(12) United States Patent
Ecker et al.

(10) Patent No.: US 7,666,588 B2
(45) Date of Patent: *Feb. 23, 2010

(54) METHODS FOR RAPID FORENSIC ANALYSIS OF MITOCHONDRIAL DNA AND CHARACTERIZATION OF MITOCHONDRIAL DNA HETEROPLASMY

(75) Inventors: David J. Ecker, Encinitas, CA (US); Richard H. Griffey, Vista, CA (US); Rangarajan Sampath, San Diego, CA (US); Steven A. Hofstadler, Oceanside, CA (US); John McNeil, La Jolla, CA (US); Stanley T. Crooke, Carlsbad, CA (US); Lawrence B. Blyn, Mission Viejo, CA (US); Thomas A. Hall, Oceanside, CA (US); Yun Jiang, Carlsbad, CA (US); James C. Hannis, Vista, CA (US); Neil White, Encinitas, CA (US); Vivek Samant, Encinitas, CA (US); Mark W. Eshoo, Solana Beach, CA (US); Jared J. Drader, Carlsbad, CA (US)

(73) Assignee: Ibis Biosciences, Inc., Carlsbad, CA (US)

( * ) Notice: Subject to any disclaimer, the term of this patent is extended or adjusted under 35 U.S.C. 154(b) by 332 days.

This patent is subject to a terminal disclaimer.

(21) Appl. No.: 10/660,998

(22) Filed: Sep. 12, 2003

(65) Prior Publication Data

US 2004/0161770 A1 Aug. 19, 2004

Related U.S. Application Data

(63) Continuation-in-part of application No. 10/323,438, filed on Dec. 18, 2002, now abandoned, and a continuation-in-part of application No. 09/798,007, filed on Mar. 2, 2001, now abandoned.

(60) Provisional application No. 60/431,319, filed on Dec. 6, 2002.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.33

(58) Field of Classification Search .............. 435/5, 435/91.2, 6; 536/24.33, 24.31, 24.32, 23.1
See application file for complete search history.

(56) References Cited

U.S. PATENT DOCUMENTS

| | | | |
|---|---|---|---|
| 4,075,475 A | 2/1978 | Risby et al. |
| 4,683,195 A | 7/1987 | Mullis et al. |
| 4,683,202 A | 7/1987 | Mullis et al. |
| 4,965,188 A | 10/1990 | Mullis et al. |
| 5,015,845 A | 5/1991 | Allen et al. |
| 5,072,115 A | 12/1991 | Zhou |
| 5,213,961 A | 5/1993 | Bunn et al. |
| 5,219,727 A | 6/1993 | Wang et al. |
| 5,436,129 A | 7/1995 | Stapleton |
| 5,451,500 A | 9/1995 | Stapleton |
| 5,472,843 A | 12/1995 | Milliman |
| 5,476,774 A | 12/1995 | Wang et al. |
| 5,484,908 A | 1/1996 | Froehler et al. |
| 5,502,177 A | 3/1996 | Matteucci et al. |
| 5,503,980 A | 4/1996 | Cantor |
| 5,504,327 A | 4/1996 | Sproch et al. |
| 5,504,329 A | 4/1996 | Mann et al. |
| 5,523,217 A | 6/1996 | Lupski et al. |
| 5,527,675 A | 6/1996 | Coull et al. |
| 5,547,835 A | 8/1996 | Koster |
| 5,567,587 A | 10/1996 | Kohne |
| 5,576,204 A | 11/1996 | Blanco et al. |
| 5,580,733 A | 12/1996 | Levis et al. |
| 5,605,798 A | 2/1997 | Koster |
| 5,608,217 A | 3/1997 | Franzen et al. |
| 5,612,179 A | 3/1997 | Simons |
| 5,622,824 A | 4/1997 | Koster |
| 5,625,184 A | 4/1997 | Vestal et al. |
| 5,645,985 A | 7/1997 | Froehler et al. |
| 5,683,869 A | 11/1997 | Ramsay Shaw et al. |
| 5,686,242 A | 11/1997 | Bruice et al. |
| 5,691,141 A | 11/1997 | Koster |
| 5,700,642 A | 12/1997 | Monforte et al. |
| 5,702,895 A | 12/1997 | Matsunaga et al. |
| 5,707,802 A | 1/1998 | Sandhu et al. |
| 5,712,125 A | 1/1998 | Uhlen |
| 5,716,825 A | 2/1998 | Hancock et al. |
| 5,727,202 A | 3/1998 | Kucala |
| 5,745,751 A | 4/1998 | Nelson et al. |
| 5,747,246 A | 5/1998 | Pannetier et al. |
| 5,747,251 A | 5/1998 | Carson et al. |
| 5,753,489 A | 5/1998 | Kistner et al. |
| 5,759,771 A | 6/1998 | Tilanus |
| 5,763,169 A | 6/1998 | Sandhu et al. |
| 5,763,588 A | 6/1998 | Matteucci et al. |

(Continued)

FOREIGN PATENT DOCUMENTS

AU 2003245488 6/2002

(Continued)

OTHER PUBLICATIONS

Aaserud et al. Accurate base composition of double-strand DNA by Mass Spectrometry. Amer Soc Mass Spectrometry, vol. 7, p. 1266-1269, 1996.*

(Continued)

*Primary Examiner*—Suryaprabha Chunduru
(74) *Attorney, Agent, or Firm*—Casimir Jones S.C.; Christopher C. Sappenfield

(57) ABSTRACT

The present invention provides methods for rapid forensic analysis of mitochondrial DNA and methods for characterizing heteroplasmy of mitochondrial DNA, which can be used to assess the progression of mitochondrial diseases.

47 Claims, 32 Drawing Sheets

U.S. PATENT DOCUMENTS

| | | |
|---|---|---|
| 5,770,367 A | 6/1998 | Southern et al. |
| 5,777,324 A | 7/1998 | Hillenkamp |
| 5,814,442 A | 9/1998 | Natarajan et al. |
| 5,828,062 A | 10/1998 | Jarrell et al. |
| 5,830,653 A | 11/1998 | Froehler et al. |
| 5,830,655 A | 11/1998 | Monforte et al. |
| 5,832,489 A | 11/1998 | Kucala |
| 5,834,255 A | 11/1998 | van Gemen et al. |
| 5,849,492 A | 12/1998 | Rogan |
| 5,849,497 A | 12/1998 | Steinman |
| 5,849,901 A | 12/1998 | Mabilat et al. |
| 5,851,765 A | 12/1998 | Koster |
| 5,845,174 A | 1/1999 | Lipschutz et al. |
| 5,864,137 A | 1/1999 | Becker et al. |
| 5,866,429 A | 2/1999 | Bloch |
| 5,869,242 A | 2/1999 | Kamb |
| 5,871,697 A | 2/1999 | Rothberg et al. |
| 5,872,003 A | 2/1999 | Koster |
| 5,876,936 A | 3/1999 | Ju |
| 5,885,775 A | 3/1999 | Haff et al. |
| 5,928,905 A | 7/1999 | Stemmer et al. |
| 5,928,906 A | 7/1999 | Koster |
| 5,965,363 A | 10/1999 | Monforte et al. |
| 5,976,798 A | 11/1999 | Parker et al. |
| 5,981,176 A | 11/1999 | Wallace |
| 5,981,190 A | 11/1999 | Israel |
| 5,994,066 A | 11/1999 | Bergeron et al. |
| 6,001,564 A | 12/1999 | Bergeron et al. |
| 6,005,096 A | 12/1999 | Matteucci et al. |
| 6,007,690 A | 12/1999 | Nelson et al. |
| 6,007,992 A | 12/1999 | Lin et al. |
| 6,015,666 A | 1/2000 | Springer et al. |
| 6,018,713 A | 1/2000 | Coli et al. |
| 6,028,183 A | 2/2000 | Lin et al. |
| 6,043,031 A | 3/2000 | Koster et al. |
| 6,046,005 A | 4/2000 | Ju et al. |
| 6,051,378 A | 4/2000 | Monforte et al. |
| 6,054,278 A | 4/2000 | Dodge et al. |
| 6,055,487 A | 4/2000 | Margery et al. |
| 6,061,686 A | 5/2000 | Gauvin et al. |
| 6,063,031 A | 5/2000 | Cundari et al. |
| 6,074,823 A | 6/2000 | Koster |
| 6,074,831 A | 6/2000 | Yakhini et al. |
| 6,090,558 A | 7/2000 | Butler et al. |
| 6,104,028 A | 8/2000 | Hunter et al. |
| 6,110,710 A | 8/2000 | Smith et al. |
| 6,111,251 A | 8/2000 | Hillenkamp |
| 6,140,053 A | 10/2000 | Koster |
| 6,146,144 A | 11/2000 | Fowler et al. |
| 6,146,854 A | 11/2000 | Koster et al. |
| 6,153,389 A | 11/2000 | Haarer et al. |
| 6,159,681 A | 12/2000 | Zebala |
| 6,180,339 B1 | 1/2001 | Sandhu et al. |
| 6,180,372 B1 | 1/2001 | Franzen |
| 6,194,144 B1 | 2/2001 | Koster |
| 6,197,498 B1 | 3/2001 | Koster |
| 6,214,555 B1 | 4/2001 | Leushner et al. |
| 6,218,118 B1 | 4/2001 | Sampson et al. |
| 6,221,587 B1 | 4/2001 | Ecker et al. |
| 6,221,601 B1 | 4/2001 | Koster et al. |
| 6,221,605 B1 | 4/2001 | Koster |
| 6,225,450 B1 | 5/2001 | Koster |
| 6,235,476 B1 | 5/2001 | Bergmann et al. |
| 6,235,478 B1 | 5/2001 | Koster |
| 6,235,480 B1 | 5/2001 | Shultz et al. |
| 6,238,871 B1 | 5/2001 | Koster |
| 6,238,927 B1 | 5/2001 | Abrams et al. |
| 6,239,159 B1 | 5/2001 | Brown et al. |
| 6,258,538 B1 | 7/2001 | Koter et al. |
| 6,261,769 B1 | 7/2001 | Everett et al. |
| 6,265,716 B1 | 7/2001 | Hunter et al. |
| 6,268,129 B1 | 7/2001 | Gut et al. |
| 6,268,131 B1 | 7/2001 | Kang et al. |
| 6,268,144 B1 | 7/2001 | Koster |
| 6,268,146 B1 | 7/2001 | Shultz |
| 6,270,973 B1 | 8/2001 | Lewiz et al. |
| 6,270,974 B1 | 8/2001 | Shultz et al. |
| 6,274,726 B1 | 8/2001 | Laugham, Jr. et al. |
| 6,277,573 B1 | 8/2001 | Koster et al. |
| 6,277,578 B1 | 8/2001 | Shultz et al. |
| 6,277,634 B1 | 8/2001 | McCall et al. |
| 6,300,076 B1 | 10/2001 | Koster |
| 6,303,297 B1 | 10/2001 | Lincoln et al. |
| 6,312,893 B1 | 11/2001 | Van Ness et al. |
| 6,312,902 B1 | 11/2001 | Shultz et al. |
| 6,322,970 B1 | 11/2001 | Little et al. |
| 6,361,940 B1 | 3/2002 | Van Ness et al. |
| 6,372,424 B1 | 4/2002 | Brow et al. |
| 6,389,428 B1 | 5/2002 | Rigault et al. |
| 6,391,551 B1 | 5/2002 | Shultz et al. |
| 6,393,367 B1 | 5/2002 | Tang et al. |
| 6,419,932 B1 | 7/2002 | Dale |
| 6,423,966 B2 | 7/2002 | Hillenkamp et al. |
| 6,428,955 B1 | 8/2002 | Koster et al. |
| 6,428,956 B1 | 8/2002 | Croooke et al. |
| 6,432,651 B1 | 8/2002 | Hughes et al. |
| 6,436,635 B1 | 8/2002 | Fu et al. |
| 6,436,640 B1 | 8/2002 | Simmons et al. |
| 6,453,244 B1 * | 9/2002 | Oefner .................. 702/20 |
| 6,458,533 B1 | 10/2002 | Felder et al. |
| 6,468,743 B1 | 10/2002 | Romick et al. |
| 6,468,748 B1 | 10/2002 | Monforte et al. |
| 6,475,143 B2 | 11/2002 | Iliff |
| 6,475,736 B1 | 11/2002 | Stanton, Jr. |
| 6,479,239 B1 | 11/2002 | Anderson et al. |
| 6,500,621 B2 | 12/2002 | Koster |
| 6,553,317 B1 | 4/2003 | Lincoln et al. |
| 6,558,902 B1 | 5/2003 | Hillenkamp |
| 6,563,025 B1 | 5/2003 | Song et al. |
| 6,566,055 B1 | 5/2003 | Monforte et al. |
| 6,582,916 B1 | 6/2003 | Schmidt et al. |
| 6,586,584 B2 | 7/2003 | McMillian et al. |
| 6,589,485 B2 | 7/2003 | Koster |
| 6,602,662 B1 | 8/2003 | Koster et al. |
| 6,605,433 B1 | 8/2003 | Fliss et al. |
| 6,610,492 B1 | 8/2003 | Stanton et al. |
| 6,613,509 B1 | 9/2003 | Chen |
| 6,613,520 B2 | 9/2003 | Ashby |
| 6,623,928 B2 | 9/2003 | Van Ness et al. |
| 6,682,889 B1 | 1/2004 | Wang et al. |
| 6,705,530 B2 | 3/2004 | Kiekhaefer |
| 6,706,530 B2 | 3/2004 | Hillencamp |
| 6,716,634 B1 | 4/2004 | Myerson |
| 6,783,939 B2 | 8/2004 | Olmsted et al. |
| 6,800,289 B2 | 10/2004 | Nagata et al. |
| 6,813,615 B1 | 11/2004 | Colasanti et al. |
| 6,836,742 B2 | 12/2004 | Brekenfeld |
| 6,852,487 B1 | 2/2005 | Barany et al. |
| 6,856,914 B1 | 2/2005 | Pelech |
| 6,875,593 B2 | 4/2005 | Froehler et al. |
| 6,906,316 B2 | 6/2005 | Sugiyama et al. |
| 6,906,319 B2 | 6/2005 | Hoyes |
| 6,914,137 B2 | 7/2005 | Baker |
| 6,994,962 B1 | 2/2006 | Thilly |
| 7,022,835 B2 | 4/2006 | Rauth et al. |
| 7,024,370 B2 | 4/2006 | Epler et al. |
| 7,217,510 B2 | 5/2007 | Ecker et al. |
| 7,255,992 B2 | 8/2007 | Ecker et al. |
| 7,226,739 B2 | 9/2007 | Ecker et al. |
| 7,312,036 B2 | 12/2007 | Sampath et al. |
| 7,321,828 B2 | 1/2008 | Cowsert et al. |
| 7,390,458 B2 | 6/2008 | Burow et al. |
| 2002/0006611 A1 | 1/2002 | Portugal et al. |
| 2002/0042112 A1 | 4/2002 | Koster et al. |

| | | |
|---|---|---|
| 2002/0042506 A1 | 4/2002 | Kristyanne et al. |
| 2002/0045178 A1 | 4/2002 | Cantor et al. |
| 2002/0120408 A1 | 8/2002 | Kreiswirth et al. |
| 2002/0137057 A1 | 9/2002 | Wold et al. |
| 2002/0138210 A1 | 9/2002 | Wilkes et al. |
| 2002/0150903 A1 | 10/2002 | Koster et al. |
| 2002/0150927 A1 | 10/2002 | Matray et al. |
| 2002/0168630 A1 | 11/2002 | Fleming et al. |
| 2003/0017487 A1 | 1/2003 | Xue et al. |
| 2003/0027135 A1 | 2/2003 | Ecker et al. |
| 2003/0039976 A1 | 2/2003 | Haff et al. |
| 2003/0050470 A1 | 3/2003 | An et al. |
| 2003/0064483 A1 | 4/2003 | Shaw et al. |
| 2003/0073112 A1 | 4/2003 | Zhang et al. |
| 2003/0082539 A1 | 5/2003 | Ecker et al. |
| 2003/0101172 A1 | 5/2003 | Ecker et al. |
| 2003/0104410 A1 | 6/2003 | Mittman |
| 2003/0113745 A1 | 6/2003 | Monforte et al. |
| 2003/0119018 A1 | 6/2003 | Omura et al. |
| 2003/0124556 A1 | 7/2003 | Ecker et al. |
| 2003/0129589 A1 | 7/2003 | Koster et al. |
| 2003/0134312 A1 | 7/2003 | Burgyone et al. |
| 2003/0148284 A1 | 8/2003 | Vision et al. |
| 2003/0167133 A1 | 9/2003 | Ecker et al. |
| 2003/0167134 A1 | 9/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0175729 A1 | 9/2003 | Van Eijk et al. |
| 2003/0186247 A1 | 10/2003 | Smarason et al. |
| 2003/0187588 A1 | 10/2003 | Ecker et al. |
| 2003/0187593 A1 | 10/2003 | Ecker et al. |
| 2003/0190605 A1 | 10/2003 | Ecker et al. |
| 2003/0190635 A1 | 10/2003 | Masswiggen |
| 2003/0194699 A1 | 10/2003 | Lewis et al. |
| 2003/0203398 A1 | 10/2003 | Bramucci et al. |
| 2003/0220844 A1 | 11/2003 | Marmellos et al. |
| 2003/0225529 A1 | 12/2003 | Ecker et al. |
| 2003/0228571 A1 | 12/2003 | Ecker et al. |
| 2004/0005555 A1 | 1/2004 | Rothman et al. |
| 2004/0014957 A1 | 1/2004 | Eldrup et al. |
| 2004/0023207 A1 | 2/2004 | Polansky |
| 2004/0023209 A1 | 2/2004 | Jonasson |
| 2004/0029129 A1 | 2/2004 | Wang et al. |
| 2004/0038206 A1 | 2/2004 | Zhang et al. |
| 2004/0038234 A1 | 2/2004 | Gut et al. |
| 2004/0038385 A1 | 2/2004 | Langlois et al. |
| 2004/0101809 A1 | 5/2004 | Weiss et al. |
| 2004/0110169 A1 | 6/2004 | Ecker et al. |
| 2004/0111221 A1 | 6/2004 | Beattie et al. |
| 2004/0117129 A1 | 6/2004 | Ecker et al. |
| 2004/0121309 A1 | 6/2004 | Ecker et al. |
| 2004/0121310 A1 | 6/2004 | Ecker et al. |
| 2004/0121311 A1 | 6/2004 | Ecker et al. |
| 2004/0121312 A1 | 6/2004 | Ecker et al. |
| 2004/0121313 A1 | 6/2004 | Ecker et al. |
| 2004/0121314 A1 | 6/2004 | Ecker et al. |
| 2004/0121315 A1 | 6/2004 | Ecker et al. |
| 2004/0121329 A1 | 6/2004 | Ecker et al. |
| 2004/0121335 A1 | 6/2004 | Ecker et al. |
| 2004/0121340 A1 | 6/2004 | Ecker et al. |
| 2004/0122598 A1 | 6/2004 | Ecker et al. |
| 2004/0122857 A1 | 6/2004 | Ecker et al. |
| 2004/0126764 A1 | 7/2004 | Lasken et al. |
| 2004/0137013 A1 | 7/2004 | Katinger et al. |
| 2004/0161770 A1 | 8/2004 | Ecker et al. |
| 2004/0180328 A1 | 9/2004 | Ecker et al. |
| 2004/0185438 A1 | 9/2004 | Ecker et al. |
| 2004/0191769 A1 | 9/2004 | Marino et al. |
| 2004/0202997 A1 | 10/2004 | Ecker et al. |
| 2004/0209260 A1 | 10/2004 | Ecker et al. |
| 2004/0219517 A1 | 11/2004 | Ecker et al. |
| 2005/0026147 A1 | 2/2005 | Walker et al. |
| 2005/0026641 A1 | 2/2005 | Hokao |
| 2005/0027459 A1 | 2/2005 | Ecker et al. |
| 2005/0065813 A1 | 3/2005 | Michelevich et al. |
| 2005/0130216 A1 | 6/2005 | Becker et al. |
| 2005/0250125 A1 | 11/2005 | Novakoff |
| 2005/0266397 A1 | 12/2005 | Ecker et al. |
| 2006/0020391 A1 | 1/2006 | Kreiswirth et al. |
| 2006/0121520 A1 | 6/2006 | Ecker et al. |
| 2006/0259249 A1 | 11/2006 | Sampath et al. |
| 2006/0275788 A1 | 12/2006 | Ecker et al. |
| 2007/0048735 A1 | 3/2007 | Ecker et al. |
| 2007/0218467 A1* | 9/2007 | Ecker et al. .................... 435/6 |
| 2008/0160512 A1 | 7/2008 | Ecker et al. |
| 2009/0004643 A1 | 1/2009 | Ecker et al. |

FOREIGN PATENT DOCUMENTS

| | | |
|---|---|---|
| AU | 2003282352 | 11/2002 |
| DE | 19732086 | 1/1999 |
| DE | 19802905 | 7/1999 |
| DE | 19824280 | 12/1999 |
| DE | 19852167 | 5/2000 |
| DE | 19943374 | 3/2001 |
| DE | 10132147 | 2/2003 |
| EP | 0620862 B1 | 4/1998 |
| EP | 0281390 | 9/1998 |
| EP | 1035219 | 9/2000 |
| EP | 02709785 | 9/2002 |
| EP | 1138782 | 2/2003 |
| EP | 1308506 | 5/2003 |
| EP | 1310571 | 5/2003 |
| EP | 1333101 | 8/2003 |
| EP | 1365031 | 11/2003 |
| EP | 1234888 | 1/2004 |
| EP | 1748072 | 1/2007 |
| FR | 2811321 | 1/2002 |
| GB | 2325002 | 11/1998 |
| GB | 2339905 | 2/2000 |
| IN | 01136/KOLNP/2003 | 2/2003 |
| JP | 5-276999 | 10/1993 |
| JP | 2004-200 | 1/2004 |
| JP | 2004-24206 | 1/2004 |
| JP | 2004-201641 | 7/2004 |
| JP | 2004-201679 | 7/2004 |
| WO | WO 88/003957 | 6/1988 |
| WO | WO 90/015157 | 12/1990 |
| WO | WO 92/08117 | 5/1992 |
| WO | WO 092/05182 | 11/1992 |
| WO | WO 92/19774 | 11/1992 |
| WO | WO 93/03186 | 2/1993 |
| WO | WO 93/08297 | 4/1993 |
| WO | WO 94/16101 | 7/1994 |
| WO | WO 94/019490 | 9/1994 |
| WO | WO 94/21822 | 9/1994 |
| WO | WO 95/04161 | 2/1995 |
| WO | WO 95/011996 | 5/1995 |
| WO | WO 95/013395 | 5/1995 |
| WO | WO 95/13396 | 5/1995 |
| WO | WO 95/031997 | 11/1995 |
| WO | 96/016186 | 5/1996 |
| WO | WO 96/29431 | 9/1996 |
| WO | WO 96/32504 | 10/1996 |
| WO | WO 96/37630 | 11/1996 |
| WO | WO97/33000 | 9/1997 |
| WO | WO 97/034909 | 9/1997 |
| WO | WO97/37041 | 10/1997 |
| WO | WO 97/47766 | 12/1997 |
| WO | WO 98/03684 | 1/1998 |
| WO | WO98/12355 | 3/1998 |
| WO | WO 98/14616 | 4/1998 |
| WO | WO 98/15652 | 4/1998 |
| WO | WO 98/20020 | 5/1998 |
| WO | WO 98/20157 | 5/1998 |

| | | |
|---|---|---|
| WO | WO98/21066 | 5/1998 |
| WO | WO 98/26095 | 6/1998 |
| WO | WO 98/31830 | 7/1998 |
| WO | WO 98/035057 | 8/1998 |
| WO | WO 98/40520 | 9/1998 |
| WO | WO98/54751 | 12/1998 |
| WO | WO 99/005319 | 2/1999 |
| WO | WO 99/05319 | 2/1999 |
| WO | WO 99/12040 | 3/1999 |
| WO | WO 99/013104 | 3/1999 |
| WO | WO99/14375 | 3/1999 |
| WO | WO 99/29898 | 6/1999 |
| WO | WO99/31278 | 6/1999 |
| WO | WO 00/063362 | 10/1999 |
| WO | WO 99/57318 | 11/1999 |
| WO | WO 99/058713 | 11/1999 |
| WO | WO 99/60183 | 11/1999 |
| WO | WO 00/066789 | 11/2000 |
| WO | WO 01/07648 | 2/2001 |
| WO | WO 01/012853 | 2/2001 |
| WO | WO 01/23604 | 4/2001 |
| WO | WO 01/023608 | 4/2001 |
| WO | WO 01/32930 | 5/2001 |
| WO | WO 01/040497 | 6/2001 |
| WO | WO 01/046404 | 6/2001 |
| WO | WO 01/51661 | 7/2001 |
| WO | WO 01/051662 | 7/2001 |
| WO | WO 01/57263 | 8/2001 |
| WO | WO 01/57518 | 8/2001 |
| WO | WO 01/73119 | 10/2001 |
| WO | WO 01/73199 | 10/2001 |
| WO | WO 01/077392 | 10/2001 |
| WO | WO 02/002811 | 1/2002 |
| WO | WO 02/10186 | 2/2002 |
| WO | WO 02/10444 | 2/2002 |
| WO | WO 02/18641 | 3/2002 |
| WO | WO 02/21108 | 3/2002 |
| WO | WO 02/22873 | 3/2002 |
| WO | WO 02/024876 | 3/2002 |
| WO | WO 02/50307 | 6/2002 |
| WO | WO 02/057491 | 7/2002 |
| WO | WO 02/070664 | 9/2002 |
| WO | WO 02/070728 | 9/2002 |
| WO | WO 02/077278 | 10/2002 |
| WO | WO 02/099034 | 12/2002 |
| WO | WO 02/099095 | 12/2002 |
| WO | WO 02/099129 | 12/2002 |
| WO | WO 02/099130 | 12/2002 |
| WO | WO 03/002750 | 1/2003 |
| WO | WO 03/008636 | 1/2003 |
| WO | WO 03/012058 | 2/2003 |
| WO | WO 03/012074 | 2/2003 |
| WO | WO 03/014382 | 2/2003 |
| WO | WO 03/016546 | 2/2003 |
| WO | WO 03/020890 | 3/2003 |
| WO | WO 03/033732 | 4/2003 |
| WO | WO 03/054162 | 7/2003 |
| WO | WO 03/054755 | 7/2003 |
| WO | WO 03/060163 | 7/2003 |
| WO | WO 03/075955 | 9/2003 |
| WO | WO 03/088979 | 10/2003 |
| WO | WO 03/093506 | 11/2003 |
| WO | WO 03/097869 | 11/2003 |
| WO | WO 03/100035 | 12/2003 |
| WO | WO 03/100068 | 12/2003 |
| WO | WO 03/104410 | 12/2003 |
| WO | WO 2004/003511 | 1/2004 |
| WO | WO 2004/011651 | 2/2004 |
| WO | WO 2004/040013 | 5/2004 |
| WO | WO 2004/044123 | 5/2004 |
| WO | WO 2004/044247 | 5/2004 |
| WO | WO 2004/052175 | 6/2004 |
| WO | WO 2004/060278 | 7/2004 |
| WO | WO 2004/070001 | 8/2004 |
| WO | WO 2004/072230 | 8/2004 |
| WO | WO 2004/072231 | 8/2004 |
| WO | WO 2004/101809 | 11/2004 |
| WO | WO 2005/003384 | 1/2005 |
| WO | WO 2005/012572 | 2/2005 |
| WO | WO 2005/024046 | 3/2005 |
| WO | WO 2005/053141 | 6/2005 |
| WO | WO 2005/054454 | 6/2005 |
| WO | WO 2005/075686 | 10/2005 |
| WO | WO 2005/091971 | 10/2005 |
| WO | WO 2005/098047 | 10/2005 |
| WO | WO 2006/089762 | 8/2006 |
| WO | WO 2006/094238 | 9/2006 |
| WO | 2006/116127 | 11/2006 |
| WO | WO 2008/118809 | 10/2008 |

OTHER PUBLICATIONS

Crespillo et al. Mitochondrial DNA sequences for 118 individuals from northeastern spain. Int J Legal Med, vol. 114, pp. 130-132, 2000.*

Gattermann et al. Heteroplasmic point mutations of mitochondrial DNA affecting subunit I of cytochrome cOxidase in two patients with acquired idiopathic sideroblastic anemia. Blood, vol. 90, No. 12, pp. 4961-4972, 1997.*

Torroni et al. Classification of European mtDNAs from an analysis of three European populations. Genetics, vol. 144, p. 1835-1850, 1996.*

Parson W et al. Population data for 101 Austrian Caucasian mitochondrial DNA d-loop sequences: Application of mtDNA sequences analysis to a forensic case. Int J Legal Med., vol. 111, pp. 124-132, 1998.*

Howell N et al. Persistent heteroplasmy of a mutation in the human mtDNA control region: Hypermutation as an apparent consequence of simple-repeat expansion/contraction. Am J Hum Genet., vol. 66, pp. 1589-1598, 2000.*

Baumer A et al. Age-related human mtDNA deletions: A heterogeneous set of deletions arising at a single pair of directly repeated sequences. Am J Hum Genet., vol. 54, pp. 618-630, 1994.*

Tatuch Y, et al. Heteroplasmic mtDNA mutation (T-G) at 8993 can cause Leigh disease when the percentage of abnormal mtDNA is high. Am J Hum Genet., vol. 50, pp. 852-858, 1992.*

Baker, et al., "Review and re-analysis of domain-specific 16S primers," J. Microbiol. Methods (2003) 55:541-555.

Benson, et al., "Advantages of *Thermococcus kodakaraenis* (KOD) DNA polymerase for PCR-mass spectrometry based analyses," J. Am. Soc. Mass Spectrom. (2003) 14:601-604.

Black. et al al., "Detection of trace levels of tricothecene mycotoxins in human urineby gas chromatography-mass spectrometry." J. Chromatog. (1986) 367:103-115.

Campbell and Huang, "Detection of California serogroup Bunyavirus in tissue culture and mosquito pools by PCR," J. Virol. Methods (1996) 57:175-179.

Chen, et al., "A universal PCR primer to detect members of the Potyviridae and its use to examine the taxonomic status of several members of the family," Arch. Virol. (2001) 146:757-766.

Conrads. et al., "16S-23S rDNA internal transcribed spacer sequences for analysis of the phylogenetic relationships among species of the genus *Fusobacterium*," Intl. J. System. Evol. Micrbiol. (2002) 52:493-499.

Dasen, et al., "Classification and identification of Propioibacteria based on ribosomal RNA genes and PCR," System. Appl. Microbiol. (1998) 21:251-259.

Deforce, et al., "Characterization of DNA oligonucleotides by coupling of capillary zone electrophoresis to electrospray ionization Q-TOF mass spectrometry," Anal. Chem. (1998) 70:3060-3068.

Demesure, et al., "A set of universal primers for amplification of polymorphic non-coding regions of mitochondrial and chloroplast DNA in plants," Mol. Ecol. (1995) 4:129-131.

Flora. et al., "Dual-micro-ESI source for precise mass determination on a quadrupole time-of-flight mass spectrometer for genomic and proteomic applications," Anal. Bioanal. Chem. (2002) 373:538-546.

Fox, et al., "Identification of *Brucella* by ribosomal-spacer-region PCR and differentiation of *Brucell canis* from other *Brucella* spp. pathogenic for humans by carbohydrate profiles," J. Clin. Microbiol. (1998) 36:3217-3222.

Fox et al., "Report of the 'Bioterrorism Workshop'", J. Microbol. Methods (2002) 51:247-254.

Griffey and Greig, "Detection of base pair mismatches in duplex DNA and RNA oligonucleotides using electrospray mass spectrometry," SPIE (1997) 2985:82-86.

Griffin, et al., "Direct genetic analysis by matrix-assisted laseer desorption/ionization mass spectrometry," proc. Natl. Acad. Sci. USA (1999) 96:6301-6306.

Hannis and Muddiman, "Accurate characterization fo the tyrosine hydroxylase forensic allele 9.3 through development of electrospray ionization Fourier transform Ion cyclotron resonance mass spectrometry," Rapid. Comm. Mass Spectrom. (1999) 13:954-962.

Hannis and Muddiman, "Genotyping short tandem repeats using flow injection and electrospray ionization Fourier transform ion cyclotron resonance mass spectrometry," Rapid. Comm. Mass Spectrom. (2001) 15:348-350.

Hannis and Muddiman, "Detection of double-stranded PCR amplicons at the attomole level electrosprayed from low nanomolar solutions using FT-ICR mass spectrometry," Fresenius J. Anal Chem. (2001) 369:246-251.

Hayashi, et al., "Phylogenetic analysis of the human gut microbiota using 16S rDNA clone libraries and strictly anaerobic culture based methods," Microbiol. Immunol. (2002) 46:535-548.

Hoffmann, et al., "Universal primer set for the full-length amplification of all influenza A viruses," Arch. Virol. (2001) 146:2275-2289.

Isola, et al., "MALDI-TOF mass spectrometric method for detection of hybridized DNA oligomers," Anal. Chem. (2001) 73:2126-2131.

Jankowski and Soler, "Mass spectrometry of DNA: Part 2' Quantitative estimation of base composition," Eur. J. Mass Spectrom. Biochem. Med. Environ. Res. (1980) 1:45-52.

Kageyama and Benno, "Rapid detection f human fecal *eubacterium* species and related genera by tested PCR method," Microbiol. Immunol. (2001) 45:315-318.

Little, et al., "Rapid sequencling of oligonucleotides by high-resolution mass spectrometry," J. Am. Chem. Soc. (1994) 116:4893-4897.

Liu, et al., "Improving the microdialysis procedure for electrospray ionization mass spectrometry of biological samples," J. Mass Spectrom. (1997) 32:425-431.

Mangrum, et al., "Solution composition and thermal denaturation for the production of single-stranded PCR amplicons: piperidine-Induced destabilization of the DNA duplex," J. Am. Soc. Mass Spectrom. (2002) 13:232-240.

McCabe, et al., "Bacterial species identification after DNA amplification with a universal primer pair," Mol. Genet. Metab. (1999) 66:205-211.

Meiyu, et al., "Detection of flaviviruses by reverse transcriptase-polymerase chain reaction with the universal primer set," Microbiol. Immunol. (1997) 41:209-213.

Moricca, et al., "Detection of *Fusarium oxysporum* f.sp. *vasinfectum* in cotton tissue by polymerase chain reaction," Plant Pathol. (1998) 47:486-494.

Muddiman, et al., "Characterization of PCR products from *Bacilli* using electrospray ionization FTICR mass spectrometry," Anal Chem. (1996) 68:3705-3712.

Nagpal, et al., "Utility of 16S-23S rRNA spacer region methodology: how similar are interspace regions within a genome and between strains for closely related organisms?," J. Microbiol. Methods (1998) 33:211-219.

Null, et al., "Preparation of single-stranded PCR products for electrospray Ionization mass spectrometry using the DNA repair enzyme lambda exonuclease," Analyst (2000) 125:619-626.

Null, et al., "Evaluation of sample preparation techniques for mass measurements of PCR products using ESI-FT-ICR mass spectrometry." Am Soc. Mass Spectrom. (2002) 13:338-344.

Null and Muddiman. "Determination of a correction to improve mass measurement accuracy of Isotopically unresolved polymerase chain reaction amplicons by electrospray ionization Fourier transform Ion cyclotron resonance mass spectrometry," Rapid Comm. Mass Spectrom. (2003) 17:1714-1722.

Null and Muddiman, "Perspectives on the use of electrospray Ionization Fourier transform ion cyclotron resonance mass spectrometry for short tandem repeat genotyping in the post genome era," J. Mass Spectrom. (2001) 36:589-606.

Null, et al., "Genotyping of simple and compound short tandem repeat loci using electrospray ionization Fourier transform ion cyclotron resonance mass spectrometry," Anal. Chem. (2001) 73:4514-4521.

Null, at al., "Implications of hydrophobicity and free energy of solvation for characterization of nucleic acids by electrospray ionization mass spectrometry," Anal. Chem. (2003) 75:1331-1339.

Peng, et al., "Rapid detection of *shigella* species in environmental sewage by an immunocapture PCR with universal primers," App. Environ. Microbiol. (2002) 68:2580-2583.

Pomerantz, et al., "Determination of oligonucleotide composition from mass spectrometrically measured molecular weight," J. Am. Soc. Mass Spectrom. (1993) 4:204-209.

Ross, et al., "Discrimination of single-nucleotide polymorphisms in human DNA using peptide nucleic acid probes detected by MALDI-TOF mass spectrometry," Anal. Chem. (1997) 69:4197-4202.

Scaramozzino, et al., "Comparison of Flavivirus universal primer pairs and development of a rapid, highly sensitive heminested reverse transcription-PCR assay for detection of flaviviruses targeted to a conserved region of the NS5 gene sequences," J. Clin. Microbiol. (2001) 39:1922-1927.

Shaver, et al., "Restriction fragment length polymorphism of rRNA operons for discrimination and intergenic spacer sequences for cataloging of *Bacilus subtilis* sub-groups," J. Microbiol. Methods (2002) 50:215-223.

Srinivasan, et al., "Matrix-assisted laser desorption/ionization time-of-flight mass spectrometry as a rapid screening method to detect mutations causing Tay-Sachs disease," Rapid Comm. Mass Spectrom. (1997) 11:1144-1150.

Steffens and Roy, "Sequence analysis of mitochondrial DNA hypervariable regions using infrared fluorescence detection," Bio/Techniques (1998) 24:1044-1046.

Wunschel, et al., "Mass spectrometric characterization of DNA for molecular biological applications: advances using MALDI and ESI," Adv. Mass Spectrom., vol. 14, Karjalainen, at al., (eds.) 1998, Elsevier, Amsterdam.

Dias Neto et al., "Shotgun sequencing of human transcriptome with ORF expressed sequence tags," *PNAS* 97(7):3491-3496.

International Search Report dated Apr. 12, 2005 for International Application No. PCT/US03/38505.

Jensen, M. A. et al., "Rapid Identification of Bacteria on the Basis of Polymerase Chain Reaction-Amplified Ribosomal DNA Spacer Polymorphisms," *Appl. Environ. Microbiol.* (1993) 59(4):945-952.

Aaserud, at al., "Accurate base composition of double-strand DNA by mass spectrometry," J. Am. Soc. Mass Spec. (1996) 7:1266-1269.

Muddiman, et al., "Length and base composition of PCR-amplified nucleic acids using mass measurements from electrospray ionization mass spectrometry," Anal. Chem. (1997) 69:1543-1549.

Wunschel, at al., "Heterogeneity in *Bacillus cereus* PCR products detected by ESI-FTICR mass spectrometry," Anal. Chem. (1998) 70:1203-1207.

Muddiman, et al., "Sequencing and characterization of larger oligonucleotides by electrospray Ionization fourier transform ion cyclotron resonance mass spectrometry," Rev. Anal.Chem. (1998) 17:1-68.

Hurst, et al., "Detection of bacterial DNA polymerase chain reaction products by matrix-assisted laser desorption/ionization mass spectrometry," Rapid. Comm. Mass. Spec. (1996) 10:377-382.

Muddiman, et al., "Precise mass measurement of a double-stranded 500 base-pair (309 kDa) polymerase chain reaction product by negative ion electrospray ionization fourier transform ion cyclotron resonance mass spectrometry," Rapid Comm. Mass Spec. (1999) 13:1201-1204.

Alves-Silva, J. et al., "The Ancestry of Brazilian mtDNA Lineages," *Am. J. Hum. Genet.* (2000) 67:444-461.

Anderson et al., "Sequence and organization of the human mitochondrial genome," *Nature* (1981) 290:457-465.

Andreasson et al., "Mitochondrial Sequence Analysis for Forensic Identification Using Pyrosequencmg Technology" *BioTechniques* (2002) 32:124-133.

Bahrmand et al., "Polymerase chain reaction of bacterial genomes with single universal primer: application to distinguishing mycobacteria species" *Molecular and Cellular Probes* (1996) 10:117-122.

Bahrmand et al., "Use of restriction enzyme analysis of amplified DNA coding for the hsp65 gene and polymerase chain reaction with universal primer for rapid differentiation of *mycobacterium* species in the clinical laboratory" *Scandinavian Journal of Infectious Diseases* (1998) 30:477-480.

Bastia et al., "Organelle DNA analysis of *Solanum* and *Brassica* somatic hybrids by PCR with 'universal primers'." *Theoretical and Applied Genetics* (2001) 102:1265-1272.

Batey et al., "Preparation of Isotopically Labeled Ribonucleotides for Multidimensional NMR Spectroscopy of RNA" *Nucleic Acids Research* (1992) 20:4515-4523.

BLAST Search results (Mar. 2006).

Boivin-Jahns et al., "Bacterial Diversity in a Deep-Subsurface Clay Environment" *Applied and Environmental Microbiology* (1996) 62:3405-3412.

Borrow et al., "SiaD PCR Elisa for confirmation and identification of serogroup Y and W135 meningococcal infections" *FEMS Microbiological Letters* (1998) 159:209-214.

Bowen et al., "The native virulence plasmid combination affects the segregational stability of a theta-replicating shuttle vector in *Bacillus anthracis* var, New Hampshire" *J. Appl. Microbiol.* (1999) 87:270-278.

Carracedo et al., "DNA commission of the international society for forensic genetics: guidelines for mitochondrial DNA typing" *Forensic Science International* (2000) 110:79-85.

Case et al., "Maternal inheritance of mitochondrial DNA polymorphisms in cultured human fibroblasts," *Somatic Cell Genetics* (1981) 7:103-108.

Cespedes et al., "Polymerase chain reaction restriction fragment length polymorphism analysis of a short fragment of the cytochrome b gene for identification of flatfish species" *J. Food Protection* (1998) 61:1684-1685.

Chang, P.-K. et al., "aflT, a MFS transporter-encoding gene located in the aflatoxin gene cluster, does not have a significant role in aflatoxin secretion," Fungal Genet.Biol. (2004) 41:911-920.

Chen et al., "Universal primers for amplification of mitochondrial small subunit ribosomal RNA-encoding gene in scleractinian corals" *Marine Biotechnology* (2000) 2:146-153.

Chen, N. et al., "The genomic sequence of ectromelia virus, the causative agent of mousepox," *Virology* (2003) 317:165-186.
Cho et al., "Application of the ribonuclease P (RNase P) RNA gene sequence for phylogenetic analysis of the gene *Saccharomonospora" International Journal of Systematic Bacteriology* (1998) 48:1223-1230.
Cornel et al., "Polymerase chain reaction species diagnostic assay for *Anopheles quadrimaculatus* cryptic species (Diptera: Culicidae) based on ribosomal DNA ITS2 sequences" *Journal of Medical Entomology* (1996) 33:109-116.
Crain et al., "Applications of mass spectrometry of the characterization of oligonucleotides and nucleic acids" *Curr. Opin. Biotechnol.* (1998) 9:25-34.
Deforce et al., "Analysis of oligonucleotides by ESI-MS" *Advances in Chromatography* (2000) 40:539-566.
Dinauer et al., "Sequence-based typing of HLA class II DQB1" *Tissue Anigens* (2000) 55:364-368.
Dubernet et al., "A PCR-based method for identification of *Lactobacilli* at the genus level" *FEMS Microbiology Letters* (2002) 214:271-275.
Elnifro et al., "PCR and Restriction Endonuclease Analysis for Rapid Identification of Adenovirus Subgenera" *Journal of Clinical Microbiology* (2000) 38:2055-2061.
EMBL Accession No. S90302, Human, Muscle, Mitochondrial Mutant, 22 nt, segment 2 of 2 (XP002436791) Nov. 26, 1993.
Esmans et al., "Liquid Chromatography—Mass Spectrometry in Nucleoside, nucleotide and modified nucleotide characterization" *J. of Chromatography A* (1998) 794:109-127.
European Search Report for 02709785.6 dated Oct. 10, 2005.
Figueiredo et al., "Identification of Brazilian flaviviruses by a simplified reverse transcription-polymerase chain reaction method using Flavivirus universal primers" *American Journal of Tropical Medicine and Hygiene* (1998) 59:357-362.
Fox et al., "Identification and Detection of Bacteria: Electrospray MS-MS Versus Derivatization/GC-MS" *Proceedings of the ERDEC Scientific Conference on Chemical and Biological Defense Research* (1994) 39-44.
Fraser et al., "The Minimal Gene Complement of Mycoplasma Genitalium" *Science* (1995) 270:397-403.
Fuerstenau et al., "Molecular Weight Determination of Megadalton DNA Electrospray Ions Using Charge Detection Time-of-flight Mass Spectrometry" *Rapid Comm. Mass Spec.* (1995) 9:1528-1538.
Fujioka et al., "Analysis of enterovirus genotypes using single-strand conformation polymorphisms of polymerase chain reaction products" *J. Virol. Meth.* (1995) 51:253-258.
Gabriel et al., "Improved mtDNA sequence analysis of forensic remains using a "mini-primer set" amplification strategy" *Journal of Forensic Sciences* (2001) 46:247-253.
Ginther et al., "Identifying individuals by sequencing mitochondrial DNA from teeth," *Nature Genetics* (1992) 2:135-138.
Giles et al., "Maternal inheritance of human mitochondrial DNA," *PNAS* (1980) 77:6715-6719.
Goto et al., "Applications of the partial 16S rDNA sequence as an index for rapid identification of species in the genus *Bacillus" J. Gen. Appl. Microbiol.* (2000) 46:1-8.
Greenberg et al., "Intraspecific nucleotide sequence variability surrounding the origin of replication in human mitochondrial DNA," *Gene* (1983) 21:33-49.
Griffin et al., "Single-nucleotide polymorphism analysis by MALDI-TOF mass spectrometry" *Trends in Biotechnology* (2000) 18:77-84.
Grzybowski "Extremely high levels of human mitochondrial DNA heteroplasmy in single hair roots" *Electrophoresis* (2000) 21:548-553.
Hahner et al., "Analysis of short tandem repeat polymorphisms by electrospray ion trap mass spectrometry" *Nucleic Acids Research* (2000) 28:E82.
Hannis et al., "Genotyping complex short tandem repeats using electrospray ionization Fourier transform ion cyclotron resonance multistage mass spectrometry" *Proceedings of SPIE—The International Society for Optical Engineering* (2000) 3926:36-47.
Haugland et al., "Identification of putative sequence specific PCR primers for detection of the toxigenic fungal species *Stachybotrys chartarum" Mol. Cell. Probes* (1998) 12:387-396.
Henchal et al., "Sensitivity and specificity of a universal primer set for the rapid diagnosis of dengue virus infections by polymerase chain reaction and nucleic acid hybridization" *American Journal of Tropical Medicine and Hygiene* (1991) 45:418-428.
Herrmann et al., "Differentiation of *Chlamydia* spp. By Sequence Determination and Restriction Endonuclease Cleavage of RNase P RNA Genes" *J. Clin. Microbiol.* (1996) 34:1897-1902.
Higgins et al., "Competitive oligonucleotide single-base extension combined with mass spectrometric detection for mutation screening" *BioTechniques* (1997) 23:710-714.
Holland et al., "Mitochondrial DNA Sequence Analysis of Human Skeletal Remains: Identification of Remains from the Vietnam War," *Journal of Forensic Sciences* (1993) 38:542-553.
Holm et al., "Removing near-neighbour redundancy from large protein sequence collections" *Bioinformatics* (1998) 14:423-429.
Honda et al., "Universal method of hypersensitive nested PCR toward forensic DNA typing" *International Congress Series* (1998) 7:28-30.
Hurst et al., "MALDI-TOF Analysis of Polymerase Chain Reaction Products from Methanotrophic Bacteria" *Anal. Chem.* (1998) 70:2693-2698.
Hutchison et al., "Maternal inheritance of mammalian mitochondrial DNA," *Nature* (1974) 251:536-538.
Ingman et al., "Mitochondrial genome variation and the origin of modern humans" *Nature* (2000) 408:708-713.
International Search Report for PCT/US02/20336 dated Feb. 3, 2003.
International Search Report for PCT/US03/38795 dated Apr. 19, 2004.

International Prelim. Exam. Report for PCT/US02/20336 dated May 12, 2004.
International Search Report for PCT/US03/38757 dated Jun. 24, 2004.
International Search Report for PCT/US03/38830 dated Aug. 25, 2004.
International Search Report for PCT/US03/38761 dated Dec. 30, 2005.
International Search Report for PCT/US2004/011877 dated Apr. 20, 2006.
International Search Report for PCT/US2005/000386 dated May 9, 2006.
International Search Report for PCT/US2005/018031 dated Jun. 28, 2006.
Jansen et al., "Genotype-by-environment Interaction in Genetic Mapping of Multiple Quantitative Trait Loci" *Theor. Appl. Genet.* (1995) 91:33-37.
Jiang et al., "Multiple Trait Analysis of Genetic Mapping for Quantitative Trait Loci Genetics" *Genetics* (1995) 140:1111-1127.
Jiang et al., "A highly efficient and automated method of purifying and desalting PCR products for analysis by electrospray ionization mass spectrometry." *Anal. Biochem.* (2003) 316:50-57.
Johnson et al., "Precise molecular weight determination of CPR products of the rRNA intergenic spacer region using electrospray quadrupole mass spectroemtry for differentiation of *B. subtilis* and *B. atrophaeus*, closely related species of bacilli" *Journal of Microbiological Methods* (2000) 40:241-254.
Jurinke et al., "Detection of hepatitis B virus DNA in serum samples via nested PCR and MALDI-TOF mass spectrometry" *Genetic Analysis: Biomolecular Engineering* (1996) 13:67-71.
Ke et al., "Development of a PCR Assay for Rapid Detection of Enterococci" *Journal of Clinical Microbiology* (1999) 37:3497-3503.
Keller et al., "Empirical Statistical Model to Estimate the Accuracy of Peptide Identifications Made by MS/MS and Database Search" *Anal. Chem* (2002) 74:5383-5392.
Kilpatrick et al., "Group-Specific Identification of Polioviruses by PCR Using Primer Containing Mixed-Base or Deoxyinosine Residues at Positions of Codon Degeneracy" *J. Clin. Microbiol.* (1996) 34:2990-2996.
Krahmer et al., "Electrospray quadrupole mass spectrometry analysis of model oligonucleotides and polymerase chain reaction products: determination of base substitutions, nucleotide additions/deletions, and chemical modifications" *Anal. Chem.* (1999) 71:2893-2900.
Krahmer et al., "MS for identification of single nucleotide polymorphisms and MS/MS for discrimination of isomeric PCR products" *Anal. Chem.* (2000) 72:4033-4040.
Kupke et al., "Molecular Characterization of Lantibiotic-synthesizing Enzyme EpiD Reveals a Function for Bacterial Dfp Proteins i Coenzyme A Biosynthesis" *Journal of Biological Chemistry* (2000) 275:31838-31846.
Lacroix et al., "PCR-Based Technique for the Detection of Bacteria in Semen and Urine" *J. Microbiol. Meth.* (1996) 26:61-71.
Lebedev, Y. et al "Oligonucleotides containing 2-aminoadenine and 5-methycytosine are more effective as primers for PCR amplification than their nonmodified counterparts" *Genetic Analysis: Biomolecular Engineering* (1996) 13:15-21.
Leif et al., "Isolation and characterization of the proton-translocating NADH: ubiquinone oxidoreductase from *Escherichia coli*" *Eur. J. Biochem.* (1995) 230:538-548.
Lewers et al., "Detection of Linked QTL for Soybean Brown Stem Rot Resistance in 'BSR 101' as Expressed in a Growth Chamber Environment" *Molecular Breeding* (1999) 5:33-42.
Li et al., "Single nucleotide polymorphism determination using primer extension and time of flight mass spectrometry" *Electrophoresis* (1999) 20:1258-1265.
Little et al., "MALDI on a Chip: Analysis of Arrays of Low-Femtomole to Subfemtomole Quantities of Synthetic Oligonucleotides and DNA Diagnostic Products Dispensed by a Piezoelectric Pipet" *Analytical Chemistry* (1997) 69:4540-4546.
Liu et al., "An unusual gene arrangement for the putative chromosome replication origin and circadian expression of dnaN in *Synechococcus* sp. Strain PCC 7942" *Gene* (1996) 172:105-109.

Loakes et al., "Nitroindoles as universal bases" *Nucleosides and Nucleotides* (1995) 14:1001-1003.
Love et al., "Cloning and sequence of the groESL heat-shock operon of *Pasteurella multocida*" *Gene* (1995) 166:179-180.
Maiwald et al., "Characterization of contaminating DNA in Taq polymerase which occurs during amplification with a primer set for Legionella 5S ribosomal RNA" *Molecular and Cellular Probes* (1994) 8:11-14.
Martemy Anov et al., "Extremely Thermostable Elongation Factor G from *Aquifex aeolicus*: Cloning, Expression, Purification, and Characterization in a Heterologous Translation System" *Protein Expr. Purif.* (2000) 18:257-261.
Matray et al., "Synthesis and properties of RNA analogs—oligoribonucleotide N3'->P5' phosphoramidates" *Nucleic Acids Res* (1999) 3976-3985.
McLafferty et al., "Comparison of Algorithms and Databases for Matching Unknown Mass Spectra" *J. Am. Soc. Mass Spectrom.* (1998).
Messmer et al., "Discrimination of *Streptococcus pneumoniae* from other upper respiratory tract streptococci by arbitrarily primed PCR" *Clinical Biochemistry* (1995) 28:567-572.
Miller et al., "A compendium of human mitochondrial DNA control region: development of an international standard forensic database," Croat Med. J. (2001) 42:315-327.
Morse et al., "Nucleotide Sequence of Part of the ropC Gene Encoding the B Subunit of DNA-Dependent RNA Polymerase from some Gram-Positive Bacteria and Comparative Amino Acid Sequence Analysis" *System Appl. Microbiol.* (1996) 19:150-157.
Muddiman et al., "Application of secondary ion and matrix-assisted laser desorption-ionization time-of-flight mass spectrometry for the quantitative analysis of biological molecules" *Mass Spectrometry Reviews* (1995) 14:383-429.
Muddiman et al., "Important aspects concerning the quantification of biomolecules by time-of-flight secondary-ion mass spectrometry" *Applied Spectroscopy* (1996) 50:161-166.
Muhammad et al., "Electrospray ionization quadrupole time-of-flight mass spectrometry and quadrupole mass spectrometry for genotyping single nucleotide substitutions in intact polymerase chain reaction products in K-ras and p53" *Rapid Commun. Mass Spectrom.* (2002) 16:2278-2285.
Mushegian et al., "A minimal gene set for ceullular life derived by comparison of complete bacterial genomes" Proc. Natl. Acad. Sci. USA (1996) 93:10268-10273.
Nakao et al., "Development of a Direct PCR Assay for Detection of the Diphtheria Toxin Gene" *J. Clin. Microbiol.* (1997) 35:1651-1655.
Naumov et al., "Discrimination of the Soil Yest Species *Williopsis saturnus* and *Williopsis suaveolens* by the Polymerase Chain Reaction with the Universal Primer N21" *Microbiology (Moscow)(Translation of Mikrobiologiya)* (2000) 69:229-233, Abstract only.
Nilsson et al., "Evaluation of mitochondrial DNA coding region assays for increased discrimination in forensic analysis" *Forensic Science International: Genetics* (2008) 2:1-8.
Nishikawa et al., "Reconstitution of active recombinant Shiga toxin (Stx)1 from recombinant Stxl-A and Stxl-B subunits independently produced by *E. coli* clones" *FEMS* (1999) 178:13-18.
Norder et al., "Typing of Hepatitis B Virus Genomes by a Simplified Polymerase Chain Reaction" *J. Med. Virol.* (1990) 31:215-221.
Paterson et al., "Fine Mapping of Quantitative Trait Loci Using Selected Overlapping Recombinant Chromosomes, in an Interspecies Cross of Tomato" *Genetics* (1990) 124:735-742.
Raaum, R. L. et al., "Catarrhine primate divergence dates estimated from complete mitochondrial genomes: concordance with fossil and nuclear DNA evidence," *J. Hum. Evol.* (2005) 48:237-257.
Reid et al., "Primary diagnosis of foot-and-mouth disease by reverse transcription polymerase chain reaction" *Journal of Virological Methods* (2000) 89:167-176.
Reilly et al., "Design and use of 16S ribosomal DNA-directed primers in competitive PCRs to enumerate proteolytic bacteria in the rumen" *Microb. Ecol.* (2002) 43:259-270.
Ross et al., "Analysis of DNA fragments from conventional and microfabricated PCR devices using delayed extraction MALDI-TOF mass spectrometry" *Anal. Chem.* (1998) 70:2067-2073.

Sala et al., "Ambiguous base pairing of the purine analogue 1-(20deoxy-B-D-ribofuranosyl)-imidazole-4-carboxamide during PCR" *Nucl. Acids Res.* (1996) 24:3302-3306.

Sauer et al., "A novel procedure for efficient genotyping of single nucleotide polymorphisms" *Nucleic Acids Research* (2000) 28:E13.

Schena M. "Genome analysis with gene expression microarrays" Bioessays (1996) 18:427-431.

Schram et al., "Mass Spectrometry of Nucleic Acid Components" *Biomedical Applications of Mass Spectrometry* (1990) 34:203-280.

Schultz et al., "Polymerase chain reaction products analyzed by charge detection mass spectrometry" *Rapid Communications in Mass Spectrometry* (1999) 13:15-20.

Senko et al., "Determination of Monoisotopic Masses and Ion Populations for Large Biomolecules from Resolved Isotopic Distributions," *J. Am. Soc. Mass Spectrom.* (1995) 6:229.

Seshardi et al., "Differential Expression of Translational Elements by Life Cycle Variants of *Coxiella burnetii*" *Infect. Immun.* (1999) 67:6026-6033.

Shaver et al., "Variation in 16S-23S rRNA intergenic spacer regions among *Bacillus subtilis* 168 isolates" *Molecular Microbiology* (2001) 42:101-109.

Stoneking et al., "Population variation of human mDNA control region sequences detected by enzymatic amplification and sequence-specific oligonucleotide probes," American Journal of Human Genetics (1991) 48:370-382.

Takahashi et al., "Characterization of gryA, gryB, grlA and grlB mutations in fluoroquinolone-resistant clinical isolates of *Staphylococcus aureus*" *J. Antimicrob. Chemother* (1998) 41:49-57.

Takeuchi et al., "Serotyping of Adenoviruses on Conjunctival Scrapings by PCR and Sequence Analysis" *Journal of Clinical Microbiology* (1999) 37:1839-1845.

Tong et al., "Ligation reaction specificities of an NAD+-dependent DNA ligase from the hyperthermophile *Aquifex aeolicus*" *Nucleic Acids Res* (2000) 28:1447-1454.

Van Aerschot et al., "In search of acyclic analogues as universal nucleosides in degenerate probes" *Nucleosides and Nucleotides* (1995) 14:1053-1056.

Van Baar et al., "Characterization of Bacteria by Matrix Assisted Laser Desorption/Ionization and Electrospray Mass Spectrometry" *FEMS Microbiol. Review* (2000) 24:195-219.

Van Camp et al., "Amplification and sequencing of variable regions in bacteria 23S ribosomal RNA genes with conserved primer sequences" *Current Microbiology* (1993) 27:147-151.

Van Der Vossen et al., "DNA based typing, identification and detection systems for food spoilage microorganisms: development and implementation" *Int. J. Food Microbiol.* (1996) 33:35-49.

Van Ert et al., "Mass spectrometry provides accurate characterization of two genetic marker types in *Bacillus anthracis*" *Biotechniques* (2004) 37:642-651.

Vanderhallen et al., "Identification of Encephalomyocarditis Virus in Clinical Samples by Reverse Transcription-PCR Followed by Genetic Typing Using Sequence Analysis" *J. Clin. Microbiol.* (1998) 36:3463-3467.

Walters et al., "Genotyping single nucleotide polymorphisms using intact polymerase chain reaction products by electrospray quadrupole mass spectrometry" *Rapid Communications in Mass Spectrometry* (2001) 15:1752-1759.

Welham et al., "The Characterization of Micro-organisms by Matrix-assisted Laser Desorption/Ionization Time-of-flight Mass Spectrometry" *Rapid Communications in Mass Spectrometry* (1998) 12:176-180.

Widjojoatmodjo et al., "Rapid Identification of Bacteria by PCR-Single-Strand Conformation Polymorphism" *Journal of Clinical Microbiology* (1994) 3002-3007.

Wolter et al., "Negative Ion FAB Mass Spectrometric Analysis of Non-Charged Key Intermediates in Oligonucleotide Synthesis: Rapid Identification of Partially Protected Dinucleoside Monophosphates" *Biomed. Environ. Mass Spectrom.* (1987) 14:111-116.

Woo et al., "Identification of *Leptospira inadai* by continuous monitoring of fluorescence during rapid cycle PCR" *Systematic and Applied Microbiology* (1998) 21:89-96.

Wunschel et al., "Discrimination Among the *B. cereus* Group, in Comparison to *B. subtilis*, by Structural Carbohydrate Profiles and Ribosomal RNA Spacer Region PCR" *System. Appl. Microbiol.* (1994) 17:625-635.

Wunschel et al., "Analysis of double-stranded polymerase chain reaction products from the *Bacillus cereus* group by electrospray ionization Fourier transform ion cyclotron resonance mass spectrometry" Rapid Communications in Mass Spectrometry (1996) 10:29-35.

Yao et al., "Mass Spectrometry Based Proteolytic Mapping for Rapid Virus Detection" *Anal. Chem.* (2002) 74:2529-2534.

Yasui et al., "A specific oligonucleotide primer for the rapid detection of *Lactobacillus lindneri* by polymerase chain reaction" *Can. J. Microbiol.* (1997) 43:157-163.

Zeng et al., "Precision Mapping of Quantitative Trait Loci" *Genetics* (1994) 136:1457-1468.

U.S. Appl. No. 90/010,209, filed Mar. 25, 2008, Kreiswirth et al.

U.S. Appl. No. 90/010,210, filed Jun. 27, 2008, Ecker et al.

Aaserud et al., "DNA sequencing with balckbody infrared radioactive dissociation of electrosprayed ions" Int. J. Mass. Spectrom. Ion Processes, (1997) 167-168: 705-712 (Reference not found in.

Adam et al., Molecular structure of the two-dimensional hexon crystalline array and of adenovirus capsid: *Acta Microbiol. Immuno. Hung.* (1998) 45:305-310.

Adam et al., "Intertype specific epitope structure of adenovirus hexon" *Acta Microbiol. Immuno. Hung.* (1998) 45:311-316.

Adam et al., "Characterization of intertype specific epitopes on adenovirus hexons" *Arch. Virol.* (1998) 143:1669-1682.

Adrian et al., "DNA restriction analysis of adenovirus prototypes 1 to 41" *Arch. Virol.* (1986) 91:277-290.

Adzhar et al., "Universal oligonucleotides for the detection of infectious bronchitis virus by the polymerase chain reaction" Avian Pathology (1996) 25:817-836.

Akalu et al., " Rapid identification of subgenera of human adenovirus by serological and PCR assays" *J. Virol Methods* (1998) 71:187-196.

Allaouchiche et al., "Clinical Impact of Rapid Oxacillin Susceptibility Testing Using a PCR Assay in Staphylococcus aureus Bactaeremia" J. Infect. (1999) 39(3):198-204.

Allawi, H.T. & Santa Lucia J., Jr. Thermodynamics and NMR of internal G.T. mismatches in DNA, Biochemistry, 36, 10581-94 (1997).

Altschuel et al., J. Mol. Biol., 215, 403-410 (1990).

Altschul et al., Nucl. Acid Res., 25:3389-3402 (1997).

Amano et al., "Detection of influenza virus: traditional approaches and development of biosensors" Anal. Bioanal. Chem. (2005) 381:156-164.

Amexis et al., "Quantiitative mutant analysis of viral quasispecies by chip-based matrix-assisted laser desorption/ionization of time-of-flight mass spectrometry" PNAS (2001) 98(21):12097-12102; Correction: 98(24):14186.

Anderson and Young, Quantitative Filter Hybridization in Nucleic Acid Hybridization (1985).

Anthony et al., "Use of the Polymerase Chain Reaction for Rapid Detection of High-Level Mupirocin Resistance in Staphylococci" Eur. J. Clin. Microbiol. Infect. Dis. (1999) 18(1):30-34.

Application for Grant by David Mitchell Lubmann dated Oct. 25, 1992 and Oct. 29, 1992.

Application for Continuation Grant by David Mitchell Lubmann dated Jun. 10, 1994 and Jun. 24, 1994.

Application for Grant by David Mitchell Lubmann dated Sep. 1, 1994 and Sep. 27, 1994.

Application for Continuation Grant by David Mitchell Lubmann dated Jun. 4, 1996 and Jun. 14, 1996.

U.S. Appl. No. 09/798,007 Office Communication Mailed May 28, 2003.

U.S. Appl. No. 09/891,793 Office Communication Mailed May 19, 2003 interview summary report.

U.S. Appl. No. 09/891,793 Office Communication Mailed May 23, 2003.

U.S. Appl. No. 09/891,793 Office Communication Mailed Jul. 22, 2008.

U.S. Appl. No. 10/156,608 Office Communication Mailed May 23, 2005.

U.S. Appl. No. 10/156,608 Office Communication Mailed Jun. 2, 2006.
U.S. Appl. No. 10/323,438 Office Communication Mailed Nov. 20, 2003.
U.S. Appl. No. 10/323,438 Office Communication Mailed Jul. 26, 2004.
U.S. Appl. No. 10/325,527 Office Communication Mailed Dec. 3, 2003.
U.S. Appl. No. 10/325,527 Office Communication Mailed Aug. 16, 2004.
U.S. Appl. No. 10/325,527 Office Communication Mailed Mar. 11, 2005.
U.S. Appl. No. 10/326,642 Office Communication Mailed Nov. 21, 2003.
U.S. Appl. No. 10/326,642 Office Communication Mailed Jul. 14, 2004.
U.S. Appl. No. 10/418,514 Office Communication Mailed Jul. 1, 2008.
U.S. Appl. No. 10/660,122 Office Communication Mailed Jul. 9, 2008.
U.S. Appl. No. 10/660,122 Office Communication Mailed Sep. 17, 2008.
U.S. Appl. No. 10/660,997 Office Communication Mailed Mar. 13, 2006.
U.S. Appl. No. 10/660,997 Office Communication Mailed May 26, 2006.
U.S. Appl. No. 10/660,997 Office Communication Mailed Sep. 18, 2006.
U.S. Appl. No. 10/660,997 Office Communication Mailed Nov. 21, 2006.
U.S. Appl. No. 10/660,997 Office Communication Mailed Apr. 26, 2007 with associated Information Disclosure Statement filed Feb. 20, 2007.
U.S. Appl. No. 10/728,486 Office Communication Mailed Jan. 23, 2008.
U.S. Appl. No. 10/728,486 Office Communication Mailed Nov. 3, 2008.
U.S. Appl. No. 10/754,415 Office Communication Mailed Jun. 12, 2008.
U.S. Appl. No. 10/754,415 Office Communication Mailed Jun. 4, 2009.
U.S. Appl. No. 10/829,826 Office Communication Mailed Jul. 6, 2007.
U.S. Appl. No. 10/829,826 Office Communication Mailed Apr. 4, 2008.
U.S. Appl. No. 10/829,826 Office Communication Mailed Dec. 10, 2008.
U.S. Appl. No. 10/844,938 Office Communication Mailed Feb. 2, 2007.
U.S. Appl. No. 10/844,938 Office Communication Mailed Aug. 7, 2007.
U.S. Appl. No. 10/844,938 Office Communication Mailed May 20, 2008.
U.S. Appl. No. 10/844,938 Office Communication Mailed Jan. 30, 2009.
U.S. Appl. No. 10/891,337 Office Communication Mailed Apr. 20, 2009.
U.S. Appl. No. 10/933,928 Office Communication Mailed Jun. 02, 2006.
U.S. Appl. No. 10/943,344 Office Communication Mailed Feb. 27, 2007.
U.S. Appl. No. 10/943,344 Office Communication Mailed May 21, 2008.
U.S. Appl. No. 10/943,344 Office Communication Mailed Feb. 23, 2009.
U.S. Appl. No. 11/059,776 Office Communication Mailed Jan. 23, 2008.
U.S. Appl. No. 11/060,135 Office Communication Mailed Mar. 25, 2008.
U.S. Appl. No. 11/060,135 Office Communication Mailed Jan. 2, 2009.
U.S. Appl. No. 11/136,134 Office Communication Mailed Jun. 20, 2007.
U.S. Appl. No. 11/136,134 Office Communication Mailed Mar. 26, 2008.
U.S. Appl. No. 11/136,134 Office Communication Mailed Oct. 31, 2008.
U.S. Appl. No. 11/136,134 Office Communication Mailed Feb. 12, 2009.
U.S. Appl. No. 11/136,134 Office Communication Mailed May 21, 2009.
U.S. Appl. No. 11/233,630 Office Communication Mailed Jun. 8, 2007.
U.S. Appl. No. 11/233,630 Office Communication Mailed Jul. 13, 2007.
U.S. Appl. No. 11/233,630 Office Communication Mailed Apr. 16, 2008.
U.S. Appl. No. 11/233,630 Office Communication Mailed Oct. 2, 2008.
U.S. Appl. No. 11/331,978 Office Communication Mailed Aug. 15, 2008.
U.S. Appl. No. 11/331,978 Office Communication Mailed Oct. 17, 2008.
U.S. Appl. No. 11/331,978 Office Communication Mailed Jun. 2, 2008 (interview summary).
U.S. Appl. No. 11/331,987 Office Communication Mailed Jul. 9, 2008.
U.S. Appl. No. 11/404,561 Office Communication Mailed May 16, 2008.
U.S. Appl. No. 11/404,561 Office Communication Mailed Feb. 4, 2009.
U.S. Appl. No. 11/409,535 Office Communication Mailed Apr. 16, 2008.
U.S. Appl. No. 11/491,376 Office Communication Mailed Oct. 31, 2008.
U.S. Appl. No. 11/491,376 Office Communication Mailed Apr. 22, 2009.
U.S. Appl. No. 11/582,859 Office Communication Mailed Oct. 21, 2008.
U.S. Appl. No. 11/582,863 Office Communication Mailed Aug. 20, 2007.
U.S. Appl. No. 11/582,863 Office Communication Mailed Jun. 17, 2008.
U.S. Appl. No. 11/582,863 Office Communication Mailed Feb. 26, 2009.
U.S. Appl. No. 11/582,930 Office Communication Mailed Sep. 14, 2007.
U.S. Appl. No. 11/582,930 Office Communication Mailed May 2, 2008.
U.S. Appl. No. 11/582,930 Office Communication Mailed Oct. 24, 2008.
U.S. Appl. No. 11/582,930 Office Communication Mailed Jan. 16, 2009.
U.S. Appl. No. 12/211,641 Office Communication Mailed Apr. 17, 2009.
U.S. Appl. No. 90/010,209 Office Communication Mailed Jun. 27, 2008.
U.S. Appl. No. 90/010,209 Office Communication Mailed Jul. 22, 2008.
U.S. Appl. No. 90/010,210 Office Communication Mailed Jun. 27, 2008.
U.S. Appl. No. 90/010,210 Office Communication Mailed Jul. 22, 2008.
Arbique et al., "Comparison of the Velogene Rapid MRSA Identification Assay, Denka MRSA-Screen Assay, and BBL Crystal MRSA ID System for rapid identification of methicillin-resistant Staphylococcus aureus" Diagn. Microbiol. Infect. Dis. (2001) 40(1-2):5-10.
Archer, G. L. et al., "Detection of Methicillin Resistance in Staphylococci by Using a DNA Probe," *Antimicrob. Agents Chemother.* (1990) 34(9): 1720-1724.
Armstrong, P. et al., "Sensitive and Specific Colorimetric Dot Assay to Detect Eastern Equine Encephalomyelitis Viral RNA in Mosquitoes After PCR Amplification" J. Med, Entomol. (1995) 32(1): 42-52.
Arnal et al., "Quantification of Hepatitis a virus in shellfish by competitive reverse transcription PCR with coextraction of standard RNA" Applied and Environmental Microbiology, American Society for Microbiology (1999) 65(1):322-326.

Aronsson et al., Persistence of the influenza A/WSN/33 virus RNA at midbrain levels of immunodefective mice, Online Publication Date: Apr. 1, 2001, Journal of the NeuroVirology 7:117-124, 2001.

Ausubel et al., Current Protocols in Molecular Biology (Relevant portions of the book).

Avellon et al. "Rapid and sensitive diagnosis of human adenovirus infections by a generic polymerase chain reaction" *J. Virol. Methods* (2001) 92:113-120.

Azevedo et al. "Detection of influenza, parainfluenza, adenovirus and respiratory syncytial virus during asthma attacks in children older than two years old." Allergol. Immunopathol. (2003) 31:311- 317.

Baba et al., "Genome and virulence determinants of high virulence community-acquired MRSA" Lancet (2002) 359:1819-1827.

Bai, J, T.H. Liu and D.M.. Lubman, "Matrix-Assisted Laser Desorption/Ionization Mass Spectrometry of Restriction Enzyme-Digested Plasmid DNA Using an Active Nafion Substrate," 8 Rapid Commun. Mass Spectrom. 687-691 (1994) ('787 reexamination).

Banik et al. "Multiplex PCR assay for rapid identification of oculopathogenic adenoviruses by amplification of the fiber and hexon genes" *J. Clin. Microbiol* (2005) 43:1064-1068.

Baron, E. J., "Genetic Aspects of Methicillin Resistance in *Staphylococcus aureus* and Methods Used for its Detection in Clinical Laboratories in the United States," *J. Chemother*. (1995) 7(Suppl. 3): 87-92.

Barr et al., "An Influenza A(H3) Reassortant Was Epidemic in Australia and New Zealand in 2003" J. Med. Virol. (2005) 76:391-397.

Barski, P. et al., "Rapid assay for detection of methicillin-resistant *Staphylococcus aureus* using multiplex PCR," *Mol. Cell Probes* (1996) 10:471-475.

Bastia et al., "Organelle DNA analysis of Solanum and Brassica somatic hybrids by PCR with 'universal primers'." *Theoretical and Applied Genetics* (2001) 102:1265-1272.

Beall, B., et al. "Survey of emm Gene Sequences and T-Antigen Types from Systemic Streptococcus pyogenes Infection Isolates Collected in San Francisco, California; Atlanta, Georgia; and Connecticut in 1994 and 1995" (1997), J. Clin. Micro. 35, 1231-1235.

Beall et al., "Sequencing emm-Specific PCR Products for Routine and Accurate Typing of Group a Streptococci" (1996) J. Clin. Micro. 34, 953-958.

Benko, M. et al., "Family Adenoviridae", Virus taxonomy, VIIIth report of the International Committee on Taxonomy of Viruses (2004) Fauquet, C.M. et al. (Eds.) Academic Press, New York, pp. 213-228.

Berencsi, G. et al., "Molecular Biological Characterization of Adenovirus DNA", Acta Microbiol. Immunol. Hung, 1998, vol. 45, Nos. 3-4; pp. 297-304.

Bisno, A.L. (1995) in Principles and Practice of Infectious Diseases, eds., Mandell, G.L., Bennett, J.E. & Dolin, R. (Churchill Livingston, New York), vol. 2, pp. 1786-1799.

Blaiotta, G. et al., "PCR detection of staphylococcal enterotoxin genes in Staphyiococcus spp. strains isolated from meat and dairy products. Evidence for new variants of seG and sel in *S. aureus* AB-8802," *J. Appl. Microbiol*. (2004) 97:719-730.

Bolton and Mccarthy, Proc. Natl. Acad. Sci. U.S.A., 48, 1390 (1962).

Bont, Thomas et al., "Matrix-assisted laser desorption/ionization time-of-flight mass spectrometry-based detection of microsatellite instabilities in coding DNA sequences: a novel approach to identify DNA-mismatch repair-deficient cancer cells," Clinical Chemistry, 49(4):552-561 Apr. 2003.

Boubaker, K. et al., "Panton-Valentine Leukocidin and Staphylococcal Skin Infections in Schoolchildren," *Emerg.Infct. Dis.* (2004) 10(1):121-124.

Bowers, K. M. et al., "Screening for methicillin resistance in *Staphylococars aureus* and coagulase-negative staphylococci: evaluation of three selective and Mastalex-MRSA latex agglutination," Br. *J. Biomed. Sci.* (2003) 60(2):71-74.

Brakstad, O. G, et al., "Multiplex polylnerase chain reaction for detection of genes for *Staphylococcus aureus* themonuclease and methicillin resistance and correlation with oxacillin resistance," *APMIS* (1993) 101:681-688.

Brakstad, O. G. et al., "Direct identification of *Staphylococcus aureus* in blood cultures by detection of the gene, encoding the thermostable nuclease or the gene product," APMIS (1995) 103:209-218.

Brandt, C.D., et al., "Infections in 18,000 Infants and Children in a Controlled Study of Respiration Tract Disease. I. Adenovirus Pathogenicity in Relation to Serologic Type and Illness Syndrome," Am. J. Epidemio.; 1969, vol. 90, No. 6, pp. 484-500.

Brayshaw, D. P., "Methicillin-resistant Staphylococcus aureus: evaluation of detection techniques on laboratory-passaged organisms," *Br. J Biomed. Sci.* (1999) 56:170-176.

Brightwell et al., "Development of internal controls for PCR detection of Bacillus anthracis" Molecular and Cellular Probes (1998) 12(6):367-377.

Brightwell , G. et a., "Genetic targets for the detection and identifiaction of Venezuelan equine encephalitis viruses," Arch. Virol (1998) 143(4): 731-742.

Bronzoni, R. V. M. et al., "Multiplex nested PCR for Brazilian *Alphavirus* diagnosis," *Trans. R. Soc. Trop. Med. Hyg.* (2004) 98(8): 456-461.

Bronzoni, R. V. M. et al., "Duplex Reverse Transcription-PCR Followed by Nested PCR Assats for Detection and Identification of Brazilan Alphaviruses and Flaviviruses." *J. Clin. Microbiol.* (2005) 43(2): 696-702.

Brown, "Advances in Molecular Diagnostics for Avian Influenza" Dev. Biol. (2006) 124:93-97.

Brownstein et al., "Modulation of Non-Templated Nucleotide Addition by Taq DNA Polymerase: Primer Modifications that Facilitate Genotyping" BioTechniques (1996) 20:1004-1010.

Brunaud et al., "T-DNA integration into the Arabidopsis genome depends on sequences of pre-insertion sites" EMBO Rep. (2002) 3(12):1152-1157.

Buck et al., "Design Strategies and Performance of Custom DNA Sequencing Primers" Biotechniques (1999) 27:528-536.

Butler "DNA profiling and quantitation of human DNA" CCQM BAWG 04122005.

Carroll, K. C. et al., "Rapid Detection of the Staphylococcal mec a Gene from BACTEC Blood Culture Bottles by the Polymerase Chain Reaction," *Am. J. Clin. Pathol.* (1996) 106:600-5.

Cattoli et al., "Comparison of three rapid detection systems for type A influenza virus on tracheal swabs of experimentally and naturally infected birds" Avian Pathology (2004) 33(4):432-437.

Cavassini, M. et al., "Evaluation of MRSA-Screen, a Simple Anti-PBP 2a Slide Latex Agglutination Kit, for Rapid Detection of Methicillin Resistance in *Staphylococcus aureus*," J. Clin. Microbial. (1999) 37(5): 1591-1594.

Chamberlin et al., "New RNA polymerase from *Escerichia coli* infected with bacteriophage T7" Nature 228:227 (1970).

Chandra, S. et al., "Virus reduction in the preparation and intravenous globulin: in vitro experiments," *Transfusion* (1999) 39(3): 249-257.

Chaves, F. et al., "Molecular Characterization of Resistance to Mupirocin in Methidlin-Susceptible and -Resistant Isolates of *Staphylococcus aureus* from Nasal Samples," *J. Clin. Microbiol.* (2004) 42(2):822-824.

Chelly et al., "Transcription of the dystrophin gene in human muscle and non-muscle tissue" Nature (1988) 333(6176):858-860.

Chen et al., "Genetic mapping of the cold-adapted phenotype of B/Ann Arbor/1/66, the master donor virus for live attenuated influenza vaccines (FluMist)" Virology (2006) 345:416-423.

Chen, Ch, K. Tang, N. Taranenko and S. Allman, "Laser Desorption Mass Spectrometry for Fast DNA Sequencing," (Nov. 1994), http://www.ornl.gove/sci/techresources/Human_Genome/publicat/94SANTA/sequencing/seqtoc.shtml ('787 reexamination).

Chmielewicz, B. et al., "Development of a PCR-Based Assay for Detection, Quantification, and Genotyping of Human Adenoviruses," Clin. Chem., 2005, vol. 51, No. 8, pp. 1365-1373.

Choi et al., "Detection and subtying of swine influenza H1N1, H1N2 and H3N2 viruses in clinical samples using two multiplex RT-PCR assays" J. Virol. Methods (2002) 102:53-59.

Choi, S. et al., "Real-Time PCR Quantification of Human Adenoviruses in Urban Rivers Indicates Genome Prevalence but Low Infectivity," Appl. Environ. Microbiol., 2005, vol. 71, No. 11, pp. 7426- 7433.

Christel, La et al., "Rapid, Automated Nucleic Acid Probe Assays Using Silicon Microstructures for Nucleic Acid Concentration" J. Biomech. Eng., 1999, 121, 22-27.

Claas, E.C.J. et al., "Internally Controlled Real-Time PCT Monitoring of Adenovirus DNA Load in Serum or Plasma of Transplant Recipients," J. Clin. Microbiol., 2005, vol. 43, No. 4, pp. 1738-1744.

Cloney, L. et al., "Rapid detection of *mecA* in methicillin resistant *Stuphylococcus aureus* using cycling probe technology," Mol. Cell Probes (1999) 13:191-197.

Couto, I. et al., "Devetopment of Methicillin Resistance in Clinical Isolates of *Staphylococcus sciuri* by Transcriptional Activation of the *mecA* Homologue Native to the Species," J. Bacteriol. (2003) 185(2):645-653.

Crawford-Miksza, L.K. et al., "Analysis of 15 Adenovirus Hexon Proteins Reveals the Location and Structure of Seven Hypervariable Regions Containing Serotype-Specific Residues," J. Virol., 1996, vol. 70, No. 3, pp. 1836-1844.

Crawford-Miksza, L.K. et al., "Adenovirus Serotype Evolution is Driven by Illegitimate Recombination in the Hypervariable Regions of the Hexon Protein," Virol., 1996, vol. 224, pp. 357- 367.

Crawfor-Miksza et al., "Strain variation in adenovirus serotypes 4 and 7a causing acute respiratory disease." (1999) 37:1107-1112.

Cui, L. et al., "Contribution of a Thickened Cell Wall and Its Glutamine Nonamidated Component to the Vancomnycin Resistance Expressed by *Staphylococcus aureus* Mu50," Antimicrob. Agents Chemother. (2000) 44(9):2276-2285.

De Sousa, M. A. et al., "Bridges from hospitals to the laboratory: genetic portraits of methicillin-resistant *Staphylococcus aureus* clones," FEMS lmmunol. Med. Microbiol. (2004) 40:101-111.

De Jong, J.C. et al., "Adenoviruses from Human Immunodeficiency Virus-Infected Individuals, Including Two Strains That Represent New Candidate Serotypes Ad50 and Ad51 of Species B1 and D, Respectively," J. Clin. Microbiol., 1999, vol. 37, No. 12, pp. 3940-3945.

Del Vecchio, V. G. et al., "Molecular Genotyping of Methicillin-Resistant *Staphylococcus aureus* via Fluorophore-Enhanced Repetitive-Sequence PCR," J. Clin. Microbiol. (1995) 33(8):2141-2144.

Denis et al., "Development of a semiquantitative PCR assay using internal standard and colorimetric detection on microwell plate for pseudorabies virus" Mol. Cell. Probes (1997) 11(6):439-448.

Deurenberg et al., "Rapid detection of Panton-Valentine leukocidin from clinical isolates of Staphylococcus aureus strains by real-time PCR" FEMS Microbiol. Lett. (2004) 240(2):225-228.

Di Guilmi, A.M. et al., "Human adenovirus serotype 3 (Ad3) and the Ad3 fiber p[protein bind to a 130-kDa membrane protein on HeLa cells," Virus Res., 1995, vol. 38, pp. 71-81.

Diep, B. A. et al., "Complete genome sequence of USA300, an epidemic clone of community acquired meticillin-resistant *Staphylococcus aureus*," Lancet (2006) 367:731-739.

Ding et al., "A high-throughput gene expression analysis technique using competitive PCR and matrix-assisted laser desorption ionization time-of-flight MS" PNAS (2003) 100(6):3059-3064.

Don Ehower, et al., "The use of primers from highly conserved pol regions to identify uncharacterized retroviruses by the polymerase chain reaction," J. Vir. Methods (1990) 28:33-46.

Donofrio et al., "Detection of influenza A and B in respiratory secretions with the polymerase chain reaction" PCR methods and applications, Cold Spring Harbor Lab. Press vol. 1, No. 4, (1992) pp. 263-268.

Doty et al., Proc. Natl. Acad. Sci. USA 46:461 (1960).

Drosten et al., New England Journal of Medicine, 2003, 348, 1967.

Ebner, K. et al., "Molecular Detection and Quantitative Analysis of the Entire Spectrum of Human Adenoviruses by a Two-Reaction Real-Time PCR Assay," J. Clin. Microbiol., 2005, vol. 43, No. 7, pp. 3049-3053.

Ebner et al., "Typing of human adenoviruses in specimens of immunosuppressed patients by PCR-fragment length analysis and real-time quantitative PCR" Journal of Clinical Microbiology (2006) 44:2808-2815.

Echavarria, M. et al., "PCR Method for Detection of Adenovirus in Urine of Healthy and Human Immunodeficiency Virus-Infected Individuals," J. Clin. Microbiol., 1998, vol. 36, No. 11, pp. 3323-3326.

Echavarria, M. et al., "Detection of Adenoviruses (AdV) in Culture-Negative Environmental Samples by PcR During an AdV-Associated Respiratory Disease Outbreak," J. Clin. Microbiol., 2000, vol. 38, No. 8, pp. 2982-2984.

Echavarria, M. et al., "Prediction of severe disseminated adenovirus infection by serum PCR," Lancet, 2001, vol. 358, pp. 384-385.

Echavarria, M. et al., "Rapid Detection of Adenovirus in Throat Swab Specimens by PCR During Respiratory Disease Outbreaks among Military Recruits", J. Clin. Microbiol., 2003, vol. 41, No. 2, pp. 810-812.

Echavarria, M. et al., "Use of PCR to demonstrate of Adenovirus Species B, C, of F as Well as Coinfection with Two Adenovirus Species in Children with Flu-Like Symptoms", J. Clin. Microbiol, 2006, vol. 44, No. 2, pp. 625-627.

Ecker et al., "Rapid identification and strain-typing of respiratory pathogens for epidemic surveillance" PNAS (2005) 102(22):8012-8017.

Ecker et al., "The Ibis T5000 Universal Biosensor: An Automated Platform for Pathogen Identification and Strain Typing" JALA (2006) 11:341-351.

Edwards, K.M. et al., "Adenovirus Infections in Young Children", Pediatrics, 1985, vol. 76, No. 3, pp. 420-424.

Ellis et al., "Molecular diagnosis of influenza" Rev. Med. Virol. (2002) 12(6):375-389.

Elsayed, S. et al., "Development and Validation of a Molecular Beacon Probe-Based Real-Time Polymerase Chain Reaction Assay for Rapid Detection of Methicillin Resistance in *Staphylococcus aureus*," Arch. Pathol. Lab. Med. (2003) 127945-849.

EMBL Accession AR321656 (Aug. 12, 2003).

EMBL Accession AB068711 (May 21, 2003).

EMBL Accession Z48571 (Jun. 9 1995).

Enright, M. C, et al., "Multilocus Sequence Typing for Characterization of Methicillin-Resistant and Methicillin-Susceptible Clones of *Staphylococcus aureus* ," J. Clin. Microbial. (2000) 38(3): 1008-1015.

Enright, M. C. et al., "The evolutionary history of methicillin-resistant *Staphylococcus aureus* (MRSA)," PNAS(2002) 99(11): 7687-7692.

Enright, M. C. et al., "The evolution of a resistant pathogen--the case of MRSA," Curr. Opin. Pharmacol. (2003) 3:474-479.

Enright, M.C., et al., "Multilocus Sequence Typing of Streptococcus pyogenes and the Relationships between emm Type and Clone" Infection and Immunity, 2001, 69, 2416-2427.

Eremeeva et al., "Evaluation of a PCR Assay for Quantitation of Rickettsia rickettsii and Closely Related Spotted Fever Group Rickettsiae" J. Clin. Microbiol. (2003) 41(12):5466-5472.

Erlich (ed.). PCR Technology, Stockton Press (1989).

Evans & Wareham, "Practical Algorithms for Universal DNA Primer Design: An Exercise in Algorithm Engineering".

European Patent Office Communication 96(2) EPC for 02709785.6 dated Nov. 20, 2006.

European Patent Office Communication for 06849755.1 dated Mar. 12, 2008.

European Supplemental Search Report for 03796752.8 dated Aug. 14, 2007.

European Supplemental Search Report for 03810055.8 dated Jul. 9, 2007.

European Supplemental Search Report for 02709785.6-2405 (PCT/US0206763) dated Oct. 12, 2005.

European Supplemental Search Report for 04752257.8 dated Feb. 15, 2006.

European Supplemental Search Report for 05751872.2 dated Jan. 28, 2008.

European Supplemental Search Report for 05856582.1 dated Nov. 10, 2008.

European Supplemental Search Report for 04775904.8 dated Jul. 25, 2008.

European Supplemental Search Report for 05856582.1 dated Nov. 10, 2008.

Facklam, R., et al., "emm Typing and Validation of Provisional M Types for Group A Streptococci" (1999) Emerging Infectious Diseases, 5, 247-253.

Fang, H. et al., "Rapid Screening and Identification of Methicillin-Resistant *Staphylococcus aureus* from Clinical Samples by Selective-Broth and Real-Time PCR Assay," *J. Clin. Microbial.* (2003) 41 (7):2894-2899.

Farrell, D. J., "The Reliability of Microscan Conventional and Rapid Panels to Identify *Staphylococcus aureus* and Detect Methicillin Resistance: an Evaluation Using the Tube Coagulase Test and *mec*A PCR," *Pathology* (1997) 29:406-410.

Fedele C G et al., "Multiplex polymerase chain reaction for the simultaneous detection and typing of polyomavirus JC, BK, and SV40 DNA in clinical samples", Journal of Virological Methods, 82(2), Oct. 1999, pp. 137-144.

Fedele C G et Al., "Quantitation of polyomavirus DNA by a competitive nested polymerase chain reaction," Journal of Virological Methods, 88(1):51-61 (Jul. 2000).

Feng, P., "Impact of molecular biology on the detection of food pathogens" Mol. Biotechnol., 1997, 7, 267-278.

Feng, P., J. AOAC Int., 1997, 80, 934-940 (Same as VanDerZee below. Use VanDerZee).

Fong, W. K., et al., "Rapid Solid-Phase Immunoassay for Detection of Methicillin-Resistant *Staphylococcus aureus* Using Cycling Probe Technology." *J. Clin. Microbiol*. (2000) 38(7): 2525-2529.

Fox, J.P. et al., "The Virus Watch Program: A Continuing Surveillance of Viral Infections in Metropolitan New York Families", Am. J. Epidemiol., 1969, vol. 89, No. 1, pp. 25-50.

Francois, P. et al., "Rapid Detection of Methicillin-Resistant *Staphylococcus aureus* Directly from Sterile or Nonsterile Clinical Samples by a New Molecular Assay," *J. Clin. Microbiol.* (2003) 41(1):254-260.

Freiberg et al. Genome-wide mRNA profiling: impact on compound evaluation and target identification in anti-bacterial research. Targets 1(1):20-29 (2002).

Freymuth et al., "Comparison of Multiplex PCR Assays and Conventional Techniques for the Diagnostic of Respiratory Virus Infections in Children Admitted to Hospital with an Acute Respiratory Illness" J. Med. Virol. (2006) 78(11):1498-1504.

Freymuth, F. et al., "Detection of respiratory syncytial virus, parainfluenzavirus 3, adenovirus and rhinovirus sequences in respiratory tract of infants by polymerase chain reaction and hybridization", Clin. Dian. Virol, 1997, vol. 8, pp. 31-40.

Fujimoto, T. et al., "Single-Tube Multiplex PCR for Rapid and Sensitive Diagnosis of Subgenus B and Other Subgenera Adenoviruses in Clinical Samples", Microbiol. Immunol., 2000, vol. 44, No. 10, pp. 821-826 (abstract only).

Fujimura, S, et al., "Characterization of the *mupA* Gene in Strains of Methicillin-Resistant *Staphylococcus aureus* with a Low Level of Resistance to Mupirocin," *Antimicrob. Agents Chemother.* (2001) 45(2):641-642.

Fujimura, S. et al., "Isoleucyl-tRNA Synthetase Mutations in *Staphylococcus aureus* Clinical Isolates and In Vitro Selection of Low-Level Mupirocin-Resistant Strains," *Antimicrob. Agents Chemother*. (2003) 47(10): 3373-3374.

Gall, J.G.D. et al., "Construction and Characterization of Hexon-Chimeric Adenoviruses: Specification of Adenovirus Serotype", J. Virol, 1998, vol. 72, No. 12, pp. 10260-10264.

Gammelin et al., "Two Subtypes of Nucleoproteins (NP) of Influenza A Viruses" Virology (1989) 170:71-80.

Garcia et al., "Quantitative Real-Time PCR Detection of Rift Valley Fever Virus and Its Application to Evaluation of Antiviral Compounds" J. Clin. Microbiol. (2001) 39(12):4456-61.

Gaydos, C.A. et al., "Adenovirus Vaccines in the U.S. Military", Military Med., 1995, vol. 160, No. 6, pp. 300-304.

Geha et al., J. Clin. Microbiol. (1994) 32:1768-1772.

GenBank Accession No. NC_000913.

Genbank Accession AF304460 (Jul. 11, 2001).

Genbank Accession No. M21150 Apr. 29, 1993.

Genbank Accession No. AF375051.1 (Jun. 26, 2001).

Genbank Accession No. Z48571 (Jun. 9, 1995).

Genbank Accession No. X84646 (Jul. 2, 1995).

Genbank GI:15922990 [online] Oct. 4, 2001 [retrieved on Jun. 22, 2008] retrieved from: http://www.ncbi.nlm.nih.gov/entrez/viewer.fcgi?I5922990:OLD08:50885 (pp. 1, 12, 15, 148, 216, 476, 722, 723, 725, 881, 1251).

Genbank GI:18542231 [online] Sep. 16, 2003 retrieved on Jun. 23, 20081 retrieved from http://www.ncbi.nlm.nih.gov/entrez/viewer.fcgi?db=nuccore&id=18542231 (2 pages).

Genbank GI:21281729 [online], publicly available at least as of May 31, 2002 retrieved on Apr. 11, 20081, retrieved from: http://www.ncbi.nlm.nih.gov/entrez/viewer.fcgi?21281729:OLD11:599579 (pp. 1, 723 and 1137).

Gendel et al., "Computational analysis of the specificity of 16S rRNA-derived signature sequences for identifying food-related microbes" Food Microbiology (1996) 13:1-15.

Gibb et al., "Development and evaluation of a 5' fluorogenic nuclease assay to detect and differentiate between Ebola Virus subtypes Zaire and Sudan", Journal of Clinical Microbiology, 39(11):4125-4130 (Nov. 2001).

Giles+A137, R.E., et al., Proc. Natl. Acad. Sci., 1980, 77, 6715-6719.

Gilbert et al., "Comparison of commercial assays for the quantitation of HBV DNA load in health care workers: calibration differences" J. Virol. Methods (2002) 100(1-2):37-47.

Gill, S. R. et al., "Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidemidis* Strain," *J. Bacteriol*. (2005) 187(7): 2426-2438.

Gilliland et al., "Analysis of cytokine mRNA and DNA: detectionf and quantitation by competitive polymerase chain reaction" PNAS (1990) 87(7):2725-2729.

Ginther, C., et al., Nature Genetics, 1992, 2, 135-138.

Gjoen et al., "Specific detection of coxsackie viruses A by the polymerase chain reaction" Clinical and Diagnostic Virology (1997) 8:183-188.

Golden et al., Pilot Study of COBAS PCR and Ligase Chain Reaction for Detection of Rectal Infections Due to Chlamydia trachomatis, J. Clin. Microbiol., 41(5):2174-2175 (May 2003).

Gravet et al., "Characterization of a novel structural member, LukE-LukD, of the bi-component staphylococcal leucotoxins family" FEBS Lett. (1998) 436(2):202-208.

Gray, G.C. et al Adenovirus Infections: Loss of Orphaned Vaccines Precipitates Military Respiratory Disease Epidemics, Clin. Infect. Diseases, 2000, vol. 31, pp. 663-670.

Grondahl, B. et al., "Rapid Identification of Nine Microorganisms Causing Acute Respiratory Tract Infections by Single-Tube Multiplex Reverse Transcription-PCR: Feasibility Study", J. Clin. Microbiol., 1999, vol. 37, No. 1, pp. 1-7.

Grundmann, H. et al., "Emergence and resurgence of meticillin-resistant *Staphylococcus aureus* as a public-health threat," *Lancet* (2006) 368: 874-885.

Gu, Z et al., "Multiplexed, Real-Time PCR for Quantitative Detection of Human Adenovirus", J. Clin. Microbiol., 2003, vol. 41, No. 10, pp. 4636-4641.

Guatelli et al., "Nucleic Acid Amplification In Vitro: Detection of Sequences with Low Copy Numbers and Application to Diagnosis of Human Immunodeficiency Virus Type 1 Infection" Clin. Microbiol. Rev. (1989) 2(2):217-226.

Haff et al., "Multiplex Genotyping of PCR Products with Mass Tag-Labeled Primers" Nucleic Acids Research (1997) 25(18):3749-3750.

Heim, A. et al., "Rapid and Quantitative Detection of Human Adenovirus DNA by Real-Time PCR", J. Med. Virol., 2003, vol. 70, pp. 228-239.

Haines, J.D., et al., "Medical response to bioterrorism: Are we prepared?" J. Okla. State Med. Assoc. 2000, 93, 187-196.

Hall et al., "Base composition analysis of human mitochondria! DNA using electrospray ionization mass spectrometry: a novel tool for the identification and differentiation of humans" Analytical Biochemistry (2005) 344:53-69.

Hamdad, F. et al., "Detection of Methicillin/Oxacillin Resistance and Typing in Aminoglycoside-Susceptible Methicillin-Resistant and Kanamycin-Tobramycin-Resistant Methicillin-Susceptible" *Microbial Drug Resistance* (2006) 12(3): 177-185.

Hamels et al., "Consensus PCR and Microarray for Diagnosis of the Genus Staphylococcus, Species, and Methicillin Resistance" BioTechniques (2001) 31(6):1364-1366.

Hammerle et al., "A sensitive PCR assay system for the quantitation of viral genome equivalents: hepatitis C virus (HCV)" Arch. Virol. (1996) 141:2103-2114.

Hannis et al., "Genotyping complex short tandem repeats using electrospray ionization Fourier transform ion cyclotron resonance multistage mass spectrometry" *Proceedings of SPIE- The International Society for Optical Engineering* (2000) 3926:36-47.

Hanssen, A.M. et al., "SCC*mec* in staphylococci: genes on the move," *FEMS Immuol. Med. Microbiol.* (2006) 46:8-20.

Hasebe, F. et al. "Combined Detection and Genotyping of *Chikungunya* Virus by a Specific Reverse Transcription-Polymerase Chain Reaction," *J. Med. Virol.* (2002) 67(3): 370-374.

Hassan et al., "Inter- and Intraspecies Variations of the 16S-23S rDNA Intergenic Spacer Region of Various Streptococcal Species" Systematic and Applied Microbiology (2003) 26(1):97-103.

Higgins, J.A., et al., *Ann. NY Acad. Sci.*, 1999, 894, 130-148.

Hill, F., et al., "Polymerase recognition of synthetic oligodeoxyribonucleotides incorporating degenerate pyrimidine and purine bases," Proc. Natl. Acad. Sci. USA 95:4258-4263 (1998).

Hiramatsu, K. et al., "The emergence and evolution of methicillin-resistant *Staphylococcus aureus*," Trends Microbiol. (2001) 9(10):486-493.

Hoffmann et al., "Rescue of influenza B virus from eight plasmids" *PNAS* (2002) 99:11411-11416.

Hofstadler et al., "Tiger: the universal biosensor" Inter. J. Mass Spectrom. (2005) 242:23-41.

Hodgson et al. Molecular Characterization of the Gene Encoding High-Level Mupirocin Resistance in *Staphylococcus aureus* J2870. Antimicrobial Agents and Chemotherapy 38(5):1205-1208, May 1994.

Holden, M. T. G. et al., "Complete genomes of two clinical *Staphylocuccus aureus* strain: Evidence for the rapid evolution of virulence and drug resistance," *PNAS* (2004) 101(26):9786-9791.

Holland, M.M. And T.J. Parsons "Mitochondrial DNA analsysis_Validation and use for forensic casework" (1999) Forensic Science Review, vol. 11, pp. 25-51.

Hongoh et al., "Evaluation of primers and PCR conditions for the analysis of 16s rRNA genes from a natural environment" Fems Microbiol. Lett. (2003) 221:299-304.

Houng, H.-S. H. et al., "Rapid type-specific diagnosis of adenovirus type 4 infection using a hexon-based quantitative fluorogenic PCR", Diagn. Microbiol. Infect. Dis., 2002, vol. 42, pp. 227-236.

Hunag, C. et al., "Detection of arboviral RNA directly from mosquito homogenates by reverse transcription-polymerase chain reaction," *J. Virol. Methods* (2001) 94(1-2): 121-128.

Huber et al., On-line cation exchange for suppression of adduct formation in negative-ion electrospray mass spectrometry of nucleic acids. Anal. Chem. (1998) 70:5288-5295.

Hung, "Detection of Sars coronavirus RNA in the cerebrospinal fluid of a patient with severe acute respiratory syndrome" Clin. Chem. (2003) 2108.

Hurdle, J. G. et al., "Analysis of Mupirocin Resistance and Fitness in *Staphylococcus aureus* by Molecular Genetic and Structural Modeling Techniques," *Antimicrob. Agents Chemother.* (2004) 48(11):4366-4376.

Ieven, M. et al., "Rapid Detection of Methicillin Resistance in Coagulase-Negative Staphylococci by Commercially Available Fluorescence Test," *J. Clin. Microbiol.* (1995) 33(8):2183-2185.

Ihle et al., "Efficient purification of DNA fragments using a protein binding membrane" *Nucleic Acids Research* (2000) 28:e76.

Inglis, T. J. et al., "Rapid Genotypic Confirmation of Methicillin Resistance," *Pathology* (1 996) 28(3):259-261.

Australian Search Report for AU 2003297687 dated Sep. 4, 2008.

Australian Search Report for AU 2003302236 dated Sep. 10, 2008.

Australian Search Report for AU 2004248107 dated Jul. 8, 2008.

Canadian patent office communication for Application No. 2,525,498 dated Apr. 7, 2009.

International Prelim. Exam. Report for PCT/US2005/033707 dated Mar. 20, 2007.

International Search Report for PCT/US02/20336 dated May 12, 2004.

International Search Report for PCT/US02/06763 dated Oct. 23, 2002.

International Search Report for PCT/US03/009802 dated Aug. 20, 2004.

International Search Report for PCT/US03/22835 dated Dec. 12, 2003.

International Search Report for PCT/US04/007236 dated Feb. 24, 2006.

International Search Report for PCT/US04/012671 dated Sep. 28, 2007.

International Search Report for PCT/US04/015123 dated Oct. 3, 2005.

International Search Report for PCT/US04/015196 dated Jul. 1, 2005.

International Search Report for PCT/US2004/028869 dated Jul. 17, 2006.

International Search Report for PCT/US04/033742 dated May 15, 2006.

International Search Report for PCT/US05/005356 dated Aug. 7, 2007.

International Search Report for PCT/US05/007022 dated Oct. 20, 2006.

International Search Report for PCT/US05/018337 dated Oct. 10, 2006.

International Search Report for PCT/US05/024799 dated Dec. 28, 2006.

International Search Report for PCT/US05/030058 dated Aug. 20, 2007.

International Search Report for PCT/US05/033707 dated Feb. 6, 2006.

International Search Report for PCT/US05/06133 dated Jul. 26, 2007.

International Search Report for PCT/US05/09557 dated Sep. 19, 2005.

International Search Report for PCT/US06/007747 dated Sep. 5, 2006.

International Search Report for PCT/US2006/040747 dated Mar. 17, 2009.

International Search Report for PCT/US06/015160 dated Oct. 10, 2006.

International Search Report for PCT/US2006/061307 dated Jan. 9, 2008.

International Search Report for PCT/US2007/020045 dated Mar. 26, 2009.

International Search Report for PCT/US2007/066194 dated Jan. 15, 2008.

International Search Report for PCT/US2008/054926 dated Jan. 26, 2009.

International Search Report for PCT/US2008/057717 dated Jan. 13, 2009.

International Search Report for PCT/US2008/057901 dated Aug. 28, 2008.

International Search Report for PCT/US2008/065332 dated Nov. 28, 2008.

Inyaku, K. et al., "Rapid Detection and Identification of Mycobacteria in Sputum Samples by Nested Polymerase Chain Reaction and Restriction Fragment Length Polymorphisms of dnaJ Heat Shock Protein Gene," 42 J. Med. Sci. 21-31 (1993) ('787 reexamination).

Iqbal et al., "A review of molecular recognition technologies for detection of biological threat agents" Biosensors & Bioelectronics, 15:549-578 (2000).

Ito, T. et al., "Structural Comparison of Three Types of Staphylococcal Cassette Chromosome *mec* Integrated in the Chromosome in Methicillin-Resistant *Staphylococcus aureus*," *Antimicrob. Agents Chemother.* (2001) 45(5): 1323-1336.

Ito, T. et al., "Insights on antibiotic resistance of *Staphylococcus aureus* from its whole genome: genomic istand Scc," *Drug Resist. Updat.* (2003) 6(1):41-52.

Jackson et al., "Mass spectrometry for genotyping: an emerging tool for molecular medicine" Molecular Medicine Today (2000) 6:271-276.

Jambrina et al., GenBank: AF005737.1 influenza B virus B/Panama/45/90 polymerase (PB2) mRNA, complete cds, (1997), pp. 1-3.

Jaulhac, B. et al., "Synthetic DNA probes for detection of genes for enterotoxins A, B, C, D, E and for TSST-1 in staphylococcal strains," *J. Appl. Bacterial*. (1992) 72(5):386-392.

Jeong, J, et al., "Early Screening of Oxacillin-Resistant *Staphylococcus aureus* and *Staphylcoccus epidermidis* from Blood Culture," *J. Korean Med. Sci* . (2002) 17: 168-172.

Jonas, D. et al., "Rapid Pcr-Based Identification of Methicillin-Resistant *Staphylococcus aureus* from Screening Swabs," *J. Clin. Microbiol*. (2002)40(5): 1821-1823.

Jurinke C et al., "Application of nested PCR and mass specctrometry for DNA based virus detection: HBV-DNA detected in the majority of isolated anti-Hbc positive sera", Genetic Analysis: Biomolecular Engineering, Elsevier Science Publishing, US, 14(3):97-102 (Jan. 3, 1998)+A627+A661.

Jurinke et al., "MALDI-TOF Mass Spectrometry. A Versatile Tool for High-Performance DNA Analysis" Molecular Biotechnology (2004) 26(2):147-163.

Kacian et al., "A Replicating RNA Molecule Suitable for a Detailed Analysis of Extracellular Evolution and Replication" Proc. Natl. Acad. Sci. USA 69:3038 (1972).

Kajon, A.E. et al., "Genome Type Analysis of Brazilian Adenovirus Strains of Serotypes 1, 2, 3, 5, and 7 Collected Between 1976 and 1995", J. Med. Virol., 1999, vol. 58, pp. 408-412.

Katano, H., et al., "Identification of Adeno-associated virus contamination in cell and virus stocks by PCR", Biotechniques, Informa Life Sciences Publishing, Westborough, MA, US, 36(4):676-680 (Apr. 2004).

Katayama, Y. et al., "Genetic Organization of the Chromosome Region Surrounding *mecA* in Clinical Staphylococcal Strains: Role of IS431-Mediated *mecI* Deletion in Expression of Resistance in med-Canying, Low-Level Methicillin-Resistant *Staphylococcus haemolyticus,*" *Antimicrob. Agents Chemother*. (2001)45(7): 1955-1963.

Kearns, A. M. et al., "Rapid detection of methicillin-resistant staphylococci by multiplex PCR," *J. Hosp. Infect*. (1999) 43:33-37.

Khan, A.S., et al., "An outbreak of Crimean-Congo haemorrhagic fever in the United Arab Emirates, 1994-1995" Am. J. Trop. Med. Hyg., 1997, 57, 519-525.

Khan, S. A. et al., "Simultaneous detection of erythromycin-resistant methylase genes *ermA* and *ermC* from *Staphylococcus* spp. By multiplex-PCR," *Mol. Cell Probes* (1999) 13:381-387.

Kidd, A.H. et al., "Rapid Subgenus Identification of Human Adenovirus Isolates by a General PPCR", J. Clin. Microbiol., 1996, vol. 34, No. 3, pp. 622-627.

Kilbourne, "Influenza Pandemics: Can We Prepare for the Unpredictable?" Viral Immunol. (2004) 17(3):350-357.

Kilbourne, "Influenza Pandemics of the 20th Century" Emerg. Infect. Dis. (2006) 12(1):9-14.

Kinney et al., American J. Trop. Med. Hyg., (1998), vol. 59, No. 6, p. 952-954.

Kolbert et al., "Branched-DNA Assay for Detection of the mecA Gene in Oxacillin-Resistant and Oxacillin-Sensitive Staphylococci" J. Clin. Microbiol. (1998) 36:2640-2644.

Krafft, A.E. et al., "Evaluation of PCR Testing of Ethanol-Fixed Nasal Swab Specimens as an Augmented Surveillance Strategy for Influenza Virus and Adenovirus Identification", J. Clin. Microbiol., 2005, vol. 43, No. 4, pp. 1768-1775.

Kramer, L. D. et al., "Dection of St. Louis Encephalitis and Western Equine Encephalomyelitis RNA in Mosquitoes Tested Without Maintainance of a Cold Chain," J. Am. Mosq. Control Assoc. (2001) 17(4): 213-215.

Kramer, L. D. et al., "Dection of Encephalitis Viruses in Mosquitoes (Diptera: Culicidea) and Avian Tissues," J. Med. Entomol. (2002) 39(2): 312-323.

Kroes et al., "Bacterial diversity within the human subgingival crevice," Proc. Natl. Acad. Sci. USA (1999) 96:14547-14552.

Kresken, M. et al., "Prevalence of mupirocin resistance in clinical isolates of *Staphylococccus aureus* and *Staphylococcus epidermidis*: results of the Antimicrobial Resistance Surveillance Study of the Paul-Ehrlich-Society for Chemotherapy, 2001," Int. J. Antimicrob. Agents (2004) 23:577-581.

Krishnan, P.U. et al., "Detection of methicillin and mupirocin resistance in *Staphylococcus aureus* isolates using conventional and molecular methods: a descriptive study from a burns unit with high prevalence of MRSA," J. Clin. Pathol. (2002) 55:745-748.

Krossoy et al., "The putative polymerase sequence of infectious anemia virus suggests a new geneus within the Orthomyxoviridae" Journal of Virology (1999) 73:2136-2142.

Ksiazek, Thomas G., et al., "A novel coronavirus associated with severe acute respiratory syndrome," New England Journal of Medicine, 348(20):1953-1966 (Apr. 10, 2003).

Kuroda, M., et al., "Whole genome Sequencing of meticillin-resistant *Staphylococcus aureus*", The Lancet, 357(9264):1225-1240 (Apr. 21, 2001).

Kwok, S. and R. Hguchi, "Avoiding false positives with PCR" Nature, 1989, 339,237-238.

Labandeira-Rey, M. et al., "Staphylococcus aureus Panton Valentine Leukocidin Causes Necrotizing Pneumonia" Sciencexpress (2007) Jan. 18.

Lamb et al., "Sequence of Interrupted and Uninterrupted mRNAs and Cloned DNA Coding for the Two Overlapping Nonstructural Proteins of Influenza Virus" Cell (1980) 21:475-485.

Lambert, A.J. et al., "Detection of North American Eastern and Western Equine Encephalitis Viruses by Nucleic Acid Amplification Assays,"*J. Clin. Microbiol*. (2003)41(1): 379-385.

Lau et al., "Nucleic acid sequence-based amplification methods to detect avian influenza virus" Biochem. Biophys. Res. Commun. (2004) 313:336-342.

Lau et al., "A real-time PCR for SARS-coronavirus incorporating target gene pre-amplification" Biochem. Biophys. Res. Comm. (2003) 312:1290-1296.

Lee, J.A. et al., "Rapid Identification of Human Adenovirus Types 3 and 7 from Respiratory Specimens via Multiplex Type-Specific PCR", J. Clin. Microbiol., 2005, vol. 43, No. 11, pp. 5509-5514.

Lee, J.H. et al., "Simultaneous Detection of Three Mosquito-Borne Encephalitis Viruses (...) with a Single-Tube Multiplex Reverse Transcriptase Polymerase Chaine Reaction Assay," *J. Am. Mosq. Control Assoc* . (2002) 18(1): 26-31.

Lengyel, A. et al., "Characterization of the Main Protein Components of Adenovirus Virion and its Possible Use in Laboratory Diagnostics", Acta Microbiol. Immunol. Hung., 1998, vol. 43, Nos. 3-4; pp. 281-283.

Leroy et al., "Diagnosis of Ebola haemorrhagic fever by RT-PCR in an epidemic setting", Journal of Medical Virology, 60:463-467 (2000).

Levi, K. et al., "Evaluation of an Isothermal Signal Amplification Method for Rapid Detection of Methicillin-Resistant Staphylococcus aureus from Patient-Screening Swabs," J. Clin. Microbiol. (2003) 41(7):3 187-3191.

Levine et al., "PCR-based detection of Bacillus anthracis in formalin-fixed tissue from a patient receiving ciprofloxacin" Journal of Clinical Microbiology (2002) 40(11):4360-4362.

Levison et al., "Recent developments of magnetic beads for use in nucleic acid purification" Journal of Chromatography (1998) A 816:107-111.

Le Cann et al., "Quantification of human astroviruses in sewage using real-time RT-PCR" Res. Microbiol. (2004) 155(1):11-15.

Li, Q.-G. et al., "Analysis of 15 Different Genome Types of Adenovirus Type 7 Isolated on Five Continents", J. Virol., 1986, vol. 60, No. 1, pp. 331-335.

Li, Q.-G. et al., "Comparison of 17 Genome Types of Adenovirus Type 3 Identified among Strains Recovered from Six Continents", J. Clin. Microbiol, 1988. vol. 26, No. 5, pp. 1009-1015.

Li, Q.-G. et al., "Genetic variability of hexon loops 1 and 2 between seven genome types of adenovirus serotype 7", Arch. Virol., 1999, vol. 144, No. 9, pp. 1739-1749.

Li et al., "Screening of the high yield influenza B virus on MDCK cell and cloning of its whole genome" International Congress Series 1263 (2004) 610-614.

Li et al., "Evolution of H9N2 influenza viruses from domestic poultry in Mainland China" Virology (2005) 340:70-83.

Liebermann, H. et al., "Mapping of linear epitopes on fibre knob of human adenovirus serotype 5", Virus Res., 2001, vol. 73, No. 2, pp. 145-151.

Liebermann, H. et al., "Mapping of Epitopes on the Fiber Knobs of Human Adenovirus Serotypes 8 and 15", Intervirology, 2002, vol. 45, pp. 59-66.

Lim et al., Genes and Development 17:991-1008 (2003).

Limbach, P.A., et al., "Enzymatic Sequencing of Oligonucleotides with Electrospray Mass Spectrometry" 42nd ASMS Conference on Mass Spectrometry (Jun. 1994) ('787 reexamination).

Limoncu, M. H. et al., "Emergence of phenotypic resistance to ciprofloxacin and levofloxacin in methicillin-resistant and methicillin-sensitive Staphylococcus aureus strains," Int. J. Antimicrob. Agents (2003) 21:420-424.

Lin et al., "Oxidative Damage to Mitochondria! DNA in Atrial Muscle of Patients with Atrial Fibrillation," Free Radical Biology and Medicine, 35(10):1310-1318 (2003).

Lin, B. et al., "Use of Oligonucleotide Microarrays for Rapid Detection and Serotyping of Acute Respiratory Disease-Associated Adenoviruses", J. Clin. Microbiol., 2004, vol. 42, No. 7, pp. 3232-3239.

Lina, G. et al., "Involvement of Panton-Valentine Leukocidin-Producing Staphylococcus aurues in Primary Skin Infections and Pneumonia," Clin. Infect. Dis. (1999) 29(5):1128-1132.

Lina, G. et al., "Bacterial Competition for Human Nasal Cavity Colonization: Role of Staphylococcal agr Alleles," Appl. Environ. Microbiol. (2003) 69(1):18-23.

Linssen, B. et al., "Development of Reverse Transcription-PCR Assays Specific for Detection of Equine Encephalitis Viruses," J. Clin. Microbiol. (2000) 38(4): 1527-1535.

Livermore, D. M., "The threat from the pink corner," Ann. Med. (2003) 35(4):226-234.

Liu et al., "Interregional Transmission of the Internal Protein Genes of H2 Influenza Virus in Migratory Ducks from North America to Eurasia" Virus Genes (2004) 29(1):81-86.

Loo, J. A et al., "Applying Charge Discrimination with Electrospray Ionization-Mass Spectrometry to Protein Analysis," J. Am. Soc. Mass. Spectrom. (1995) 6:1098-1104.

Lott, "Nucleotide Sequence Analysis of the 5-8s rDNA and Adjacent ITS2 Region of Candida albicans and Related Species" Yeast, 9:1199-1206 (1999).

Louie, L. et al., "Evaluation of Three Rapid Methods for Detection of Methicillin Resistance in Staphylococcus aureus," J. Clin. Microbiol. (2000) 38(6):2170-2173.

Lovseth, A. et al., "Modified Multiplex PCR Method for Detection of Pyrogenic Exotoxin Genes in Staphylococcal Isolates," J. Clin. Microbiol. (2004) 42(8):3869-3872.

Lu, X. et al., "Molecular typing of human adenoviruses by PCR and sequencing of a partial region of the hexon gene", Arch. Virol.,., 2006, vol. 15, No. 8, pp. 1587-1602.

Ludwig, S.L. et al., "Prevalence of Antibodies to Adenovirus Serotypes 4 and 7 among Unimmunized US Army Trainees: Results of Retrospective Nationwide Seroprevalence Survey", J. Infect. Dis., (1998) 178, pp. 1776-1778.

Ma, X. X. et al., "Novel Type of Staphylococcal Cassette Chromosome mec Identified in Community-Acquired Methicillin-Resistant Staphylococcus aureus Strains," Antimicrob. Agents Chemother. (2002) 46(4):1147-1152.

Mack and Sninsky, "A sensitive method for the identification of uncharacterized viruses related to known virus groups: Hepadnavirus model system," Proc. Natl. Acad. Sci. USA (1988) 85:6977-6981.

Magnuson, VL, "Substrate nucleotide-determined non-templated addition of adenine by Taq DNA polymerase: Implications for PCR-based genotyping and cloning" Biotechniques, 21:700-709 (Oct. 1996).

Malasig, M.D. et al., "Simplified Microneutralization Test for Serotyping Adenovirus Isolates", J. Clin. Microbiol., 2001, vol. 39, No. 8, pp. 2984-2986.

Manian, F. A,, "Asymptomatic Nasal Carriage of Mupirocin-Resistant, Methicillin-Resistant Staphylococcus aureus (MRSA) in a Pet Dog Associated with MRSA Infection in Household Contacts," Clin. Infect. Dis. (2003) 36:e26-e28.

Marmur et al., "Strand Separation and Specific Recombination in Deoxyribonucleic Acids: Biological Studies" Proc. Natl. Acad. Sci. USA 46:453 (1960).

Martineau, F. et al., "Species-Specific and Ubiquitous-DNA-Based Assays for Rapid Identification of Staphylococcus aureus," J. Clin. Microbial. (1998) 36(3):618-623.

Martineau, F. et al., "Development of a PCR Assay for Identification of Staphylococci at Genus and Species Levels," J. Clin. Microbial. (2001) 39(7):2541-2547.

Martin-Lopez, J. V. et al., "Simultaneous PCR detection of ica cluster and methicillin and mupirocin resistance genes in catheter-isolated Staphylococcus," Int. Microbial. (2004) 7:63-66.

Mason et al., "Diversity and linkage of replication and mobilisation genes in Bacillus rolling circle-replicating plasmids from diverse geographical origins" FEMS Microbiol. Ecol. 2002,42:235-241.

Matsuoka, M. et al., "Characteristic expression of three genes, msr(A), mph(C) and erm(Y), that confer resistance to macrolide antibiotics on Staphylococcus aureus," FEMS Microbiol. Lett. (2003) 220:287-293.

May, "Percent sequence identity: The need to be explicit" Structure (2004) 12(5):737-738.

McLuckey, S.A., et al., "Ion Trap Tandem Mass Spectrometry Applied to Small Multiply Charged Oligonucleotides with a Modified Base," 5 J. Am. Soc. Mass. Spectrom. 740-747 (1994) (787 reexamination).

Mehrotra et al., "Multiplex PCR for detection of genes for Staphylococcus aureus enterotoxins, exfoliative toxins, toxic shock syndrome toxin 1, and methicillin resistance", Journal of Clinical Microbiology, Washington, DC US 38(3):1032-1035 (Mar. 1, 2000)+A256.

Mellor et al., "Genotype Dependence of Hepatitis C Virus Load Measurement in Commercially Available Quantitative Assays" J. Clin. Microbiol. (1999) 37(8):2525-2532.

Merlino, J. et at., "New Chromogenic Identification and Detection of Staphylococcus aureus and Methicillin-Resistant S. aureus." J. Clin. Microbiol (2000) 38(6): 2378-2380.

Merlino, J. et al., "Rapid Detection of Non-Multidrug-Resistant and Multidrug-Resistant Methicillin-Resistant Staphylococcus aureus Using Cycling Probe Technology for the mecA Gene," Eur. J. Clin. Microbiol. Infect. Dis. (2003) 22: 322.323.

Metzgar, D. et al., "PCR Analysis of Egyptian Respiratory Adenovirus Isolates, Including Identification of Species, Serotypes and Coinfections", J. Clin. Microbiol., 2005, vol. 43, No. 11, p. 5743-5752.

Miragaia, M. et al., "Genetic Diversity among Methicillin-Resistant Staphylococcus epidemidis (MRSE)," Microbial Drug Resistance (2005) 11(2):83-93.

Miura-Ochiai, R. et al., "Quantitative detection and rapid identification of human adenoviruses", J. Clin. Microbiol., 2007, vol. 45, No. 3, pp. 958-967.

Monroy, A.M. et al., "Exvaluation of Reverse Transcriptase Polymerase Chain Reaction for the Detection of Eastern Equine Encephalumyelitis Virus during Vector Surveillance," J. Med. Entomol. (1996) 33(3): 449-457.

Moore et al., "Development and Evaluation of a Real-Time Nucleic Acid Sequence Based Amplification Assay for Rapid Detection of Influenza A" J. Med. Virol. (2004) 74(4):619-628.

Morinaga, N. er al., "Purification, Cloning and Charactarizarion of Variant LukE-LukD with Strong Leukocidal Activity of Staphylococcal Bi-Component Leukotoxin Family," Microbiol. Immunol. (2003) 47(1):81-90.

Murakami, K. et al., "Identification of Methicillin-Resistant Strains of Staphylococci by Polymerase Chain Reaction," J. Clin. Microbiol. (1991) 29(10):2240-2244.

Na et al., "Detection and typing of respiratory adenoviruses in a single-tube multiplex polymerase chain reaction" Journal of Medical Virology (2002) 66:512-517.

Nagy, M. et al., "Sequence Analysis of Porcine Adenovirus Serotype 5 Fibre Gene: Evidence for Recombination", Virus Genes, 2002, vol. 24, No. 2, pp. 181-185.

Nakagawa et al., "Gene sequences and specific detection for Panton-Valentine leukocidin" Biochem. Biophys. Res. Commun. (2005) 328(4):995-1002.

Narita et al., "Phage conversion of Panton-Valentine leukocidin in Staphylococcus aureus: molecular analysis of a PVL-converting phage, phiSLT" Gene (2001) 268(1-2):195-206.

Neumann et al., "Host Range Restriction and Pathogenicity in the Context of Influenza Pandemic" Emerg. Infect. Dis. (2006) 12(6):881-886.

New England Biolabs Catalog (1998-1999) pp. 1, 79, 121, 284.

Newcombe et al. "PCR of peripheral blood for diagnosis of meningococcal disease" (1996) 34:1637-1640.

Ng et al., "Serial analysis of the plasma concentration of SARScoronavirus RNA in pediatric patients with severe acute respiratory syndrome" Clin. Chem. (2003) 49:2085.

Ng et al., "Quantitative analysis and prognostic implication of SARS coronavirus RNA in the plasma and serum of patients with severe acute respiratory syndrome" Clin. Chem. (2003)49:1976-1980.

Nordhoff, E., et al., "Matrix Assisted Laser Desorption/Ionization Mass Spectrometry of Nucleic Acids with Wavelengths in the Ultraviolet and Infrared" 6 Rapid Commun. Mass Spectrom. 771- 776 (1992) ('787 reexamination).

Nubel et al., "PCR primers to amplify 16S rRNA genes from Cyanobacteria," Applied and Environmental Microbiology, 63(8):3327-3332 (Aug. 1997).

Nunes, E. L. et al., "Detection of ileS-2 Gene Encoding Mupirocin Resistance in Methicillin-Resistant Staphylococcus aureus by Multiplex PCR" Diagn. Microbiol. Infect. Dis. (1999) 34(2): 77-81.

Nygren et al., "Quantification of HIV-1 Using Multiple Quantitative Polymerase Chain Reaction Standards and Bioluminometric Detection" Anal. Biochem. (2001) 288(1):28-38.

Oberacher H et al., "Increased foresnic efficiency of DNA fingerprints through simultaneous resolution of length and nucleotide variability by high-performance mass spectrometry," Human Mutation 29(3):427-432 (Mar. 2008)+A613+A714.

Oberacher et al., "Analysis of polymerase chain reaction products by on-line liquid chromatography mass spectrometry for genotyping of polymeric short tandem repeat Ioci" (2001) 73:5109-5115.

Oberste, et al., "Molecular phylogeny and proposed classification of the Simian picornaviruses," J. Virol. (2002) 76:1244-1251.

Oberste, et al., "Improved molecular identification of enteroviruses by RT-PCRand amplicon sequencing," J. Clin. Virol. (2003) 26:375-377.

Oberste, et al., "Molecular epidemiology and type-specific detection of echovirus 11 isolates from the Americas, Europe, Africa, Australia, southern Asia and the Middle East," Virus Res. (2003) 91:241- 248.

O'Guinn, M.L. et al., "Field Detection of Eastern Equine Encephalitis Virus in the Amazon Basin Region of Peru Using Reverse Transcription-Polymerase Chain Reaction Adapted for Field Identification of Arthropod-Borne Pathogens," Am. J. Trop. Med. Hyg. (2004) 70(2): 164-171.

Oizumi, N, et al., "Relationship between mutations in the DNA gyrase and topoisomerase IV genes and nadifloxacin resistance in clinically isolated quinolone-resistant Staphylococcus aureus," Journal of Infection and Chemotherapy: Official Journal of the Japan Society of Chemotherapy, 7(3):191-194 (Sep. 2001).

Okada, M. et al., "Detection and sequence-based typing of human adenoviruses using sensitive universal primer sets for the hexon gene", Arch. Virol., 2007, vol. 152, No. 1, pp. 1-9.

Okuma, K. et al., "Dissemination of New Methicillin-Resistant Staphylococcus aureus Clones in the Community," J. Clin. Mcrobiol. (2002) 40(11):4289-4294.

Oliveira, D. C. et al., "Genetic Organization of the Downstream Region of the mecA Element in Methicillin-Resistant Staphylococcus aureus Isolates Carrying Different Polymorphisms of This Region," Antimicrob. dients Chemother. (2000) 44(7): 1906-1910.

Oliveira, D. C. et al., "Multiplex PCR Strategy for Rapid Identification of Structural Types and Variants of the mec Element in Methicillin- Resistant Staphylococcus aureus," Antimicrob. Agents Chemother. (2002) 46(7):2155-2161.

Osiowy, C. et al., "Direct Detection of Respiratory Syncytial Virus, Parainfluenze Virus, and Adenovirus in Clinical Respiratory Specimens by a Multiplex Reverse Transcription-PCR Assay", J. Clin. Microbiol., 1998, vol. 36, No. 11, pp. 3149-3154.

Ounissi, H. et al., "Gene Homogeneity for Aminoglycoside-Modifying Enzymes in Gram-Positive Cocci," Antimicrob. Agents Chemother. (1990) 34(11):2164-2168.

Pastorino, B. et al., "Development of a TaqMan PCR assay without RNA extraction step for the detection and quantification of African Chikungunya viruses," J. Virol. Methods (2005) 124(1-2): 65-71.

Pawa, A. et al., "Co-transfer of plasmids in association with conjugative transfer of mupirocin or mupirocin and penicillin resistance in methicillin-resistant Staphylococcus aureus;" J. Med. Microbiol. (2000) 49: 1103-1107.

Payne et al. Antimicrobials: The challenge of antibiotic resistant bacterial pathogens: the medical need, the market and prospects for new antimicrobial agents. Current Opinion in Microbiology 7:435-438 (2004).

Perez-Roth, E. et al., "Multiplex PCR for Simultaneous Identification of Staphylococcus aureus and Detection of Methicillin and Mupirocin Resistance," J. Clin. Microbial. (2001) 39(11):4037-4041.

Peters et al., "Quantification of the detection of Pneumocystis carinii by DNA amplification" Mol. Cell. Probes (1992) 6:115-117.

Pfeffer, M. et al., "Genus-Specific Detection of Alphaviruses by a Semi-Nested Reverse Transcription-Polymerase Chain Reaction," Am. J. Trop. Med Hyg. (1 997) 57(6): 709-718.

Pfeffer, M. et al., "Specific Detection of Chikungunya Virus Using a RT-PCR/Nested PCR Combination," J. Vet. Med. B (2002) 49(1): 49-54.

Pieles, U, et al., Matrix-Assisted Laser Desorption Ionization Time-of-Flight Spectrometry: A Powerful Tool for the Mass and Sequence Analysis of Natural and Modified Oligonucleotides 21 Nucleic Acids Res. 3191-3196 (1993) ('787 reexamination).

Pillai, S.D., :Rapid molecular detection of microbial pathogens: breakthroughs and challenges Arch Virol., 1997, 13 Suppl., 67-82.

Piper, J. et al., "Commercially Available Technique for Rapid Laboratory Detection of Methicillin Resistance Among Staphylococcus aureus," Diagn. Microbial. Infect. Dis. (1988) 11(3): 177-180.

Poddar, Sk., "Detection of adenovirus using PCR and molecular beacon", J. Virol. Methods., 1999, vol. 82, No. 1, pp. 19-26.

Pring-Akerblom, P., et al., "PCR-based detection and typing of human adenoviruses in clinical samples", Res. Virol., 1997, vol. 148, No. 3, pp. 225-231.

Pring-Akerblom, P., et al., "Multiplex Polymerase Chain Reaction for Subgenus-Specific Detection of Human Adenoviruses in Clinical Samples", J. Med. Virol., 1999, vol. 58, No. 1, pp. 87-92.

Promega T4 Polynucleotide Kinase, Promega Technical Bulletin No. 519, Jul. 2002.

Puthavathana et al., "Molecular characterization of the complete genome of human influenza H5N1 virus isolates from Thailand" J. Gen. Virol. (2005) 86:423-433.

Qadri, S. M. et al., "Rapid Detection of Methicillin-Resistant Staphylococcus aureus by Crystal MRSA ID System,"J. Clin. Microbiol. (1994) 32(7):1830-1832.

Ramisse et al., "Identification and characterization of Bacillus anthracis by multiplex PCR analysis of sequences on plasmids pX01 and pX02 and chromosomal DNA" FEMS Microbiology Letters (1996) 145(1):9-16.

Rangarajan, Sampath, et al., "Rapid identification of emerging infectious agents using PCR and electrospray ionization mass spectrometry" Ann. N. Y. Acad. Of Sci (2007) 1102:109-120.

Reischl, Frontiers Biosci., 1996, 1, Application of Molecular Biology-Based Methods to the Diagnosis of Infectious Diseases 1, e72-e77.

Reischl, U. et al., "Rapid Identification of Methicillin-Resistant Staphylococcuss aureus and Simultaneous Species Confirmation Using Real-Time Fluorescence PCR," J. Clin. Microbiol. (2000) 38(6):2429-2433.

Roberts, M.M. et al., "Three-Dimensional Structure of the Adenovirus Major Coat Protein Hexon", Science, 1986, vol. 232, No. 4754, pp. 1148-1151.

Robinson, D. A. et al., "Multilocus sequence typing and the evolution of methicillin-resistant Staphylococcus aureus," Clin. Microbiol. Infect. (2004) 10:92-97.

Rong et al., "Design and Application of 60mer oligonucleotide microarray in SARS coronavirus detection", Chinese Sci. Bull., 2003, 48, 1165-1169.

Ruan et al., Comparative full-length genome sequence analysis of 14 SARS coronavirus isolates and common mutations associated with the putative origins of infection, Lancet (2003) 361:1832.

Rota et al., "Sequencing of a cDNA clone of the nucleoprotein gene of influenza B/Ann Arbor/1/86" Nucleic Acids Research (1989) 17:3595.

Ruest et al., "Comparison of the Directigen Flu A+B test, the QuickVue Influenza Test, and Clinical Case Definition to Viral Culture and Reverse Transcription-PCR for Rapid Diagnosis of Influenza Virus Infection" J. Clin. Microbiol. (2003) 41(8):3487-3493.

Rupf et al., "Quantitative determination of Streptococcus mutans by using competitive polymerase chain reaction" Eur. J. Oral. Sci. (1999) 107(2):75-81.

Russell, K.L. et al., "Transmission Dynamics and Prospective Environmental Sampling of Adenovirus in a Military Recruit Setting", J. Infect. Dis., 2006, vol. 194, No. 7, pp. 877-885.

Sabat, a. et al., "Comparison of PCR-Based Methods for Typing Staphylococcus aureus Isolates," J. Clin. Microbiol. (2006) 44(10):3804-3807.

Sackesen, C. et al., "Use of polymerase chain reaction for detection of adenovirus in children with or without wheezing", Turk. J. Pediatr., 2005, vol. 47, No. 3, pp. 227-231.

Sakai, H. et al., "Simultaneous Detection of Staphylococcus aureus and Coagulase-Negative Staphylococci in Positive Blood Cultures by Real-Time PCR with Two Fluorescence Resonance Energy Transfer Probe Sets," J. Clin. Microbiol. (2004) 42(12):5739-5744.

Sambrook et al., Molecular Cloning: A Laboratory Manual, 2nd Edition, Cold Spring Harbor Press, Cold Spring Harbor, NY 1989.

Sampath et al., "Rapid Identification of Emerging Pathogens: Coronavirus" Emerg. Infect. Dis. (2005) 11(3):373-379.

Sanchez et al., "Detection and Molecular Characterizatio of Ebola viruses causing disease in human and nonhuman primates" The Journal of Infectious Diseases, 179(1):5164-5169 (1991).

Sanchez, J.L. et al., "Epidemic of Adenovirus-Induced Respiratory Illness Among US Military Recruits: Epidemiologic and Immunologic Risk Factors in Healthy, Young adults", J. Med. Virol., 2001, vol. 65, No. 4, pp. 710-718.

Sanchez-Seco, M. P. et al., "A generic nested-RT-PCR followed by sequencing for detection and identification of members of the alphavirus genus," J. Virol. Methods (2001) 95(1-2): 153-161.

Sarantis, H. et al., "Comprehensive Detection and Serotyping of Human Adenoviruses by PCR and Sequencing", J. Clin. Microbial., 2004, vol. 42, No. 9, pp. 3963-3969.

Schmidt et al., "Analysis of a marine pikoplankton community by 16s rRNA gene cloning and sequencing," J. Bacteriol. (1991) 173:4371-4378.

Schmitz, F. J. et al., "Specific information concerning taxonomy, pathogenicity and methicillin resistance of staphylococci obtained by a multiplex PCR." J. Med. Microbiol. (1997) 46:773-778.

Schmitz, F. J. et al., "Development of a multiplex-PCR for direct detection of the genes for enterotoxin B and C, and toxic shock syndrome toxin-1 in Staphylococcus aureus isolates," J. Med. Microbiol. (1998) 47(4):335-340.

Schmitz, F. J. et al., "Development of Resistance to Ciprofloxacin, Rifampin, and Mupirocin in Methicillin-Susceptible and -Resistant Staphylococcus aureus Isolates," Antimicrob. Agents Chemother. (2000) 44(11): 3229-3231.

Schwartz, M, et al., "Prenatal diagnosis of alpha-1-antitrypsin deficiency using polymerase chain reaction (Pcr). Comparison of conventional RFLP methods with PCR used in combination with allele specific oligonucleotides or RFLP analysis," 36 Clin. Genet. 419-426 (1989) ('787 reexamination).

Schweiger et al., "Application of a Fluorogenic PCR Assay for Typing and Subtyping of Influenza Viruses in Respiratory Samples" J. Clin. Microbiol. (2000) 38(4):1552-1558.

Sciacchitano et al., "Analysis of polymerase chain reaction-amplified DNA fragments of clostridium botulinum type E neurotoxin gene by high performance capillary electrophoresis." J. Liq. Chromatogr. Relat. Technol. (1996) 19:2165-2178.

Scott-Taylor, T.H. et al., "Conserved Sequences of the Adenovirus Genome for Detection of all Human Adenovirus Types by Hybridization", J. Clin. Microbiol., 1992, vol. 30, No. 7, pp. 1703-1710.
Seifarth, et al., "Rapid identification of all known retroviral reverse transcriptase sequences with a novel versatile detection assay," AIDS Res. Human Retrovir. (2000) 16:721-729.
Sellner, L. N. et al., "Sensitive detection of Ross River virus - a one-tube nested RT-PCR," *J. Virol. Methods* (1994) 49(1): 47-58.
Sellner, L., "A Single-Tube Nested RT-PCR for the Detection of Ross River Virus," Methods Mol. Biol. (1998) 92: 145-152.
Shi et al., "Design and application of 60mer oligonucleotide microarray in SARS coronavirus detection" Chinese Sci. Bull. (2003) 48:1165-1169.
Shimaoka, M. et al., "Development of Enzyme-Labeled Oligonucleotide Probe for Detection of mecA gene in Methicillin-Resistant Staphylococcus aureus," J. Clin. Microbiol (1994) 32(8): 1866-1869.
Shimaoka, M. et al., "Detection of the gene for toxic shock syndrome toxin 1 in Siaphylococcus aureus by enzyme-labelled oligonucleotideprobes," J. Med. Microbiol. (1996)44:215-218.
Shrestha, N. K. et al., "Rapid Identification of Staphylococcus aureus and the mecA Gene from BacT/Alert Blood Culture Bottles by Using the Lightcycler System," J. Clin. Microbiol. (2002) 40(1):2659-2661.
Simonsen et al., "The Impact of Influenza Epidemics on Hospitalizations" J. Infect. Dis. (2000) 181:831-837.
Skov, R L. et al., "Evaluation of a new 3-h hybridization method for detecting the mecA gene in Staphylococcus aureus and comparison with existing genotypic and phenotypic susceptibility testing methods," J. Antimicrob. Chemother. (1999) 43: 467-475.
Smirnov et al. "Application of DNA-binding polymers for preparation of DNA for analysis by matrix-assisted laser desorption/ionization mass spectrometry." Rapid Comm in Mass Spectrometry (2001) 15:1427-1432.
Smith and Waterman, Adv. Appl. Math., 1981, 2,482-489.
Song et al., "Identification of cry11-type genes from Bacilus thuringiensis strains and characterization of a novel cry11-type gene" App. Environ. Microbiol. (2003) 69:5207-5211.
Spackman et al., "Development of a real-time reverse transcriptase PCR assay for type A influenza virus and the avian H5 and H7 hemagglutinin subtypes" Journal of Clinical Microbiology (2002) 40:3256-3260.
Spiess, et al., Trehalose is a potent PCR enhancer: Lowering of DNA melting temperature and thermal stabilization of Taq polymerase by the disaccharide trehalose, In: Clinical Chemistry, 2004, 50(7):1256-1259.
Stephensen CB et al., "Phylogenetic analysis of a highly conserved region of the polymerase gene from 11 coronaviruses and development ofa consensus polymerase chain reaction assay" Virus Research Amsterdam NL, 60(2):181-189 (Apr. 1, 1999).
Stone et al., "Rapid detection and simultaneous subtype differentiation of influenza a viruses by real time Pcr" (2004) *Journal of Virological Methods* (2004) 117:103-112.
Stratagene, 1988 Catalog, p. 39.
Strommenger, B. et al., "Multiplex PCR Assay for Simultaneous Detection of Nine Clinically Relevant Antibiotic Resistance Genes in Staphylococcus aureus," J. Clin. Microbial. (2003) 41(9):4089 4094.
Studdert, M. J. et al., "Polymerase chain reaction tests for the identification of Ross River, Kunjin and Murray Valley encephalitis virus infections in horses," *Aust. Vet. J.* (2003) 81(1-2): 76-80.
Stuhlmeier, R et al., "Fast, simultaneous, and sensitive detection of staphylococci," J. Clin. Pathol. (2003) 56:782-785.
Sundsfjord, A. et al., "Genetic methods for detection of antimicrobial resistance," APMIS (2004) 112:815-837.
Swanborg, R.H., "Human herpesvirus 6 and Chlamydia pneumoniae as etiologic agents in multiple sclerosis—a critical review"Microbes and Infection, 4:1327-1333 (2002).
Swaminathan, B., et al., Emerging Infectious Diseases, 2001, 7, 382-389.
Swenson, J. M. et al., "Pet-romance of Eight Methods, Including Two New Rapid Methods, for Detection of Oxacillin Resistance in a Challenge Set of Staphylococcus aureus Organisms," J. Clin. Microbial. (2001) 39(10):3785-3788.
Takahata M, et al., "Mutations in the gyrA and gr1A genes of quinolone-resistant clinical isolates of methicillin-resistant Staphylococcus aureus," The Journal of Antimicrobial Chemotherapy, 38(3):543- 546 (Sep. 1996).

Takayama, R. et al., "Quantification of Adenovirus Species B and C Viremia by Real-Time PCR in Adults and Children Undergoing Stem Cell Transplantation", J. Med. Virol., 2007, vol. 79, No. 3, pp. 278-284.

Talaat et al., "Genome-directed primers for selective labeling of bacterial transcripts for DNA microarray analysis" *Nature Biotechnology* 17:676-682.

Tan, T. Y., "Use of molecular techniques for the detection of antibiotic resistance in bacteria," Expert. Rev. Mol. Diagn. (2003) 3(1):93-103.

Tanabe, F. et al., "The Properties and mec A Gene of the Methicillin-Resistant Staphylccoccus aureus Isolated in Fukushima Medical College Hospital," Fukushima J. Med. Sci (1993) 39(1):35-42.

Tang, K., "Matrix-Assisted Laser Desorption/Ionization Mass Spectrometry of Oligonucleotides," Dissertation submitted to the Faculty of VAnderbilt University (Aug. 1994) ('787 reexamination).

Tang, K, N. I. Taranenko, S.L. Allman, L.Y. Chang and C.H. Chen, "Double-Stranded DNA Analysis by Matrix Assisted Laser Desorption/Ionization," 42nd ASMA Conference on Mass Spectrometry (Jun. 1994) ('787 reexamination).

Tang, K, N. I. Taranenko, S.L. Allman, L.Y. Chang and C.H. Chen, "Detection of 500-Nucleotide DNA by Laser Desorption Mass Spectrometry," Rapid Commun. Mass Spectrom. 727-730 (Sep. 1994) ('787 reexamination).

Tarassishin, L. et al., "Adenovirus core protein VII displays a linear epitope conserved in a range of human adenoviruses", J. Gen. Virol., 1999, vol. 80, pp. 47-50.

Tarassishin, L. et al., "An epitope on the adenovirus fibre tail is common to all human subgroups", Ach. Virol., 2000, vol. 145, pp. 805-811.

Taubenberger et al., "Characterization of the 1918 influenza virus polymerase genes" Nature (2005) 437:889-893.

Taylor, L.H., et al., Philos. Trans. R. Soc. Lond B. Biol. Sci. 2001, 356, 983-989.

Tenover, F. C. et al., "Characterization of a Strain of Community-Associated Methicillin-Resistant Slaphylococcus aureus Widely Disseminated in the United States," J. Clin.Microbiol. (2006) 44(1):108- 118.

Teramura, T. et al., "Quantitative detection of serum adenovirus in a transplant recipient", Lancet, 2002, vol. 359, pp. 1945.

Thiel, et al., "Infectious RNA transcribed in vitro from a cDNA copy of the human coronavirus genome cloned in vaccinia virus" J. Gen. Virology 2001 82:1273-1281.

Thompson et al., "Influenza-Associated Hospitalizations in the United States" JAMA (2004) 292:1333-1340.

Thompson et al., Nucleic Acid Res., 22, 4673-80.

Tokue, Y. et al., "Comparison of a Polymerase Chain Reaction Assay and a Conventional Microbiologic Method for Detection of Methicillin-Resistant Slaphylococcus aureus," Antimicrob. Agents Chemother. (1992) 36(1):6-9.

Top, F., Jr., "Control of Adenovirus Acute Respiratory Disease in U.S. Army Trainees", Yale J. Biol. Med., 1975, vol. 48, pp. 185-195.

Towner, K. J. et al., "Development and evaluation of a PCR-based immunoassay for the rapid detection of methicillin-resistant Staphylococcus aureus," J. Med. Microbial. (1998) 47:607-613.

Tsuneyoshi et al., "Mass spectrometric gene diagnosis of one-base substitution from polymerase chain reaction amplified human DNA" (1997) 11:719-722.

Tsunoda et al., Time and Memory Efficient Algorithm for Extracting Palindromic and Repetitive Subsequences in Nucleic Acid Sequences Pacific Symposium on Biocomputing (1999)4:202-213.

Udo, E. E. et al., "Rapid detection of methicillin resistance in staphylococci using a slide latex agglutination kit," Int. J Antimicrob. Agents. (2000) 15(1):19-24.

Udo, E. E. et al., "Genetic analysis of methicillin-resistant Staphylococcus aureus expressing high-and low-level mupirocin resistance."J. Med. Microbiol. (2001) 50:909-515.

Udo, E. E. et al., "A chromosomal location of the mupA gene in Staphylococcus aureus expressing high-level mupirocin resistance," J. Antimicrob. Chemother. (2003) 51:1283-1286.

Unal et al., J. Clin. Microbiol. (1992) 30:1685-1691.

Unpublished U.S. Appl. No. 10/323,186 filed Dec. 18, 2002.
Unpublished U.S. Appl. No. 10/323,187 filed Dec. 18, 2002.
Unpublished U.S. Appl. No. 10/324,721 filed Dec. 18, 2002.
Unpublished U.S. Appl. No. 10/728,486 filed Dec. 5, 2003.
Unpublished U.S. Appl. No. 11/209,439 filed Aug. 23, 2005.
Unpublished U.S. Appl. No. 60/604,329 filed Aug. 24, 2004.
Unpublished U.S. Appl. No. 60/632,862 filed Dec. 3, 2004.
Unpublished U.S. Appl. No. 60/639,068 filed Dec. 22, 2004.
Unpublished U.S. Appl. No. 60/648,188 filed Jan. 28, 2005.
Unpublished U.S. Appl. No. 60/658,248 filed Mar. 3, 2005.
Unpublished U.S. Appl. No. 90/010,209 filed Jun. 27, 2008.
Unpublished U.S. Appl. No. 90/010,210 filed Jun. 27, 2008.

Upton, a. et al., "Mupirocin and Staphylococcus aureus: a recent paradigm of emerging antibiotic resistance," J. Antimicrob. Chemother. (2003) 51: 613-617.

Vabret, a., et al., "Development of a PCRand hybridization-based assay (PCR Adenovirus Consensusä) for the detection and the species identification of adenoviruses in respiratory specimens", J. Clin. Virol., 2004, vol. 31, No. 2, pp. 116-122.

Van Der Zee, et al., "Rapid and alternative screening methods for microbiological analysis" J. AOAC Int., 1997, 80, 934-940.

Van Dinten et al., " Proteolytic Processing of the Open Reading Frame 1b-Encoded Part of Arterivirus Replicase Is Mediated by nsp4 Serine Protease and Is Essential for Virus Replication" J. Virology, 1999, vol. 73, pp. 2027-2037.

Van Elden et al., "Simultaneous Detection of Influenza Viruses A and B Using Real-Time Quantitative PCR" J. Clin. Microbiol. (2001) 39(1):196-200.

Van Elden et al., "Clinical diagnosis of influenza virus infection: evaluation of diagnostic tools in general practice" Br. J. Gen. Pract. (2001) 51:630-634.

Van Leeuwen, W. B. et al., "Rapid Detection of Methicillin-Resistance in Staphylococus aureus Isolates by the Mrsa-Screen Latex Agglutination Test,"J. Clin. Microbiol. (1999) 37(9):3029-3030.

Van Leeuwen, W. B. et al., "Multilocus Sequence Typing of Staphylococcus aureus with DNA Array Technology," J. Clin. Microbiol. (2003) 41(7):3323-3326.

Vannuffel, P. et al.. "Specific Detection of Methicillin-Resistant Staphylococcus Species by Multiplex PCR," J. Clin Microbiol. (1995) 33(11):2864-2867.

Vannuffel, P. et al., "Rapid and Specific Molecular Identification of Methicillin-Resistant Staphylococcus aureus in Endotracheal Aspirates from Mechanically Ventilated Patients," J Clin. Microbiol. (1998) 36(8):2366-2368.

Videla, C. et al., "Genomic analysis of adenovirus isolated from Argentinean children with acute lower respiratory infections", J. Clin. Virol., 1999, vol. 14, pp. 67-71.

Vilchez, Regis a et al., "Detection of polyomavirus simian virus 40 tumor antigen DNA in Aids related systemic non-Hodgkin lymphoma," J. Aids Journal of Acquired Immune Deficiency Syndromes, 29(2):109-116 (Feb. 1, 2002).

Voelter C et al., "Screening human tumor samples with a broad-spectrum polymerase chain reaction method for the detection of polyomaviruses", Virology, Academic Press, Orlando, US 237(2):389-396 (Oct. 1997).

Volokhov et al. Microarray analysis of erythromycin resistance determinants. Journal of Applied Microbiology 95:787-798 (2003).

Von Eiff, C. et al., "Pathogenesis of infections due to coagulase-negative staphylococci," Lancet Infect. Dis. (2002) 2:677-685.

Walker, E. S. et al., "A Decline in Mupimcin Resistance in Methicillin-Resistant Staphylococcus aureus Accompanied Administrative Control of Prescriptions," J. Clin. Microbiol. (2004) 42(6):2792-2795.

Wallace, et al., "The Enigma of Endonuclease VII. DNA Repair," 2:441-453 (2003).

Wallet, F. et al., "Choice of a routine method for detecting methicillin-resistance in staphylococci,"I Antimicrob. Chemother. (1996) 37:901-909.

Ward et al, "Design and performance testing of quantitative real time PCR assays for influenza A and B viral load measurement" Journal of Clinical Virology (2004) 29:179-188.

Weissenbacher, M. et al., "Etiologic and Clinical Evaluation of Acute Lower Respiratory Tract Infections in Young Argentinean Children: an Overview", Rev. Infect. Dis., 1990, vol. 12, Suppl. 8; pp. S889-898.

Wertheim, H. F. et al., "Effect of Mupirocin Treatment on Nasal, Pharyngeal, and Perineal Carriage of *Staphylococcus aureus* in Healthy Adults," Antimicrob. Agents Chemother. (2005) 49(4):1465-1467.

Whiley, David M et al., "Simultaneous detection and differentiation of human polyomaviruses JC and BK by a rapid and sensitive PCR-ELAHA assay and a survey of the JCV subtypes within an Australian population," Journal of Medical Virology, 72(3):467-472 (Mar. 2004).

Wichelhaus, T. A. et al., "Rapid Detection of Epidemic Strains of Methicillin-Resistant *Staphylococcus aureus*," J. Clin. Microbiol. (1999) 37(3):690-693.

Wickham, T.J., "Targeting adenovirus", Gene Therapy, 2000, vol. 7, pp. 110-114.

Winger et al., "High resolution accurate mass measurements of biomolecules using a new electrospray ionization ion cyclotron resonance mass spectrometer" J. Am. Soc. Mass Spectrom. 4, 566, 1993.

Wood, S.R. et al., "Rapid Detection and Serotyping of Adenovirus by Direct Immunofluorescence", J. Med. Virol., 1997, vol. 51, No. 3, pp. 198-201.

Wright et al., "Typing and Subtyping of Influenza Viruses in Clinical Samples by PCR" J. Clin. Microbiol. (1995) 33(5):1180-1184.

Wu et al., "Genetic Organization of the mecA Region in Methicillin-Susceptible and Methicillin-Resistant Strains of *Staphylococcus sciuri*" J. Bacteriol. (1998) 180(2):236-242.

Wu et al., "Establishment of a fluorescent polymerase chain reaction method for the detection of SARS-associated coronavirus and its clinical application" Chin. Med. J. (2003) 116:988-990.

Xu et al., "Intercontinental Circulation of Human Influenza A(H1N2) Reassortant Viruses During the 2001-2002 Influenza Season" J. Infect. Dis. (2002):186:1490-1493.

Xu, W. et al., "Species-Specific Identification of Human Adenoviruses by a Multiplex PCR Assay", J. Clin. Microbiol., 2000, vol. 38, No. 11, pp. 4114-4120.

Xu, W. et al., "Type-Specific Identification of Human Adenovirus, 3, 7, and 21 by a Multiplex PCR Assay", J. Med. Virol., 2001, vol. 64, No. 4, pp. 537-542.

Yun, H J et al., "Increased antibacterial activity of OW286, a novel fluoronaphthyridone antibiotic, against *Staphylococcus aureus* strains with defined mutations in DNA gyrase and toposiomerase IV", International Journal of Antimicrobial Agents, Amsterdam, NL, 25(4):334-337 (Apr. 1, 2005).

Zhang et al., "Detectiona and identification of human influenza viruses by the polymerase chain reaction" J. Virol. Methods (1991) 33(1-2):165-189.

Zhang, K. et al., "New Quadriplex PCR Assay for Detection of Methicillin and Mupirocin Resistance and Simultaneous Discrimination of *Staphylococcus aureus* from Coagulase-Negative Staphylococci," J. Clin. Microbiol. (2004) 42(11):4947-4955.

Zhang, Y.-Q. et al., "Genome-based analysis of virulence genes in a non-biofilm-forming *Staphylococcus epidemidis* strain (ATCC 12228):" Mol. Microbiol. (2003) 49(6):1577-1593.

\* cited by examiner

FIG. 1G
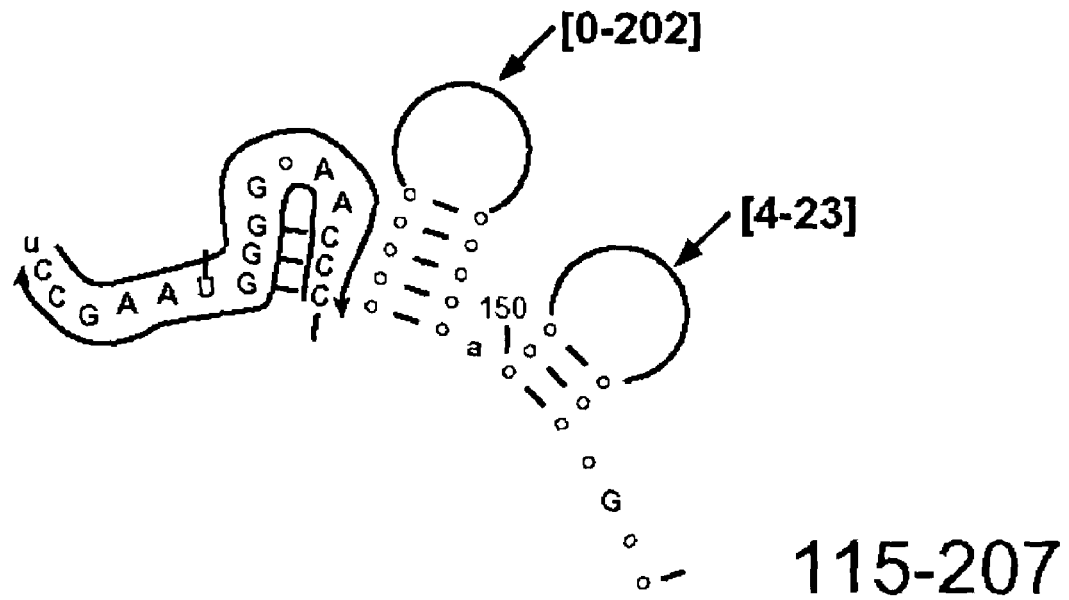
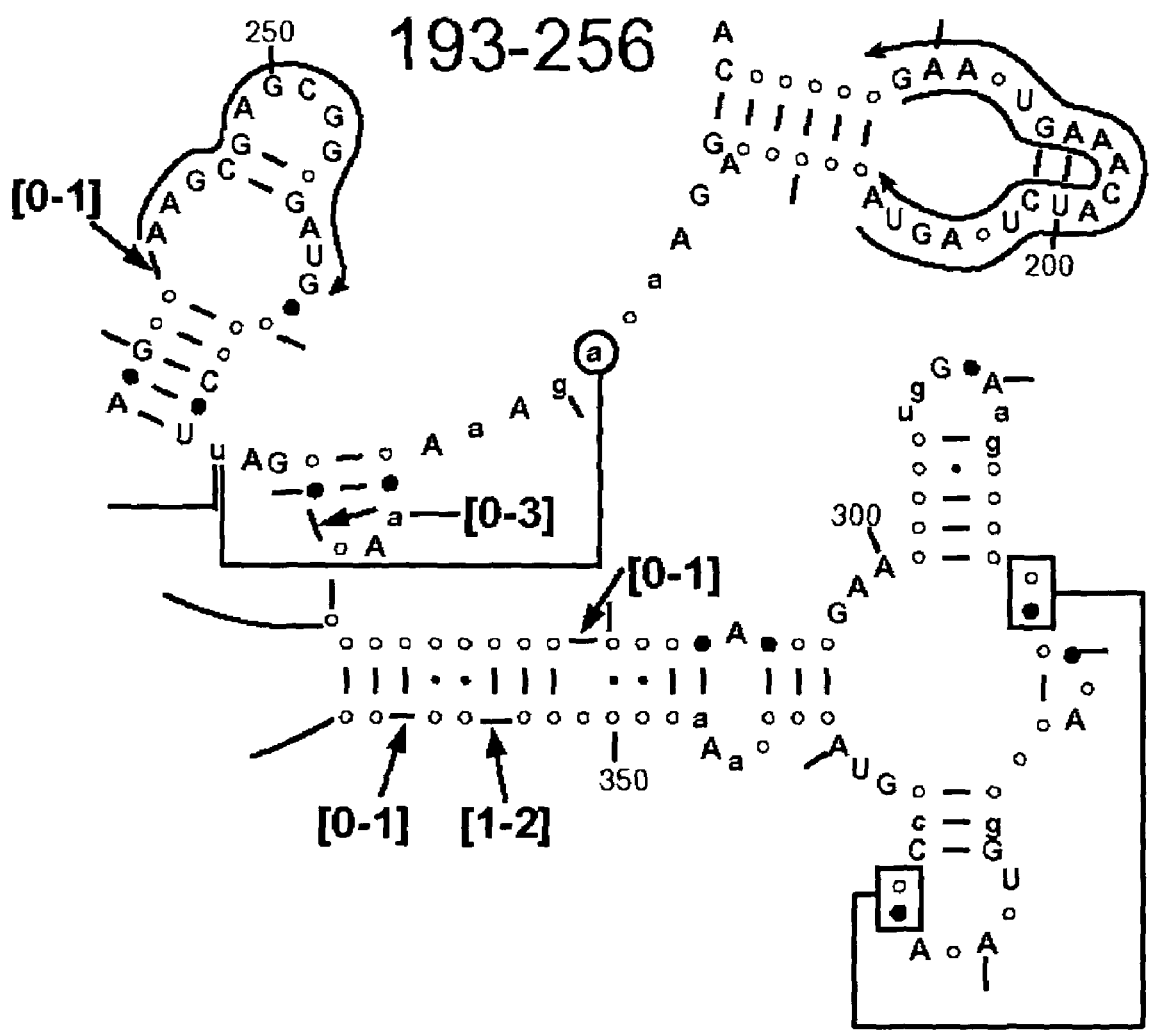

FIG. 5

B. anthracis ($A_{14}G_9C_{14}T_9$) $MW_{meas}$ = 14072.2)

B. anthracis* ($A_1A^*_{13}G_9C_{14}T_9$) $MW_{meas}$ = 14280.9)

13500    14000    14500
MW

Flavi RdRp 2453-2493

| | | |
|---|---|---|
| ▦ Dengue virus type | ☐ Japanese encephalitis virus | ▤ Tick-borne encephalitis virus |
| ☐ Dengue virus type | ■ Kunjin virus | ▦ West Nile virus |
| ■ Dengue virus type | ☐ Murray valley encephalitis virus | ☐ Yellow fever virus |

Figure 20B

MS Approach Succeeds Where Conventional Sequencing Fails

Sequences differ in length by one base in the 'C' stretch. Both variants appear in digest data. Sequencing profile also points to a length variation in this region: Example trace: 040803_81_A1_HV1-1_1560F_A11.AB1 (SEQ ID NO: 46)

Good sequence up to C stretch, then length variation causes double-read

Same thing with opposite read: 040803_83_A1_HV1-1_1561R_C11.AB1 (SEQ ID NO: 47)

MS detects multiple species simultaneously while sequencing requires pure sample for maximum information content Ratio of short to long alleles is 1:3

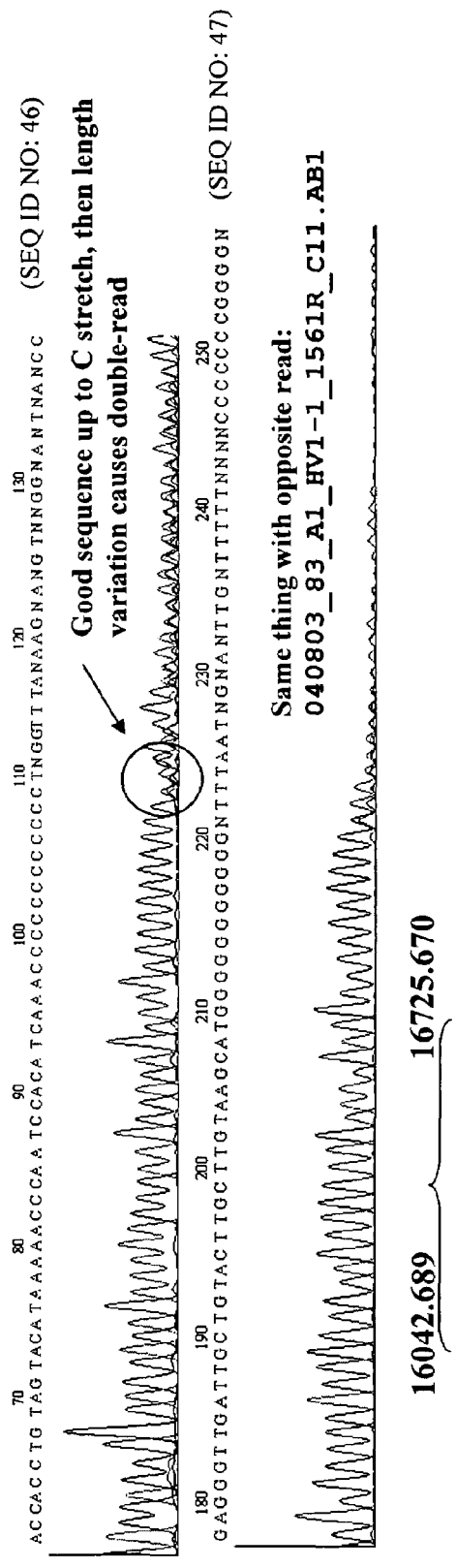
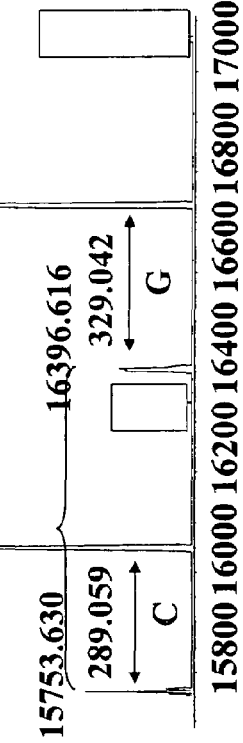

METHODS FOR RAPID FORENSIC ANALYSIS OF MITOCHONDRIAL DNA AND CHARACTERIZATION OF MITOCHONDRIAL DNA HETEROPLASMY

CROSS-REFERENCE TO RELATED APPLICATIONS

This application is a continuation-in-part of U.S. application Ser. No. 10/323,438 filed Dec. 18, 2002 now abandoned, which is incorporated herein by reference in its entirety. This application is also a continuation-in-part of U.S. application Ser. No. 09/798,007 filed Mar. 2, 2001 now abandoned, which is incorporated herein by reference in its entirety. This application also claims priority to U.S. provisional application Ser. No. 60/431,319 filed Dec. 6, 2002, which is incorporated herein by reference in its entirety.

STATEMENT OF GOVERNMENT SUPPORT

This invention was made with United States Government support under DARPA contract MDA-972-03C-0112. The United States Government has certain rights in the invention.

FIELD OF THE INVENTION

This invention relates to the field of mitochondrial DNA analysis. The invention enables the rapid and accurate identification of individuals and eukaryotic organisms by forensics methods as well as characterization of mitochondrial DNA heteroplasmy and prediction of onset of mitochondrial diseases.

BACKGROUND OF THE INVENTION

Mitochondrial DNA (mtDNA) is found in eukaryotes and differs from nuclear DNA in its location, its sequence, its quantity in the cell, and its mode of inheritance. The nucleus of the cell contains two sets of 23 chromosomes, one paternal set and one maternal set. However, cells may contain hundreds to thousands of mitochondria, each of which may contain several copies of mtDNA. Nuclear DNA has many more bases than mtDNA, but mtDNA is present in many more copies than nuclear DNA. This characteristic of mtDNA is useful in situations where the amount of DNA in a sample is very limited. Typical sources of DNA recovered from crime scenes include hair, bones, teeth, and body fluids such as saliva, semen, and blood.

In humans, mitochondrial DNA is inherited strictly from the mother (Case J. T. and Wallace, D. C., Somatic Cell Genetics, 1981, 7, 103-108; Giles, R. E. et al. Proc. Natl. Acad. Sci. 1980, 77, 6715-6719; Hutchison, C. A. et al. Nature, 1974, 251, 536-538). Thus, the mtDNA sequences obtained from maternally related individuals, such as a brother and a sister or a mother and a daughter, will exactly match each other in the absence of a mutation. This characteristic of mtDNA is advantageous in missing persons cases as reference mtDNA samples can be supplied by any maternal relative of the missing individual (Ginther, C. et al. Nature Genetics, 1992, 2, 135-138; Holland, M. M. et al. Journal of Forensic Sciences, 1993, 38, 542-553; Stoneking, M. et al. American Journal of Human Genetics, 1991, 48, 370-382).

The human mtDNA genome is approximately 16,569 bases in length and has two general regions: the coding region and the control region. The coding region is responsible for the production of various biological molecules involved in the process of energy production in the cell. The control region is responsible for regulation of the mtDNA molecule. Two regions of mtDNA within the control region have been found to be highly polymorphic, or variable, within the human population (Greenberg, B. D. et al. Gene, 1983, 21, 33-49). These two regions are termed "hypervariable Region I" (HVR1), which has an approximate length of 342 base pairs (bp), and "hypervariable Region II" (HVR2), which has an approximate length of 268 bp. Forensic mtDNA examinations are performed using these two regions because of the high degree of variability found among individuals.

Approximately 610 bp of mtDNA are currently sequenced in forensic mtDNA analysis. Recording and comparing mtDNA sequences would be difficult and potentially confusing if all of the bases were listed. Thus, mtDNA sequence information is recorded by listing only the differences with respect to a reference DNA sequence. By convention, human mtDNA sequences are described using the first complete published mtDNA sequence as a reference (Anderson, S. et al., Nature, 1981, 290, 457-465). This sequence is commonly referred to as the Anderson sequence. It is also called the Cambridge reference sequence or the Oxford sequence. Each base pair in this sequence is assigned a number. Deviations from this reference sequence are recorded as the number of the position demonstrating a difference and a letter designation of the different base. For example, a transition from A to G at Position 263 would be recorded as 263 G. If deletions or insertions of bases are present in the mtDNA, these differences are denoted as well.

In the United States, there are seven laboratories currently conducting forensic mtDNA examinations: the FBI Laboratory; Laboratory Corporation of America (LabCorp) in Research Triangle Park, North Carolina; Mitotyping Technologies in State College, Pa.; the Bode Technology Group (BTG) in Springfield, Va.; the Armed Forces DNA Identification Laboratory (AFDIL) in Rockville, Md.; BioSynthesis, Inc. in Lewisville, Tex.; and Reliagene in New Orleans, La.

Mitochondrial DNA analyses have been admitted in criminal proceedings from these laboratories in the following states as of April 1999: Alabama, Arkansas, Florida, Indiana, Illinois, Maryland, Michigan, New Mexico, North Carolina, Pennsylvania, South Carolina, Tennessee, Texas, and Washington. Mitochondrial DNA has also been admitted and used in criminal trials in Australia, the United Kingdom, and several other European countries.

Since 1996, the number of individuals performing mitochondrial DNA analysis at the FBI Laboratory has grown from 4 to 12, with more personnel expected in the near future. Over 150 mitochondrial DNA cases have been completed by the FBI Laboratory as of March 1999, and dozens more await analysis. Forensic courses are being taught by the FBI Laboratory personnel and other groups to educate forensic scientists in the procedures and interpretation of mtDNA sequencing. More and more individuals are learning about the value of mtDNA sequencing for obtaining useful information from evidentiary samples that are small, degraded, or both. Mitochondrial DNA sequencing is becoming known not only as an exclusionary tool but also as a complementary technique for use with other human identification procedures. Mitochondrial DNA analysis will continue to be a powerful tool for law enforcement officials in the years to come as other applications are developed, validated, and applied to forensic evidence.

Presently, the forensic analysis of mtDNA is rigorous and labor-intensive. Currently, only 1-2 cases per month per analyst can be performed. Several molecular biological techniques are combined to obtain a mtDNA sequence from a sample. The steps of the mtDNA analysis process include primary visual analysis, sample preparation, DNA extraction, polymerase chain reaction (PCR) amplification, postamplification quantification of the DNA, automated DNA sequencing, and data analysis. Another complicating factor in the forensic analysis of mtDNA is the occurrence of heteroplasmy wherein the pool of mtDNAs in a given cell is heterogeneous due to mutations in individual mtDNAs. There are two forms of heteroplasmy found in mtDNA. Sequence heteroplasmy (also known as point heteroplasmy) is the occurrence of more than one base at a particular position or positions in the mtDNA sequence. Length heteroplasmy is the occurrence of more than one length of a stretch of the same base in a mtDNA sequence as a result of insertion of nucleotide residues. Heteroplasmy is a problem for forensic investigators since a sample from a crime scene can differ from a sample from a suspect by one base pair and this difference may be interpreted as sufficient evidence to eliminate that individual as the suspect. Hair samples from a single individual can contain heteroplasmic mutations at vastly different concentrations and even the root and shaft of a single hair can differ. The detection methods currently available to molecular biologists cannot detect low levels of heteroplasmy. Furthermore, if present, length heteroplasmy will adversely affect sequencing runs by resulting in an out-of-frame sequence that cannot be interpreted.

Mass spectrometry provides detailed information about the molecules being analyzed, including high mass accuracy. It is also a process that can be easily automated. Low-resolution MS may be unreliable when used to detect some known agents, if their spectral lines are sufficiently weak or sufficiently close to those from other living organisms in the sample. DNA chips with specific probes can only determine the presence or absence of specifically anticipated organisms. Because there are hundreds of thousands of species of benign bacteria, some very similar in sequence to threat organisms, even arrays with 10,000 probes lack the breadth needed to detect a particular organism.

Antibodies face more severe diversity limitations than arrays. If antibodies are designed against highly conserved targets to increase diversity, the false alarm problem will dominate, again because threat organisms are very similar to benign ones. Antibodies are only capable of detecting known agents in relatively uncluttered environments.

Several groups have described detection of PCR products using high resolution electrospray ionization-Fourier transform-ion cyclotron resonance mass spectrometry (ESI-FT-ICR MS). Accurate measurement of exact mass combined with knowledge of the number of at least one nucleotide allowed calculation of the total base composition for PCR duplex products of approximately 100 base pairs. (Aaserud et al., *J. Am. Soc. Mass Spec.*, 1996, 7, 1266-1269; Muddiman et al., *Anal. Chem.*, 1997, 69, 1543-1549; Wunschel et al., *Anal. Chem.*, 1998, 70, 1203-1207; Muddiman et al., *Rev. Anal. Chem.*, 1998, 17, 1-68). Electrospray ionization-Fourier transform-ion cyclotron resistance (ESI-FT-ICR) MS may be used to determine the mass of double-stranded, 500 base-pair PCR products via the average molecular mass (Hurst et al., *Rapid Commun. Mass Spec.* 1996, 10, 377-382). The use of matrix-assisted laser desorption ionization-time of flight (MALDI-TOF) mass spectrometry for characterization of PCR products has been described. (Muddiman et al., *Rapid Commun. Mass Spec.*, 1999, 13, 1201-1204). However, the degradation of DNAs over about 75 nucleotides observed with MALDI limited the utility of this method.

U.S. Pat. No. 5,849,492 describes a method for retrieval of phylogenetically informative DNA sequences which comprise searching for a highly divergent segment of genomic DNA surrounded by two highly conserved segments, designing the universal primers for PCR amplification of the highly divergent region, amplifying the genomic DNA by PCR technique using universal primers, and then sequencing the gene to determine the identity of the organism.

U.S. Pat. No. 5,965,363 discloses methods for screening nucleic acids for polymorphisms by analyzing amplified target nucleic acids using mass spectrometric techniques and to procedures for improving mass resolution and mass accuracy of these methods.

WO 99/14375 describes methods, PCR primers and kits for use in analyzing preselected DNA tandem nucleotide repeat alleles by mass spectrometry.

WO 98/12355 discloses methods of determining the mass of a target nucleic acid by mass spectrometric analysis, by cleaving the target nucleic acid to reduce its length, making the target single-stranded and using MS to determine the mass of the single-stranded shortened target. Also disclosed are methods of preparing a double-stranded target nucleic acid for MS analysis comprising amplification of the target nucleic acid, binding one of the strands to a solid support, releasing the second strand and then releasing the first strand which is then analyzed by MS. Kits for target nucleic acid preparation are also provided.

PCT WO97/33000 discloses methods for detecting mutations in a target nucleic acid by nonrandomly fragmenting the target into a set of single-stranded nonrandom length fragments and determining their masses by MS.

U.S. Pat. No. 5,605,798 describes a fast and highly accurate mass spectrometer-based process for detecting the presence of a particular nucleic acid in a biological sample for diagnostic purposes.

WO 98/21066 describes processes for determining the sequence of a particular target nucleic acid by mass spectrometry. Processes for detecting a target nucleic acid present in a biological sample by PCR amplification and mass spectrometry detection are disclosed, as are methods for detecting a target nucleic acid in a sample by amplifying the target with primers that contain restriction sites and tags, extending and cleaving the amplified nucleic acid, and detecting the presence of extended product, wherein the presence of a DNA fragment of a mass different from wild-type is indicative of a mutation. Methods of sequencing a nucleic acid via mass spectrometry methods are also described.

WO 97/37041, WO 99/31278 and U.S. Pat. No. 5,547,835 describe methods of sequencing nucleic acids using mass spectrometry. U.S. Pat. Nos. 5,622,824, 5,872,003 and 5,691,141 describe methods, systems and kits for exonuclease-mediated mass spectrometric sequencing.

Thus, there is a need for a method for bioagent detection and identification which is both specific and rapid, and in which no nucleic acid sequencing is required. The present invention addresses this need.

SUMMARY OF THE INVENTION

The present invention is directed to methods of identifying an individual by obtaining mitochondrial DNA from the individual, amplifying the mitochondrial DNA with intelligent primers to obtain at least one amplification product, determining the molecular mass of the amplification product and comparing the molecular mass with a database of molecular masses calculated from known sequences of mitochondrial DNAs indexed to known individuals, wherein a match between said molecular mass of the amplification product and the calculated molecular mass of a known sequence in the database identifies the individual.

Furthermore, this present invention is directed to methods of determining the identity of protists or fungi by a process analogous to the process described above, and determining the geographic spread of fungi and protists by analysis of samples obtained from a plurality of geographic locations.

The present invention is also directed to methods of characterizing the heteroplasmy of a sample of mitochondrial DNA by amplifying the mitochondrial DNA with intelligent primers to obtain a plurality of amplification products, determining the molecular masses and relative abundances of the plurality of amplification products, thereby characterizing said heteroplasmy. Furthermore, the present invention is directed to using these methods to characterize the heteroplasmy of a plurality of samples of mitochondrial DNA taken from an individual at different points of the lifetime of said individual to investigate the rate of naturally occurring mutations in mitochondrial DNA. These methods can also be used to initiate a prediction of the rate of onset of mitochondrial disease.

BRIEF DESCRIPTION OF THE DRAWINGS

FIGS. 1A-1H and FIG. 2 are consensus diagrams that show examples of conserved regions from 16S rRNA (FIGS. 1A-1, 1A-2, 1A-3, 1A-4, and 1A-5), 23S rRNA (3'-half, FIGS. 1B, 1C, and 1D; 5'-half, FIGS. 1E-F), 23S rRNA Domain I (FIG. 1G), 23S rRNA Domain IV (FIG. 1H) and 16S rRNA Domain III (FIG. 2) which are suitable for use in the present invention. Lines with arrows are examples of regions to which intelligent primer pairs for PCR are designed. The label for each primer pair represents the starting and ending base number of the amplified region on the consensus diagram. Bases in capital letters are greater than 95% conserved; bases in lower case letters are 90-95% conserved, filled circles are 80-90% conserved; and open circles are less than 80% conserved. The label for each primer pair represents the starting and ending base number of the amplified region on the consensus diagram. The nucleotide sequence of the 16S rRNA consensus sequence is SEQ ID NO:3 and the nucleotide sequence of the 23S rRNA consensus sequence is SEQ ID NO:4.

FIG. 2 shows a typical primer amplified region from the 16S rRNA Domain III shown in FIG. 1A-1.

FIG. 5 shows the deconvoluted mass spectra of a *Bacillus anthracis* region with and without the mass tag phosphorothioate A (A*). The two spectra differ in that the measured molecular weight of the mass tag-containing sequence is greater than the unmodified sequence.

FIG. 20B indicates that, whereas sequencing fails to resolve the variants due to the length heteroplasmy, mass determination detects multiple species simultaneously and also indicates abundance ratios. In this case, the ratio of variant 1 (SEQ ID NO:46, top sequence) to variant 2 (SEQ ID NO:47)(short to long alleles) is 1:3.

DESCRIPTION OF EMBODIMENTS

A. Introduction

Figures 1, 1A:
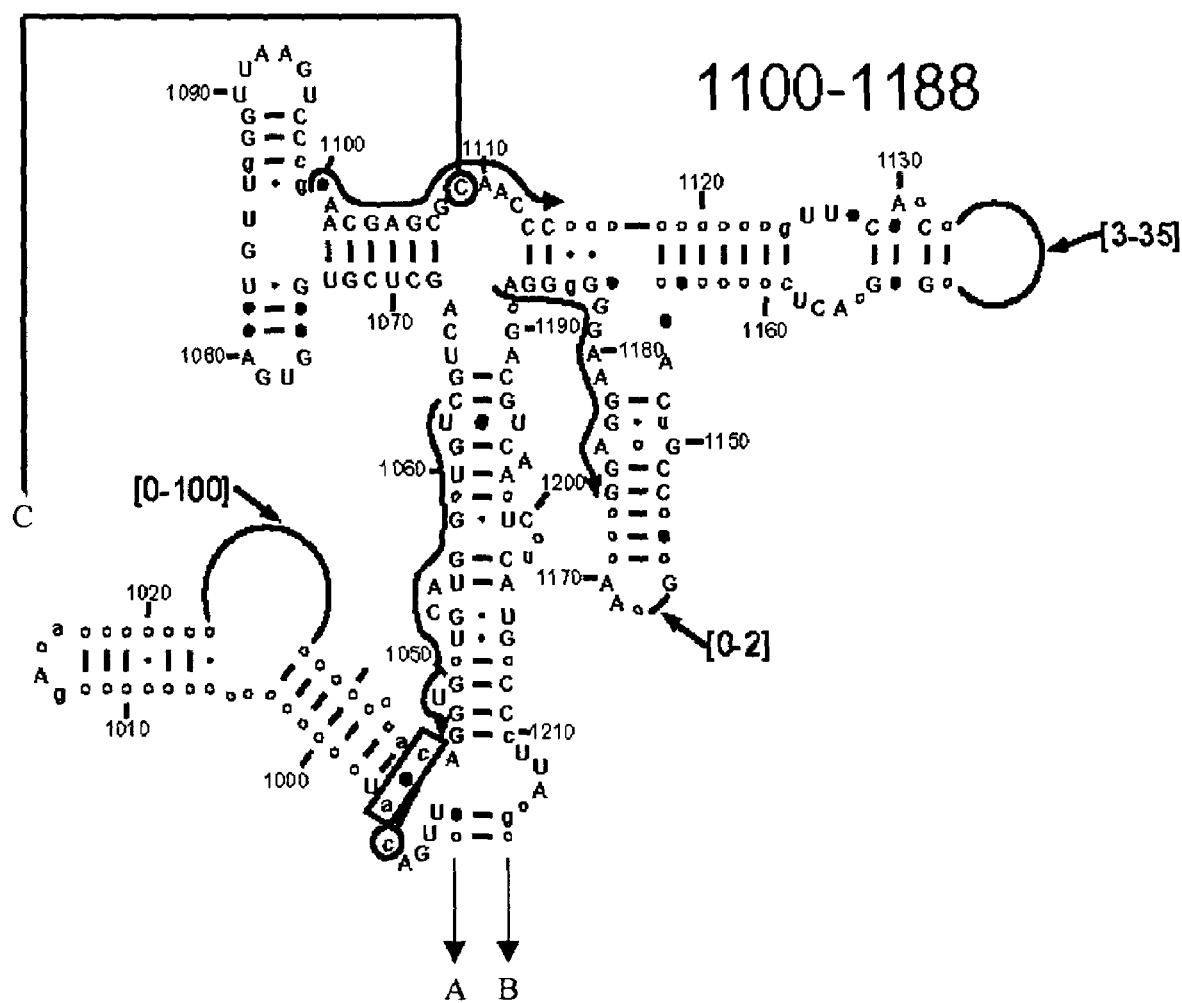
Figures 1, 1A, 2:
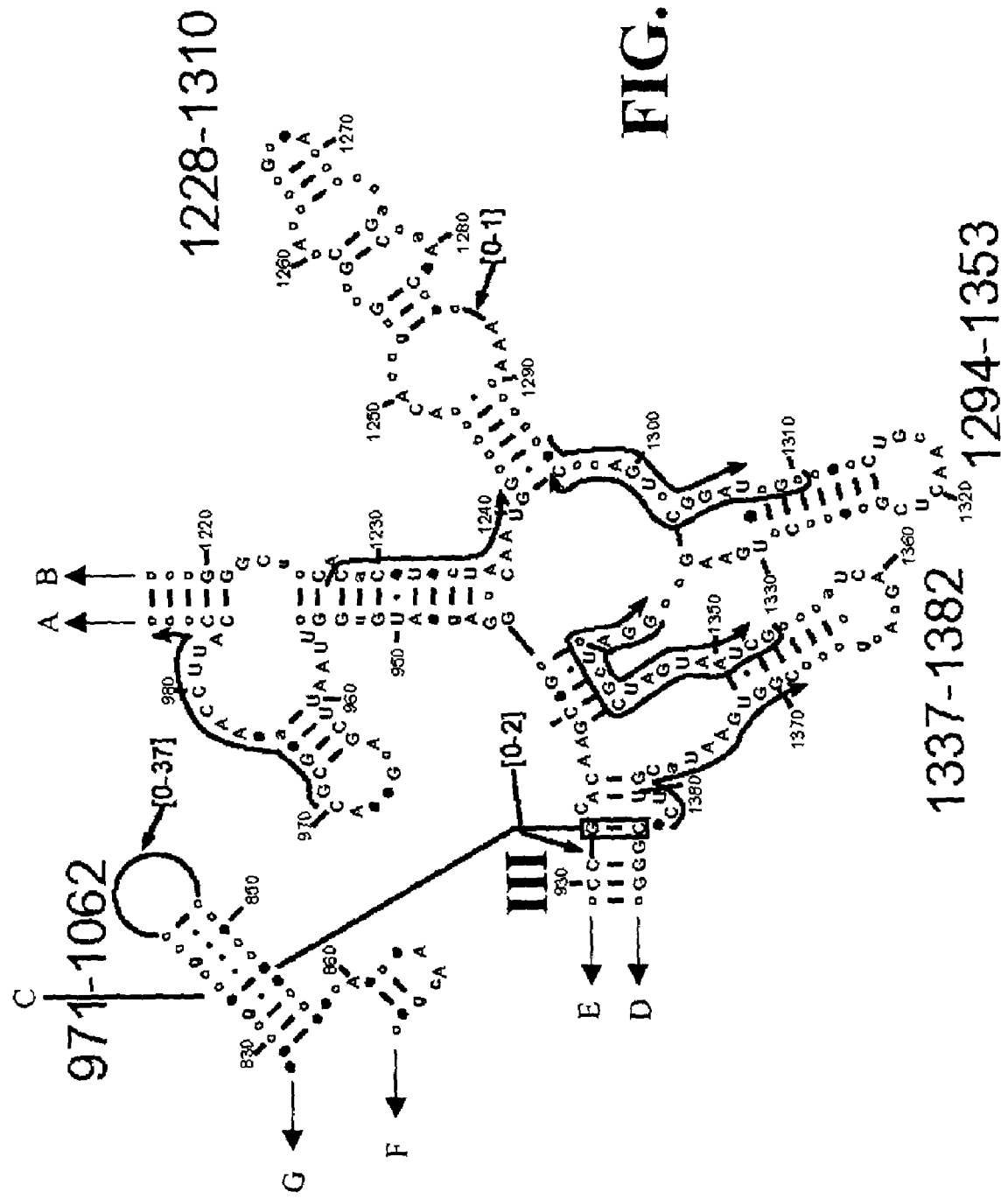
Figures 1, 1A, 2, 3:
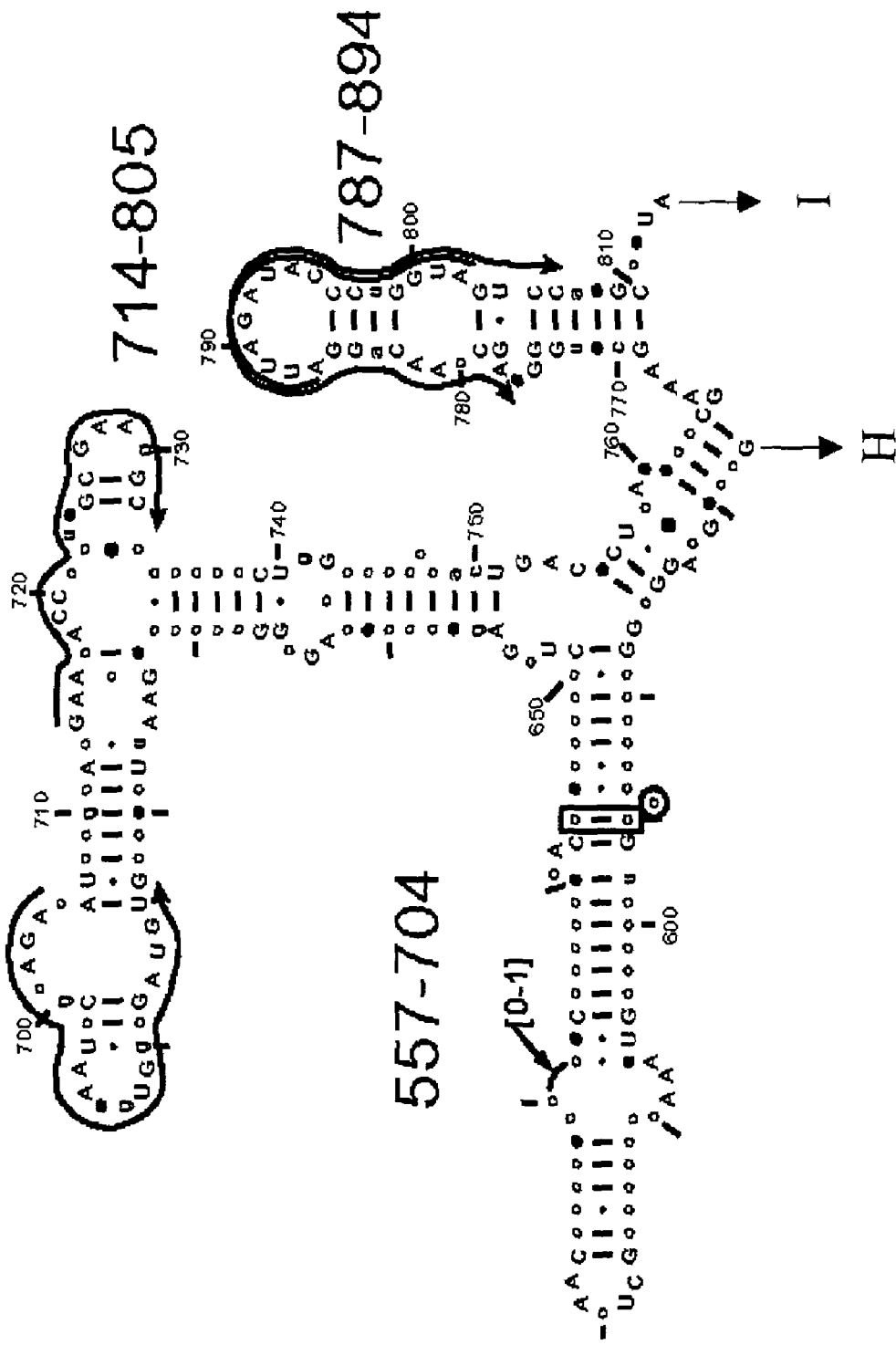

The present invention provides, inter alia, methods for detection and identification of bioagents in an unbiased manner using "bioagent identifying amplicons." "Intelligent primers" are selected to hybridize to conserved sequence regions of nucleic acids derived from a bioagent and which bracket variable sequence regions to yield a bioagent identifying amplicon which can be amplified and which is amenable to molecular mass determination. The molecular mass then provides a means to uniquely identify the bioagent without a requirement for prior knowledge of the possible identity of the bioagent. The molecular mass or corresponding "base composition signature" (BCS) of the amplification product is then matched against a database of molecular masses or base composition signatures. Furthermore, the method can be applied to rapid parallel "multiplex" analyses, the results of which can be employed in a triangulation identification strategy. The present method provides rapid throughput and does not require nucleic acid sequencing of the amplified target sequence for bioagent detection and identification.

B. Bioagents

In the context of this invention, a "bioagent" is any organism, cell, or virus, living or dead, or a nucleic acid derived from such an organism, cell or virus. Examples of bioagents include, but are not limited to, cells, including but not limited to, cells, including but not limited to human clinical samples, bacterial cells and other pathogens) viruses, fungi, and protists, parasites, and pathogenicity markers (including but not limited to: pathogenicity islands, antibiotic resistance genes, virulence factors, toxin genes and other bioregulating compounds). Samples may be alive or dead or in a vegetative state (for example, vegetative bacteria or spores) and may be encapsulated or bioengineered. In the context of this invention, a "pathogen" is a bioagent which causes a disease or disorder.

Despite enormous biological diversity, all forms of life on earth share sets of essential, common features in their genomes. Bacteria, for example have highly conserved sequences in a variety of locations on their genomes. Most notable is the universally conserved region of the ribosome but there are also conserved elements in other non-coding RNAs, including RNAse P and the signal recognition particle (SRP) among others. Bacteria have a common set of absolutely required genes. About 250 genes are present in all bacterial species (*Proc. Natl. Acad. Sci. U.S.A.*, 1996, 93, 10268; *Science*, 1995, 270, 397), including tiny genomes like Mycoplasma, Ureaplasma and Rickettsia. These genes encode proteins involved in translation, replication, recombination and repair, transcription, nucleotide metabolism, amino acid metabolism, lipid metabolism, energy generation, uptake, secretion and the like. Examples of these proteins are DNA polymerase III beta, elongation factor TU, heat shock protein groEL, RNA polymerase beta, phosphoglycerate kinase, NADH dehydrogenase, DNA ligase, DNA topoisomerase and elongation factor G. Operons can also be targeted using the present method. One example of an operon is the bfp operon from enteropathogenic *E. coli*. Multiple core chromosomal genes can be used to classify bacteria at a genus or genus species level to determine if an organism has threat potential. The methods can also be used to detect pathogenicity markers (plasmid or chromosomal) and antibiotic resistance genes to confirm the threat potential of an organism and to direct countermeasures.

C. Selection of "Bioagent Identifying Amplicons"

Since genetic data provide the underlying basis for identification of bioagents by the methods of the present invention, it is necessary to select segments of nucleic acids which ideally provide enough variability to distinguish each individual bioagent and whose molecular mass is amenable to molecular mass determination. In one embodiment of the present invention, at least one polynucleotide segment is amplified to facilitate detection and analysis in the process of identifying the bioagent. Thus, the nucleic acid segments which provide enough variability to distinguish each individual bioagent and whose molecular masses are amenable to molecular mass determination are herein described as "bioagent identifying amplicons." The term "amplicon" as used herein, refers to a segment of a polynucleotide which is amplified in an amplification reaction.

As used herein, "intelligent primers" are primers that are designed to bind to highly conserved sequence regions of a bioagent identifying amplicon that flank an intervening variable region and yield amplification products which ideally provide enough variability to distinguish each individual bioagent, and which are amenable to molecular mass analysis. By the term "highly conserved," it is meant that the sequence regions exhibit between about 80-100%, or between about 90-100%, or between about 95-100% identity. The molecular mass of a given amplification product provides a means of identifying the bioagent from which it was obtained, due to the variability of the variable region. Thus design of intelligent primers requires selection of a variable region with appropriate variability to resolve the identity of a given bioagent. Bioagent identifying amplicons are ideally specific to the identity of the bioagent. A plurality of bioagent identifying amplicons selected in parallel for distinct bioagents which contain the same conserved sequences for hybridization of the same pair of intelligent primers are herein defined as "correlative bioagent identifying amplicons."

In one embodiment, the bioagent identifying amplicon is a portion of a ribosomal RNA (rRNA) gene sequence. With the complete sequences of many of the smallest microbial genomes now available, it is possible to identify a set of genes that defines "minimal life" and identify composition signatures that uniquely identify each gene and organism. Genes that encode core life functions such as DNA replication, transcription, ribosome structure, translation, and transport are distributed broadly in the bacterial genome and are suitable regions for selection of bioagent identifying amplicons. Ribosomal RNA (rRNA) genes comprise regions that provide useful base composition signatures. Like many genes involved in core life functions, rRNA genes contain sequences that are extraordinarily conserved across bacterial domains interspersed with regions of high variability that are more specific to each species. The variable regions can be utilized to build a database of base composition signatures. The strategy involves creating a structure-based alignment of sequences of the small (16S) and the large (23S) subunits of the rRNA genes. For example, there are currently over 13,000 sequences in the ribosomal RNA database that has been created and maintained by Robin Gutell, University of Texas at Austin, and is publicly available on the Institute for Cellular and Molecular Biology web page on the world wide web of the Internet at, for example, "rna.icmb.utexas.edu" There is also a publicly available rRNA database created and maintained by the University of Antwerp, Belgium on the world wide web of the Internet at, for example, "rrna.uia.ac.be."

These databases have been analyzed to determine regions that are useful as bioagent identifying amplicons. The characteristics of such regions include: a) between about 80 and 100%, or greater than about 95% identity among species of the particular bioagent of interest, of upstream and downstream nucleotide sequences which serve as sequence amplification primer sites; b) an intervening variable region which exhibits no greater than about 5% identity among species; and c) a separation of between about 30 and 1000 nucleotides, or no more than about 50-250 nucleotides, or no more than about 60-100 nucleotides, between the conserved regions.

As a non-limiting example, for identification of *Bacillus* species, the conserved sequence regions of the chosen bioagent identifying amplicon must be highly conserved among all *Bacillus* species while the variable region of the bioagent identifying amplicon is sufficiently variable such that the molecular masses of the amplification products of all species of *Bacillus* are distinguishable.

Bioagent identifying amplicons amenable to molecular mass determination are either of a length, size or mass compatible with the particular mode of molecular mass determination or compatible with a means of providing a predictable fragmentation pattern in order to obtain predictable fragments of a length compatible with the particular mode of molecular mass determination. Such means of providing a predictable fragmentation pattern of an amplification product include, but are not limited to, cleavage with restriction enzymes or cleavage primers, for example.

Identification of bioagents can be accomplished at different levels using intelligent primers suited to resolution of each individual level of identification. "Broad range survey" intelligent primers are designed with the objective of identifying a bioagent as a member of a particular division of bioagents. A "bioagent division" is defined as group of bioagents above the species level and includes but is not limited to: orders, families, classes, clades, genera or other such groupings of bioagents above the species level. As a non-limiting example, members of the *Bacillus/Clostridia* group or gamma-proteobacteria group may be identified as such by employing broad range survey intelligent primers such as primers which target 16S or 23S ribosomal RNA.

In some embodiments, broad range survey intelligent primers are capable of identification of bioagents at the species level. One main advantage of the detection methods of the present invention is that the broad range survey intelligent primers need not be specific for a particular bacterial species, or even genus, such as *Bacillus* or *Streptomyces*. Instead, the primers recognize highly conserved regions across hundreds of bacterial species including, but not limited to, the species described herein. Thus, the same broad range survey intelligent primer pair can be used to identify any desired bacterium because it will bind to the conserved regions that flank a variable region specific to a single species, or common to several bacterial species, allowing unbiased nucleic acid amplification of the intervening sequence and determination of its molecular weight and base composition. For example, the 16S_971-1062, 16S_1228-1310 and 16S_1100-1188 regions are 98-99% conserved in about 900 species of bacteria (16S≠16S rRNA, numbers indicate nucleotide position). In one embodiment of the present invention, primers used in the present method bind to one or more of these regions or portions thereof.

Due to their overall conservation, the flanking rRNA primer sequences serve as good intelligent primer binding sites to amplify the nucleic acid region of interest for most, if not all, bacterial species. The intervening region between the sets of primers varies in length and/or composition, and thus provides a unique base composition signature. Examples of intelligent primers that amplify regions of the 16S and 23S rRNA are shown in FIGS. 1A-1H. A typical primer amplified region in 16S rRNA is shown in FIG. 2. The arrows represent primers that bind to highly conserved regions which flank a variable region in 16S rRNA domain II. The amplified region is the stem-loop structure under "1100-1188." It is advantageous to design the broad range survey intelligent primers to minimize the number of primers required for the analysis, and to allow detection of multiple members of a bioagent division using a single pair of primers. The advantage of using broad range survey intelligent primers is that once a bioagent is broadly identified, the process of further identification at species and sub-species levels is facilitated by directing the choice of additional intelligent primers.

"Division-wide" intelligent primers are designed with an objective of identifying a bioagent at the species level. As a non-limiting example, a *Bacillus anthracis, Bacillus cereus* and *Bacillus thuringiensis* can be distinguished from each other using division-wide intelligent primers. Division-wide intelligent primers are not always required for identification at the species level because broad range survey intelligent primers may provide sufficient identification resolution to accomplishing this identification objective.

"Drill-down" intelligent primers are designed with an objective of identifying a sub-species characteristic of a bioagent. A "sub-species characteristic" is defined as a property imparted to a bioagent at the sub-species level of identification as a result of the presence or absence of a particular segment of nucleic acid. Such sub-species characteristics include, but are not limited to, strains, sub-types, pathogenicity markers such as antibiotic resistance genes, pathogenicity islands, toxin genes and virulence factors. Identification of such sub-species characteristics is often critical for determining proper clinical treatment of pathogen infections.

Chemical Modifications of Intelligent Primers

Ideally, intelligent primer hybridization sites are highly conserved in order to facilitate the hybridization of the primer. In cases where primer hybridization is less efficient due to lower levels of conservation of sequence, intelligent primers can be chemically modified to improve the efficiency of hybridization.

For example, because any variation (due to codon wobble in the $3^{rd}$ position) in these conserved regions among species is likely to occur in the third position of a DNA triplet, oligonucleotide primers can be designed such that the nucleotide corresponding to this position is a base which can bind to more than one nucleotide, referred to herein as a "universal base." For example, under this "wobble" pairing, inosine (I) binds to U, C or A; guanine (G) binds to U or C, and uridine (U) binds to U or C. Other examples of universal bases include nitroindoles such as 5-nitroindole or 3-nitropyrrole (Loakes et al., *Nucleosides and Nucleotides,* 1995, 14, 1001-1003), the degenerate nucleotides dP or dK (Hill et al.), an acyclic nucleoside analog containing 5-nitroindazole (Van Aerschot et al., *Nucleosides and Nucleotides,* 1995, 14, 1053-1056) or the purine analog 1-(2-deoxy-β-D-ribofuranosyl)-imidazole-4-carboxamide (Sala et al., *Nucl. Acids Res.,* 1996, 24, 3302-3306).

In another embodiment of the invention, to compensate for the somewhat weaker binding by the "wobble" base, the oligonucleotide primers are designed such that the first and second positions of each triplet are occupied by nucleotide analogs which bind with greater affinity than the unmodified nucleotide. Examples of these analogs include, but are not limited to, 2,6-diaminopurine which binds to thymine, propyne T which binds to adenine and propyne C and phenoxazines, including G-clamp, which binds to G. Propynylated pyrimidines are described in U.S. Pat. Nos. 5,645,985, 5,830,653 and 5,484,908, each of which is commonly owned and incorporated herein by reference in its entirety. Propynylated primers are claimed in U.S. Ser. No. 10/294,203 which is also commonly owned and incorporated herein by reference in entirety. Phenoxazines are described in U.S. Pat. Nos. 5,502,177, 5,763,588, and 6,005,096, each of which is incorporated herein by reference in its entirety. G-clamps are described in U.S. Pat. Nos. 6,007,992 and 6,028,183, each of which is incorporated herein by reference in its entirety.

D. Characterization of Bioagent Identifying Amplicons

A theoretically ideal bioagent detector would identify, quantify, and report the complete nucleic acid sequence of every bioagent that reached the sensor. The complete sequence of the nucleic acid component of a pathogen would provide all relevant information about the threat, including its identity and the presence of drug-resistance or pathogenicity markers. This ideal has not yet been achieved. However, the present invention provides a straightforward strategy for obtaining information with the same practical value based on analysis of bioagent identifying amplicons by molecular mass determination.

In some cases, a molecular mass of a given bioagent identifying amplicon alone does not provide enough resolution to unambiguously identify a given bioagent. For example, the molecular mass of the bioagent identifying amplicon obtained using the intelligent primer pair "16S_971" would be 55622 Da for both *E. coli* and *Salmonella typhimurium*. However, if additional intelligent primers are employed to analyze additional bioagent identifying amplicons, a "triangulation identification" process is enabled. For example, the "16S_1100" intelligent primer pair yields molecular masses of 55009 and 55005 Da for *E. coli* and *Salmonella typhimurium*, respectively. Furthermore, the "23S_855" intelligent primer pair yields molecular masses of 42656 and 42698 Da for *E. coli* and *Salmonella typhimurium*, respectively. In this basic example, the second and third intelligent primer pairs provided the additional "fingerprinting" capability or resolution to distinguish between the two bioagents.

In another embodiment, the triangulation identification process is pursued by measuring signals from a plurality of bioagent identifying amplicons selected within multiple core genes. This process is used to reduce false negative and false positive signals, and enable reconstruction of the origin of hybrid or otherwise engineered bioagents. In this process, after identification of multiple core genes, alignments are created from nucleic acid sequence databases. The alignments are then analyzed for regions of conservation and variation, and bioagent identifying amplicons are selected to distinguish bioagents based on specific genomic differences. For example, identification of the three part toxin genes typical of *B. anthracis* (Bowen et al., *J. Appl. Microbiol.*, 1999, 87, 270-278) in the absence of the expected signatures from the *B. anthracis* genome would suggest a genetic engineering event.

The triangulation identification process can be pursued by characterization of bioagent identifying amplicons in a massively parallel fashion using the polymerase chain reaction (PCR), such as multiplex PCR, and mass spectrometric (MS) methods. Sufficient quantities of nucleic acids should be present for detection of bioagents by MS. A wide variety of techniques for preparing large amounts of purified nucleic acids or fragments thereof are well known to those of skill in the art. PCR requires one or more pairs of oligonucleotide primers that bind to regions which flank the target sequence(s) to be amplified. These primers prime synthesis of a different strand of DNA, with synthesis occurring in the direction of one primer towards the other primer. The primers, DNA to be amplified, a thermostable DNA polymerase (e.g. Taq polymerase), the four deoxynucleotide triphosphates, and a buffer are combined to initiate DNA synthesis. The solution is denatured by heating, then cooled to allow annealing of newly added primer, followed by another round of DNA synthesis. This process is typically repeated for about 30 cycles, resulting in amplification of the target sequence.

Although the use of PCR is suitable, other nucleic acid amplification techniques may also be used, including ligase chain reaction (LCR) and strand displacement amplification (SDA). The high-resolution MS technique allows separation of bioagent spectral lines from background spectral lines in highly cluttered environments.

In another embodiment, the detection scheme for the PCR products generated from the bioagent(s) incorporates at least three features. First, the technique simultaneously detects and differentiates multiple (generally about 6-10) PCR products. Second, the technique provides a molecular mass that uniquely identifies the bioagent from the possible primer sites. Finally, the detection technique is rapid, allowing multiple PCR reactions to be run in parallel.

E. Mass Spectrometric Characterization of Bioagent Identifying Amplicons

Mass spectrometry (MS)-based detection of PCR products provides a means for determination of BCS which has several advantages. MS is intrinsically a parallel detection scheme without the need for radioactive or fluorescent labels, since every amplification product is identified by its molecular mass. The current state of the art in mass spectrometry is such that less than femtomole quantities of material can be readily analyzed to afford information about the molecular contents of the sample. An accurate assessment of the molecular mass of the material can be quickly obtained, irrespective of whether the molecular weight of the sample is several hundred, or in excess of one hundred thousand atomic mass units (amu) or Daltons. Intact molecular ions can be generated from amplification products using one of a variety of ionization techniques to convert the sample to gas phase. These ionization methods include, but are not limited to, electrospray ionization (ES), matrix-assisted laser desorption ionization (MALDI) and fast atom bombardment (FAB). For example, MALDI of nucleic acids, along with examples of matrices for use in MALDI of nucleic acids, are described in WO 98/54751 (Genetrace, Inc.).

In some embodiments, large DNAs and RNAs, or large amplification products therefrom, can be digested with restriction endonucleases prior to ionization. Thus, for example, an amplification product that was 10 kDa could be digested with a series of restriction endonucleases to produce a panel of, for example, 100 Da fragments. Restriction endonucleases and their sites of action are well known to the skilled artisan. In this manner, mass spectrometry can be performed for the purposes of restriction mapping.

Upon ionization, several peaks are observed from one sample due to the formation of ions with different charges. Averaging the multiple readings of molecular mass obtained from a single mass spectrum affords an estimate of molecular mass of the bioagent. Electrospray ionization mass spectrometry (ESI-MS) is particularly useful for very high molecular weight polymers such as proteins and nucleic acids having molecular weights greater than 10 kDa, since it yields a distribution of multiply-charged molecules of the sample without causing a significant amount of fragmentation.

The mass detectors used in the methods of the present invention include, but are not limited to, Fourier transform ion cyclotron resonance mass spectrometry (FT-ICR-MS), ion trap, quadrupole, magnetic sector, time of flight (TOF), Q-TOF, and triple quadrupole.

In general, the mass spectrometric techniques which can be used in the present invention include, but are not limited to, tandem mass spectrometry, infrared multiphoton dissociation and pyrolytic gas chromatography mass spectrometry (PGC-MS). In one embodiment of the invention, the bioagent detection system operates continually in bioagent detection mode using pyrolytic GC-MS without PCR for rapid detection of increases in biomass (for example, increases in fecal contamination of drinking water or of germ warfare agents). To achieve minimal latency, a continuous sample stream flows directly into the PGC-MS combustion chamber. When an increase in biomass is detected, a PCR process is automatically initiated. Bioagent presence produces elevated levels of large molecular fragments from, for example, about 100-7,000 Da which are observed in the PGC-MS spectrum. The observed mass spectrum is compared to a threshold level and when levels of biomass are determined to exceed a predetermined threshold, the bioagent classification process described hereinabove (combining PCR and MS, such as FT-ICR MS) is initiated. Optionally, alarms or other processes (halting ventilation flow, physical isolation) are also initiated by this detected biomass level.

The accurate measurement of molecular mass for large DNAs is limited by the adduction of cations from the PCR reaction to each strand, resolution of the isotopic peaks from natural abundance $^{13}C$ and $^{15}N$ isotopes, and assignment of the charge state for any ion. The cations are removed by in-line dialysis using a flow-through chip that brings the solution containing the PCR products into contact with a solution containing ammonium acetate in the presence of an electric field gradient orthogonal to the flow. The latter two problems are addressed by operating with a resolving power of >100,000 and by incorporating isotopically depleted nucleotide triphosphates into the DNA. The resolving power of the instrument is also a consideration. At a resolving power of 10,000, the modeled signal from the $[M-14H+]^{14-}$ charge state of an 84mer PCR product is poorly characterized and assignment of the charge state or exact mass is impossible. At a resolving power of 33,000, the peaks from the individual isotopic components are visible. At a resolving power of 100,000, the isotopic peaks are resolved to the baseline and assignment of the charge state for the ion is straightforward. The $[^{13}C, ^{15}N]$-depleted triphosphates are obtained, for example, by growing microorganisms on depleted media and harvesting the nucleotides (Batey et al., *Nucl. Acids Res.*, 1992, 20, 4515-4523).

While mass measurements of intact nucleic acid regions are believed to be adequate to determine most bioagents, tandem mass spectrometry (MS") techniques may provide more definitive information pertaining to molecular identity or sequence. Tandem MS involves the coupled use of two or more stages of mass analysis where both the separation and detection steps are based on mass spectrometry. The first stage is used to select an ion or component of a sample from which further structural information is to be obtained. The selected ion is then fragmented using, e.g., blackbody irradiation, infrared multiphoton dissociation, or collisional activation. For example, ions generated by electrospray ionization (ESI) can be fragmented using IR multiphoton dissociation. This activation leads to dissociation of glycosidic bonds and the phosphate backbone, producing two series of fragment ions, called the w-series (having an intact 3' terminus and a 5' phosphate following internal cleavage) and the a-Base series (having an intact 5' terminus and a 3' furan).

The second stage of mass analysis is then used to detect and measure the mass of these resulting fragments of product ions. Such ion selection followed by fragmentation routines can be performed multiple times so as to essentially completely dissect the molecular sequence of a sample.

If there are two or more targets of similar molecular mass, or if a single amplification reaction results in a product which has the same mass as two or more bioagent reference standards, they can be distinguished by using mass-modifying "tags." In this embodiment of the invention, a nucleotide analog or "tag" is incorporated during amplification (e.g., a 5-(trifluoromethyl) deoxythymidine triphosphate) which has a different molecular weight than the unmodified base so as to improve distinction of masses. Such tags are described in, for example, PCT WO97/33000, which is incorporated herein by reference in its entirety. This further limits the number of possible base compositions consistent with any mass. For example, 5-(trifluoromethyl)deoxythymidine triphosphate can be used in place of dTTP in a separate nucleic acid amplification reaction. Measurement of the mass shift between a conventional amplification product and the tagged product is used to quantitate the number of thymidine nucleotides in each of the single strands. Because the strands are complementary, the number of adenosine nucleotides in each strand is also determined.

Figures 1, 1A, 2, 3, 4:
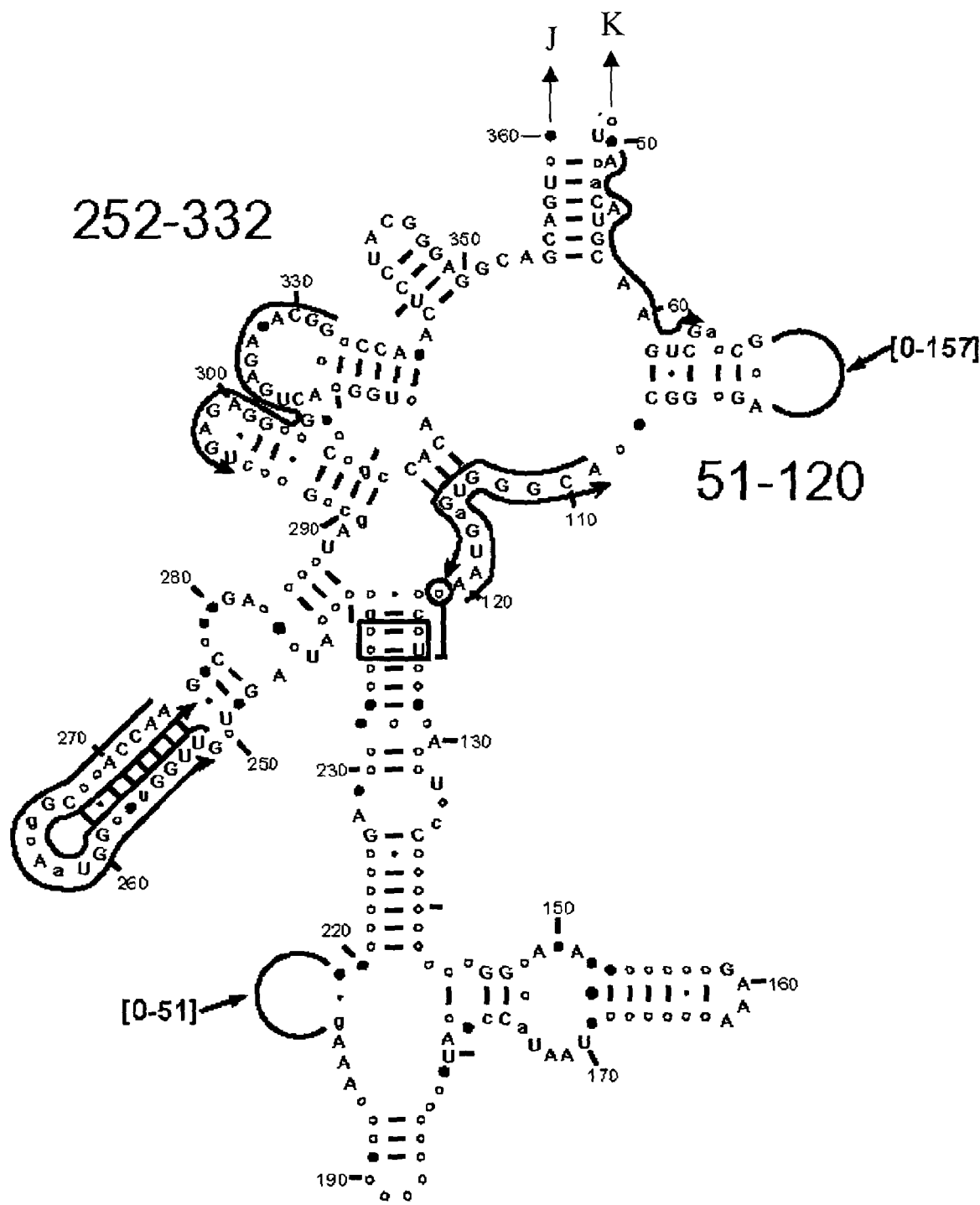

In another amplification reaction, the number of G and C residues in each strand is determined using, for example, the cytidine analog 5-methylcytosine (5-meC) or propyne C. The combination of the A/T reaction and G/C reaction, followed by molecular weight determination, provides a unique base composition. This method is summarized in FIG. 4 and Table 1.

TABLE 1

| Mass tag | Double strand sequence | Single strand Sequence | Total mass this strand | Base info this strand | Base info other strand | Total base comp. Top strand | Total base comp. Bottom strand |
|---|---|---|---|---|---|---|---|
| T*mass (T* − T) = x | T*ACGT*ACGT* AT*GCAT*GCA | T*ACGT*ACGT* | 3x | 3T | 3A | 3T 2A 2C 2G | 3A 2T 2G 2C |
| | | AT*GCAT*GCA | 2x | 2T | 2A | | |

TABLE 1-continued

| Mass tag | Double strand sequence | Single strand Sequence | Total mass this strand | Base info this strand | Base info other strand | Total base comp. Top strand | Total base comp. Bottom strand |
|---|---|---|---|---|---|---|---|
| C*mass (C* − C) = y | TAC*GTAC*GT ATGC*ATGC*A | TAC*GTAC*GT | 2x | 2C | 2G | | |
| | | ATGC*ATGC*A | 2x | 2C | 2G | | |

Figures 1, 1A, 2, 3, 4, 5:
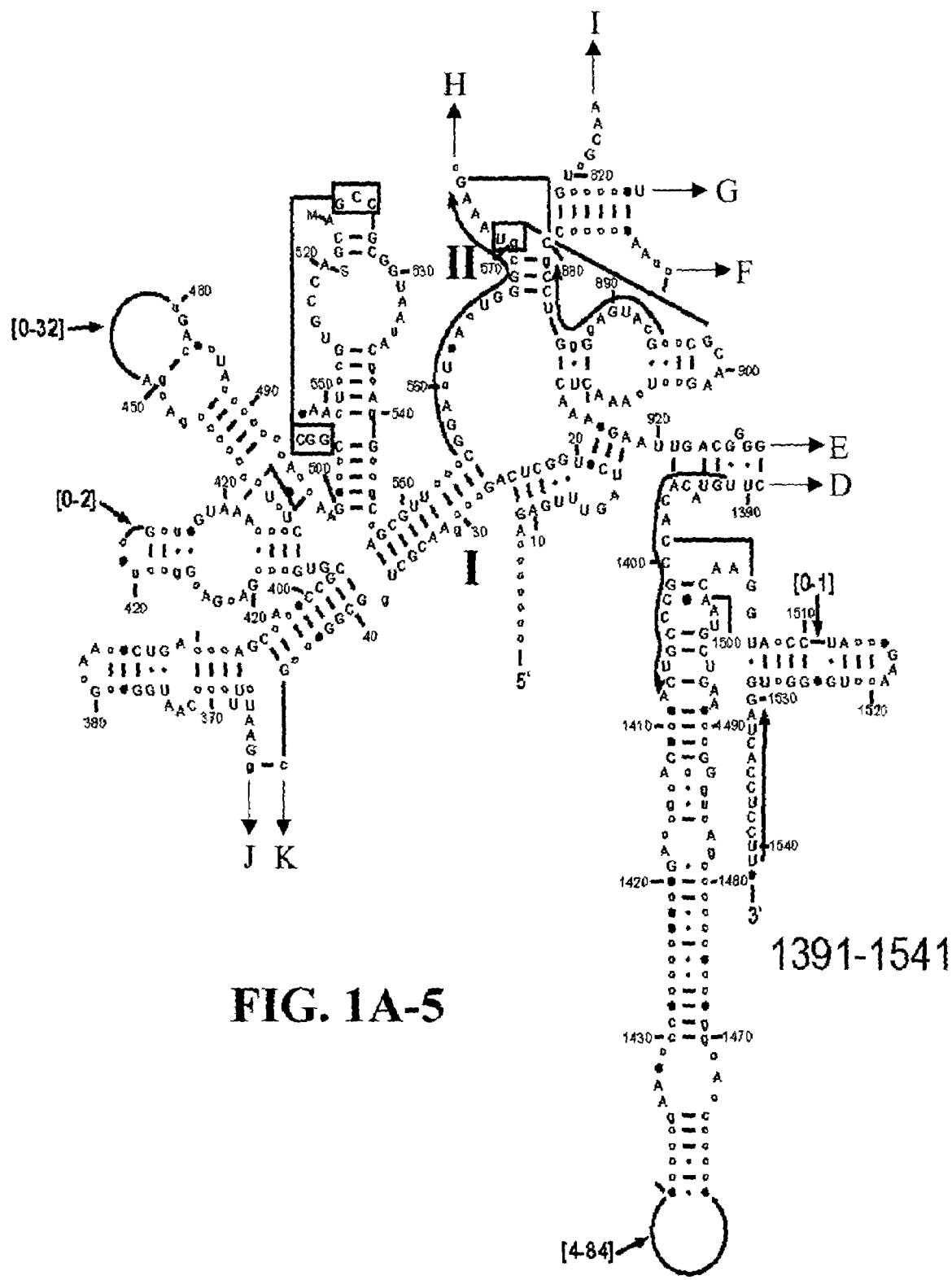
Figure 1B:
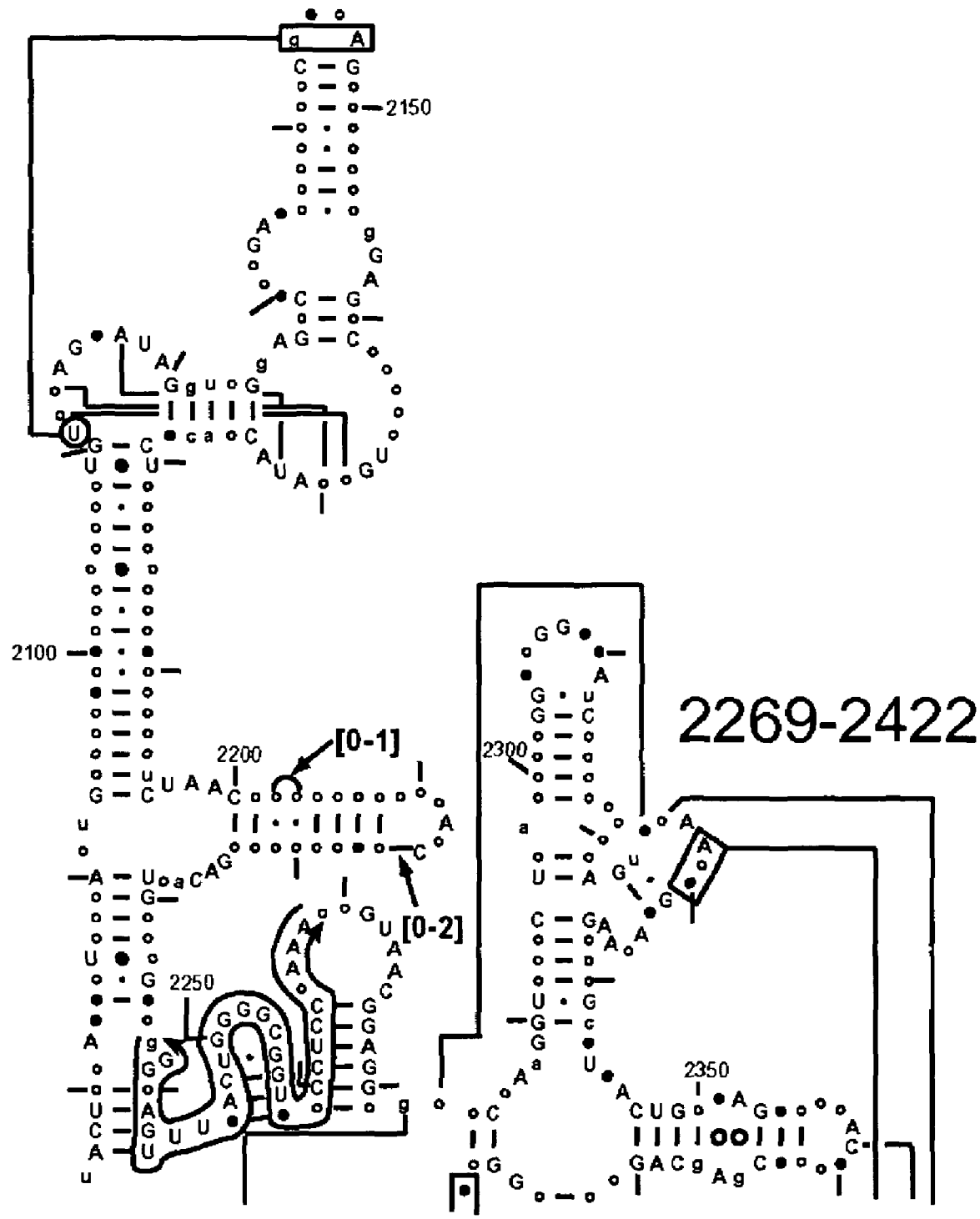
Figure 1C:
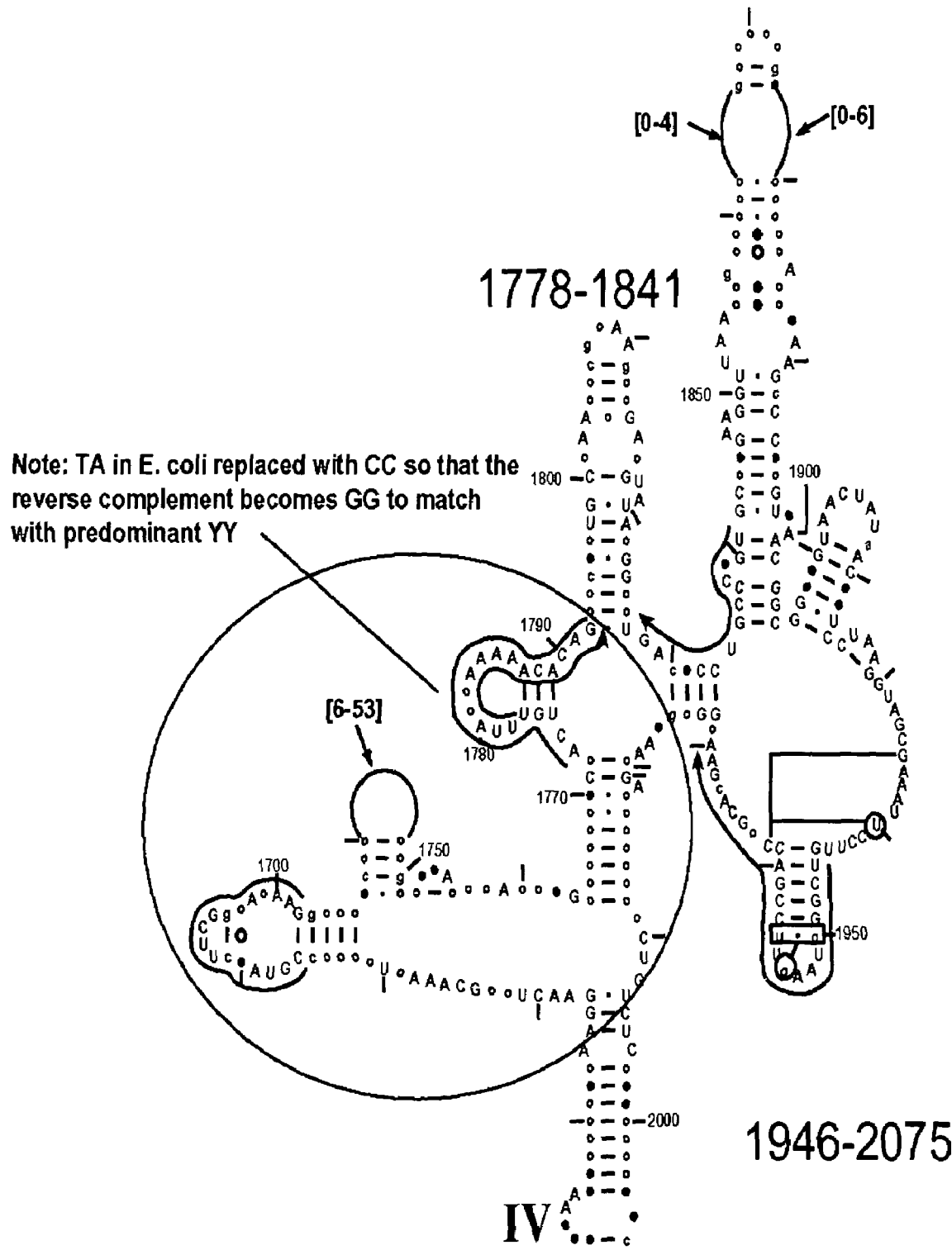
Figure 1D:
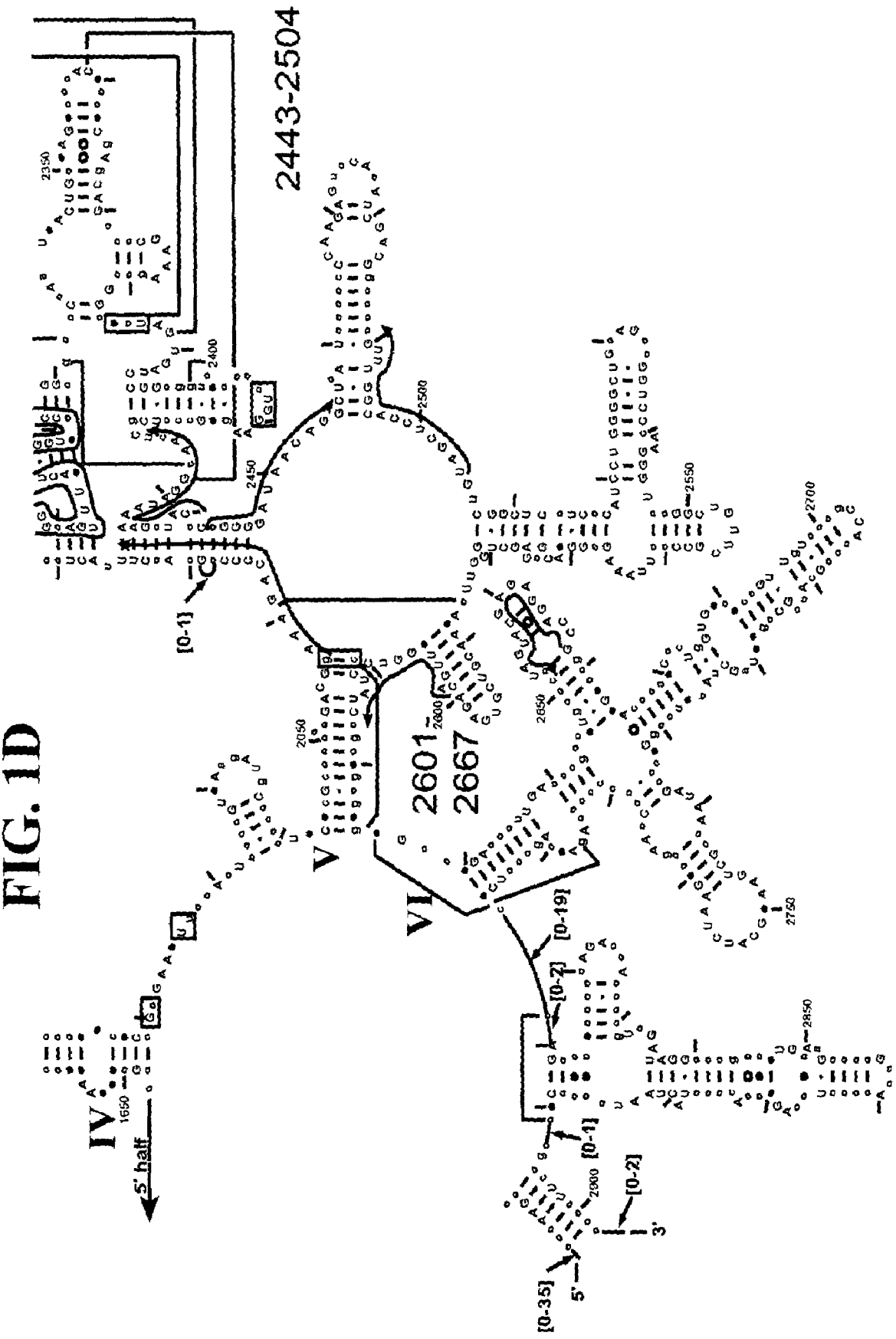
Figure 1E:
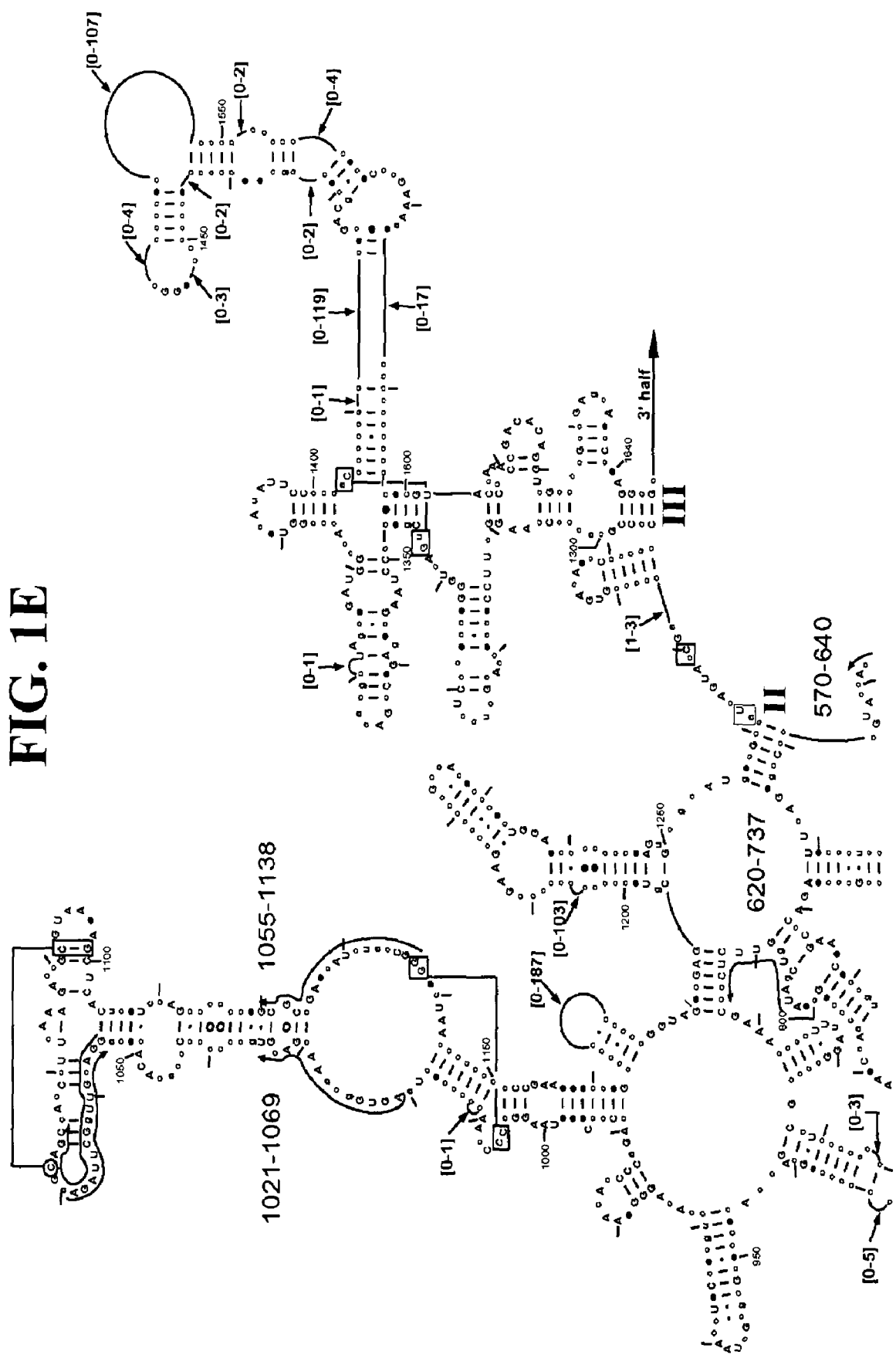
Figure 1F:
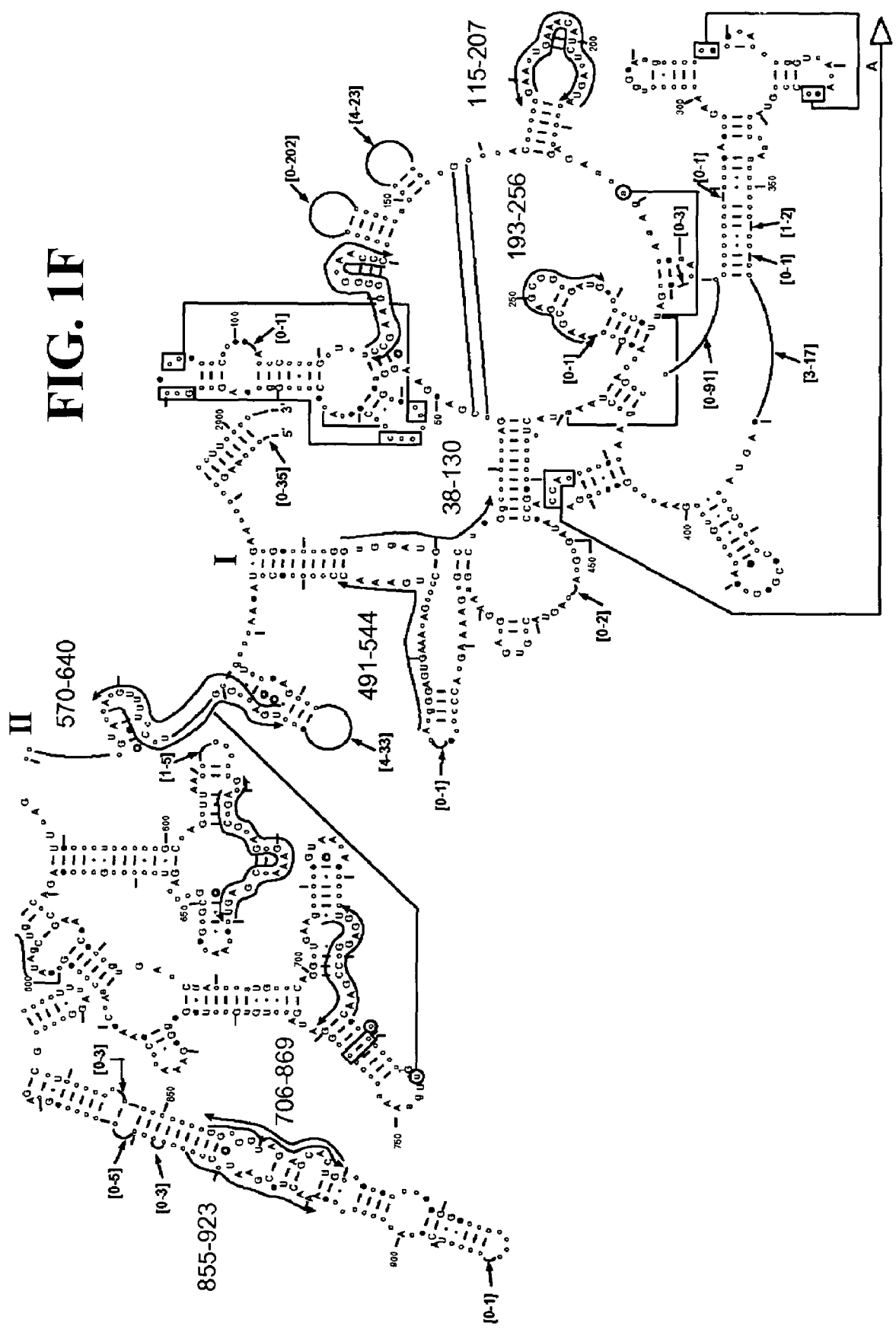
Figure 1H:
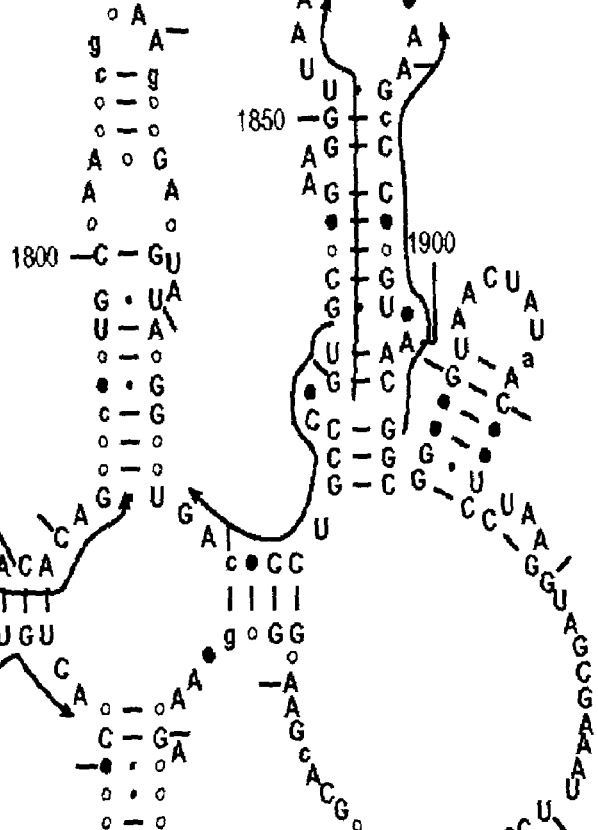
Figure 2:
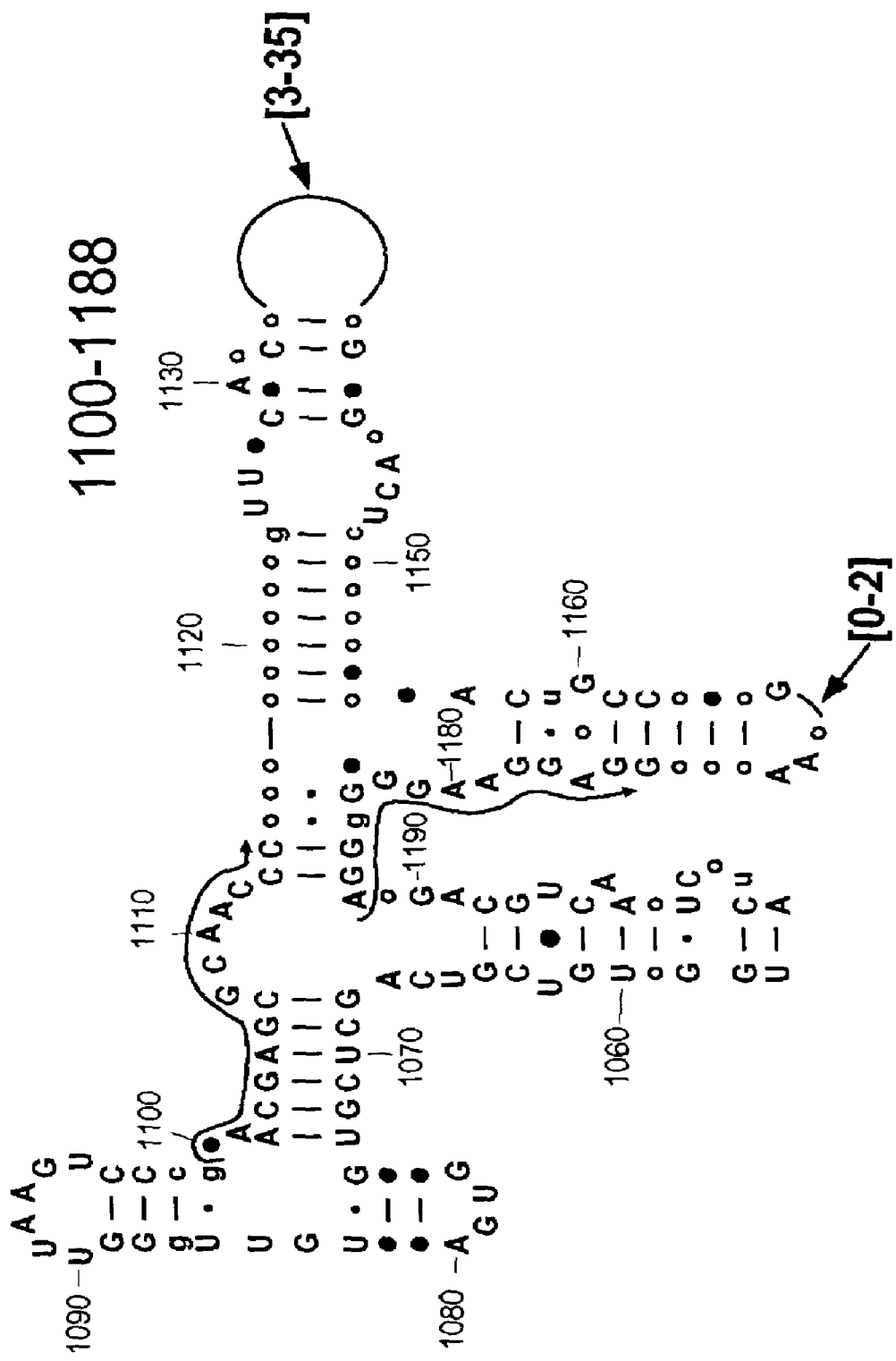
Figure 3:
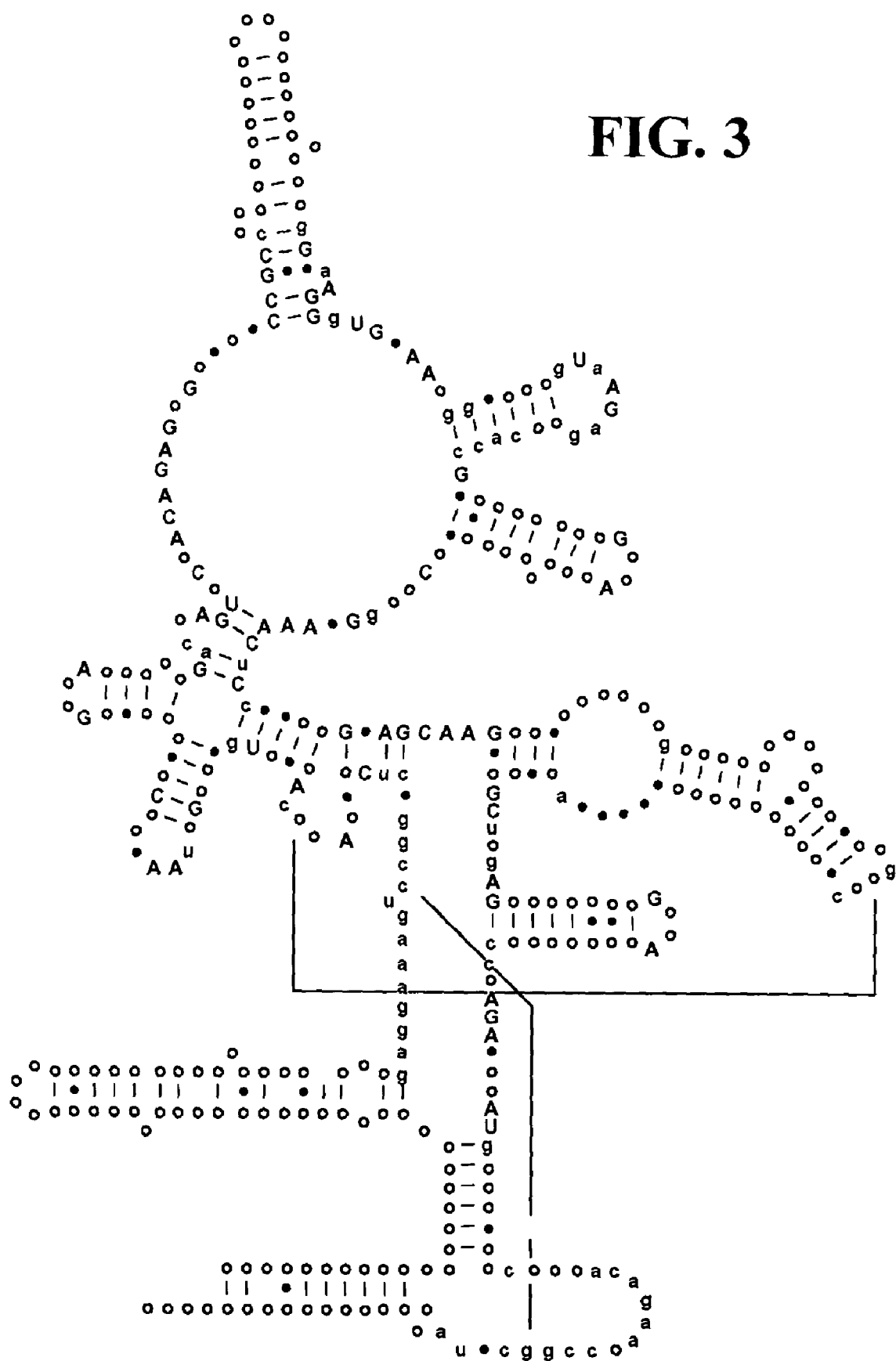
FIG. 3 is a schematic diagram showing conserved regions in RNase P. Bases in capital letters are greater than 90% conserved; bases in lower case letters are 80-90% conserved; filled circles designate bases which are 70-80% conserved; and open circles designate bases that are less than 70% conserved.
Figure 4:
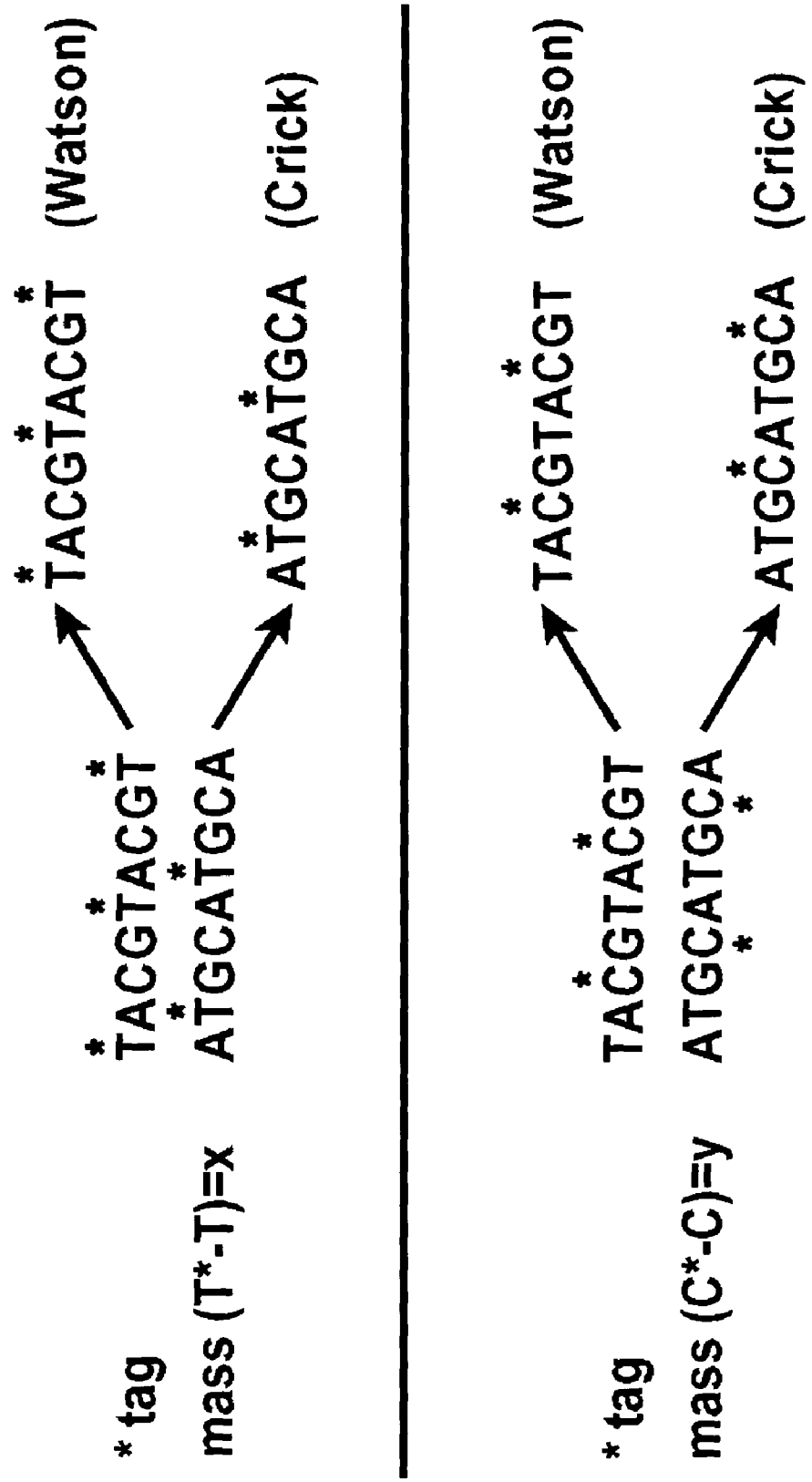
FIG. 4 is a schematic diagram of base composition signature determination using nucleotide analog "tags" to determine base composition signatures.

The mass tag phosphorothioate A (A*) was used to distinguish a *Bacillus anthracis* cluster. The *B. anthracis* ($A_{14}G_9Cl_{14}T_9$) had an average MW of 14072.26, and the *B. anthracis* ($A_1A^*_{13}G_9Cl_4T_9$) had an average molecular weight of 14281.11 and the phosphorothioate A had an average molecular weight of +16.06 as determined by ESI-TOF MS. The deconvoluted spectra are shown in FIG. 5.

In another example, assume the measured molecular masses of each strand are 30,000.115 Da and 31,000.115 Da respectively, and the measured number of dT and dA residues are (30,28) and (28,30). If the molecular mass is accurate to 100 ppm, there are 7 possible combinations of dG+dC possible for each strand. However, if the measured molecular mass is accurate to 10 ppm, there are only 2 combinations of dG+dC, and at 1 ppm accuracy there is only one possible base composition for each strand.

Signals from the mass spectrometer may be input to a maximum-likelihood detection and classification algorithm such as is widely used in radar signal processing. The detection processing uses matched filtering of BCS observed in mass-basecount space and allows for detection and subtraction of signatures from known, harmless organisms, and for detection of unknown bioagent threats. Comparison of newly observed bioagents to known bioagents is also possible, for estimation of threat level, by comparing their BCS to those of known organisms and to known forms of pathogenicity enhancement, such as insertion of antibiotic resistance genes or toxin genes.

Processing may end with a Bayesian classifier using log likelihood ratios developed from the observed signals and average background levels. The program emphasizes performance predictions culminating in probability-of-detection versus probability-of-false-alarm plots for conditions involving complex backgrounds of naturally occurring organisms and environmental contaminants. Matched filters consist of a priori expectations of signal values given the set of primers used for each of the bioagents. A genomic sequence database (e.g. GenBank) is used to define the mass basecount matched filters. The database contains known threat agents and benign background organisms. The latter is used to estimate and subtract the signature produced by the background organisms. A maximum likelihood detection of known background organisms is implemented using matched filters and a running-sum estimate of the noise covariance. Background signal strengths are estimated and used along with the matched filters to form signatures which are then subtracted the maximum likelihood process is applied to this "cleaned up" data in a similar manner employing matched filters for the organisms and a running-sum estimate of the noise-covariance for the cleaned up data.

F. Base Composition Signatures as Indices of Bioagent Identifying Amplicons

Although the molecular mass of amplification products obtained using intelligent primers provides a means for identification of bioagents, conversion of molecular mass data to a base composition signature is useful for certain analyses. As used herein, a "base composition signature" (BCS) is the exact base composition determined from the molecular mass of a bioagent identifying amplicon. In one embodiment, a BCS provides an index of a specific gene in a specific organism.

Figure 18:
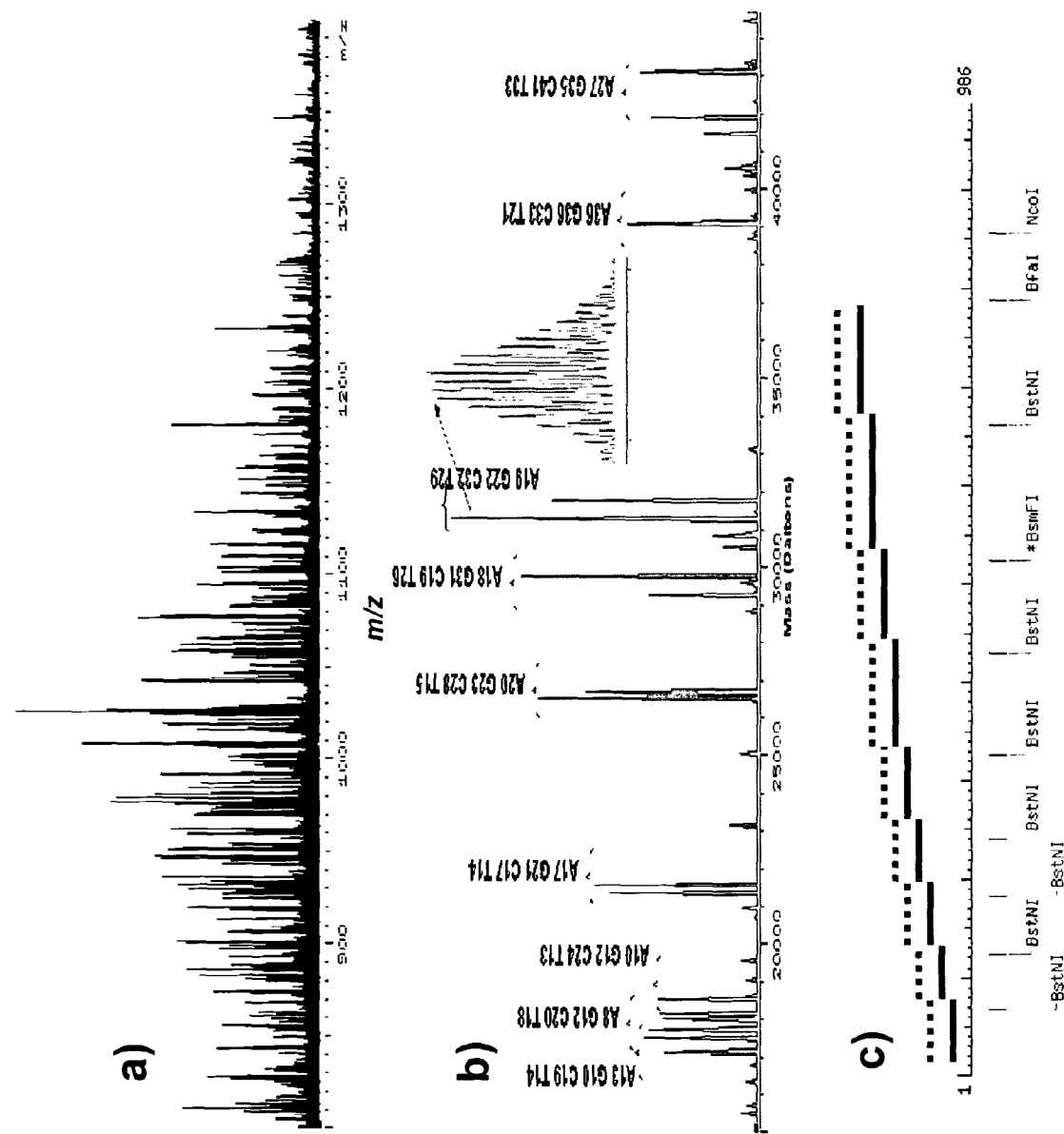
FIG. 18 shows: a) a representative ESI-FTICR mass spectrum of a restriction digest of a 986 bp region of the 16S ribosomal gene from *E. coli* K12 digested with a mixture of BstNI, BsmFI, BfaI, and NcoI, b) a deconvoluted representation (neutral mass) of the above spectrum showing the base compositions derived from accurate mass measurements of each fragment; and c) a representative reconstructed restriction map showing complete base composition coverage for nucleotides 1-856. The NcoI did not cut.

Base compositions, like sequences, vary slightly from isolate to isolate within species. It is possible to manage this diversity by building "base composition probability clouds" around the composition constraints for each species. This permits identification of organisms in a fashion similar to sequence analysis. A "pseudo four-dimensional plot" can be used to visualize the concept of base composition probability clouds (FIG. 18). Optimal primer design requires optimal choice of bioagent identifying amplicons and maximizes the separation between the base composition signatures of individual bioagents. Areas where clouds overlap indicate regions that may result in a misclassification, a problem which is overcome by selecting primers that provide information from different bioagent identifying amplicons, ideally maximizing the separation of base compositions. Thus, one aspect of the utility of an analysis of base composition probability clouds is that it provides a means for screening primer sets in order to avoid potential misclassifications of BCS and bioagent identity. Another aspect of the utility of base composition probability clouds is that they provide a means for predicting the identity of a bioagent whose exact measured BCS was not previously observed and/or indexed in a BCS database due to evolutionary transitions in its nucleic acid sequence.

It is important to note that, in contrast to probe-based techniques, mass spectrometry determination of base composition does not require prior knowledge of the composition in order to make the measurement, only to interpret the results. In this regard, the present invention provides bioagent classifying information similar to DNA sequencing and phylogenetic analysis at a level sufficient to detect and identify a given bioagent. Furthermore, the process of determination of a previously unknown BCS for a given bioagent (for example, in a case where sequence information is unavailable) has downstream utility by providing additional bioagent indexing information with which to populate BCS databases. The process of future bioagent identification is thus greatly improved as more BCS indexes become available in the BCS databases.

Another embodiment of the present invention is a method of surveying bioagent samples that enables detection and identification of all bacteria for which sequence information is available using a set of twelve broad-range intelligent PCR primers. Six of the twelve primers are "broad range survey primers" herein defined as primers targeted to broad divisions of bacteria (for example, the *Bacillus/Clostridia* group or gamma-proteobacteria). The other six primers of the group of twelve primers are "division-wide" primers herein defined as primers which provide more focused coverage and higher resolution. This method enables identification of nearly 100% of known bacteria at the species level. A further example of this embodiment of the present invention is a method herein designated "survey/drill-down" wherein a subspecies characteristic for detected bioagents is obtained using additional primers. Examples of such a subspecies characteristic include but are not limited to: antibiotic resistance, pathogenicity island, virulence factor, strain type, sub-species type, and clade group. Using the survey/drill-down method, bioagent detection, confirmation and a subspecies characteristic can be provided within hours. Moreover, the survey/drill-down method can be focused to identify bioengineering events such as the insertion of a toxin gene into a bacterial species that does not normally make the toxin.

G. Fields of Application of the Present Invention

The present methods allow extremely rapid and accurate detection and identification of bioagents compared to existing methods. Furthermore, this rapid detection and identification is possible even when sample material is impure. The methods leverage ongoing biomedical research in virulence, pathogenicity, drug resistance and genome sequencing into a method which provides greatly improved sensitivity, specificity and reliability compared to existing methods, with lower rates of false positives. Thus, the methods are useful in a wide variety of fields, including, but not limited to, those fields discussed below.

1. Forensics Methods

In other embodiments of the invention, the methods disclosed herein can be used for forensics. As used herein, "forensics" is the study of evidence discovered at a crime or accident scene and used in a court of law. "Forensic science" is any science used for the purposes of the law, in particular the criminal justice system, and therefore provides impartial scientific evidence for use in the courts of law, and in a criminal investigation and trial. Forensic science is a multi-disciplinary subject, drawing principally from chemistry and biology, but also from physics, geology, psychology and social science, for example.

The process of human identification is a common objective of forensics investigations. For example, there exists a need for rapid identification of humans wherein human remains and/or biological samples are analyzed. Such remains or samples may be associated with war-related casualties, aircraft crashes, and acts of terrorism, for example. Analysis of mtDNA enables a rule-in/rule-out identification process for persons for whom DNA profiles from a maternal relative are available. Human identification by analysis of mtDNA can also be applied to human remains and/or biological samples obtained from crime scenes.

Nucleic acid segments which provide enough variability to distinguish each individual bioagent and whose molecular masses are amenable to molecular mass determination are herein described as "bioagent identifying amplicons." The bioagent identifying amplicons used in the present invention for analysis of mitochondrial DNA are defined as "mitochondrial DNA identifying amplicons."

Forensic scientists generally use two highly variable regions of human mtDNA for analysis. These regions are designated "hypervariable regions 1 and 2" (HVR1 and HVR2—which contain 341 and 267 base pairs respectively). These hypervariable regions, or portions thereof, provide one non-limiting example of mitochondrial DNA identifying amplicons.

A mtDNA analysis begins when total genomic DNA is extracted from biological material, such as a tooth, blood sample, or hair. The polymerase chain reaction (PCR) is then used to amplify, or create many copies of, the two hypervariable portions of the non-coding region of the mtDNA molecule, using flanking primers. Care is taken to eliminate the introduction of exogenous DNA during both the extraction and amplification steps via methods such as the use of pre-packaged sterile equipment and reagents, aerosol-resistant barrier pipette tips, gloves, masks, and lab coats, separation of pre- and post-amplification areas in the lab using dedicated reagents for each, ultraviolet irradiation of equipment, and autoclaving of tubes and reagent stocks. In casework, questioned samples are always processed before known samples and they are processed in different laboratory rooms. When adequate amounts of PCR product are amplified to provide all the necessary information about the two hypervariable regions, sequencing reactions are performed. These chemical reactions use each PCR product as a template to create a new complementary strand of DNA in which some of the nucleotide residues that make up the DNA sequence are labeled with dye. The strands created in this stage are then separated according to size by an automated sequencing machine that uses a laser to "read" the sequence, or order, of the nucleotide bases. Where possible, the sequences of both hypervariable regions are determined on both strands of the double-stranded DNA molecule, with sufficient redundancy to confirm the nucleotide substitutions that characterize that particular sample. At least two forensic analysts independently assemble the sequence and then compare it to a standard, commonly used, reference sequence. The entire process is then repeated with a known sample, such as blood or saliva collected from a known individual. The sequences from both samples, about 780 bases long each, are compared to determine if they match. The analysts assess the results of the analysis and determine if any portions of it need to be repeated. Finally, in the event of an inclusion or match, the SWGDAM mtDNA database, which is maintained by the FBI, is searched for the mitochondrial sequence that has been observed for the samples. The analysts can then report the number of observations of this type based on the nucleotide positions that have been read. A written report can be provided to the submitting agency.

2. Determination and Quantitation of Mitochondrial DNA Heteroplasmy

In one embodiment of the present invention, the methods disclosed herein for rapid identification of bioagents using base composition signatures are employed for analysis of human mtDNA. The advantages provided by this embodiment of the present invention include, but are not limited to, efficiency of mass determination of amplicons over sequence determination, and the ability to resolve mixtures of mtDNA amplicons arising from heteroplasmy. Such mixtures invariably cause sequencing failures.

In another embodiment of the present invention, the methods disclosed herein for mtDNA analysis can be used to identify the presence of heteroplasmic variants and to determine their relative abundances. As used herein, "mitochondrial diseases" are defined as diseases arising from defects in mitochondrial function which often arise as a result of mutations and heteroplasmy. If the defect is in the mitochondrial rather than the nuclear genome unusual patterns of inheritance can be observed. This embodiment can be used to determine rates of naturally occurring mutations contributing to heteroplasmy and to predict the onset of mitochondrial diseases arising from heteroplasmy. Examples of mitochondrial diseases include, but are not limited to: Alpers Disease, Barth syndrome, Beta-oxidation Defects, Carnitine-Acyl-Carnitine Deficiency, Carnitine Deficiency, Co-Enzyme Q10 Deficiency, Complex I Deficiency, Complex II Deficiency, Complex III Deficiency, Complex IV Deficiency, Complex V Deficiency, COX Deficiency, CPEO, CPT I Deficiency, CPT II Deficiency, Glutaric Aciduria Type II, KSS, Lactic Acidosis, LCAD, LCHAD, Leigh Disease or Syndrome, LHON, Lethal Infantile Cardiomyopathy, Luft Disease, MAD, MCA, MELAS, MERRF, Mitochondrial Cytopathy, Mitochondrial DNA Depletion, Mitochondrial Encephalopathy, Mitochondrial Myopathy, MNGIE, NARP, Pearson Syndrome, Pyruvate Carboxylase Deficiency, Pyruvate Dehydrogenase Deficiency, Respiratory Chain, SCAD, SCHAD, VLCAD, and the like (found at the united mitochondrial disease foundation website).

In another embodiment of the present invention, the methods disclosed herein can be used to rapidly determine the identity of a fungus or a protist by analysis of its mtDNA.

In addition, epidemiologists, for example, can use the present methods to determine the geographic origin of a particular strain of a protist or fungus. For example, a particular strain of bacteria or virus may have a sequence difference that is associated with a particular area of a country or the world and identification of such a sequence difference can lead to the identification of the geographic origin and epidemiological tracking of the spread of the particular disease, disorder or condition associated with the detected protist or fungus. In addition, carriers of particular DNA or diseases, such as mammals, non-mammals, birds, insects, and plants, can be tracked by screening their mtDNA. Diseases, such as malaria, can be tracked by screening the mtDNA of commensals such as mosquitoes.

The present method can also be used to detect single nucleotide polymorphisms (SNPs), or multiple nucleotide polymorphisms, rapidly and accurately. A SNP is defined as a single base pair site in the genome that is different from one individual to another. The difference can be expressed either as a deletion, an insertion or a substitution, and is frequently linked to a disease state. Because they occur every 100-1000 base pairs, SNPs are the most frequently bound type of genetic marker in the human genome.

For example, sickle cell anemia results from an A-T transition, which encodes a valine rather than a glutamic acid residue. Oligonucleotide primers may be designed such that they bind to sequences that flank a SNP site, followed by nucleotide amplification and mass determination of the amplified product. Because the molecular masses of the resulting product from an individual who does not have sickle cell anemia is different from that of the product from an individual who has the disease, the method can be used to distinguish the two individuals. Thus, the method can be used to detect any known SNP in an individual and thus diagnose or determine increased susceptibility to a disease or condition.

In one embodiment, blood is drawn from an individual and peripheral blood mononuclear cells (PBMC) are isolated and simultaneously tested, preferably in a high-throughput screening method, for one or more SNPs using appropriate primers based on the known sequences which flank the SNP region. The National Center for Biotechnology Information maintains a publicly available database of SNPs on the world wide web of the Internet at, for example, "ncbi.nlm.nih.gov/SNP/."

The method of the present invention can also be used for blood typing. The gene encoding A, B or O blood type can differ by four single nucleotide polymorphisms. If the gene contains the sequence CGTGGTGACCCTT (SEQ ID NO:5), antigen A results. If the gene contains the sequence CGTCGTCACCGCTA (SEQ ID NO:6) antigen B results. If the gene contains the sequence CGTGGT-ACCCCTT (SEQ ID NO:7), blood group 0 results ("-" indicates a deletion). These sequences can be distinguished by designing a single primer pair which flanks these regions, followed by amplification and mass determination.

While the present invention has been described with specificity in accordance with certain of its embodiments, the following examples serve only to illustrate the invention and are not intended to limit the same.

EXAMPLES

Example 1

Nucleic Acid Isolation and PCR

In one embodiment, nucleic acid is isolated from the organisms and amplified by PCR using standard methods prior to BCS determination by mass spectrometry. Nucleic acid is isolated, for example, by detergent lysis of bacterial cells, centrifugation and ethanol precipitation. Nucleic acid isolation methods are described in, for example, *Current Protocols in Molecular Biology* (Ausubel et al.) and *Molecular Cloning; A Laboratory Manual* (Sambrook et al.). The nucleic acid is then amplified using standard methodology, such as PCR, with primers which bind to conserved regions of the nucleic acid which contain an intervening variable sequence as described below.

General Genomic DNA Sample Prep Protocol: Raw samples are filtered using Supor-200 0.2 μm membrane syringe filters (VWR International). Samples are transferred to 1.5 ml eppendorf tubes pre-filled with 0.45 g of 0.7 mm Zirconia beads followed by the addition of 350 μl of ATL buffer (Qiagen, Valencia, Calif.). The samples are subjected to bead beating for 10 minutes at a frequency of 19 l/s in a Retsch Vibration Mill (Retsch). After centrifugation, samples are transferred to an S-block plate (Qiagen) and DNA isolation is completed with a BioRobot 8000 nucleic acid isolation robot (Qiagen).

Swab Sample Protocol. Allegiance S/P brand culture swabs and collection/transport system are used to collect samples. After drying, swabs are placed in 17×100 mm culture tubes (VWR International) and the genomic nucleic acid isolation is carried out automatically with a Qiagen Mdx robot and the Qiagen QIAamp DNA Blood BioRobot Mdx genomic preparation kit (Qiagen, Valencia, Calif.).

Example 2

Mass Spectrometry

FTICR Instrumentation: The FTICR instrument is based on a 7 tesla actively shielded superconducting magnet and modified Bruker Daltonics Apex II 70e ion optics and vacuum chamber. The spectrometer is interfaced to a LEAP PAL autosampler and a custom fluidics control system for high throughput screening applications. Samples are analyzed directly from 96-well or 384-well microtiter plates at a rate of about 1 sample/minute. The Bruker data-acquisition platform is supplemented with a lab-built ancillary NT datastation which controls the autosampler and contains an arbitrary waveform generator capable of generating complex rf-excite waveforms (frequency sweeps, filtered noise, stored waveform inverse Fourier transform (SWIFT), etc.) for sophisticated tandem MS experiments. For oligonucleotides in the 20-30-mer regime typical performance characteristics include mass resolving power in excess of 100,000 (FWHM), low ppm mass measurement errors, and an operable m/z range between 50 and 5000 m/z.

Modified ESI Source. In sample-limited analyses, analyte solutions are delivered at 150 nL/minute to a 30 mm i.d. fused-silica ESI emitter mounted on a 3-D micromanipulator. The ESI ion optics consists of a heated metal capillary, an rf-only hexapole, a skimmer cone, and an auxiliary gate electrode. The 6.2 cm rf-only hexapole is comprised of 1 mm diameter rods and is operated at a voltage of 380 Vpp at a frequency of 5 MHz. A lab-built electro-mechanical shutter can be employed to prevent the electrospray plume from entering the inlet capillary unless triggered to the "open" position via a TTL pulse from the data station. When in the "closed" position, a stable electrospray plume is maintained between the ESI emitter and the face of the shutter. The back face of the shutter arm contains an elastomeric seal that can be positioned to form a vacuum seal with the inlet capillary. When the seal is removed, a 1 mm gap between the shutter blade and the capillary inlet allows constant pressure in the external ion reservoir regardless of whether the shutter is in the open or closed position. When the shutter is triggered, a "time slice" of ions is allowed to enter the inlet capillary and is subsequently accumulated in the external ion reservoir. The rapid response time of the ion shutter (<25 ms) provides reproducible, user defined intervals during which ions can be injected into and accumulated in the external ion reservoir.

Apparatus for Infrared Multiphoton Dissociation. A 25 watt CW $CO_2$ laser operating at 10.6 μm has been interfaced to the spectrometer to enable infrared multiphoton dissociation (IRMPD) for oligonucleotide sequencing and other tandem MS applications. An aluminum optical bench is positioned approximately 1.5 m from the actively shielded superconducting magnet such that the laser beam is aligned with the central axis of the magnet. Using standard IR-compatible mirrors and kinematic mirror mounts, the unfocused 3 mm laser beam is aligned to traverse directly through the 3.5 mm holes in the trapping electrodes of the FTICR trapped ion cell and longitudinally traverse the hexapole region of the external ion guide finally impinging on the skimmer cone. This scheme allows IRMPD to be conducted in an m/z selective manner in the trapped ion cell (e.g. following a SWIFT isolation of the species of interest), or in a broadband mode in the high pressure region of the external ion reservoir where collisions with neutral molecules stabilize IRMPD-generated metastable fragment ions resulting in increased fragment ion yield and sequence coverage.

Example 3

Identification of Bioagents

Table 2 shows a small cross section of a database of calculated molecular masses for over 9 primer sets and approximately 30 organisms. The primer sets were derived from rRNA alignment. Examples of regions from rRNA consensus alignments are shown in FIGS. 1A-1C. Lines with arrows are examples of regions to which intelligent primer pairs for PCR are designed. The primer pairs are >95% conserved in the bacterial sequence database (currently over 10,000 organisms). The intervening regions are variable in length and/or composition, thus providing the base composition "signature" (BCS) for each organism. Primer pairs were chosen so the total length of the amplified region is less than about 80-90 nucleotides. The label for each primer pair represents the starting and ending base number of the amplified region on the consensus diagram.

Included in the short bacterial database cross-section in Table 2 are many well known pathogens/biowarfare agents (shown in bold/red typeface) such as *Bacillus anthracis* or *Yersinia pestis* as well as some of the bacterial organisms found commonly in the natural environment such as *Streptomyces*. Even closely related organisms can be distinguished from each other by the appropriate choice of primers. For instance, two low G+C organisms, *Bacillus anthracis* and *Staph aureus*, can be distinguished from each other by using the primer pair defined by 16S_1337 or 23S_855 (ΔM of 4 Da).

TABLE 2

Cross Section Of A Database Of Calculated Molecular Masses[1]

| | Primer Regions | | | | | | | | |
|---|---|---|---|---|---|---|---|---|---|
| Bug Name | 16S_971 | 16S_1100 | 16S_1337 | 16S_1294 | 16S_1228 | 23S_1021 | 23S_855 | 23S_193 | 23S_115 |
| *Acinetobacter calcoaceticus* | 55619.1 | 55004 | 28446.7 | 35854.9 | 51295.4 | 30299 | 42654 | 39557.5 | 54999 |
| *Bacillus anthracis* | 55005 | 54388 | 28448 | 35238 | 51296 | 30295 | 42651 | 39560 | 56850 |
| *Bacillus cereus* | 55622.1 | 54387.9 | 28447.6 | 35854.9 | 51296.4 | 30295 | 42651 | 39560.5 | 56850.3 |
| *Bordetella bronchiseptica* | 56857.3 | 51300.4 | 28446.7 | 35857.9 | 51307.4 | 30299 | 42653 | 39559.5 | 51920.5 |
| *Borrelia burgdorferi* | 56231.2 | 55621.1 | 28440.7 | 35852.9 | 51295.4 | 30297 | 42029.9 | 38941.4 | 52524.6 |
| *Brucella abortus* | 58098 | 55011 | 28448 | 35854 | 50683 | | | | |
| *Campylobacter jejuni* | 58088.5 | 54386.9 | 29061.8 | 35856.9 | 50674.3 | 30294 | 42032.9 | 39558.5 | 45732.5 |
| *Chlamydia pnuemoniae* | 55000 | 55007 | 29063 | 35855 | 50676 | 30295 | 42036 | 38941 | 56230 |
| *Clostridium botullinum* | 55006 | 53767 | 28445 | 35855 | 51291 | 30300 | 42656 | 39562 | 54999 |
| *Clostridium difficile* | 56855.3 | 54386.9 | 28444.7 | 35853.9 | 51296.4 | 30294 | 41417.8 | 39556.5 | 55612.2 |
| *Enterococcus faecalis* | 55620.1 | 54387.9 | 28447.6 | 35858.9 | 51296.4 | 30297 | 42652 | 39559.5 | 56849.3 |
| *Escherichia coli* | 55622 | 55009 | 28445 | 35857 | 51301 | 30301 | 42656 | 39562 | 54999 |
| *Francisella tularensis* | 53769 | 54385 | 28445 | 35856 | 51298 | | | | |
| *Haemophilus influenzae* | 55620.1 | 55006 | 28444.7 | 35855.9 | 51298.4 | 30298 | 42656 | 39560.5 | 55613.1 |
| *Klebsiella pneumoniae* | 55622.1 | 55008 | 28442.7 | 35856.9 | 51297.4 | 30300 | 42655 | 39562.5 | 55000 |
| *Legionella pneumophila* | 55618 | 55626 | 28446 | 35857 | 51303 | | | | |
| *Mycobacterium avium* | 54390.9 | 55631.1 | 29064.8 | 35858.9 | 51915.5 | 30298 | 42656 | 38942.4 | 56241.2 |
| *Mycobacterium leprae* | 54389.9 | 55629.1 | 29064.8 | 35860.9 | 51917.5 | 30298 | 42656 | 39559.5 | 56240.2 |
| *Mycobacterium tuberculosis* | 54390.9 | 55629.1 | 29064.8 | 35860.9 | 51301.4 | 30299 | 42656 | 39560.5 | 56243.2 |

TABLE 2-continued Cross Section Of A Database Of Calculated Molecular Masses[1]

| Bug Name | Primer Regions | | | | | | | | |
|---|---|---|---|---|---|---|---|---|---|
| | 16S_971 | 16S_1100 | 16S_1337 | 16S_1294 | 16S_1228 | 23S_1021 | 23S_855 | 23S_193 | 23S_115 |
| *Mycoplasma genitalium* | 53143.7 | 45115.4 | 29061.8 | 35854.9 | 50671.3 | 30294 | 43264.1 | 39558.5 | 56842.4 |
| *Mycoplasma pneumoniae* | 53143.7 | 45118.4 | 29061.8 | 35854.9 | 50673.3 | 30294 | 43264.1 | 39559.5 | 56843.4 |
| *Neisseria gonorrhoeae* | 55627.1 | 54389.9 | 28445.7 | 35855.9 | 51302.4 | 30300 | 42649 | 39561.5 | 55000 |
| Pseudomonas aeruginosa | 55623 | 55010 | 28443 | 35858 | 51301 | 30298 | 43272 | 39558 | 55619 |
| Rickettsia prowazekii | 58093 | 55621 | 28448 | 35853 | 50677 | 30293 | 42650 | 39559 | 53139 |
| Rickettsia rickettsii | 58094 | 55623 | 28448 | 35853 | 50679 | 30293 | 42648 | 39559 | 53755 |
| Salmonella typhimurium | 55622 | 55005 | 28445 | 35857 | 51301 | 30301 | 42658 | | |
| Shigella dysenteriae | 55623 | 55009 | 28444 | 35857 | 51301 | | | | |
| *Staphylococcus aureus* | 56854.3 | 54386.9 | 28443.7 | 35852.9 | 51294.4 | 30298 | 42655 | 39559.5 | 57466.4 |
| *Streptomyces* | 54389.9 | 59341.6 | 29063.8 | 35858.9 | 51300.4 | | | 39563.5 | 56864.3 |
| *Treponema pallidum* | 56245.2 | 55631.1 | 28445.7 | 35851.9 | 51297.4 | 30299 | 42034.9 | 38939.4 | 57473.4 |
| Vibrio cholerae | 55625 | 55626 | 28443 | 35857 | 52536 | 29063 | 30303 | 35241 | 50675 |
| *Vibrio parahaemolyticus* | 54384.9 | 55626.1 | 28444.7 | 34620.7 | 50064.2 | | | | |
| Yersinia pestis | 55620 | 55626 | 28443 | 35857 | 51299 | | | | |

[1]Molecular mass distribution of PCR amplified regions for a selection of organisms (rows) across various primer pairs (columns). Pathogens are shown in bold. Empty cells indicate presently incomplete or missing data.

Figure 6:
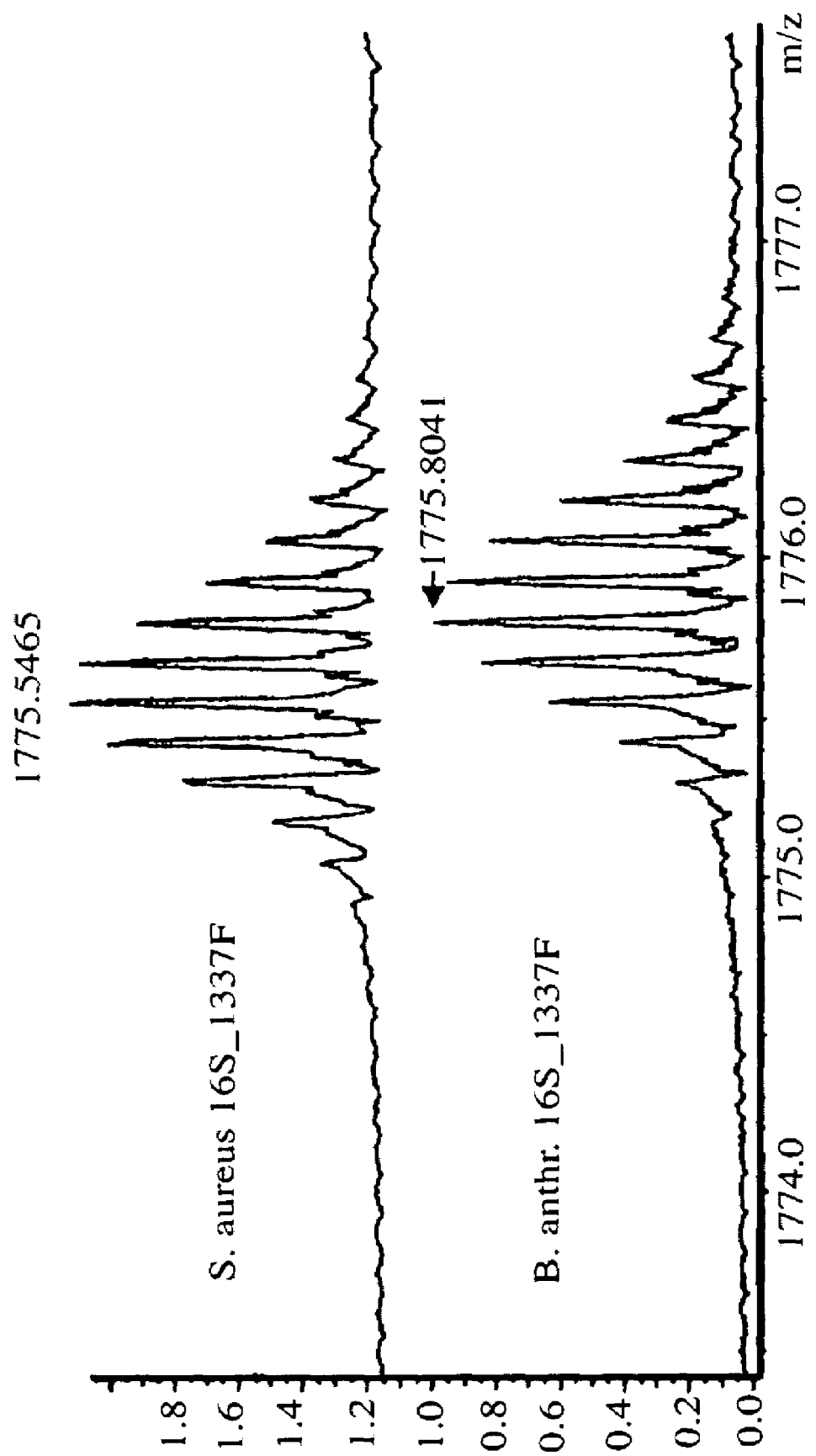
FIG. 6 shows base composition signature (BCS) spectra from PCR products from *Staphylococcus aureus* (*S. aureus* 16S_1337F) and *Bacillus anthracis* (*B. anthr.* 16S_1337F), amplified using the same primers. The two strands differ by only two (AT—>CG) substitutions and are clearly distinguished on the basis of their BCS.
Figure 7:
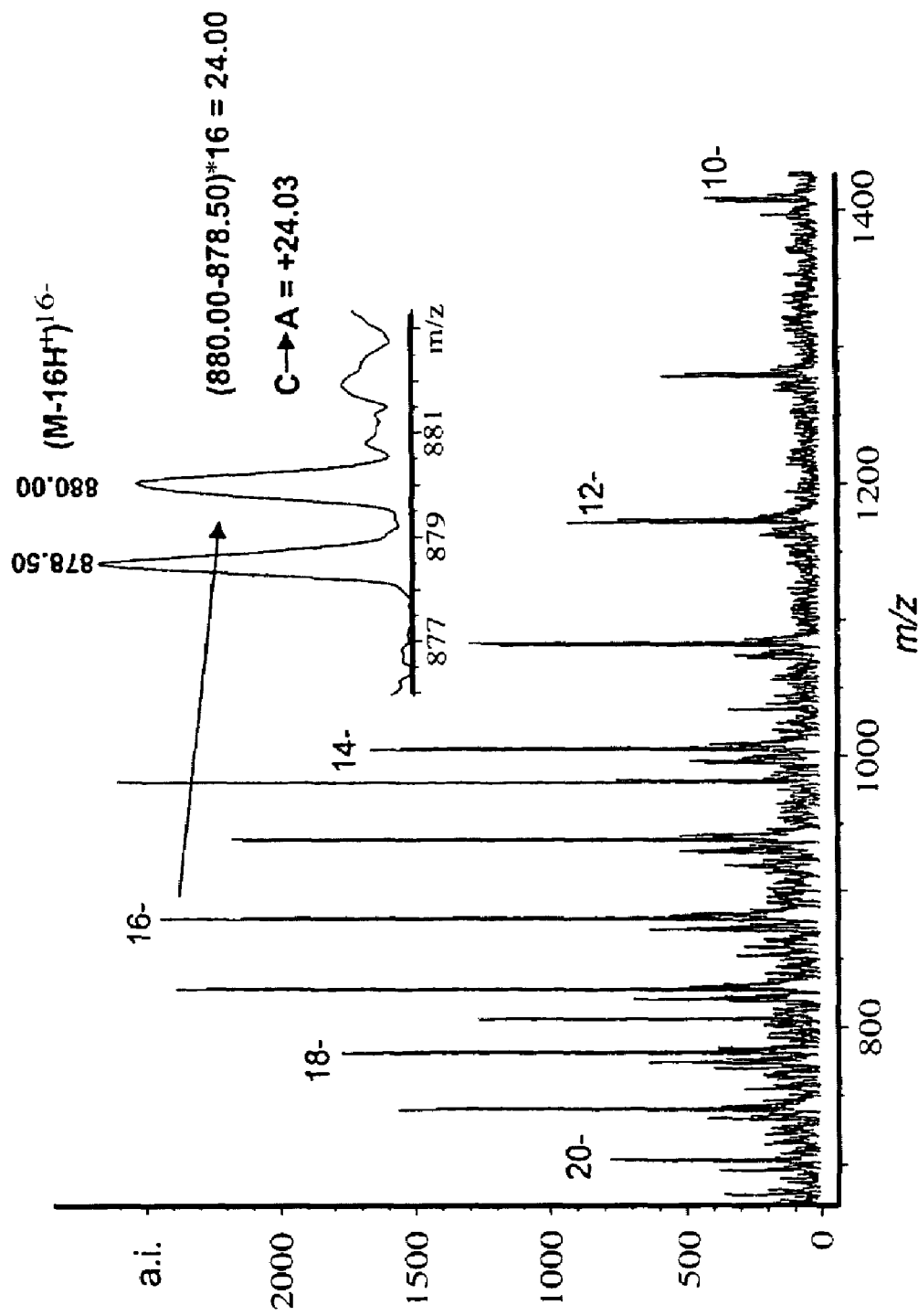
FIG. 7 shows that a single difference between two sequences (A14 in *B. anthracis* vs. A15 in *B. cereus*) can be easily detected using ESI-TOF mass spectrometry.

FIG. 6 shows the use of ESI-FT-ICR MS for measurement of exact mass. The spectra from 46 mer PCR products originating at position 1337 of the 16S rRNA from *S. aureus* (upper) and *B. anthracis* (lower) are shown. These data are from the region of the spectrum containing signals from the $[M-8H+]^{8-}$ charge states of the respective 5'-3' strands. The two strands differ by two (AT→CG) substitutions, and have measured masses of 14206.396 and 14208.373+0.010 Da, respectively. The possible base compositions derived from the masses of the forward and reverse strands for the *B. anthracis* products are listed in Table 3.

TABLE 3

Possible base composition for *B. anthracis* products

| Calc. Mass | Error | Base Comp. |
|---|---|---|
| 14208.2935 | 0.079520 | A1 G17 C10 T18 |
| 14208.3160 | 0.056980 | A1 G20 C15 T10 |
| 14208.3386 | 0.034440 | A1 G23 C20 T2 |
| 14208.3074 | 0.065560 | A6 G11 C3 T26 |
| 14208.3300 | 0.043020 | A6 G14 C8 T18 |
| 14208.3525 | 0.020480 | A6 G17 C13 T10 |
| 14208.3751 | 0.002060 | A6 G20 C18 T2 |
| 14208.3439 | 0.029060 | A11 G8 C1 T26 |
| 14208.3665 | 0.006520 | A11 G11 C6 T18 |
| 14208.3890 | 0.016020 | A11 G14 C11 T10 |
| 14208.4116 | 0.038560 | A11 G17 C16 T2 |
| 14208.4030 | 0.029980 | A16 G8 C4 T18 |
| 14208.4255 | 0.052520 | A16 G11 C9 T10 |
| 14208.4481 | 0.075060 | A16 G14 C14 T2 |
| 14208.4395 | 0.066480 | A21 G5 C2 T18 |
| 14208.4620 | 0.089020 | A21 G8 C7 T10 |
| 14079.2624 | 0.080600 | A0 G14 C13 T19 |
| 14079.2849 | 0.058060 | A0 G17 C18 T11 |
| 14079.3075 | 0.035520 | A0 G20 C23 T3 |
| 14079.2538 | 0.089180 | A5 G5 C1 T35 |
| 14079.2764 | 0.066640 | A5 G8 C6 T27 |
| 14079.2989 | 0.044100 | A5 G11 C11 T19 |
| 14079.3214 | 0.021560 | A5 G14 C16 T11 |
| 14079.3440 | 0.000980 | A5 G17 C21 T3 |
| 14079.3129 | 0.030140 | A10 G5 C4 T27 |
| 14079.3354 | 0.007600 | A10 G8 C9 T19 |
| 14079.3579 | 0.014940 | A10 G11 C14 T11 |
| 14079.3805 | 0.037480 | A10 G14 C19 T3 |
| 14079.3494 | 0.006360 | A15 G2 C2 T27 |
| 14079.3719 | 0.028900 | A15 G5 C7 T19 |
| 14079.3944 | 0.051440 | A15 G8 C12 T11 |
| 14079.4170 | 0.073980 | A15 G11 C17 T3 |

TABLE 3-continued

Possible base composition for *B. anthracis* products

| Calc. Mass | Error | Base Comp. |
|---|---|---|
| 14079.4084 | 0.065400 | A20 G2 C5 T19 |
| 14079.4309 | 0.087940 | A20 G5 C10 T13 |

Among the 16 compositions for the forward strand and the 18 compositions for the reverse strand that were calculated, only one pair (shown in bold) are complementary, corresponding to the actual base compositions of the *B. anthracis* PCR products.

Example 4

BCS of Region from *Bacillus anthracis* and *Bacillus cereus*

A conserved Bacillus region from *B. anthracis* ($Al_{14}G_9Cl_{14}T_9$) and *B. cereus* ($Al_{15}G_9Cl_{13}T_9$) having a C to A base change was synthesized and subjected to ESI-TOF MS. The results are shown in FIG. 7 in which the two regions are clearly distinguished using the method of the present invention (MW=14072.26 vs. 14096.29).

Example 5

Identification of Additional Bioagents

In other examples of the present invention, the pathogen Vibrio cholera can be distinguished from *Vibrio parahemolyticus* with ΔM>600 Da using one of three 16S primer sets shown in Table 2 (16S_971, 16S_1228 or 16S_1294) as shown in Table 4. The two mycoplasma species in the list (*M. genitalium* and *M. pneumoniae*) can also be distinguished from each other, as can the three mycobacteriae. While the direct mass measurements of amplified products can identify and distinguish a large number of organisms, measurement of the base composition signature provides dramatically enhanced resolving power for closely related organisms. In cases such as *Bacillus anthracis* and *Bacillus cereus* that are virtually indistinguishable from each other based solely on mass differences, compositional analysis or fragmentation patterns are used to resolve the differences. The single base difference between the two organisms yields different fragmentation patterns, and despite the presence of the ambiguous/unidentified base N at position 20 in *B. anthracis*, the two organisms can be identified.

Tables 4a-b show examples of primer pairs from Table 1 which distinguish pathogens from background.

TABLE 4a

| Organism name | 23S_855 | 16S_1337 | 23S_1021 |
|---|---|---|---|
| *Bacillus anthracis* | 42650.98 | 28447.65 | 30294.98 |
| *Staphylococcus aureus* | 42654.97 | 28443.67 | 30297.96 |

TABLE 4b

| Organism name | 16S_971 | 16S_1294 | 16S_1228 |
|---|---|---|---|
| *Vibrio cholerae* | 55625.09 | 35856.87 | 52535.59 |
| *Vibrio parahaemolyticus* | 54384.91 | 34620.67 | 50064.19 |

Table 5 shows the expected molecular weight and base composition of region 16S_1100-1188 in *Mycobacterium avium* and *Streptomyces* sp.

TABLE 5

| Region | Organism name | Length | Molecular weight | Base comp. |
|---|---|---|---|---|
| 16S_1100-1188 | *Mycobacterium avium* | 82 | 25624.1728 | $A_{16}G_{32}C_{18}T_{16}$ |
| 16S_1100-1188 | *Streptomyces* sp. | 96 | 29904.871 | $A_{17}G_{38}C_{27}T_{14}$ |

Table 6 shows base composition (single strand) results for 16S_1100-1188 primer amplification reactions different species of bacteria. Species which are repeated in the table (e.g., *Clostridium botulinum*) are different strains which have different base compositions in the 16S_1100-1188 region.

TABLE 6

| Organism name | Base comp. | Organism name | Base comp. |
|---|---|---|---|
| *Mycobacterium avium* | $A_{16}G_{32}C_{18}T_{16}$ | *Vibrio cholerae* | $A_{23}G_{30}C_{21}T_{16}$ |
| *Streptomyces* sp. | $A_{17}G_{38}C_{27}T_{14}$ | Aeromonas hydrophila | $A_{23}G_{31}C_{21}T_{15}$ |
| *Ureaplasma urealyticum* | $A_{18}G_{30}C_{17}T_{17}$ | Aeromonas salmonicida | $A_{23}G_{31}C_{21}T_{15}$ |
| *Streptomyces* sp. | $A_{19}G_{36}C_{24}T_{18}$ | *Mycoplasma genitalium* | $A_{24}G_{19}C_{12}T_{18}$ |
| *Mycobacterium leprae* | $A_{20}G_{32}C_{22}T_{16}$ | *Clostridium botulinum* | $A_{24}G_{25}C_{18}T_{20}$ |
| M. tuberculosis | $A_{20}G_{33}C_{21}T_{16}$ | *Bordetella bronchiseptica* | $A_{24}G_{26}C_{19}T_{14}$ |
| Nocardia asteroides | $A_{20}G_{33}C_{21}T_{16}$ | *Francisella tularensis* | $A_{24}G_{26}C_{19}T_{19}$ |
| *Fusobacterium necroforum* | $A_{21}G_{26}C_{22}T_{18}$ | Bacillus anthracis | $A_{24}G_{26}C_{20}T_{18}$ |
| *Listeria monocytogenes* | $A_{21}G_{27}C_{19}T_{19}$ | Campylobacter jejuni | $A_{24}G_{26}C_{20}T_{18}$ |
| *Clostridium botulinum* | $A_{21}G_{27}C_{19}T_{21}$ | Staphylococcus aureus | $A_{24}G_{26}C_{20}T_{18}$ |
| *Neisseria gonorrhoeae* | $A_{21}G_{28}C_{21}T_{18}$ | *Helicobacter pylori* | $A_{24}G_{26}C_{20}T_{19}$ |
| *Bartonella quintana* | $A_{21}G_{30}C_{22}T_{16}$ | *Helicobacter pylori* | $A_{24}G_{26}C_{21}T_{18}$ |
| *Enterococcus faecalis* | $A_{22}G_{27}C_{20}T_{19}$ | *Moraxella catarrhalis* | $A_{24}G_{26}C_{23}T_{16}$ |
| *Bacillus megaterium* | $A_{22}G_{28}C_{20}T_{18}$ | *Haemophilus influenzae* Rd | $A_{24}G_{28}C_{20}T_{17}$ |
| *Bacillus subtilis* | $A_{22}G_{28}C_{21}T_{17}$ | Chlamydia trachomatis | $A_{24}G_{28}C_{21}T_{16}$ |
| *Pseudomonas aeruginosa* | $A_{22}G_{29}C_{23}T_{15}$ | Chlamydophila pneumoniae | $A_{24}G_{28}C_{21}T_{16}$ |
| *Legionella pneumophila* | $A_{22}G_{32}C_{20}T_{16}$ | C. pneumonia AR39 | $A_{24}G_{28}C_{21}T_{16}$ |
| *Mycoplasma pneumoniae* | $A_{23}G_{20}C_{14}T_{16}$ | *Pseudomonas putida* | $A_{24}G_{29}C_{21}T_{16}$ |
| *Clostridium botulinum* | $A_{23}G_{26}C_{20}T_{19}$ | Proteus vulgaris | $A_{24}G_{30}C_{21}T_{15}$ |
| *Enterococcus faecium* | $A_{23}G_{26}C_{21}T_{18}$ | Yersinia pestis | $A_{24}G_{30}C_{21}T_{15}$ |
| *Acinetobacter calcoaceti* | $A_{23}G_{26}C_{21}T_{19}$ | Yersinia pseudotuberculos | $A_{24}G_{30}C_{21}T_{15}$ |
| Leptospira borgpeterseni | $A_{23}G_{26}C_{24}T_{15}$ | *Clostridium botulinum* | $A_{25}G_{24}C_{18}T_{21}$ |
| Leptospira interrogans | $A_{23}G_{26}C_{24}T_{15}$ | *Clostridium tetani* | $A_{25}G_{25}C_{18}T_{20}$ |
| *Clostridium perfringens* | $A_{23}G_{27}C_{19}T_{19}$ | *Francisella tularensis* | $A_{25}G_{25}C_{19}T_{19}$ |
| Bacillus anthracis | $A_{23}G_{27}C_{20}T_{18}$ | *Acinetobacter calcoacetic* | $A_{25}G_{26}C_{20}T_{19}$ |
| Bacillus cereus | $A_{23}G_{27}C_{20}T_{18}$ | *Bacteriodes fragilis* | $A_{25}G_{27}C_{16}T_{22}$ |
| Bacillus thuringiensis | $A_{23}G_{27}C_{20}T_{18}$ | *Chlamydophila psittaci* | $A_{25}G_{27}C_{21}T_{16}$ |
| *Aeromonas hydrophila* | $A_{23}G_{29}C_{21}T_{16}$ | *Borrelia burgdorferi* | $A_{25}G_{29}C_{17}T_{19}$ |
| *Escherichia coli* | $A_{23}G_{29}C_{21}T_{16}$ | *Streptobacillus monilifor* | $A_{26}G_{26}C_{20}T_{16}$ |
| *Pseudomonas putida* | $A_{23}G_{29}C_{21}T_{17}$ | *Rickettsia prowazekii* | $A_{26}G_{28}C_{18}T_{18}$ |
| Escherichia coli | $A_{23}G_{29}C_{22}T_{15}$ | *Rickettsia rickettsii* | $A_{26}G_{28}C_{20}T_{16}$ |
| Shigella dysenteriae | $A_{23}G_{29}C_{22}T_{15}$ | *Mycoplasma mycoides* | $A_{28}G_{23}C_{16}T_{20}$ The same organism having different base compositions are different strains. Groups of organisms which are highlighted or in italics have the same base compositions in the amplified region. Some of these organisms can be distinguished using multiple primers. For example, *Bacillus anthracis* can be distinguished from *Bacillus cereus* and *Bacillus thuringiensis* using the primer 16S_971-1062 (Table 7). Other primer pairs which produce unique base composition signatures are shown in Table 6 (bold). Clusters containing very similar threat and ubiquitous non-threat organisms (e.g. anthracis cluster) are distinguished at high resolution with focused sets of primer pairs. The known biowarfare agents in Table 6 are *Bacillus anthracis, Yersinia pestis, Francisella tularensis* and *Rickettsia prowazekii*.

distinguishes *B. anthracis* from other species of Bacillus such as *B. thuringiensis* and B. cereus.

Example 7

B. anthracis ESI-TOF Synthetic 16S_1228 Duplex

Figure 9:
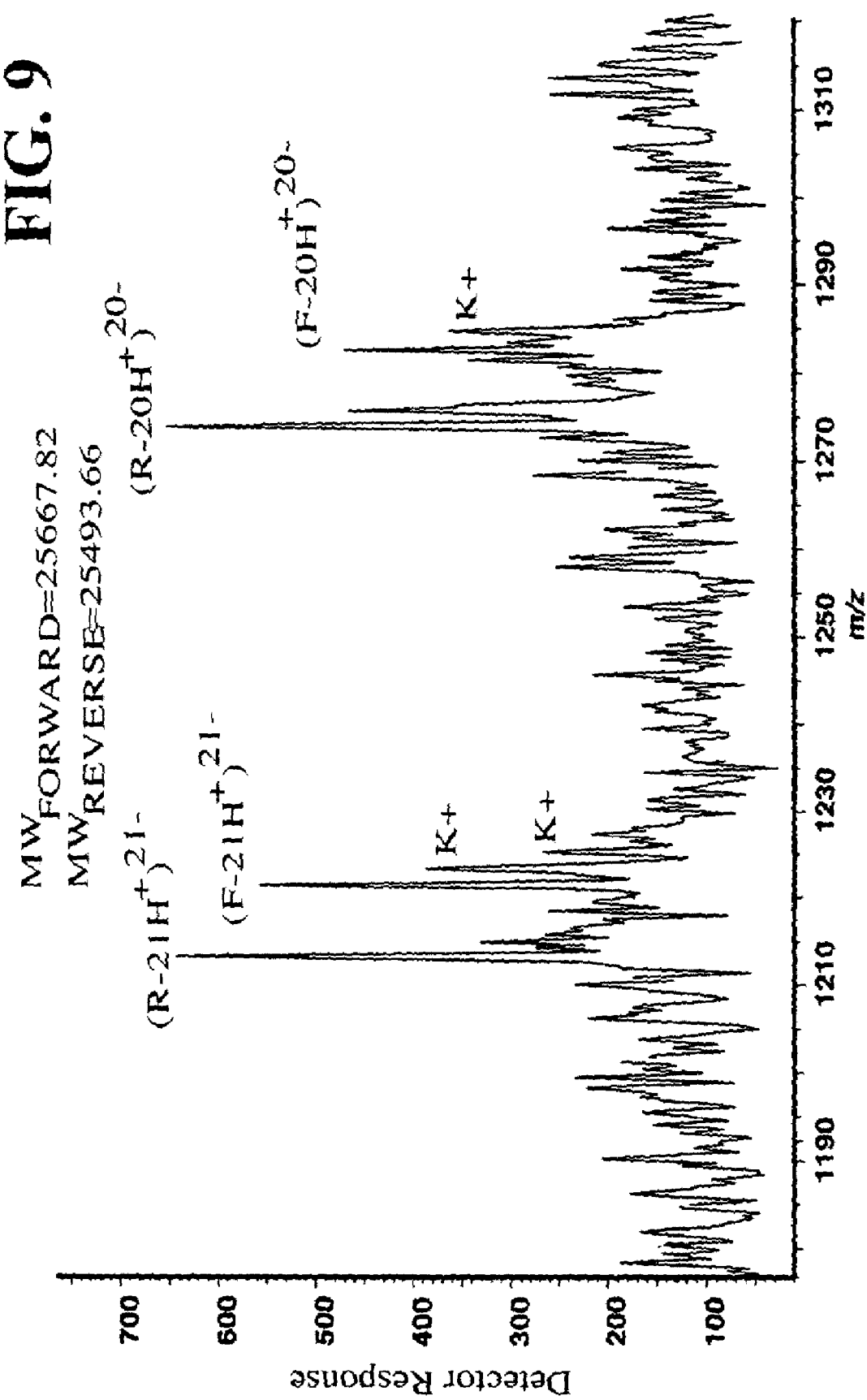
FIG. 9 is an ESI-TOF of a *B. anthracis* synthetic 16S_ 1228 duplex (reverse and forward strands). The technique easily distinguishes between the forward and reverse strands.

An ESI-TOF MS spectrum was obtained from an aqueous solution containing 5 μM each of synthetic analogs of the expected forward and reverse PCR products from the nucleotide 1228 region of the *B. anthracis* 16S rRNA gene. The results (FIG. 9) show that the molecular weights of the forward and reverse strands can be accurately determined and

TABLE 7

| Organism | 16S_971-1062 | 16S_1228-1310 | 16S_1100-1188 |
|---|---|---|---|
| *Aeromonas hydrophila* | $A_{21}G_{29}C_{22}T_{20}$ | $A_{22}G_{27}C_{21}T_{13}$ | $A_{23}G_{31}C_{21}T_{15}$ |
| *Aeromonas salmonicida* | $A_{21}G_{29}C_{22}T_{20}$ | $A_{22}G_{27}C_{21}T_{13}$ | $A_{23}G_{31}C_{21}T_{15}$ |
| *Bacillus anthracis* | $\mathbf{A_{21}G_{27}C_{22}T_{22}}$ | $A_{24}G_{22}C_{19}T_{18}$ | $A_{23}G_{27}C_{20}T_{18}$ |
| *Bacillus cereus* | $A_{22}G_{27}C_{21}T_{22}$ | $A_{24}G_{22}C_{19}T_{18}$ | $A_{23}G_{27}C_{20}T_{18}$ |
| *Bacillus thuringiensis* | $A_{22}G_{27}C_{21}T_{22}$ | $A_{24}G_{22}C_{19}T_{18}$ | $A_{23}G_{27}C_{20}T_{18}$ |
| *Chlamydia trachomatis* | $A_{22}G_{26}C_{20}T_{23}$ | $\mathbf{A_{24}G_{23}C_{19}T_{16}}$ | $A_{24}G_{28}C_{21}T_{16}$ |
| *Chlamydia pneumoniae* AR39 | $A_{26}G_{23}C_{20}T_{22}$ | $A_{26}G_{22}C_{16}T_{18}$ | $A_{24}G_{28}C_{21}T_{16}$ |
| *Leptospira borgpetersenii* | $A_{22}G_{26}C_{20}T_{21}$ | $A_{22}G_{25}C_{21}T_{15}$ | $A_{23}G_{26}C_{24}T_{15}$ |
| *Leptospira interrogans* | $A_{22}G_{26}C_{20}T_{21}$ | $A_{22}G_{25}C_{21}T_{15}$ | $A_{23}G_{26}C_{24}T_{15}$ |
| *Mycoplasma genitalium* | $A_{28}G_{23}C_{15}T_{22}$ | $\mathbf{A_{30}G_{18}C_{15}T_{19}}$ | $\mathbf{A_{24}G_{19}C_{12}T_{18}}$ |
| *Mycoplasma pneumoniae* | $A_{28}G_{23}C_{15}T_{22}$ | $\mathbf{A_{27}G_{19}C_{16}T_{20}}$ | $\mathbf{A_{23}G_{20}C_{14}T_{16}}$ |
| *Escherichia coli* | $A_{22}G_{28}C_{20}T_{22}$ | $A_{24}G_{25}C_{21}T_{13}$ | $A_{23}G_{29}C_{22}T_{15}$ |
| *Shigella dysenteriae* | $\mathbf{A_{22}G_{28}C_{21}T_{21}}$ | $A_{24}G_{25}C_{21}T_{13}$ | $A_{23}G_{29}C_{22}T_{15}$ |
| *Proteus vulgaris* | $\mathbf{A_{23}G_{26}C_{22}T_{21}}$ | $A_{26}G_{24}C_{19}T_{14}$ | $A_{24}G_{30}C_{21}T_{15}$ |
| *Yersinia pestis* | $A_{24}G_{25}C_{21}T_{22}$ | $A_{25}G_{24}C_{20}T_{14}$ | $A_{24}G_{30}C_{21}T_{15}$ |
| *Yersinia pseudotuberculosis* | $A_{24}G_{25}C_{21}T_{22}$ | $A_{25}G_{24}C_{20}T_{14}$ | $A_{24}G_{30}C_{21}T_{15}$ |
| *Francisella tularensis* | $\mathbf{A_{20}G_{25}C_{21}T_{23}}$ | $\mathbf{A_{23}G_{26}C_{17}T_{17}}$ | $\mathbf{A_{24}G_{26}C_{19}T_{19}}$ |
| *Rickettsia prowazekii* | $\mathbf{A_{21}G_{26}C_{24}T_{25}}$ | $\mathbf{A_{24}G_{23}C_{16}T_{19}}$ | $\mathbf{A_{26}G_{28}C_{18}T_{18}}$ |
| *Rickettsia rickettsii* | $\mathbf{A_{21}G_{26}C_{25}T_{24}}$ | $\mathbf{A_{24}G_{24}C_{17}T_{17}}$ | $\mathbf{A_{26}G_{28}C_{20}T_{16}}$ |

The sequence of *B. anthracis* and *B. cereus* in region 16S_971 is shown below. Shown in bold is the single base difference between the two species which can be detected using the methods of the present invention. *B. anthracis* has an ambiguous base at position 20.

```
B. anthracis_16S_971                         (SEQ ID NO:1)
GCGAAGAACCUUACCAGGUNUUGACAUC
CUCUGACAACCCUAGAGAUAGGGCU
UCUCCUUCGGGAGCAGAGUGACAGGUG
GUGCAUGGUU B. cereus_16S_971                            (SEQ ID NO:2)
GCGAAGAACCUUACCAGGUCUUGACAUC
CUCUGAAAACCCUAGAGAUAGGGCU
UCUCCUUCGGGAGCAGAGUGACAGGUG
GUGCAUGGUU
```

Example 6

ESI-TOF MS of sspE 56-mer Plus Calibrant

Figure 8:
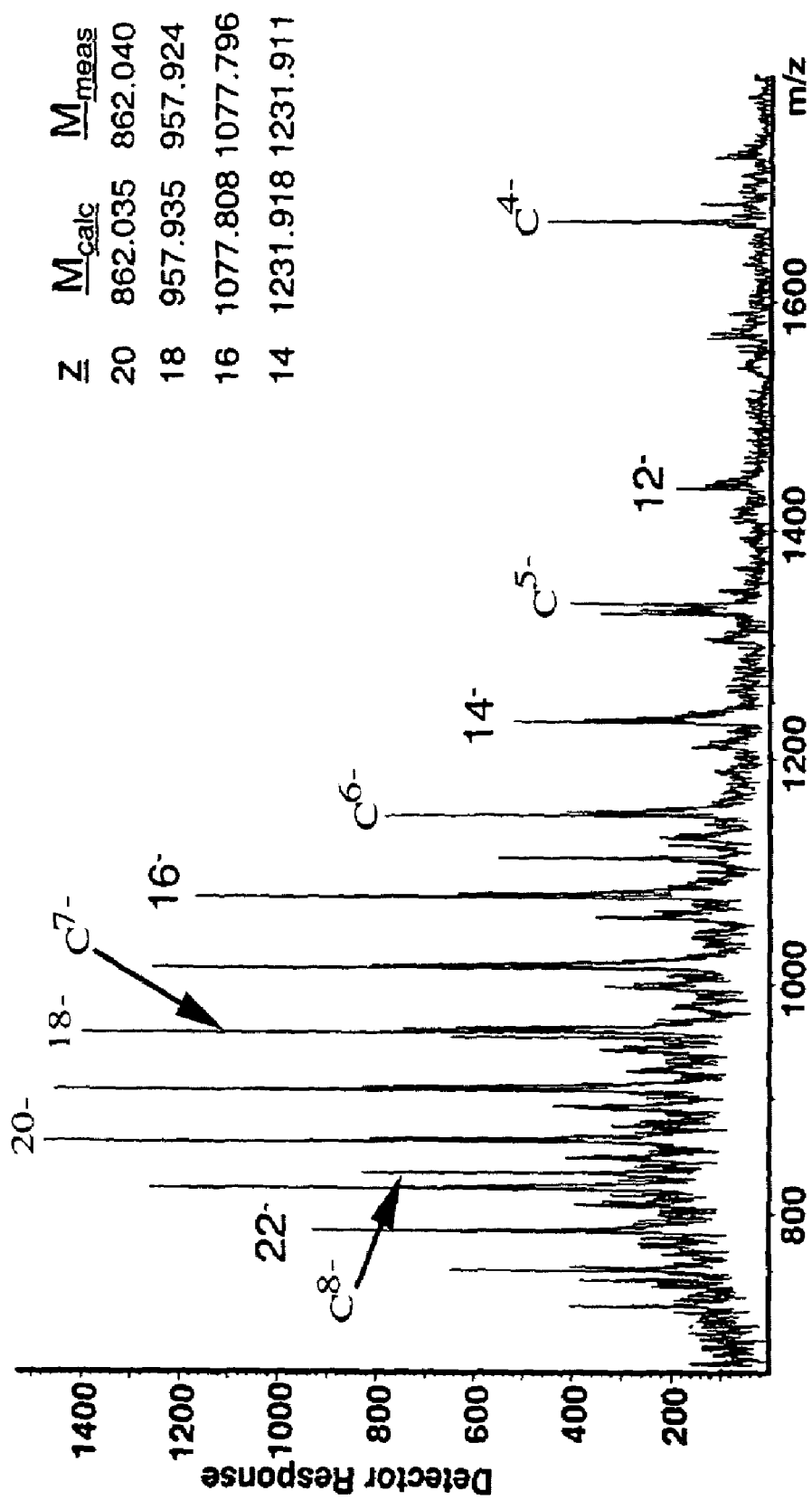
FIG. 8 is an ESI-TOF of *Bacillus anthracis* spore coat protein sspE 56mer plus calibrant. The signals unambiguously identify *B. anthracis* versus other Bacillus species.

The mass measurement accuracy that can be obtained using an internal mass standard in the ESI-MS study of PCR products is shown in FIG. 8. The mass standard was a 20-mer phosphorothioate oligonucleotide added to a solution containing a 56-mer PCR product from the *B. anthracis* spore coat protein sspE. The mass of the expected PCR product easily distinguish the two strands. The $[M-21H^+]^{21-}$ and $[M-20H+]^{20-}$ charge states are shown.

Example 8

ESI-FTICR-MS of Synthetic *B. anthracis* 16S_1337 46 Base Pair Duplex

Figure 10:
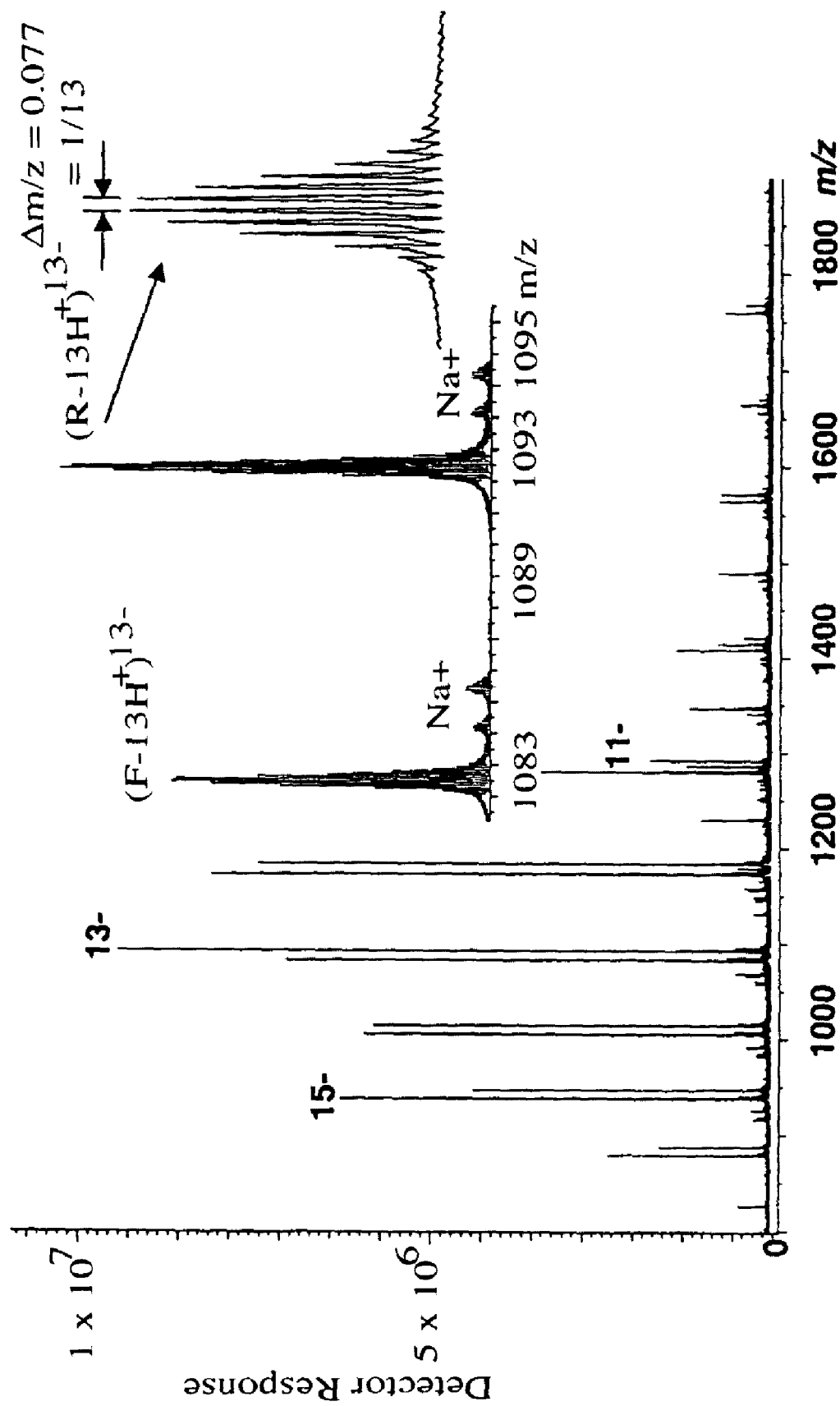
FIG. 10 is an ESI-FTICR-MS of a synthetic *B. anthracis* 16S_1337 46 base pair duplex.

An ESI-FTICR-MS spectrum was obtained from an aqueous solution containing 5 μM each of synthetic analogs of the expected forward and reverse PCR products from the nucleotide 1337 region of the *B. anthracis* 16S rRNA gene. The results (FIG. 10) show that the molecular weights of the strands can be distinguished by this method. The $[M-16H^+]^{16-}$ through $[M-10H^+]^{10-}$ charge states are shown. The insert highlights the resolution that can be realized on the FTICR-MS instrument, which allows the charge state of the ion to be determined from the mass difference between peaks differing by a single 13C substitution.

Example 9

Figure 11:
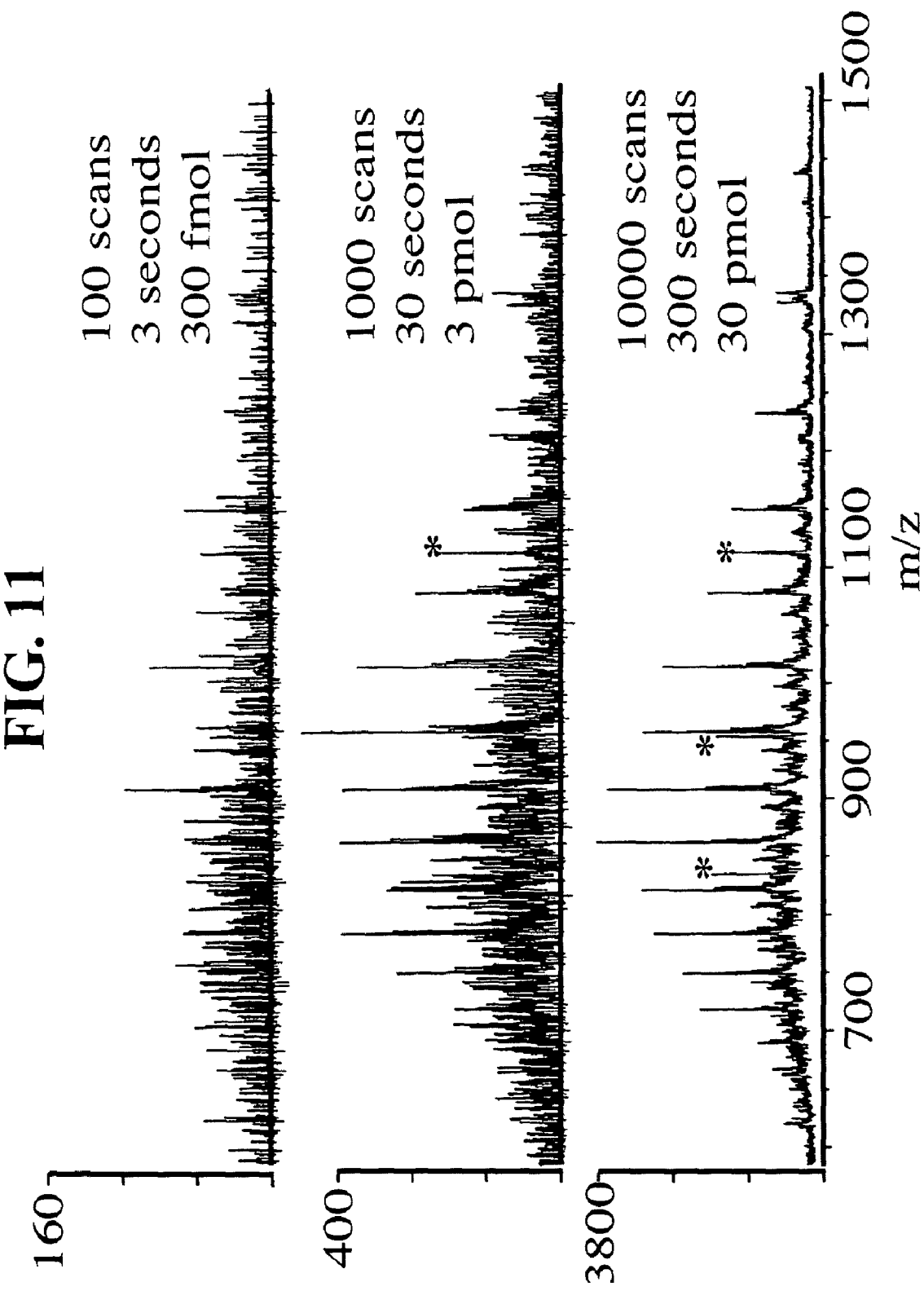
FIG. 11 is an ESI-TOF-MS of a 56mer oligonucleotide (3 scans) from the *B. anthracis* saspB gene with an internal mass standard. The internal mass standards are designated by asterisks.

ESI-TOF MS of 56-mer Oligonucleotide from saspB Gene of *B. anthracis* with Internal Mass Standard ESI-TOF MS spectra were obtained on a synthetic 56-mer oligonucleotide (5 μM) from the saspB gene of *B. anthracis* containing an internal mass standard at an ESI of 1.7 μL/min as a function of sample consumption. The results (FIG. 11)

show that the signal to noise is improved as more scans are summed, and that the standard and the product are visible after only 100 scans.

Example 10

Figure 12:
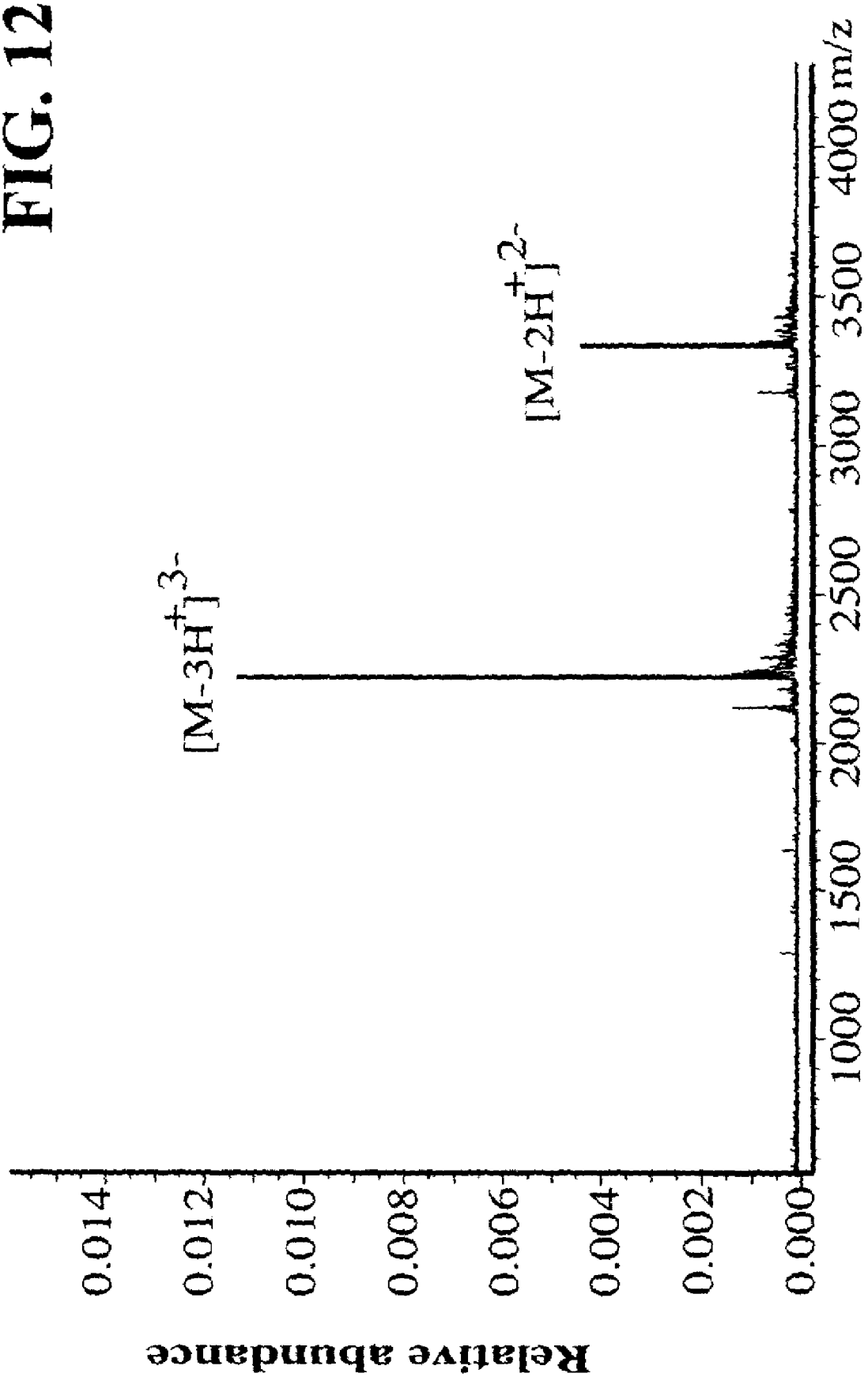
FIG. 12 is an ESI-TOF-MS of an internal standard with 5 mM TBA-TFA buffer showing that charge stripping with tributylammonium trifluoroacetate reduces the most abundant charge state from [M-8H+]8− to [M-3H+]3−.
Figure 13:
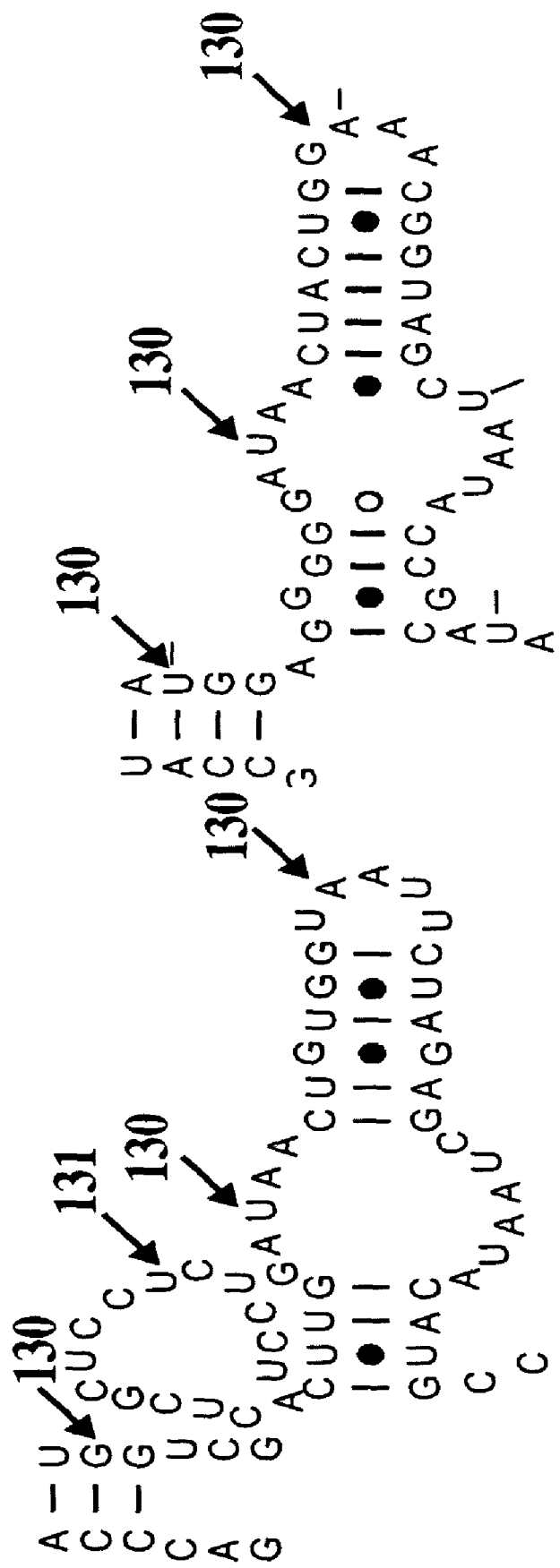
FIG. 13 is a portion of a secondary structure defining database according to one embodiment of the present invention, where two examples of selected sequences are displayed graphically thereunder.
Figure 14:
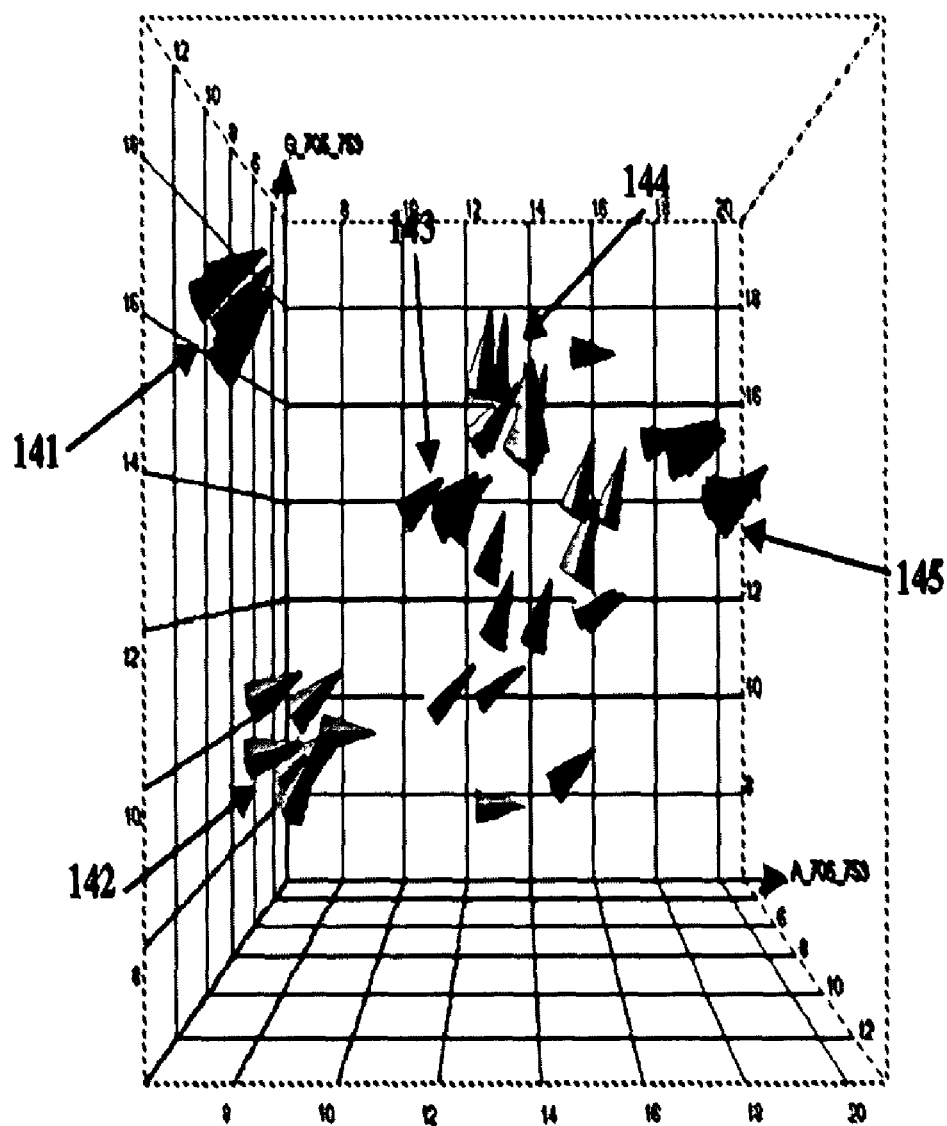
FIG. 14 is a three dimensional graph demonstrating the grouping of sample molecular weight according to species.
Figure 15:
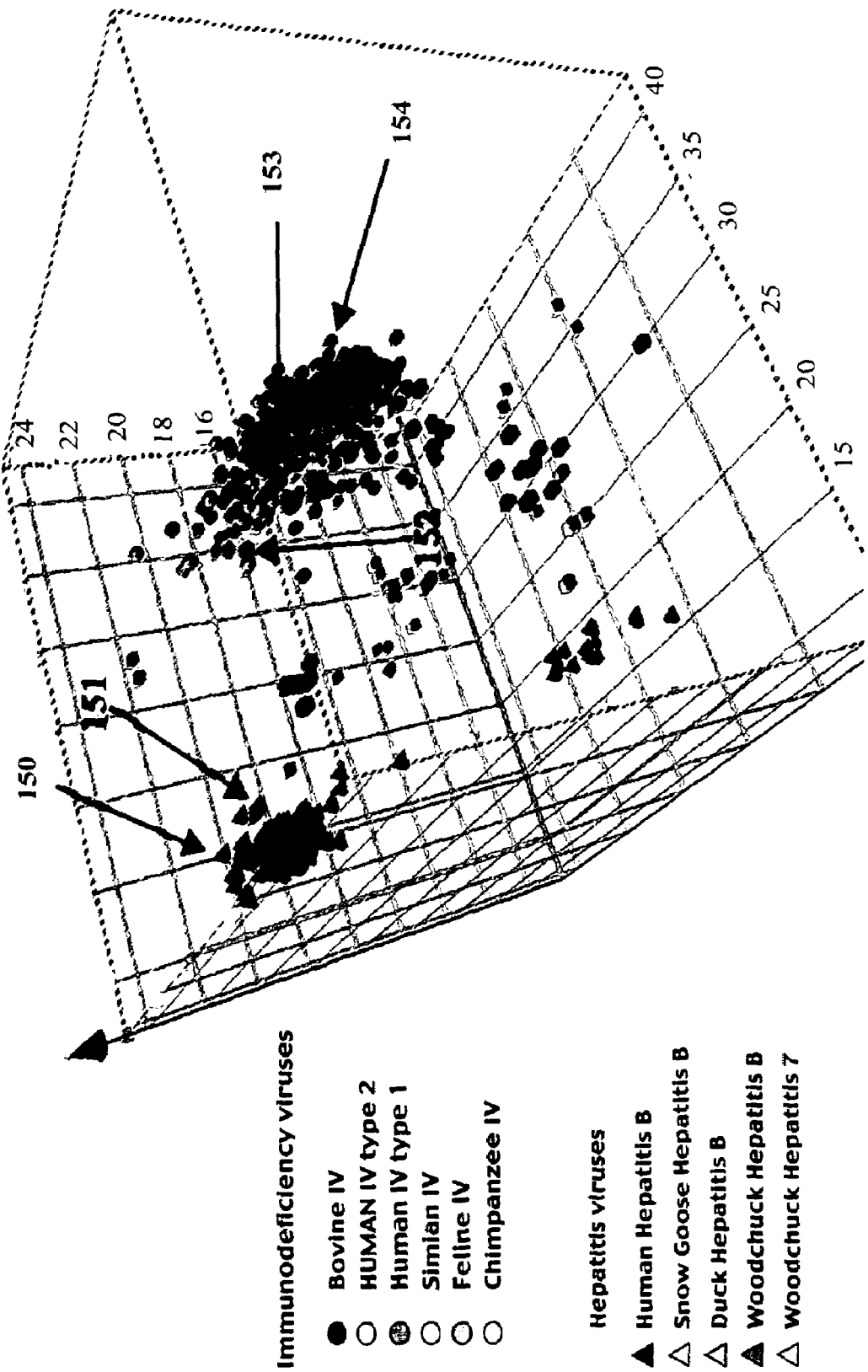
FIG. 15 is a three dimensional graph demonstrating the grouping of sample molecular weights according to species of virus and mammal infected.
Figure 16:
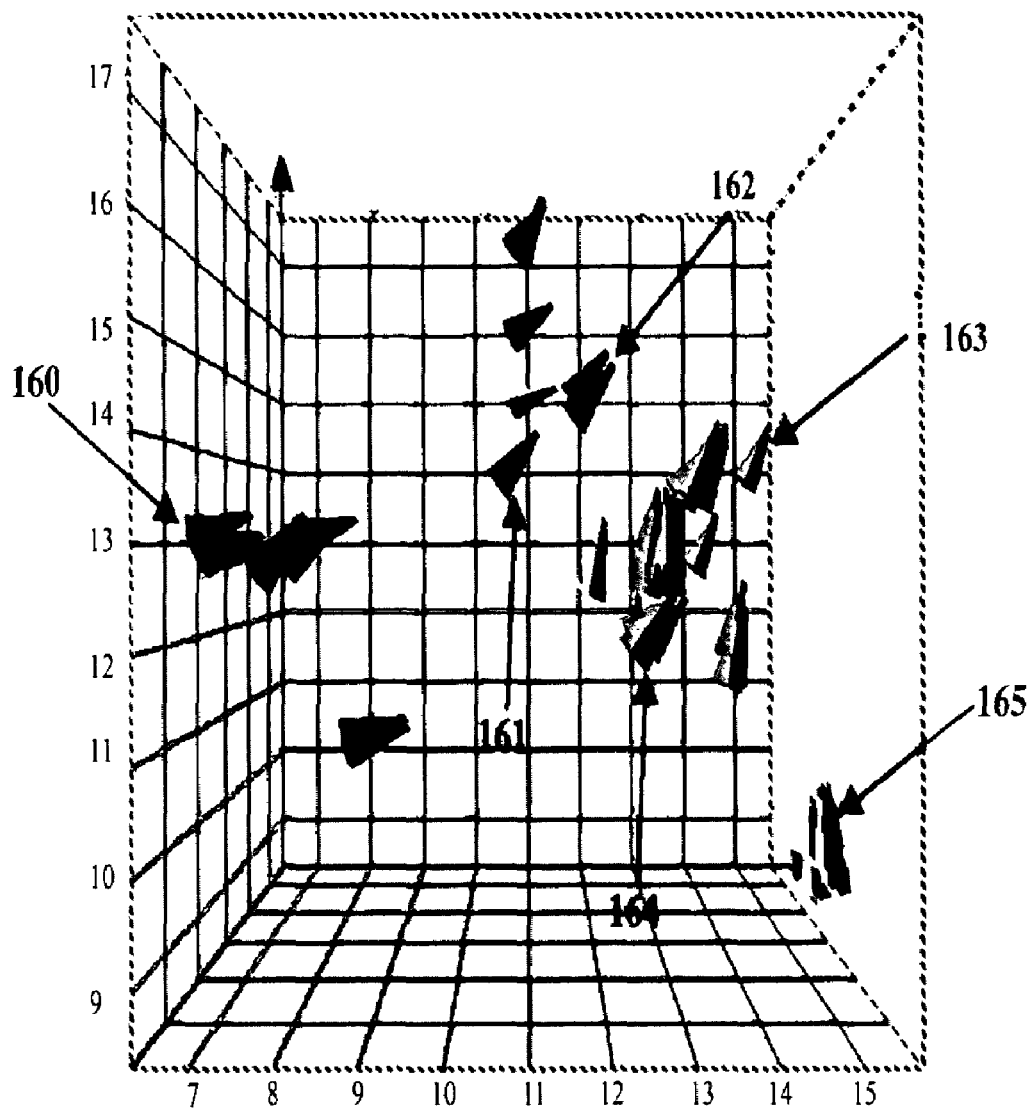
FIG. 16 is a three dimensional graph demonstrating the grouping of sample molecular weights according to species of virus, and animal-origin of infectious agent.
Figure 17:
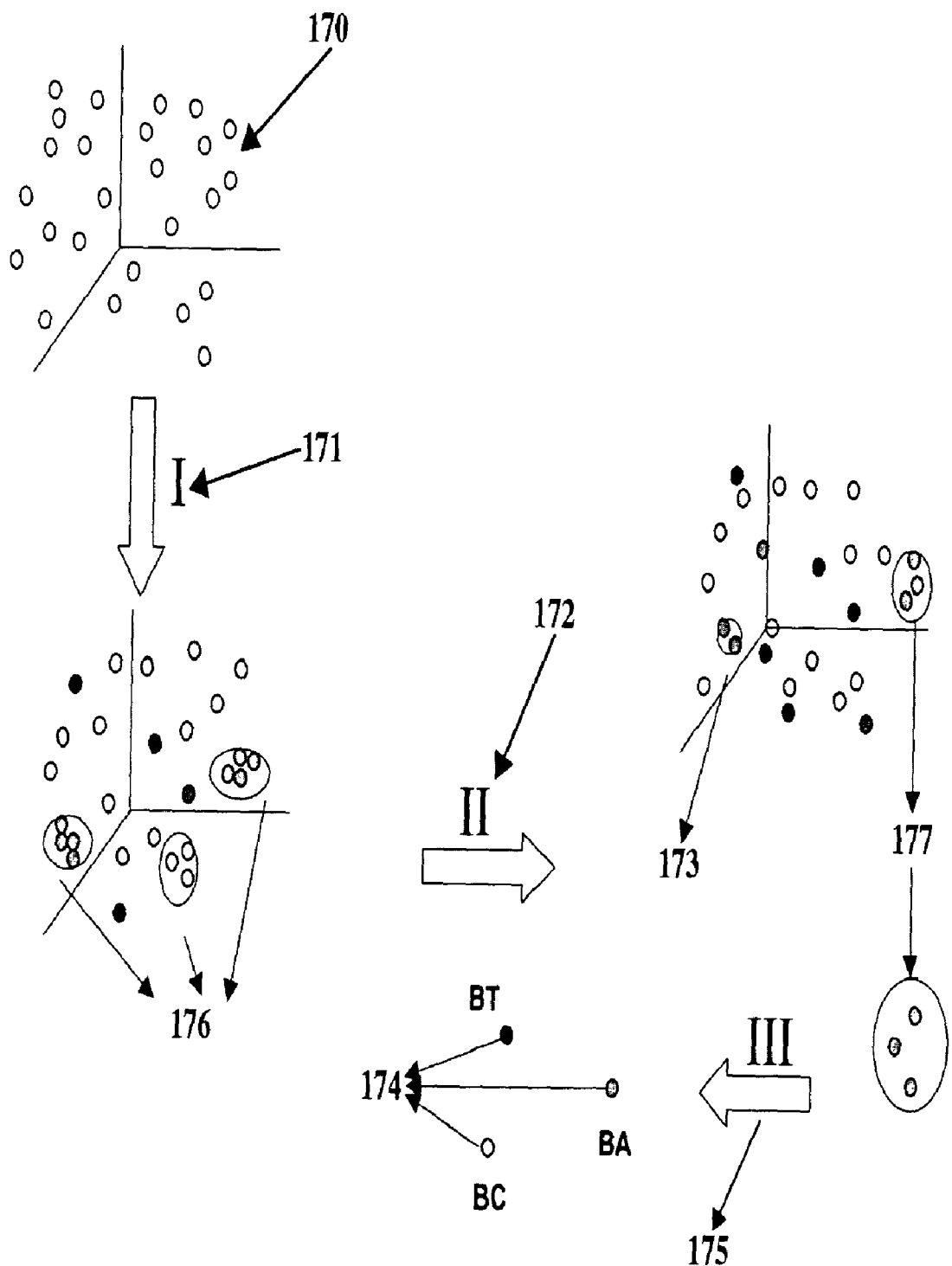
FIG. 17 is a figure depicting how the triangulation method of the present invention provides for the identification of an unknown bioagent without prior knowledge of the unknown agent. The use of different primer sets to distinguish and identify the unknown is also depicted as primer sets I, II and III within this figure. A three dimensional graph depicts all of bioagent space (170), including the unknown bioagent, which after use of primer set I (171) according to a method according to the present invention further differentiates and classifies bioagents according to major classifications (176) which, upon further analysis using primer set II (172) differentiates the unknown agent (177) from other, known agents (173) and finally, the use of a third primer set (175) further specifies subgroups within the family of the unknown (174).

ESI-TOF MS of an Internal Standard with Tributylammonium (TBA)-trifluoroacetate (TFA) Buffer An ESI-TOF-MS spectrum of a 20-mer phosphorothioate mass standard was obtained following addition of 5 mM TBA-TFA buffer to the solution. This buffer strips charge from the oligonucleotide and shifts the most abundant charge state from $[M-8H^+]^{8-}$ to $[M-3H^+]^{3-}$ (FIG. 12).

Example 11

Master Database Comparison

The molecular masses obtained through Examples 1-10 are compared to molecular masses of known bioagents stored in a master database to obtain a high probability matching molecular mass.

Example 12

Master Data Base Interrogation over the Internet

The same procedure as in Example 11 is followed except that the local computer did not store the Master database. The Master database is interrogated over an internet connection, searching for a molecular mass match.

Example 13

Master Database Updating

The same procedure as in example 11 is followed except the local computer is connected to the internet and has the ability to store a master database locally. The local computer system periodically, or at the user's discretion, interrogates the Master database, synchronizing the local master database with the global Master database. This provides the current molecular mass information to both the local database as well as to the global Master database. This further provides more of a globalized knowledge base.

Example 14

Global Database Updating

The same procedure as in example 13 is followed except there are numerous such local stations throughout the world. The synchronization of each database adds to the diversity of information and diversity of the molecular masses of known bioagents.

Example 15

Biochemical Processing of Large Amplification Products for Analysis by Mass Spectrometry In the example illustrated in FIG. 18, a primer pair which amplifies a 986 bp region of the 16S ribosomal gene in *E. coli* (K12) was digested with a mixture of 4 restriction enzymes: BstNI, BsmFI, BfaI, and NcoI. FIG. 18(*a*) illustrates the complexity of the resulting ESI-FTICR mass spectrum which contains multiple charge states of multiple restriction fragments. Upon mass deconvolution to neutral mass, the spectrum is significantly simplified and discrete oligonucleotide pairs are evident (FIG. 18(*b*)). When base compositions are derived from the masses of the restriction fragments, perfect agreement is observed for the known sequence of nucleotides 1-856 (FIG. 18(*c*); the batch of NcoI enzyme used in this experiment was inactive and resulted in a missed cleavage site and a 197-mer fragment went undetected as it is outside the mass range of the mass spectrometer under the conditions employed. Interestingly however, both a forward and reverse strand were detected for each fragment measured (solid and dotted lines in, respectively) within 2 ppm of the predicted molecular weights resulting in unambiguous determination of the base composition of 788 nucleotides of the 985 nucleotides in the amplicon. The coverage map offers redundant coverage as both 5' to 3' and 3' to 5' fragments are detected for fragments covering the first 856 nucleotides of the amplicon.

This approach is in many ways analogous to those widely used in MS-based proteomics studies in which large intact proteins are digested with trypsin, or other proteolytic enzyme(s), and the identity of the protein is derived by comparing the measured masses of the tryptic peptides with theoretical digests. A unique feature of this approach is that the precise mass measurements of the complementary strands of each digest product allow one to derive a de novo base composition for each fragment, which can in turn be "stitched together" to derive a complete base composition for the larger amplicon. An important distinction between this approach and a gel-based restriction mapping strategy is that, in addition to determination of the length of each fragment, an unambiguous base composition of each restriction fragment is derived. Thus, a single base substitution within a fragment (which would not be resolved on a gel) is readily observed using this approach. Because this study was performed on a 7 Tesla ESI-FTICR mass spectrometer, better than 2 ppm mass measurement accuracy was obtained for all fragments. Interestingly, calculation of the mass measurement accuracy required to derive unambiguous base compositions from the complementary fragments indicates that the highest mass measurement accuracy actually required is only 15 ppm for the 139 bp fragment (nucleotides 525-663). Most of the fragments were in the 50-70 bp size-range which would require mass accuracy of only ~50 ppm for unambiguous base composition determination. This level of performance is achievable on other more compact, less expensive MS platforms such as the ESI-TOF suggesting that the methods developed here could be widely deployed in a variety of diagnostic and human forensic arenas.

This example illustrates an alternative approach to derive base compositions from larger PCR products. Because the amplicons of interest cover many strain variants, for some of which complete sequences are not known, each amplicon can be digested under several different enzymatic conditions to ensure that a diagnostically informative region of the amplicon is not obscured by a "blind spot" which arises from a mutation in a restriction site. The extent of redundancy required to confidently map the base composition of amplicons from different markers, and determine which set of restriction enzymes should be employed and how they are most effectively used as mixtures can be determined. These parameters will be dictated by the extent to which the area of interest is conserved across the amplified region, the compatibility of the various restriction enzymes with respect to digestion protocol (buffer, temperature, time) and the degree of coverage required to discriminate one amplicon from another.

Example 16

Analysis of 10 Human Blood Mitochondrial DNA Samples Provided by the FBI

Ten different samples of human DNA provided by the FBI were subjected to rapid mtDNA analysis by the method of the present invention. Intelligent primers (SEQ ID NOs: 8-17 in Table 8) were selected to amplify portions of HVR1 and HVR2. Additional intelligent primers were designed to mtDNA regions other than HVR1 and HVR2 (SEQ ID NOs: 18-43). The primers described below are generally 10-50 nucleotides in length, 15-35 nucleotides in length, or 18-30 nucleotides in length.

TABLE 8

Intelligent Primer Pairs for Analysis of mtDNA

| Primer Pair Name | Forward Primer Sequence | Forward SEQ ID NO: | Reverse Primer Sequence | Reverse SEQ ID NO: |
|---|---|---|---|---|
| HMTHV2_AND RSN_76_353_ TMOD | TCACGCGATAGCATTGCG | 8 | TGGTTTGGCAGAGATGTGTTTA AGT | 9 |
| HMTHV2_AND RSN_29_429_ TMOD | TCTCACGGGAGCTCTCCATGC | 10 | TCTGTTAAAAGTGCATACCGCC A | 11 |
| HMTHV1_AND RSN_16065_ 16410_TMOD | TGACTCACCCATCAACAACCGC | 12 | TGAGGATGGTGGTCAAGGGAC | 13 |
| HMTHV1_AND RSN_16065_ 16354_TMOD | TGACTCACCCATCAACAACCGC | 14 | TGGATTTGACTGTAATGTGCTA | 15 |
| HMTHV1_AND RSN_16064_ 16359 | TGACTCACCCATCAACAACCGC | 16 | TGAAGGGATTTGACTGTAATGT GCTATG | 17 |
| HMT_ASN_16 036_522 | GAAGCAGATTTGGGTACCACC | 18 | GTGTGTGTGCTGGGTAGGATG | 19 |
| HMT_ASN_81 62_8916 | TACGGTCAATGCTCTGAAATCT GTGG | 20 | TGGTAAGAAGTGGGCTAGGGCA TT | 21 |
| HMT_ASN_12 438_13189 | TTATGTAAAATCCATTGTCGCA TCCACC | 22 | TGGTGATAGCGCCTAAGCATAG TG | 23 |
| HMT_ASN_14 629_15353 | TCCCATTACTAAACCCACACTC AACAG | 24 | TTTCGTGCAAGAATAGGAGGTG GAG | 25 |
| HMT_ASN_94 35_10188 | TAAGGCCTTCGATACGGGATAA TCCTA | 26 | TAGGGTCGAAGCCGCACTCG | 27 |
| HMT_ASN_10 753_11500 | TACTCCAATGCTAAAACTAATC GTCCCAAC | 28 | TGTGAGGCGTATTATACCATAG CCG | 29 |
| HMT_ASN_15 369_16006 | TCCTAGGAATCACCTCCCATTC CGA | 30 | TAGAATCTTAGCTTTGGGTGCT AATGGTG | 31 |
| HMT_ASN_13 461_14206 | TGGCAGCCTAGCATTAGCAGGA ATA | 32 | TGGCTGAACATTGTTTGTTGGT GT | 33 |
| HMT_ASN_34 52_4210 | TCGCTGACGCCATAAAACTCTT CAC | 34 | TAAGTAATGCTAGGGTGAGTGG TAGGAAG | 35 |
| HMT_ASN_77 34_8493 | TAACTAATACTAACATCTCAGA CGCTCAGGA | 36 | TTTATGGGCTTTGGTGAGGGAG GTA | 37 |
| HMT_ASN_63 09_7058 | TACTCCCACCCTGGAGCCTC | 38 | TGCTCCTATTGATAGGACATAG TGGAAGTG | 39 |
| HMT_ASN_76 44_8371 | TTATCACCTTTCATGATCACGC CCT | 40 | TGGCATTTCACTGTAAAGAGGT GTTGG | 41 |
| HMT_ASN_26 26_3377 | TGTATGAATGGCTCCACGAGGG T | 42 | TCGGTAAGCATTAGGAATGCCA TTGC | 43 |

Figure 19:
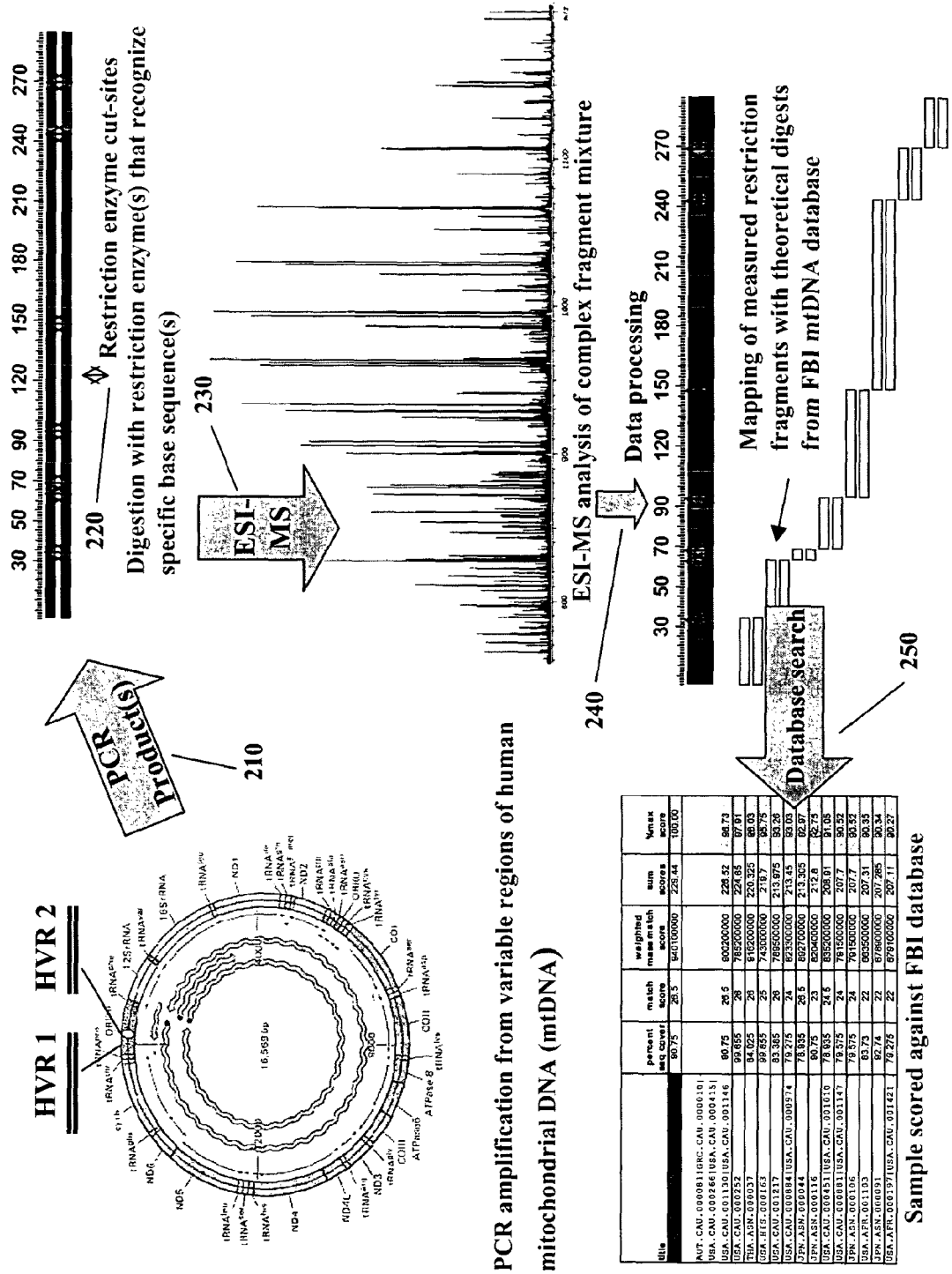
FIG. 19 indicates the process of mtDNA analysis. After amplification by PCR (210), the PCR products were subjected to restriction digests (220) with RsaI for HVR1 and a combination of HpaII, HpyCH4IV, PacI and EaeI for HVR2 in order to obtain amplicon segments suitable for analysis by FTICR-MS (240). The data were processed to obtain mass data for each amplicon segment (250) which were then compared to the masses calculated for theoretical digests from the FBI mtDNA database by a scoring scheme (260).

The process of the analysis is shown in FIG. 19. After amplification by PCR (210), the PCR products were subjected to restriction digests (220) with RsaI for HVR1 and a combination of HpaII, HpyCH4IV, PacI and EaeI for HVR2 in order to obtain amplicon segments suitable for analysis by FTICR-MS (230). The data were processed to obtain mass data for each amplicon segment (240) which were then compared to the masses calculated for theoretical digests from the FBI mtDNA database by a scoring scheme (250). Digestion pattern matches were scored by the sum of (i) the percentage of expected complete digest fragments observed, (ii) the percentage of fragments with a "floating" percentage of potential incomplete digest fragments (to increase sensitivity for incomplete digestion—these are assigned lower weight), (iii) the percentage of the sequence covered by matched masses, (iv) the number of mass peaks accounted for in the theoretical database digest, and (v) the weighted score for matched peaks, weighted by their observed abundance. HVR1 and HVR2 scores were combined and all database entries were sorted by high score. Even in the absence of an exact match in the database, the majority of entries can be ruled out by observing a much lower match score than the maximum score. One with relevant skill in the art will recognize that development of such scoring procedures is can be accomplished without undue experimentation.

Figure 20A:
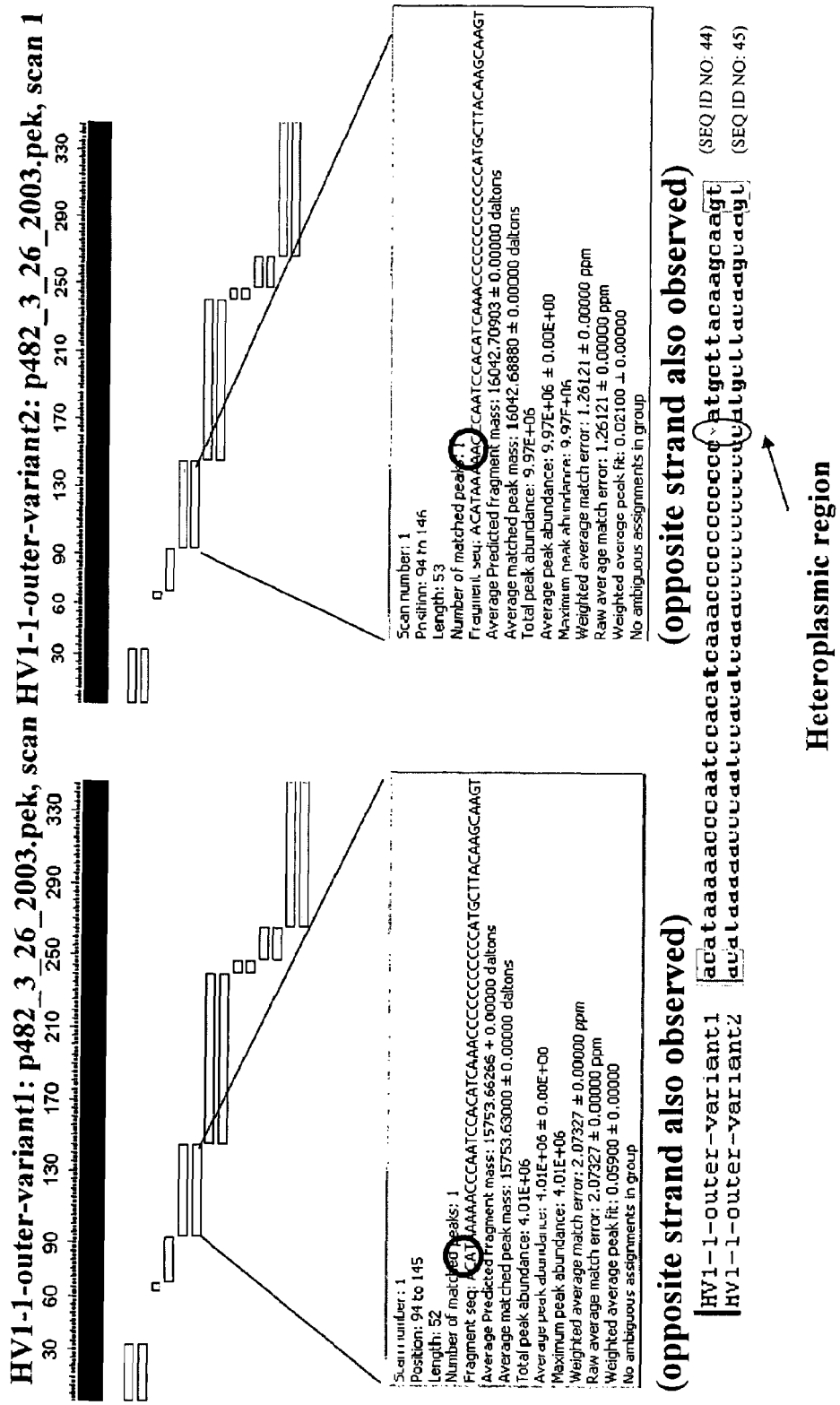
FIG. 20A indicates predicted and actual mass data with scoring parameters for length heteroplasmy (HVR1-1-outer-variants 1 and 2) in the digest segment from position 94 to 145 (variant 1)(SEQ ID NO:44)/146 (variant 2)(SEQ ID NO:45) are shown.

The results of analysis of sample 1 are shown in FIGS. 20A and 20B. In this example, the utility of mass determination of amplicon digest segments is indicated. In FIG. 20A, predicted and actual mass data with scoring parameters for length heteroplasmy (HV1-1-outer-variants 1 and 2) in the digest segment from position 94 to 145 (variant 1)/146 (variant 2) are shown. FIG. 20B indicates that, whereas sequencing fails to resolve the variants due to the length heteroplasmy, mass determination detects multiple species simultaneously and indicates abundance ratios. In this case, the ratio of variant 1 to variant 2 (short to long alleles) is 1:3. Thus, in addition to efficiency of characterization of individual digested amplicon fragments, the relative abundances of heteroplasmic variants can be determined.

Of the 10 samples analyzed by the present methods, 9 samples were verified as being consistent with members of the FBI database. The remaining sample could not be analyzed due to a failure of PCR to produce an amplification product.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety

What is claimed is:

1. A forensic method of mitochondrial DNA analysis comprising the steps of:
providing a forensic evidence sample;
amplifying two or more segments of mitochondrial DNA obtained from said forensic evidence sample to obtain two or more amplification products;
determining the molecular masses of said two or more amplification products by mass spectrometry, without sequencing said two or more amplification products; and
comparing said molecular masses of said two or more amplification products with at least one database comprising a plurality of known molecular masses from said two or more segments of mitochondrial DNA from a plurality of subjects, thereby reaching a forensic conclusion.

2. The forensic method of claim 1, further comprising digesting said two or more amplification products with one or more restriction enzymes to produce restriction fragments before said mass spectrometry.

3. The forensic method of claim 2, wherein said one or more restriction enzymes are selected from the group consisting of RsaI, HpaII, HpyCH4IV, PacI, and EaeI.

4. The forensic method of claim 2, further comprising determining the molecular masses of said restriction fragments by mass spectrometry, without sequencing said restriction fragments.

5. The forensic method of claim 2, further comprising comparing said molecular masses of said restriction fragments with at least one database comprising a plurality of known molecular masses from said two or more segments of mitochondrial DNA from a plurality of subjects, thereby reaching a forensic conclusion.

6. The forensic method of claim 1, wherein said subjects are animals.

7. The forensic method of claim 6, wherein said animals are humans.

8. The forensic method of claim 1, wherein said subjects are nonhuman eukaryotic organisms, fungi, parasites or protozoa.

9. The forensic method of claim 1, wherein said two or more segments of mitochondrial DNA comprise a portion of a hypervariable region of mitochondrial DNA.

10. The forensic method of claim 9, wherein said hypervariable region comprises at least one of HVR1 or HVR2.

11. The forensic method of claim 1, wherein said two or more amplification products are generated from two or more hypervariable portions of the noncoding region of mitochondrial DNA using flanking primers.

12. The forensic method of claim 1, wherein said two or more segments of mitochondrial DNA comprise the entire mitochondrial DNA of said subject.

13. The forensic method of claim 1, wherein said forensic conclusion comprises identification of at least one subject from whom said forensic evidence sample is obtained by comparing said molecular masses of said two or more amplification products with said plurality of known molecular masses in said at least one database.

14. The forensic method of claim 13, wherein said forensic conclusion is the identification of a criminal.

15. The forensic method of claim 13, wherein said forensic conclusion is the identification of a crime victim.

16. The method of 1, further comprising determining the relative amounts of said one or more amplification products from the abundance of mass spectral peaks corresponding to said one or more amplification products.

17. The forensic method of claim 1, wherein said forensic conclusion further comprises determining the movement of at least one subject from whom said forensic evidence sample is obtained by mitochondrial DNA analysis of a plurality of forensic evidence samples obtained from a plurality of locations.

18. The forensic method of claim 1, wherein said mass spectrometry is electrospray Fourier transform ion cyclotron resonance mass spectrometry.

19. The forensic method of claim 1, wherein said at least one database is a Federal Bureau of Investigation mitochondrial DNA database.

20. A forensic method of mitochondrial DNA analysis comprising the steps of:
   providing a forensic evidence sample;
   amplifying two or more segments of mitochondrial DNA obtained from said forensic evidence sample to obtain two or more amplification products;
   determining the molecular masses of said two or more amplification products by mass spectrometry, without sequencing said two or more amplification products;
   calculating base compositions of said two or more amplification products from said molecular masses; and
   comparing said base compositions of said two or more amplification products with at least one database comprising a plurality of known base compositions from said two or more segments of mitochondrial DNA from a plurality of subjects, thereby reaching a forensic conclusion.

21. The forensic method of claim 20, further comprising digesting said two or more amplification products with one or more restriction enzymes to produce restriction fragments before said mass spectrometry.

22. The forensic method of claim 21, wherein said one or more restriction enzymes are selected from the group consisting of RsaI , HpaII, HpyCH4IV, PacI, and EaeI.

23. The forensic method of claim 21, further comprising determining the base compositions of said restriction fragments by mass spectrometry, without sequencing said restriction fragments.

24. The forensic method of claim 21, further comprising comparing said base compositions of said restriction fragments with at least one database comprising a plurality of known base compositions from said two or more segments of mitochondrial DNA from a plurality of subjects, thereby reaching a forensic conclusion.

25. The forensic method of claim 20, wherein said subjects are animals.

26. The forensic method of claim 25, wherein said animals are humans.

27. The forensic method of claim 20, wherein said subjects are nonhuman eukaryotic organisms, fungi, parasites or protozoa.

28. The forensic method of claim 20, wherein said two or more segments of mitochondrial DNA comprise a portion of a hypervariable region of mitochondrial DNA.

29. The forensic method of claim 28, wherein said hypervariable region comprises at least one of HVR1 or HVR2.

30. The forensic method of claim 20, wherein said two or more amplification products are generated from two hypervariable portions of the noncoding region of mitochondrial DNA using flanking primers.

31. The forensic method of claim 20, wherein said two or more segments of mitochondrial DNA comprise the entire mitochondrial DNA of said subject.

32. The forensic method of claim 20, wherein said forensic conclusion comprises identification of at least one subject from whom said forensic evidence sample is obtained by comparing said molecular masses of said two or more amplification products with said plurality of known molecular masses in said at least one database.

33. The forensic method of claim 32, wherein said forensic conclusion is the identification of a criminal.

34. The forensic method of claim 32, wherein said forensic conclusion is the identification of a crime victim.

35. The method of 20, further comprising determining the relative amounts of said two or more amplification products from the abundance of mass spectral peaks corresponding to said two or more amplification products.

36. The forensic method of claim 20, wherein said forensic conclusion further comprises determining the movement of at least one subject from whom said forensic evidence sample is obtained by mitochondrial DNA analysis of a plurality of forensic evidence samples obtained from a plurality of locations.

37. The forensic method of claim 20, wherein said mass spectrometry is electrospray Fourier transform ion cyclotron resonance mass spectrometry.

38. The forensic method of claim 20, wherein said at least one database is a Federal Bureau of Investigation mitochondrial DNA database.

39. A method of characterizing heteroplasmy of two or more segments of mitochondrial DNA of a subject comprising the steps of:
   providing a sample from said subject;
   amplifying said two or more segments of mitochondrial DNA from said sample with two or more primer pairs to obtain a plurality of amplification products;
   determining molecular masses of said plurality of amplification products by mass spectrometry, without sequencing said plurality of amplification products; and
   determining base compositions of said plurality of amplification products thereby characterizing said heteroplasmy.

40. The method of claim 39, wherein said heteroplasmy is selected from the group consisting of length heteroplasmy, nucleotide polymorphism heteroplasmy, or both length heteroplasmy and nucleotide polymorphism heteroplasmy.

41. The method of claim 39, further comprising obtaining a plurality of samples of mitochondrial DNA from said subject at different ages of the individual, wherein the characterization of heteroplasmy indicates the rate of naturally occurring mutations in mitochondrial DNA.

42. The method of claim 39, further comprising comparing said heteroplasmy in said two or more segments of mitochondrial DNA from said sample with at least one database comprising a plurality of base compositions from said two or more segments of mitochondrial DNA from a plurality of subjects with one or more mitochondrial diseases, wherein said comparing correlates said heteroplasmy with the onset of said one or more mitochondrial diseases in a subject.

43. The method of claim 42, wherein said one or more mitochondrial diseases are selected from the group consisting of Alpers Disease, Barth syndrome, Beta-oxidation Defects, Carnitine-Acyl-Carnitine Deficiency, Carnitine Deficiency, Co-Enzyme Q10 Deficiency, Complex I Deficiency, Complex II Deficiency, Complex III Deficiency, Complex IV Deficiency, Complex V Deficiency, COX Deficiency, CPEO, CPT I Deficiency, CPT II Deficiency, Glutaric Aciduria Type II, KSS, Lactic Acidosis, LCAD, LCHAD, Leigh Disease or Syndrome, LHON, Lethal Infantile Cardiomyopathy, Luft Disease, MAD, MCA, MELAS, MERRF, Mitochondrial Cytopathy, Mitochondrial DNA Depletion, Mitochondrial Encephalopathy, Mitochondrial Myopathy, MNGIE, NARP, Pearson Syndrome, Pyruvate Carboxylase Deficiency, Pyruvate Dehydrogenase Deficiency, Respiratory Chain, SCAD, SCHAD, or VLCAD.

44. The method of claim 39, wherein said mass spectrometry is electrospray Fourier transform ion cyclotron resonance mass spectrometry.

45. The method of claim 39, wherein said sample from said subject is a forensic evidence sample.

46. The forensic method of claim 1, wherein said forensic conclusion comprises identification of a missing person, detection and identification of a known bioagent, detection and identification of an unknown bioagent, elimination of an individual as a crime suspect, identification of an individual as a crime suspect, identification of a location as a crime scene, identification of a location as an accident scene, identification of evidence useful in a court of law, identification of evidence useful in a criminal investigation, or identification of one or more biological samples from a crime scene.

47. The forensic method of claim 20, wherein said forensic conclusion comprises identification of a missing person, detection and identification of a known bioagent, detection and identification of an unknown bioagent, elimination of an individual as a crime suspect, identification of an individual as a crime suspect, identification of a location as a crime scene, identification of a location as an accident scene, identification of evidence useful in a court of law, identification of evidence useful in a criminal investigation, or identification of one or more biological samples from a crime scene.

\* \* \* \* \*

```
                         SEQUENCE LISTING

<160> NUMBER OF SEQ ID NOS: 47

<210> SEQ ID NO 1
<211> LENGTH: 90
<212> TYPE: RNA
<213> ORGANISM: Bacillus anthracis
<220> FEATURE:
<221> NAME/KEY: misc_feature
<222> LOCATION: (20)..(20)
<223> OTHER INFORMATION: N = A, U, G or C

<400> SEQUENCE: 1
gcgaagaacc uuaccaggun uugacauccu cugacaaccc uagagauagg gcuucuccuu      60
cgggagcaga gugacaggug gugcaugguu                                      90

<210> SEQ ID NO 2
<211> LENGTH: 90
<212> TYPE: RNA
<213> ORGANISM: Bacillus cereus

<400> SEQUENCE: 2
gcgaagaacc uuaccagguc uugacauccu cugaaaaccc uagagauagg gcuucuccuu      60
cgggagcaga gugacaggug gugcaugguu                                      90

<210> SEQ ID NO 3
<211> LENGTH: 1542
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 16S rRNA consensus sequence
<220> FEATURE:
<221> NAME/KEY: misc_feature
<222> LOCATION: (1)..(7)
<223> OTHER INFORMATION: N= A, U, G or C
<220> FEATURE:
```

```
<221> NAME/KEY: misc_feature
<222> LOCATION: (19)..(19)
<223> OTHER INFORMATION: N= A, U, G or C
<220> FEATURE:
<221> NAME/KEY: misc_feature
<222> LOCATION: (28)..(30)
<223> OTHER INFORMATION: N= A, U, G or C
<220> FEATURE:
<221> NAME/KEY: misc_feature
<222> LOCATION: (43)..(45)
<223> OTHER INFORMATION: N= A, U, G or C
<220> FEATURE:
<221> NAME/KEY: misc_feature
<222> LOCATION: (48)..(48)
<223> OTHER INFORMATION: N= A, U, G or C
<220> FEATURE:
<221> NAME/KEY: misc_feature
<222> LOCATION: (50)..(50)
<223> OTHER INFORMATION: N= A, U, G or C
<220> FEATURE:
<221> NAME/KEY: misc_feature
<222> LOCATION: (52)..(52)
<223> OTHER INFORMATION: N= A, U, G or C
<220> FEATURE:
<221> NAME/KEY: misc_feature
<222> LOCATION: (66)..(66)
<223> OTHER INFORMATION: N= A, U, G or C
<220> FEATURE:
<221> NAME/KEY: misc_feature
<222> LOCATION: (69)..(100)
<223> OTHER INFORMATION: N= A, U, G or C
<220> FEATURE:
<221> NAME/KEY: misc_feature
<222> LOCATION: (103)..(103)
<223> OTHER INFORMATION: N= A, U, G or C
<220> FEATURE:
<221> NAME/KEY: misc_feature
<222> LOCATION: (107)..(108)
<223> OTHER INFORMATION: N= A, U, G or C
<220> FEATURE:
<221> NAME/KEY: misc_feature
<222> LOCATION: (121)..(122)
<223> OTHER INFORMATION: N= A, U, G or C
<220> FEATURE:
<221> NAME/KEY: misc_feature
<222> LOCATION: (124)..(124)
<223> OTHER INFORMATION: N= A, U, G or C
<220> FEATURE:
<221> NAME/KEY: misc_feature
<222> LOCATION: (126)..(129)
<223> OTHER INFORMATION: N= A, U, G or C
<220> FEATURE:
<221> NAME/KEY: misc_feature
<222> LOCATION: (131)..(132)
<223> OTHER INFORMATION: N= A, U, G or C
<220> FEATURE:
<221> NAME/KEY: misc_feature
<222> LOCATION: (134)..(134)
<223> OTHER INFORMATION: N= A, U, G or C
<220> FEATURE:
<221> NAME/KEY: misc_feature
<222> LOCATION: (137)..(145)
<223> OTHER INFORMATION: N= A, U, G or C
<220> FEATURE:
<221> NAME/KEY: misc_feature
<222> LOCATION: (148)..(148)
<223> OTHER INFORMATION: N= A, U, G or C
<220> FEATURE:
<221> NAME/KEY: misc_feature
<222> LOCATION: (150)..(150)
<223> OTHER INFORMATION: N= A, U, G or C
<220> FEATURE:
<221> NAME/KEY: misc_feature
<222> LOCATION: (152)..(158)
<223> OTHER INFORMATION: N= A, U, G or C
<220> FEATURE:
<221> NAME/KEY: misc_feature
<222> LOCATION: (163)..(169)
<223> OTHER INFORMATION: N= A, U, G or C
```

-continued

```
<220> FEATURE:
<221> NAME/KEY: misc_feature
<222> LOCATION: (177)..(178)
<223> OTHER INFORMATION: N= A, U, G or C
<220> FEATURE:
<221> NAME/KEY: misc_feature
<222> LOCATION: (181)..(194)
<223> OTHER INFORMATION: N= A, U, G or C
<220> FEATURE:
<221> NAME/KEY: misc_feature
<222> LOCATION: (199)..(226)
<223> OTHER INFORMATION: N= A, U, G or C
<220> FEATURE:
<221> NAME/KEY: misc_feature
<222> LOCATION: (229)..(237)
<223> OTHER INFORMATION: N= A, U, G or C
<220> FEATURE:
<221> NAME/KEY: misc_feature
<222> LOCATION: (239)..(242)
<223> OTHER INFORMATION: N= A, U, G or C
<220> FEATURE:
<221> NAME/KEY: misc_feature
<222> LOCATION: (245)..(245)
<223> OTHER INFORMATION: N= A, U, G or C
<220> FEATURE:
<221> NAME/KEY: misc_feature
<222> LOCATION: (248)..(248)
<223> OTHER INFORMATION: N= A, U, G or C
<220> FEATURE:
<221> NAME/KEY: misc_feature
<222> LOCATION: (250)..(250)
<223> OTHER INFORMATION: N= A, U, G or C
<220> FEATURE:
<221> NAME/KEY: misc_feature
<222> LOCATION: (257)..(258)
<223> OTHER INFORMATION: N= A, U, G or C
<220> FEATURE:
<221> NAME/KEY: misc_feature
<222> LOCATION: (264)..(264)
<223> OTHER INFORMATION: N= A, U, G or C
<220> FEATURE:
<221> NAME/KEY: misc_feature
<222> LOCATION: (268)..(269)
<223> OTHER INFORMATION: N= A, U, G or C
<220> FEATURE:
<221> NAME/KEY: misc_feature
<222> LOCATION: (276)..(276)
<223> OTHER INFORMATION: n is a, c, g, or u
<220> FEATURE:
<221> NAME/KEY: misc_feature
<222> LOCATION: (278)..(280)
<223> OTHER INFORMATION: N= A, U, G or C
<220> FEATURE:
<221> NAME/KEY: misc_feature
<222> LOCATION: (283)..(286)
<223> OTHER INFORMATION: N= A, U, G or C
<220> FEATURE:
<221> NAME/KEY: misc_feature
<222> LOCATION: (291)..(291)
<223> OTHER INFORMATION: N= A, U, G or C
<220> FEATURE:
<221> NAME/KEY: misc_feature
<222> LOCATION: (293)..(294)
<223> OTHER INFORMATION: N= A, U, G or C
<220> FEATURE:
<221> NAME/KEY: misc_feature
<222> LOCATION: (303)..(304)
<223> OTHER INFORMATION: N= A, U, G or C
<220> FEATURE:
<221> NAME/KEY: misc_feature
<222> LOCATION: (306)..(307)
<223> OTHER INFORMATION: N= A, U, G or C
<220> FEATURE:
<221> NAME/KEY: misc_feature
<222> LOCATION: (309)..(309)
<223> OTHER INFORMATION: N= A, U, G or C
<220> FEATURE:
<221> NAME/KEY: misc_feature
<222> LOCATION: (316)..(316)
```

```
<223> OTHER INFORMATION: N= A, U, G or C
<220> FEATURE:
<221> NAME/KEY: misc_feature
<222> LOCATION: (320)..(320)
<223> OTHER INFORMATION: N= A, U, G or C
<220> FEATURE:
<221> NAME/KEY: misc_feature
<222> LOCATION: (328)..(328)
<223> OTHER INFORMATION: N= A, U, G or C
<220> FEATURE:
<221> NAME/KEY: misc_feature
<222> LOCATION: (333)..(333)
<223> OTHER INFORMATION: N= A, U, G or C
<220> FEATURE:
<221> NAME/KEY: misc_feature
<222> LOCATION: (337)..(337)
<223> OTHER INFORMATION: N= A, U, G or C
<220> FEATURE:
<221> NAME/KEY: misc_feature
<222> LOCATION: (359)..(360)
<223> OTHER INFORMATION: N= A, U, G or C
<220> FEATURE:
<221> NAME/KEY: misc_feature
<222> LOCATION: (366)..(366)
<223> OTHER INFORMATION: N= A, U, G or C
<220> FEATURE:
<221> NAME/KEY: misc_feature
<222> LOCATION: (369)..(371)
<223> OTHER INFORMATION: N= A, U, G or C
<220> FEATURE:
<221> NAME/KEY: misc_feature
<222> LOCATION: (378)..(379)
<223> OTHER INFORMATION: N= A, U, G or C
<220> FEATURE:
<221> NAME/KEY: misc_feature
<222> LOCATION: (381)..(381)
<223> OTHER INFORMATION: N= A, U, G or C
<220> FEATURE:
<221> NAME/KEY: misc_feature
<222> LOCATION: (384)..(385)
<223> OTHER INFORMATION: N= A, U, G or C
<220> FEATURE:
<221> NAME/KEY: misc_feature
<222> LOCATION: (390)..(392)
<223> OTHER INFORMATION: N= A, U, G or C
<220> FEATURE:
<221> NAME/KEY: misc_feature
<222> LOCATION: (396)..(396)
<223> OTHER INFORMATION: N= A, U, G or C
<220> FEATURE:
<221> NAME/KEY: misc_feature
<222> LOCATION: (398)..(399)
<223> OTHER INFORMATION: N= A, U, G or C
<220> FEATURE:
<221> NAME/KEY: misc_feature
<222> LOCATION: (407)..(409)
<223> OTHER INFORMATION: N= A, U, G or C
<220> FEATURE:
<221> NAME/KEY: misc_feature
<222> LOCATION: (412)..(412)
<223> OTHER INFORMATION: N= A, U, G or C
<220> FEATURE:
<221> NAME/KEY: misc_feature
<222> LOCATION: (415)..(415)
<223> OTHER INFORMATION: N= A, U, G or C
<220> FEATURE:
<221> NAME/KEY: misc_feature
<222> LOCATION: (418)..(419)
<223> OTHER INFORMATION: N= A, U, G or C
<220> FEATURE:
<221> NAME/KEY: misc_feature
<222> LOCATION: (421)..(423)
<223> OTHER INFORMATION: N= A, U, G or C
<220> FEATURE:
<221> NAME/KEY: misc_feature
<222> LOCATION: (425)..(425)
<223> OTHER INFORMATION: N= A, U, G or C
<220> FEATURE:
<221> NAME/KEY: misc_feature
```

```
<222> LOCATION: (427)..(427)
<223> OTHER INFORMATION: N= A, U, G or C
<220> FEATURE:
<221> NAME/KEY: misc_feature
<222> LOCATION: (433)..(435)
<223> OTHER INFORMATION: N= A, U, G or C
<220> FEATURE:
<221> NAME/KEY: misc_feature
<222> LOCATION: (438)..(438)
<223> OTHER INFORMATION: N= A, U, G or C
<220> FEATURE:
<221> NAME/KEY: misc_feature
<222> LOCATION: (440)..(446)
<223> OTHER INFORMATION: N= A, U, G or C
<220> FEATURE:
<221> NAME/KEY: misc_feature
<222> LOCATION: (449)..(449)
<223> OTHER INFORMATION: N= A, U, G or C
<220> FEATURE:
<221> NAME/KEY: misc_feature
<222> LOCATION: (452)..(479)
<223> OTHER INFORMATION: N= A, U, G or C
<220> FEATURE:
<221> NAME/KEY: misc_feature
<222> LOCATION: (484)..(485)
<223> OTHER INFORMATION: N= A, U, G or C
<220> FEATURE:
<221> NAME/KEY: misc_feature
<222> LOCATION: (488)..(494)
<223> OTHER INFORMATION: N= A, U, G or C
<220> FEATURE:
<221> NAME/KEY: misc_feature
<222> LOCATION: (496)..(497)
<223> OTHER INFORMATION: N= A, U, G or C
<220> FEATURE:
<221> NAME/KEY: misc_feature
<222> LOCATION: (501)..(503)
<223> OTHER INFORMATION: N= A, U, G or C
<220> FEATURE:
<221> NAME/KEY: misc_feature
<222> LOCATION: (508)..(508)
<223> OTHER INFORMATION: N= A, U, G or C
<220> FEATURE:
<221> NAME/KEY: misc_feature
<222> LOCATION: (513)..(513)
<223> OTHER INFORMATION: N= A, U, G or C
<220> FEATURE:
<221> NAME/KEY: misc_feature
<222> LOCATION: (538)..(538)
<223> OTHER INFORMATION: N= A, U, G or C
<220> FEATURE:
<221> NAME/KEY: misc_feature
<222> LOCATION: (542)..(543)
<223> OTHER INFORMATION: N= A, U, G or C
<220> FEATURE:
<221> NAME/KEY: misc_feature
<222> LOCATION: (546)..(546)
<223> OTHER INFORMATION: N= A, U, G or C
<220> FEATURE:
<221> NAME/KEY: misc_feature
<222> LOCATION: (553)..(555)
<223> OTHER INFORMATION: N= A, U, G or C
<220> FEATURE:
<221> NAME/KEY: misc_feature
<222> LOCATION: (560)..(560)
<223> OTHER INFORMATION: N= A, U, G or C
<220> FEATURE:
<221> NAME/KEY: misc_feature
<222> LOCATION: (562)..(562)
<223> OTHER INFORMATION: N= A, U, G or C
<220> FEATURE:
<221> NAME/KEY: misc_feature
<222> LOCATION: (564)..(564)
<223> OTHER INFORMATION: N= A, U, G or C
<220> FEATURE:
<221> NAME/KEY: misc_feature
<222> LOCATION: (576)..(576)
<223> OTHER INFORMATION: N= A, U, G or C
<220> FEATURE:
```

-continued

```
<221> NAME/KEY: misc_feature
<222> LOCATION: (578)..(580)
<223> OTHER INFORMATION: N= A, U, G or C
<220> FEATURE:
<221> NAME/KEY: misc_feature
<222> LOCATION: (582)..(582)
<223> OTHER INFORMATION: N= A, U, G or C
<220> FEATURE:
<221> NAME/KEY: misc_feature
<222> LOCATION: (586)..(586)
<223> OTHER INFORMATION: N= A, U, G or C
<220> FEATURE:
<221> NAME/KEY: misc_feature
<222> LOCATION: (589)..(596)
<223> OTHER INFORMATION: N= A, U, G or C
<220> FEATURE:
<221> NAME/KEY: misc_feature
<222> LOCATION: (599)..(603)
<223> OTHER INFORMATION: N= A, U, G or C
<220> FEATURE:
<221> NAME/KEY: misc_feature
<222> LOCATION: (606)..(606)
<223> OTHER INFORMATION: N= A, U, G or C
<220> FEATURE:
<221> NAME/KEY: misc_feature
<222> LOCATION: (610)..(616)
<223> OTHER INFORMATION: N= A, U, G or C
<220> FEATURE:
<221> NAME/KEY: misc_feature
<222> LOCATION: (620)..(620)
<223> OTHER INFORMATION: N= A, U, G or C
<220> FEATURE:
<221> NAME/KEY: misc_feature
<222> LOCATION: (624)..(633)
<223> OTHER INFORMATION: N= A, U, G or C
<220> FEATURE:
<221> NAME/KEY: misc_feature
<222> LOCATION: (635)..(641)
<223> OTHER INFORMATION: N= A, U, G or C
<220> FEATURE:
<221> NAME/KEY: misc_feature
<222> LOCATION: (644)..(650)
<223> OTHER INFORMATION: N= A, U, G or C
<220> FEATURE:
<221> NAME/KEY: misc_feature
<222> LOCATION: (653)..(653)
<223> OTHER INFORMATION: N= A, U, G or C
<220> FEATURE:
<221> NAME/KEY: misc_feature
<222> LOCATION: (657)..(662)
<223> OTHER INFORMATION: N= A, U, G or C
<220> FEATURE:
<221> NAME/KEY: misc_feature
<222> LOCATION: (665)..(665)
<223> OTHER INFORMATION: N= A, U, G or C
<220> FEATURE:
<221> NAME/KEY: misc_feature
<222> LOCATION: (668)..(673)
<223> OTHER INFORMATION: N= A, U, G or C
<220> FEATURE:
<221> NAME/KEY: misc_feature
<222> LOCATION: (679)..(682)
<223> OTHER INFORMATION: N= A, U, G or C
<220> FEATURE:
<221> NAME/KEY: misc_feature
<222> LOCATION: (689)..(689)
<223> OTHER INFORMATION: N= A, U, G or C
<220> FEATURE:
<221> NAME/KEY: misc_feature
<222> LOCATION: (694)..(694)
<223> OTHER INFORMATION: N= A, U, G or C
<220> FEATURE:
<221> NAME/KEY: misc_feature
<222> LOCATION: (698)..(698)
<223> OTHER INFORMATION: N= A, U, G or C
<220> FEATURE:
<221> NAME/KEY: misc_feature
<222> LOCATION: (701)..(701)
<223> OTHER INFORMATION: N= A, U, G or C
```

-continued

```
<220> FEATURE:
<221> NAME/KEY: misc_feature
<222> LOCATION: (705)..(705)
<223> OTHER INFORMATION: N= A, U, G or C
<220> FEATURE:
<221> NAME/KEY: misc_feature
<222> LOCATION: (708)..(709)
<223> OTHER INFORMATION: N= A, U, G or C
<220> FEATURE:
<221> NAME/KEY: misc_feature
<222> LOCATION: (711)..(711)
<223> OTHER INFORMATION: N= A, U, G or C
<220> FEATURE:
<221> NAME/KEY: misc_feature
<222> LOCATION: (713)..(713)
<223> OTHER INFORMATION: N= A, U, G or C
<220> FEATURE:
<221> NAME/KEY: misc_feature
<222> LOCATION: (717)..(717)
<223> OTHER INFORMATION: N= A, U, G or C
<220> FEATURE:
<221> NAME/KEY: misc_feature
<222> LOCATION: (721)..(722)
<223> OTHER INFORMATION: N= A, U, G or C
<220> FEATURE:
<221> NAME/KEY: misc_feature
<222> LOCATION: (724)..(724)
<223> OTHER INFORMATION: N= A, U, G or C
<220> FEATURE:
<221> NAME/KEY: misc_feature
<222> LOCATION: (733)..(738)
<223> OTHER INFORMATION: N= A, U, G or C
<220> FEATURE:
<221> NAME/KEY: misc_feature
<222> LOCATION: (743)..(748)
<223> OTHER INFORMATION: N= A, U, G or C
<220> FEATURE:
<221> NAME/KEY: misc_feature
<222> LOCATION: (755)..(755)
<223> OTHER INFORMATION: N= A, U, G or C
<220> FEATURE:
<221> NAME/KEY: misc_feature
<222> LOCATION: (758)..(758)
<223> OTHER INFORMATION: N= A, U, G or C
<220> FEATURE:
<221> NAME/KEY: misc_feature
<222> LOCATION: (760)..(763)
<223> OTHER INFORMATION: N= A, U, G or C
<220> FEATURE:
<221> NAME/KEY: misc_feature
<222> LOCATION: (771)..(771)
<223> OTHER INFORMATION: N= A, U, G or C
<220> FEATURE:
<221> NAME/KEY: misc_feature
<222> LOCATION: (776)..(776)
<223> OTHER INFORMATION: N= A, U, G or C
<220> FEATURE:
<221> NAME/KEY: misc_feature
<222> LOCATION: (780)..(780)
<223> OTHER INFORMATION: N= A, U, G or C
<220> FEATURE:
<221> NAME/KEY: misc_feature
<222> LOCATION: (808)..(808)
<223> OTHER INFORMATION: N= A, U, G or C
<220> FEATURE:
<221> NAME/KEY: misc_feature
<222> LOCATION: (811)..(812)
<223> OTHER INFORMATION: N= A, U, G or C
<220> FEATURE:
<221> NAME/KEY: misc_feature
<222> LOCATION: (819)..(819)
<223> OTHER INFORMATION: N= A, U, G or C
<220> FEATURE:
<221> NAME/KEY: misc_feature
<222> LOCATION: (822)..(826)
<223> OTHER INFORMATION: N= A, U, G or C
<220> FEATURE:
<221> NAME/KEY: misc_feature
<222> LOCATION: (828)..(831)
```

```
<223> OTHER INFORMATION: N= A, U, G or C
<220> FEATURE:
<221> NAME/KEY: misc_feature
<222> LOCATION: (833)..(835)
<223> OTHER INFORMATION: N= A, U, G or C
<220> FEATURE:
<221> NAME/KEY: misc_feature
<222> LOCATION: (837)..(859)
<223> OTHER INFORMATION: N= A, U, G or C
<220> FEATURE:
<221> NAME/KEY: misc_feature
<222> LOCATION: (861)..(863)
<223> OTHER INFORMATION: N= A, U, G or C
<220> FEATURE:
<221> NAME/KEY: misc_feature
<222> LOCATION: (868)..(870)
<223> OTHER INFORMATION: N= A, U, G or C
<220> FEATURE:
<221> NAME/KEY: misc_feature
<222> LOCATION: (874)..(878)
<223> OTHER INFORMATION: N= A, U, G or C
<220> FEATURE:
<221> NAME/KEY: misc_feature
<222> LOCATION: (895)..(896)
<223> OTHER INFORMATION: N= A, U, G or C
<220> FEATURE:
<221> NAME/KEY: misc_feature
<222> LOCATION: (903)..(904)
<223> OTHER INFORMATION: N= A, U, G or C
<220> FEATURE:
<221> NAME/KEY: misc_feature
<222> LOCATION: (906)..(906)
<223> OTHER INFORMATION: N= A, U, G or C
<220> FEATURE:
<221> NAME/KEY: misc_feature
<222> LOCATION: (916)..(916)
<223> OTHER INFORMATION: N= A, U, G or C
<220> FEATURE:
<221> NAME/KEY: misc_feature
<222> LOCATION: (929)..(929)
<223> OTHER INFORMATION: N= A, U, G or C
<220> FEATURE:
<221> NAME/KEY: misc_feature
<222> LOCATION: (932)..(932)
<223> OTHER INFORMATION: N= A, U, G or C
<220> FEATURE:
<221> NAME/KEY: misc_feature
<222> LOCATION: (941)..(941)
<223> OTHER INFORMATION: N= A, U, G or C
<220> FEATURE:
<221> NAME/KEY: misc_feature
<222> LOCATION: (943)..(943)
<223> OTHER INFORMATION: N= A, U, G or C
<220> FEATURE:
<221> NAME/KEY: misc_feature
<222> LOCATION: (948)..(948)
<223> OTHER INFORMATION: N= A, U, G or C
<220> FEATURE:
<221> NAME/KEY: misc_feature
<222> LOCATION: (955)..(955)
<223> OTHER INFORMATION: N= A, U, G or C
<220> FEATURE:
<221> NAME/KEY: misc_feature
<222> LOCATION: (965)..(965)
<223> OTHER INFORMATION: N= A, U, G or C
<220> FEATURE:
<221> NAME/KEY: misc_feature
<222> LOCATION: (967)..(968)
<223> OTHER INFORMATION: N= A, U, G or C
<220> FEATURE:
<221> NAME/KEY: misc_feature
<222> LOCATION: (974)..(974)
<223> OTHER INFORMATION: N= A, U, G or C
<220> FEATURE:
<221> NAME/KEY: misc_feature
<222> LOCATION: (976)..(976)
<223> OTHER INFORMATION: N= A, U, G or C
<220> FEATURE:
<221> NAME/KEY: misc_feature
```

```
<222> LOCATION: (986)..(990)
<223> OTHER INFORMATION: N= A, U, G or C
<220> FEATURE:
<221> NAME/KEY: misc_feature
<222> LOCATION: (998)..(1012)
<223> OTHER INFORMATION: N= A, U, G or C
<220> FEATURE:
<221> NAME/KEY: misc_feature
<222> LOCATION: (1015)..(1015)
<223> OTHER INFORMATION: N= A, U, G or C
<220> FEATURE:
<221> NAME/KEY: misc_feature
<222> LOCATION: (1017)..(1043)
<223> OTHER INFORMATION: N= A, U, G or C
<220> FEATURE:
<221> NAME/KEY: misc_feature
<222> LOCATION: (1051)..(1051)
<223> OTHER INFORMATION: N= A, U, G or C
<220> FEATURE:
<221> NAME/KEY: misc_feature
<222> LOCATION: (1059)..(1059)
<223> OTHER INFORMATION: N= A, U, G or C
<220> FEATURE:
<221> NAME/KEY: misc_feature
<222> LOCATION: (1075)..(1076)
<223> OTHER INFORMATION: N= A, U, G or C
<220> FEATURE:
<221> NAME/KEY: misc_feature
<222> LOCATION: (1082)..(1082)
<223> OTHER INFORMATION: N= A, U, G or C
<220> FEATURE:
<221> NAME/KEY: misc_feature
<222> LOCATION: (1100)..(1100)
<223> OTHER INFORMATION: N= A, U, G or C
<220> FEATURE:
<221> NAME/KEY: misc_feature
<222> LOCATION: (1115)..(1123)
<223> OTHER INFORMATION: N= A, U, G or C
<220> FEATURE:
<221> NAME/KEY: misc_feature
<222> LOCATION: (1127)..(1127)
<223> OTHER INFORMATION: N= A, U, G or C
<220> FEATURE:
<221> NAME/KEY: misc_feature
<222> LOCATION: (1129)..(1129)
<223> OTHER INFORMATION: N= A, U, G or C
<220> FEATURE:
<221> NAME/KEY: misc_feature
<222> LOCATION: (1131)..(1131)
<223> OTHER INFORMATION: N= A, U, G or C
<220> FEATURE:
<221> NAME/KEY: misc_feature
<222> LOCATION: (1133)..(1141)
<223> OTHER INFORMATION: N= A, U, G or C
<220> FEATURE:
<221> NAME/KEY: misc_feature
<222> LOCATION: (1143)..(1143)
<223> OTHER INFORMATION: N= A, U, G or C
<220> FEATURE:
<221> NAME/KEY: misc_feature
<222> LOCATION: (1145)..(1145)
<223> OTHER INFORMATION: N= A, U, G or C
<220> FEATURE:
<221> NAME/KEY: misc_feature
<222> LOCATION: (1150)..(1156)
<223> OTHER INFORMATION: N= A, U, G or C
<220> FEATURE:
<221> NAME/KEY: misc_feature
<222> LOCATION: (1163)..(1165)
<223> OTHER INFORMATION: N= A, U, G or C
<220> FEATURE:
<221> NAME/KEY: misc_feature
<222> LOCATION: (1167)..(1168)
<223> OTHER INFORMATION: N= A, U, G or C
<220> FEATURE:
<221> NAME/KEY: misc_feature
<222> LOCATION: (1171)..(1173)
<223> OTHER INFORMATION: N= A, U, G or C
<220> FEATURE:
```

```
<221> NAME/KEY: misc_feature
<222> LOCATION: (1183)..(1183)
<223> OTHER INFORMATION: N= A, U, G or C
<220> FEATURE:
<221> NAME/KEY: misc_feature
<222> LOCATION: (1189)..(1189)
<223> OTHER INFORMATION: N= A, U, G or C
<220> FEATURE:
<221> NAME/KEY: misc_feature
<222> LOCATION: (1198)..(1198)
<223> OTHER INFORMATION: N= A, U, G or C
<220> FEATURE:
<221> NAME/KEY: misc_feature
<222> LOCATION: (1201)..(1201)
<223> OTHER INFORMATION: N= A, U, G or C
<220> FEATURE:
<221> NAME/KEY: misc_feature
<222> LOCATION: (1207)..(1207)
<223> OTHER INFORMATION: N= A, U, G or C
<220> FEATURE:
<221> NAME/KEY: misc_feature
<222> LOCATION: (1214)..(1214)
<223> OTHER INFORMATION: N= A, U, G or C
<220> FEATURE:
<221> NAME/KEY: misc_feature
<222> LOCATION: (1216)..(1219)
<223> OTHER INFORMATION: N= A, U, G or C
<220> FEATURE:
<221> NAME/KEY: misc_feature
<222> LOCATION: (1225)..(1225)
<223> OTHER INFORMATION: N= A, U, G or C
<220> FEATURE:
<221> NAME/KEY: misc_feature
<222> LOCATION: (1231)..(1231)
<223> OTHER INFORMATION: N= A, U, G or C
<220> FEATURE:
<221> NAME/KEY: misc_feature
<222> LOCATION: (1233)..(1233)
<223> OTHER INFORMATION: N= A, U, G or C
<220> FEATURE:
<221> NAME/KEY: misc_feature
<222> LOCATION: (1243)..(1247)
<223> OTHER INFORMATION: N= A, U, G or C
<220> FEATURE:
<221> NAME/KEY: misc_feature
<222> LOCATION: (1251)..(1252)
<223> OTHER INFORMATION: N= A, U, G or C
<220> FEATURE:
<221> NAME/KEY: misc_feature
<222> LOCATION: (1254)..(1254)
<223> OTHER INFORMATION: N= A, U, G or C
<220> FEATURE:
<221> NAME/KEY: misc_feature
<222> LOCATION: (1256)..(1257)
<223> OTHER INFORMATION: N= A, U, G or C
<220> FEATURE:
<221> NAME/KEY: misc_feature
<222> LOCATION: (1260)..(1260)
<223> OTHER INFORMATION: N= A, U, G or C
<220> FEATURE:
<221> NAME/KEY: misc_feature
<222> LOCATION: (1262)..(1265)
<223> OTHER INFORMATION: N= A, U, G or C
<220> FEATURE:
<221> NAME/KEY: misc_feature
<222> LOCATION: (1267)..(1268)
<223> OTHER INFORMATION: N= A, U, G or C
<220> FEATURE:
<221> NAME/KEY: misc_feature
<222> LOCATION: (1270)..(1274)
<223> OTHER INFORMATION: N= A, U, G or C
<220> FEATURE:
<221> NAME/KEY: misc_feature
<222> LOCATION: (1278)..(1278)
<223> OTHER INFORMATION: N= A, U, G or C
<220> FEATURE:
<221> NAME/KEY: misc_feature
<222> LOCATION: (1281)..(1281)
<223> OTHER INFORMATION: N= A, U, G or C
```

```
<220> FEATURE:
<221> NAME/KEY: misc_feature
<222> LOCATION: (1283)..(1286)
<223> OTHER INFORMATION: N= A, U, G or C
<220> FEATURE:
<221> NAME/KEY: misc_feature
<222> LOCATION: (1290)..(1294)
<223> OTHER INFORMATION: N= A, U, G or C
<220> FEATURE:
<221> NAME/KEY: misc_feature
<222> LOCATION: (1297)..(1298)
<223> OTHER INFORMATION: N= A, U, G or C
<220> FEATURE:
<221> NAME/KEY: misc_feature
<222> LOCATION: (1302)..(1302)
<223> OTHER INFORMATION: N= A, U, G or C
<220> FEATURE:
<221> NAME/KEY: misc_feature
<222> LOCATION: (1308)..(1308)
<223> OTHER INFORMATION: N= A, U, G or C
<220> FEATURE:
<221> NAME/KEY: misc_feature
<222> LOCATION: (1310)..(1313)
<223> OTHER INFORMATION: N= A, U, G or C
<220> FEATURE:
<221> NAME/KEY: misc_feature
<222> LOCATION: (1324)..(1327)
<223> OTHER INFORMATION: N= A, U, G or C
<220> FEATURE:
<221> NAME/KEY: misc_feature
<222> LOCATION: (1329)..(1329)
<223> OTHER INFORMATION: N= A, U, G or C
<220> FEATURE:
<221> NAME/KEY: misc_feature
<222> LOCATION: (1335)..(1336)
<223> OTHER INFORMATION: N= A, U, G or C
<220> FEATURE:
<221> NAME/KEY: misc_feature
<222> LOCATION: (1340)..(1340)
<223> OTHER INFORMATION: N= A, U, G or C
<220> FEATURE:
<221> NAME/KEY: misc_feature
<222> LOCATION: (1354)..(1356)
<223> OTHER INFORMATION: N= A, U, G or C
<220> FEATURE:
<221> NAME/KEY: misc_feature
<222> LOCATION: (1362)..(1362)
<223> OTHER INFORMATION: N= A, U, G or C
<220> FEATURE:
<221> NAME/KEY: misc_feature
<222> LOCATION: (1364)..(1364)
<223> OTHER INFORMATION: N= A, U, G or C
<220> FEATURE:
<221> NAME/KEY: misc_feature
<222> LOCATION: (1366)..(1368)
<223> OTHER INFORMATION: N= A, U, G or C
<220> FEATURE:
<221> NAME/KEY: misc_feature
<222> LOCATION: (1383)..(1383)
<223> OTHER INFORMATION: N= A, U, G or C
<220> FEATURE:
<221> NAME/KEY: misc_feature
<222> LOCATION: (1388)..(1388)
<223> OTHER INFORMATION: N= A, U, G or C
<220> FEATURE:
<221> NAME/KEY: misc_feature
<222> LOCATION: (1409)..(1411)
<223> OTHER INFORMATION: N= A, U, G or C
<220> FEATURE:
<221> NAME/KEY: misc_feature
<222> LOCATION: (1414)..(1414)
<223> OTHER INFORMATION: N= A, U, G or C
<220> FEATURE:
<221> NAME/KEY: misc_feature
<222> LOCATION: (1416)..(1417)
<223> OTHER INFORMATION: N= A, U, G or C
<220> FEATURE:
<221> NAME/KEY: misc_feature
<222> LOCATION: (1420)..(1428)
```

```
<223> OTHER INFORMATION: N= A, U, G or C
<220> FEATURE:
<221> NAME/KEY: misc_feature
<222> LOCATION: (1431)..(1432)
<223> OTHER INFORMATION: N= A, U, G or C
<220> FEATURE:
<221> NAME/KEY: misc_feature
<222> LOCATION: (1436)..(1447)
<223> OTHER INFORMATION: N= A, U, G or C
<220> FEATURE:
<221> NAME/KEY: misc_feature
<222> LOCATION: (1449)..(1454)
<223> OTHER INFORMATION: N= A, U, G or C
<220> FEATURE:
<221> NAME/KEY: misc_feature
<222> LOCATION: (1456)..(1465)
<223> OTHER INFORMATION: N= A, U, G or C
<220> FEATURE:
<221> NAME/KEY: misc_feature
<222> LOCATION: (1467)..(1467)
<223> OTHER INFORMATION: N= A, U, G or C
<220> FEATURE:
<221> NAME/KEY: misc_feature
<222> LOCATION: (1469)..(1469)
<223> OTHER INFORMATION: N= A, U, G or C
<220> FEATURE:
<221> NAME/KEY: misc_feature
<222> LOCATION: (1472)..(1481)
<223> OTHER INFORMATION: N= A, U, G or C
<220> FEATURE:
<221> NAME/KEY: misc_feature
<222> LOCATION: (1484)..(1484)
<223> OTHER INFORMATION: N= A, U, G or C
<220> FEATURE:
<221> NAME/KEY: misc_feature
<222> LOCATION: (1489)..(1491)
<223> OTHER INFORMATION: N= A, U, G or C
<220> FEATURE:
<221> NAME/KEY: misc_feature
<222> LOCATION: (1508)..(1508)
<223> OTHER INFORMATION: N= A, U, G or C
<220> FEATURE:
<221> NAME/KEY: misc_feature
<222> LOCATION: (1511)..(1511)
<223> OTHER INFORMATION: N= A, U, G or C
<220> FEATURE:
<221> NAME/KEY: misc_feature
<222> LOCATION: (1514)..(1516)
<223> OTHER INFORMATION: N= A, U, G or C
<220> FEATURE:
<221> NAME/KEY: misc_feature
<222> LOCATION: (1520)..(1521)
<223> OTHER INFORMATION: N= A, U, G or C
<220> FEATURE:
<221> NAME/KEY: misc_feature
<222> LOCATION: (1524)..(1524)
<223> OTHER INFORMATION: N= A, U, G or C
<220> FEATURE:
<221> NAME/KEY: misc_feature
<222> LOCATION: (1527)..(1527)
<223> OTHER INFORMATION: N= A, U, G or C
<220> FEATURE:
<221> NAME/KEY: misc_feature
<222> LOCATION: (1542)..(1542)
<223> OTHER INFORMATION: n is a, c, g, or u

<400> SEQUENCE: 3
nnnnnnnaga guuugaucnu ggcucagnnn gaacgcuggc ggnnngcnun anacaugcaa      60
gucgancgnn nnnnnnnnnn nnnnnnnnnn nnnnnnnnnn agnggcnnac gggugaguaa     120
nncnunnnna nnunccnnnn nnnnnggnan annnnnnnga aannnnnnnu aauaccnnau     180
nnnnnnnnnn nnnnaaagnn nnnnnnnnnn nnnnnnnnnn nnnnnngann nnnnnnngnn     240
nnaunagnun guuggunngg uaanggcnna ccaagncnnn gannnnuagc ngnncugaga     300
ggnngnncng ccacanuggn acugaganac ggnccanacu ccuacgggag gcagcagunn     360
```

```
ggaaunuunn ncaauggnng naanncugan nnagcnannc cgcgugnnng angangnnnu      420
nnngnungua aannncunun nnnnnngang annnnnnnnn nnnnnnnnnn nnnnnnnnnu      480
gacnnuannn nnnnannaag nnncggcnaa cuncgugcca gcagccgcgg uaauacgnag      540
gnngcnagcg uunnncggan unanugggcg uaaagngnnn gnaggnggnn nnnnnngunn      600
nnngunaaan nnnnnngcun aacnnnnnnn nnncnnnnnn nacnnnnnnn cungagnnnn      660
nnagnggnnn nnngaauunn nnguguagng gugnaauncg naganaunng nangaanacc      720
nnungcgaag gcnnnnnncu ggnnnnnnac ugacncunan nnncgaaagc nugggnagcn      780
aacaggauua gauacccugg uaguccangc nnuaaacgnu gnnnnnunnn ngnnngnnnn      840
nnnnnnnnnn nnnnnnnnna nnaacgnnnn uaannnnncc gccugggag uacgnncgca       900 agnnunaaac ucaaangaau ugacggggnc cngcacaagc ngnggagnau guggnuuaau      960
ucgangnnac gcgnanaacc uuaccnnnnn uugacaunnn nnnnnnnnnn nngananann     1020
nnnnnnnnnn nnnnnnnnnn nnacaggug nugcauggnu gucgucagcu cgugnnguga     1080
gnuguugggu uaaguccgn aacgagcgca accnnnnnn nnnguucna ncnnnnnnn          1140 ngngnacucn nnnnnnacug ccnnngnaa nnnggaggaa ggnggggang acgucaanuc      1200
nucaugnccc uuangnnnng ggcuncacac nuncuacaau ggnnnnnaca nngngnngcn     1260
annnngnnan nnnnagcnaa ncnnnnaaan nnnnucnnag uncggaungn nnncugcaac    1320
ucgnnnncnu gaagnnggan ucgcuaguaa ucgnnnauca gnangnnncg gugaauacgu     1380
ucncgggncu uguacacacc gcccgucann ncangnnagn nnnnnnnncc nnaagnnnnn     1440
nnnnnnncnn nnnngnnnnn nnnnncnang gnnnnnnnnn nganugggnn naagucguaa    1500
caagguancc nuannngaan nugnggnugg aucaccuccu un                       1542

<210> SEQ ID NO 4
<211> LENGTH: 2904
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 23S rRNA consensus sequence
<220> FEATURE:
<221> NAME/KEY: misc_feature
<222> LOCATION: (1)..(4)
<223> OTHER INFORMATION: N= A, U, G or C
<220> FEATURE:
<221> NAME/KEY: misc_feature
<222> LOCATION: (8)..(12)
<223> OTHER INFORMATION: N= A, U, G or C
<220> FEATURE:
<221> NAME/KEY: misc_feature
<222> LOCATION: (16)..(16)
<223> OTHER INFORMATION: N= A, U, G or C
<220> FEATURE:
<221> NAME/KEY: misc_feature
<222> LOCATION: (18)..(22)
<223> OTHER INFORMATION: N= A, U, G or C
<220> FEATURE:
<221> NAME/KEY: misc_feature
<222> LOCATION: (34)..(34)
<223> OTHER INFORMATION: N= A, U, G or C
<220> FEATURE:
<221> NAME/KEY: misc_feature
<222> LOCATION: (38)..(43)
<223> OTHER INFORMATION: N= A, U, G or C
<220> FEATURE:
<221> NAME/KEY: misc_feature
<222> LOCATION: (46)..(46)
<223> OTHER INFORMATION: N= A, U, G or C
```

```
<220> FEATURE:
<221> NAME/KEY: misc_feature
<222> LOCATION: (50)..(50)
<223> OTHER INFORMATION: N= A, U, G or C
<220> FEATURE:
<221> NAME/KEY: misc_feature
<222> LOCATION: (57)..(57)
<223> OTHER INFORMATION: N= A, U, G or C
<220> FEATURE:
<221> NAME/KEY: misc_feature
<222> LOCATION: (59)..(65)
<223> OTHER INFORMATION: N= A, U, G or C
<220> FEATURE:
<221> NAME/KEY: misc_feature
<222> LOCATION: (67)..(68)
<223> OTHER INFORMATION: N= A, U, G or C
<220> FEATURE:
<221> NAME/KEY: misc_feature
<222> LOCATION: (70)..(72)
<223> OTHER INFORMATION: N= A, U, G or C
<220> FEATURE:
<221> NAME/KEY: misc_feature
<222> LOCATION: (74)..(75)
<223> OTHER INFORMATION: N= A, U, G or C
<220> FEATURE:
<221> NAME/KEY: misc_feature
<222> LOCATION: (77)..(79)
<223> OTHER INFORMATION: N= A, U, G or C
<220> FEATURE:
<221> NAME/KEY: misc_feature
<222> LOCATION: (82)..(83)
<223> OTHER INFORMATION: N= A, U, G or C
<220> FEATURE:
<221> NAME/KEY: misc_feature
<222> LOCATION: (86)..(87)
<223> OTHER INFORMATION: N= A, U, G or C
<220> FEATURE:
<221> NAME/KEY: misc_feature
<222> LOCATION: (89)..(96)
<223> OTHER INFORMATION: N= A, U, G or C
<220> FEATURE:
<221> NAME/KEY: misc_feature
<222> LOCATION: (98)..(102)
<223> OTHER INFORMATION: N= A, U, G or C
<220> FEATURE:
<221> NAME/KEY: misc_feature
<222> LOCATION: (104)..(104)
<223> OTHER INFORMATION: N= A, U, G or C
<220> FEATURE:
<221> NAME/KEY: misc_feature
<222> LOCATION: (107)..(109)
<223> OTHER INFORMATION: N= A, U, G or C
<220> FEATURE:
<221> NAME/KEY: misc_feature
<222> LOCATION: (111)..(111)
<223> OTHER INFORMATION: N= A, U, G or C
<220> FEATURE:
<221> NAME/KEY: misc_feature
<222> LOCATION: (113)..(113)
<223> OTHER INFORMATION: N= A, U, G or C
<220> FEATURE:
<221> NAME/KEY: misc_feature
<222> LOCATION: (125)..(125)
<223> OTHER INFORMATION: N= A, U, G or C
<220> FEATURE:
<221> NAME/KEY: misc_feature
<222> LOCATION: (131)..(148)
<223> OTHER INFORMATION: N= A, U, G or C
<220> FEATURE:
<221> NAME/KEY: misc_feature
<222> LOCATION: (150)..(177)
<223> OTHER INFORMATION: N= A, U, G or C
<220> FEATURE:
<221> NAME/KEY: misc_feature
<222> LOCATION: (179)..(181)
<223> OTHER INFORMATION: N= A, U, G or C
<220> FEATURE:
<221> NAME/KEY: misc_feature
<222> LOCATION: (184)..(188)
```

-continued

```
<223> OTHER INFORMATION: N= A, U, G or C
<220> FEATURE:
<221> NAME/KEY: misc_feature
<222> LOCATION: (192)..(192)
<223> OTHER INFORMATION: N= A, U, G or C
<220> FEATURE:
<221> NAME/KEY: misc_feature
<222> LOCATION: (203)..(203)
<223> OTHER INFORMATION: N= A, U, G or C
<220> FEATURE:
<221> NAME/KEY: misc_feature
<222> LOCATION: (208)..(212)
<223> OTHER INFORMATION: N= A, U, G or C
<220> FEATURE:
<221> NAME/KEY: misc_feature
<222> LOCATION: (218)..(218)
<223> OTHER INFORMATION: N= A, U, G or C
<220> FEATURE:
<221> NAME/KEY: misc_feature
<222> LOCATION: (224)..(225)
<223> OTHER INFORMATION: N= A, U, G or C
<220> FEATURE:
<221> NAME/KEY: misc_feature
<222> LOCATION: (228)..(231)
<223> OTHER INFORMATION: N= A, U, G or C
<220> FEATURE:
<221> NAME/KEY: misc_feature
<222> LOCATION: (236)..(236)
<223> OTHER INFORMATION: N= A, U, G or C
<220> FEATURE:
<221> NAME/KEY: misc_feature
<222> LOCATION: (238)..(241)
<223> OTHER INFORMATION: N= A, U, G or C
<220> FEATURE:
<221> NAME/KEY: misc_feature
<222> LOCATION: (246)..(246)
<223> OTHER INFORMATION: N= A, U, G or C
<220> FEATURE:
<221> NAME/KEY: misc_feature
<222> LOCATION: (257)..(259)
<223> OTHER INFORMATION: N= A, U, G or C
<220> FEATURE:
<221> NAME/KEY: misc_feature
<222> LOCATION: (261)..(261)
<223> OTHER INFORMATION: N= A, U, G or C
<220> FEATURE:
<221> NAME/KEY: misc_feature
<222> LOCATION: (263)..(264)
<223> OTHER INFORMATION: N= A, U, G or C
<220> FEATURE:
<221> NAME/KEY: misc_feature
<222> LOCATION: (267)..(267)
<223> OTHER INFORMATION: N= A, U, G or C
<220> FEATURE:
<221> NAME/KEY: misc_feature
<222> LOCATION: (269)..(293)
<223> OTHER INFORMATION: N= A, U, G or C
<220> FEATURE:
<221> NAME/KEY: misc_feature
<222> LOCATION: (295)..(297)
<223> OTHER INFORMATION: N= A, U, G or C
<220> FEATURE:
<221> NAME/KEY: misc_feature
<222> LOCATION: (301)..(305)
<223> OTHER INFORMATION: N= A, U, G or C
<220> FEATURE:
<221> NAME/KEY: misc_feature
<222> LOCATION: (309)..(309)
<223> OTHER INFORMATION: N= A, U, G or C
<220> FEATURE:
<221> NAME/KEY: misc_feature
<222> LOCATION: (313)..(321)
<223> OTHER INFORMATION: N= A, U, G or C
<220> FEATURE:
<221> NAME/KEY: misc_feature
<222> LOCATION: (323)..(325)
<223> OTHER INFORMATION: N= A, U, G or C
<220> FEATURE:
<221> NAME/KEY: misc_feature
```

```
<222> LOCATION: (329)..(329)
<223> OTHER INFORMATION: N= A, U, G or C
<220> FEATURE:
<221> NAME/KEY: misc_feature
<222> LOCATION: (331)..(331)
<223> OTHER INFORMATION: N= A, U, G or C
<220> FEATURE:
<221> NAME/KEY: misc_feature
<222> LOCATION: (333)..(334)
<223> OTHER INFORMATION: N= A, U, G or C
<220> FEATURE:
<221> NAME/KEY: misc_feature
<222> LOCATION: (337)..(337)
<223> OTHER INFORMATION: N= A, U, G or C
<220> FEATURE:
<221> NAME/KEY: misc_feature
<222> LOCATION: (341)..(344)
<223> OTHER INFORMATION: N= A, U, G or C
<220> FEATURE:
<221> NAME/KEY: misc_feature
<222> LOCATION: (348)..(370)
<223> OTHER INFORMATION: N= A, U, G or C
<220> FEATURE:
<221> NAME/KEY: misc_feature
<222> LOCATION: (375)..(377)
<223> OTHER INFORMATION: N= A, U, G or C
<220> FEATURE:
<221> NAME/KEY: misc_feature
<222> LOCATION: (379)..(382)
<223> OTHER INFORMATION: N= A, U, G or C
<220> FEATURE:
<221> NAME/KEY: misc_feature
<222> LOCATION: (384)..(384)
<223> OTHER INFORMATION: N= A, U, G or C
<220> FEATURE:
<221> NAME/KEY: misc_feature
<222> LOCATION: (387)..(387)
<223> OTHER INFORMATION: N= A, U, G or C
<220> FEATURE:
<221> NAME/KEY: misc_feature
<222> LOCATION: (389)..(390)
<223> OTHER INFORMATION: N= A, U, G or C
<220> FEATURE:
<221> NAME/KEY: misc_feature
<222> LOCATION: (392)..(395)
<223> OTHER INFORMATION: N= A, U, G or C
<220> FEATURE:
<221> NAME/KEY: misc_feature
<222> LOCATION: (398)..(399)
<223> OTHER INFORMATION: N= A, U, G or C
<220> FEATURE:
<221> NAME/KEY: misc_feature
<222> LOCATION: (403)..(405)
<223> OTHER INFORMATION: N= A, U, G or C
<220> FEATURE:
<221> NAME/KEY: misc_feature
<222> LOCATION: (407)..(410)
<223> OTHER INFORMATION: N= A, U, G or C
<220> FEATURE:
<221> NAME/KEY: misc_feature
<222> LOCATION: (416)..(421)
<223> OTHER INFORMATION: N= A, U, G or C
<220> FEATURE:
<221> NAME/KEY: misc_feature
<222> LOCATION: (425)..(425)
<223> OTHER INFORMATION: N= A, U, G or C
<220> FEATURE:
<221> NAME/KEY: misc_feature
<222> LOCATION: (435)..(441)
<223> OTHER INFORMATION: N= A, U, G or C
<220> FEATURE:
<221> NAME/KEY: misc_feature
<222> LOCATION: (446)..(446)
<223> OTHER INFORMATION: N= A, U, G or C
<220> FEATURE:
<221> NAME/KEY: misc_feature
<222> LOCATION: (451)..(451)
<223> OTHER INFORMATION: N= A, U, G or C
<220> FEATURE:
```

```
<221> NAME/KEY: misc_feature
<222> LOCATION: (453)..(453)
<223> OTHER INFORMATION: N= A, U, G or C
<220> FEATURE:
<221> NAME/KEY: misc_feature
<222> LOCATION: (455)..(456)
<223> OTHER INFORMATION: N= A, U, G or C
<220> FEATURE:
<221> NAME/KEY: misc_feature
<222> LOCATION: (462)..(462)
<223> OTHER INFORMATION: N= A, U, G or C
<220> FEATURE:
<221> NAME/KEY: misc_feature
<222> LOCATION: (467)..(467)
<223> OTHER INFORMATION: N= A, U, G or C
<220> FEATURE:
<221> NAME/KEY: misc_feature
<222> LOCATION: (475)..(475)
<223> OTHER INFORMATION: N= A, U, G or C
<220> FEATURE:
<221> NAME/KEY: misc_feature
<222> LOCATION: (482)..(482)
<223> OTHER INFORMATION: N= A, U, G or C
<220> FEATURE:
<221> NAME/KEY: misc_feature
<222> LOCATION: (487)..(491)
<223> OTHER INFORMATION: N= A, U, G or C
<220> FEATURE:
<221> NAME/KEY: misc_feature
<222> LOCATION: (493)..(493)
<223> OTHER INFORMATION: N= A, U, G or C
<220> FEATURE:
<221> NAME/KEY: misc_feature
<222> LOCATION: (504)..(504)
<223> OTHER INFORMATION: N= A, U, G or C
<220> FEATURE:
<221> NAME/KEY: misc_feature
<222> LOCATION: (507)..(508)
<223> OTHER INFORMATION: N= A, U, G or C
<220> FEATURE:
<221> NAME/KEY: misc_feature
<222> LOCATION: (518)..(522)
<223> OTHER INFORMATION: N= A, U, G or C
<220> FEATURE:
<221> NAME/KEY: misc_feature
<222> LOCATION: (524)..(524)
<223> OTHER INFORMATION: N= A, U, G or C
<220> FEATURE:
<221> NAME/KEY: misc_feature
<222> LOCATION: (527)..(527)
<223> OTHER INFORMATION: N= A, U, G or C
<220> FEATURE:
<221> NAME/KEY: misc_feature
<222> LOCATION: (530)..(532)
<223> OTHER INFORMATION: N= A, U, G or C
<220> FEATURE:
<221> NAME/KEY: misc_feature
<222> LOCATION: (535)..(537)
<223> OTHER INFORMATION: N= A, U, G or C
<220> FEATURE:
<221> NAME/KEY: misc_feature
<222> LOCATION: (540)..(553)
<223> OTHER INFORMATION: N= A, U, G or C
<220> FEATURE:
<221> NAME/KEY: misc_feature
<222> LOCATION: (557)..(558)
<223> OTHER INFORMATION: N= A, U, G or C
<220> FEATURE:
<221> NAME/KEY: misc_feature
<222> LOCATION: (563)..(563)
<223> OTHER INFORMATION: N= A, U, G or C
<220> FEATURE:
<221> NAME/KEY: misc_feature
<222> LOCATION: (571)..(571)
<223> OTHER INFORMATION: N= A, U, G or C
<220> FEATURE:
<221> NAME/KEY: misc_feature
<222> LOCATION: (573)..(574)
<223> OTHER INFORMATION: N= A, U, G or C
```

```
<220> FEATURE:
<221> NAME/KEY: misc_feature
<222> LOCATION: (578)..(580)
<223> OTHER INFORMATION: N= A, U, G or C
<220> FEATURE:
<221> NAME/KEY: misc_feature
<222> LOCATION: (582)..(582)
<223> OTHER INFORMATION: N= A, U, G or C
<220> FEATURE:
<221> NAME/KEY: misc_feature
<222> LOCATION: (584)..(584)
<223> OTHER INFORMATION: N= A, U, G or C
<220> FEATURE:
<221> NAME/KEY: misc_feature
<222> LOCATION: (587)..(587)
<223> OTHER INFORMATION: N= A, U, G or C
<220> FEATURE:
<221> NAME/KEY: misc_feature
<222> LOCATION: (590)..(593)
<223> OTHER INFORMATION: N= A, U, G or C
<220> FEATURE:
<221> NAME/KEY: misc_feature
<222> LOCATION: (595)..(599)
<223> OTHER INFORMATION: N= A, U, G or C
<220> FEATURE:
<221> NAME/KEY: misc_feature
<222> LOCATION: (602)..(602)
<223> OTHER INFORMATION: N= A, U, G or C
<220> FEATURE:
<221> NAME/KEY: misc_feature
<222> LOCATION: (605)..(605)
<223> OTHER INFORMATION: N= A, U, G or C
<220> FEATURE:
<221> NAME/KEY: misc_feature
<222> LOCATION: (610)..(618)
<223> OTHER INFORMATION: N= A, U, G or C
<220> FEATURE:
<221> NAME/KEY: misc_feature
<222> LOCATION: (620)..(620)
<223> OTHER INFORMATION: N= A, U, G or C
<220> FEATURE:
<221> NAME/KEY: misc_feature
<222> LOCATION: (623)..(623)
<223> OTHER INFORMATION: N= A, U, G or C
<220> FEATURE:
<221> NAME/KEY: misc_feature
<222> LOCATION: (626)..(626)
<223> OTHER INFORMATION: N= A, U, G or C
<220> FEATURE:
<221> NAME/KEY: misc_feature
<222> LOCATION: (629)..(629)
<223> OTHER INFORMATION: N= A, U, G or C
<220> FEATURE:
<221> NAME/KEY: misc_feature
<222> LOCATION: (634)..(634)
<223> OTHER INFORMATION: N= A, U, G or C
<220> FEATURE:
<221> NAME/KEY: misc_feature
<222> LOCATION: (640)..(642)
<223> OTHER INFORMATION: N= A, U, G or C
<220> FEATURE:
<221> NAME/KEY: misc_feature
<222> LOCATION: (645)..(646)
<223> OTHER INFORMATION: N= A, U, G or C
<220> FEATURE:
<221> NAME/KEY: misc_feature
<222> LOCATION: (648)..(648)
<223> OTHER INFORMATION: N= A, U, G or C
<220> FEATURE:
<221> NAME/KEY: misc_feature
<222> LOCATION: (652)..(654)
<223> OTHER INFORMATION: N= A, U, G or C
<220> FEATURE:
<221> NAME/KEY: misc_feature
<222> LOCATION: (658)..(662)
<223> OTHER INFORMATION: N= A, U, G or C
<220> FEATURE:
<221> NAME/KEY: misc_feature
<222> LOCATION: (664)..(667)
```

-continued

```
<223> OTHER INFORMATION: N= A, U, G or C
<220> FEATURE:
<221> NAME/KEY: misc_feature
<222> LOCATION: (672)..(672)
<223> OTHER INFORMATION: N= A, U, G or C
<220> FEATURE:
<221> NAME/KEY: misc_feature
<222> LOCATION: (677)..(677)
<223> OTHER INFORMATION: N= A, U, G or C
<220> FEATURE:
<221> NAME/KEY: misc_feature
<222> LOCATION: (679)..(681)
<223> OTHER INFORMATION: N= A, U, G or C
<220> FEATURE:
<221> NAME/KEY: misc_feature
<222> LOCATION: (686)..(686)
<223> OTHER INFORMATION: N= A, U, G or C
<220> FEATURE:
<221> NAME/KEY: misc_feature
<222> LOCATION: (690)..(692)
<223> OTHER INFORMATION: N= A, U, G or C
<220> FEATURE:
<221> NAME/KEY: misc_feature
<222> LOCATION: (696)..(697)
<223> OTHER INFORMATION: N= A, U, G or C
<220> FEATURE:
<221> NAME/KEY: misc_feature
<222> LOCATION: (702)..(702)
<223> OTHER INFORMATION: N= A, U, G or C
<220> FEATURE:
<221> NAME/KEY: misc_feature
<222> LOCATION: (708)..(712)
<223> OTHER INFORMATION: N= A, U, G or C
<220> FEATURE:
<221> NAME/KEY: misc_feature
<222> LOCATION: (717)..(717)
<223> OTHER INFORMATION: N= A, U, G or C
<220> FEATURE:
<221> NAME/KEY: misc_feature
<222> LOCATION: (719)..(723)
<223> OTHER INFORMATION: N= A, U, G or C
<220> FEATURE:
<221> NAME/KEY: misc_feature
<222> LOCATION: (730)..(730)
<223> OTHER INFORMATION: N= A, U, G or C
<220> FEATURE:
<221> NAME/KEY: misc_feature
<222> LOCATION: (737)..(744)
<223> OTHER INFORMATION: N= A, U, G or C
<220> FEATURE:
<221> NAME/KEY: misc_feature
<222> LOCATION: (753)..(758)
<223> OTHER INFORMATION: N= A, U, G or C
<220> FEATURE:
<221> NAME/KEY: misc_feature
<222> LOCATION: (765)..(766)
<223> OTHER INFORMATION: N= A, U, G or C
<220> FEATURE:
<221> NAME/KEY: misc_feature
<222> LOCATION: (771)..(772)
<223> OTHER INFORMATION: N= A, U, G or C
<220> FEATURE:
<221> NAME/KEY: misc_feature
<222> LOCATION: (774)..(774)
<223> OTHER INFORMATION: N= A, U, G or C
<220> FEATURE:
<221> NAME/KEY: misc_feature
<222> LOCATION: (776)..(776)
<223> OTHER INFORMATION: N= A, U, G or C
<220> FEATURE:
<221> NAME/KEY: misc_feature
<222> LOCATION: (779)..(779)
<223> OTHER INFORMATION: N= A, U, G or C
<220> FEATURE:
<221> NAME/KEY: misc_feature
<222> LOCATION: (784)..(785)
<223> OTHER INFORMATION: N= A, U, G or C
<220> FEATURE:
<221> NAME/KEY: misc_feature
```

```
<222> LOCATION: (787)..(787)
<223> OTHER INFORMATION: N= A, U, G or C
<220> FEATURE:
<221> NAME/KEY: misc_feature
<222> LOCATION: (790)..(790)
<223> OTHER INFORMATION: N= A, U, G or C
<220> FEATURE:
<221> NAME/KEY: misc_feature
<222> LOCATION: (792)..(792)
<223> OTHER INFORMATION: N= A, U, G or C
<220> FEATURE:
<221> NAME/KEY: misc_feature
<222> LOCATION: (796)..(798)
<223> OTHER INFORMATION: N= A, U, G or C
<220> FEATURE:
<221> NAME/KEY: misc_feature
<222> LOCATION: (800)..(801)
<223> OTHER INFORMATION: N= A, U, G or C
<220> FEATURE:
<221> NAME/KEY: misc_feature
<222> LOCATION: (815)..(816)
<223> OTHER INFORMATION: N= A, U, G or C
<220> FEATURE:
<221> NAME/KEY: misc_feature
<222> LOCATION: (822)..(825)
<223> OTHER INFORMATION: N= A, U, G or C
<220> FEATURE:
<221> NAME/KEY: misc_feature
<222> LOCATION: (832)..(835)
<223> OTHER INFORMATION: N= A, U, G or C
<220> FEATURE:
<221> NAME/KEY: misc_feature
<222> LOCATION: (838)..(838)
<223> OTHER INFORMATION: N= A, U, G or C
<220> FEATURE:
<221> NAME/KEY: misc_feature
<222> LOCATION: (840)..(854)
<223> OTHER INFORMATION: N= A, U, G or C
<220> FEATURE:
<221> NAME/KEY: misc_feature
<222> LOCATION: (857)..(857)
<223> OTHER INFORMATION: N= A, U, G or C
<220> FEATURE:
<221> NAME/KEY: misc_feature
<222> LOCATION: (870)..(879)
<223> OTHER INFORMATION: N= A, U, G or C
<220> FEATURE:
<221> NAME/KEY: misc_feature
<222> LOCATION: (882)..(894)
<223> OTHER INFORMATION: N= A, U, G or C
<220> FEATURE:
<221> NAME/KEY: misc_feature
<222> LOCATION: (898)..(899)
<223> OTHER INFORMATION: N= A, U, G or C
<220> FEATURE:
<221> NAME/KEY: misc_feature
<222> LOCATION: (901)..(908)
<223> OTHER INFORMATION: N= A, U, G or C
<220> FEATURE:
<221> NAME/KEY: misc_feature
<222> LOCATION: (914)..(914)
<223> OTHER INFORMATION: N= A, U, G or C
<220> FEATURE:
<221> NAME/KEY: misc_feature
<222> LOCATION: (920)..(920)
<223> OTHER INFORMATION: N= A, U, G or C
<220> FEATURE:
<221> NAME/KEY: misc_feature
<222> LOCATION: (923)..(938)
<223> OTHER INFORMATION: N= A, U, G or C
<220> FEATURE:
<221> NAME/KEY: misc_feature
<222> LOCATION: (940)..(940)
<223> OTHER INFORMATION: N= A, U, G or C
<220> FEATURE:
<221> NAME/KEY: misc_feature
<222> LOCATION: (943)..(944)
<223> OTHER INFORMATION: N= A, U, G or C
<220> FEATURE:
```

-continued

```
<221> NAME/KEY: misc_feature
<222> LOCATION: (946)..(947)
<223> OTHER INFORMATION: N= A, U, G or C
<220> FEATURE:
<221> NAME/KEY: misc_feature
<222> LOCATION: (949)..(951)
<223> OTHER INFORMATION: N= A, U, G or C
<220> FEATURE:
<221> NAME/KEY: misc_feature
<222> LOCATION: (953)..(953)
<223> OTHER INFORMATION: N= A, U, G or C
<220> FEATURE:
<221> NAME/KEY: misc_feature
<222> LOCATION: (955)..(955)
<223> OTHER INFORMATION: N= A, U, G or C
<220> FEATURE:
<221> NAME/KEY: misc_feature
<222> LOCATION: (957)..(957)
<223> OTHER INFORMATION: N= A, U, G or C
<220> FEATURE:
<221> NAME/KEY: misc_feature
<222> LOCATION: (961)..(962)
<223> OTHER INFORMATION: N= A, U, G or C
<220> FEATURE:
<221> NAME/KEY: misc_feature
<222> LOCATION: (964)..(964)
<223> OTHER INFORMATION: N= A, U, G or C
<220> FEATURE:
<221> NAME/KEY: misc_feature
<222> LOCATION: (966)..(968)
<223> OTHER INFORMATION: N= A, U, G or C
<220> FEATURE:
<221> NAME/KEY: misc_feature
<222> LOCATION: (971)..(972)
<223> OTHER INFORMATION: N= A, U, G or C
<220> FEATURE:
<221> NAME/KEY: misc_feature
<222> LOCATION: (974)..(974)
<223> OTHER INFORMATION: N= A, U, G or C
<220> FEATURE:
<221> NAME/KEY: misc_feature
<222> LOCATION: (979)..(979)
<223> OTHER INFORMATION: N= A, U, G or C
<220> FEATURE:
<221> NAME/KEY: misc_feature
<222> LOCATION: (984)..(984)
<223> OTHER INFORMATION: N= A, U, G or C
<220> FEATURE:
<221> NAME/KEY: misc_feature
<222> LOCATION: (991)..(991)
<223> OTHER INFORMATION: N= A, U, G or C
<220> FEATURE:
<221> NAME/KEY: misc_feature
<222> LOCATION: (993)..(994)
<223> OTHER INFORMATION: N= A, U, G or C
<220> FEATURE:
<221> NAME/KEY: misc_feature
<222> LOCATION: (996)..(998)
<223> OTHER INFORMATION: N= A, U, G or C
<220> FEATURE:
<221> NAME/KEY: misc_feature
<222> LOCATION: (1004)..(1004)
<223> OTHER INFORMATION: N= A, U, G or C
<220> FEATURE:
<221> NAME/KEY: misc_feature
<222> LOCATION: (1008)..(1008)
<223> OTHER INFORMATION: N= A, U, G or C
<220> FEATURE:
<221> NAME/KEY: misc_feature
<222> LOCATION: (1011)..(1018)
<223> OTHER INFORMATION: N= A, U, G or C
<220> FEATURE:
<221> NAME/KEY: misc_feature
<222> LOCATION: (1026)..(1026)
<223> OTHER INFORMATION: N= A, U, G or C
<220> FEATURE:
<221> NAME/KEY: misc_feature
<222> LOCATION: (1030)..(1030)
<223> OTHER INFORMATION: N= A, U, G or C
```

```
<220> FEATURE:
<221> NAME/KEY: misc_feature
<222> LOCATION: (1033)..(1033)
<223> OTHER INFORMATION: N= A, U, G or C
<220> FEATURE:
<221> NAME/KEY: misc_feature
<222> LOCATION: (1037)..(1042)
<223> OTHER INFORMATION: N= A, U, G or C
<220> FEATURE:
<221> NAME/KEY: misc_feature
<222> LOCATION: (1044)..(1045)
<223> OTHER INFORMATION: N= A, U, G or C
<220> FEATURE:
<221> NAME/KEY: misc_feature
<222> LOCATION: (1047)..(1047)
<223> OTHER INFORMATION: N= A, U, G or C
<220> FEATURE:
<221> NAME/KEY: misc_feature
<222> LOCATION: (1051)..(1053)
<223> OTHER INFORMATION: N= A, U, G or C
<220> FEATURE:
<221> NAME/KEY: misc_feature
<222> LOCATION: (1058)..(1058)
<223> OTHER INFORMATION: N= A, U, G or C
<220> FEATURE:
<221> NAME/KEY: misc_feature
<222> LOCATION: (1078)..(1078)
<223> OTHER INFORMATION: N= A, U, G or C
<220> FEATURE:
<221> NAME/KEY: misc_feature
<222> LOCATION: (1080)..(1080)
<223> OTHER INFORMATION: N= A, U, G or C
<220> FEATURE:
<221> NAME/KEY: misc_feature
<222> LOCATION: (1083)..(1083)
<223> OTHER INFORMATION: N= A, U, G or C
<220> FEATURE:
<221> NAME/KEY: misc_feature
<222> LOCATION: (1089)..(1090)
<223> OTHER INFORMATION: N= A, U, G or C
<220> FEATURE:
<221> NAME/KEY: misc_feature
<222> LOCATION: (1097)..(1097)
<223> OTHER INFORMATION: N= A, U, G or C
<220> FEATURE:
<221> NAME/KEY: misc_feature
<222> LOCATION: (1106)..(1107)
<223> OTHER INFORMATION: N= A, U, G or C
<220> FEATURE:
<221> NAME/KEY: misc_feature
<222> LOCATION: (1110)..(1110)
<223> OTHER INFORMATION: N= A, U, G or C
<220> FEATURE:
<221> NAME/KEY: misc_feature
<222> LOCATION: (1113)..(1119)
<223> OTHER INFORMATION: N= A, U, G or C
<220> FEATURE:
<221> NAME/KEY: misc_feature
<222> LOCATION: (1124)..(1124)
<223> OTHER INFORMATION: N= A, U, G or C
<220> FEATURE:
<221> NAME/KEY: misc_feature
<222> LOCATION: (1127)..(1128)
<223> OTHER INFORMATION: N= A, U, G or C
<220> FEATURE:
<221> NAME/KEY: misc_feature
<222> LOCATION: (1131)..(1131)
<223> OTHER INFORMATION: N= A, U, G or C
<220> FEATURE:
<221> NAME/KEY: misc_feature
<222> LOCATION: (1134)..(1134)
<223> OTHER INFORMATION: N= A, U, G or C
<220> FEATURE:
<221> NAME/KEY: misc_feature
<222> LOCATION: (1139)..(1139)
<223> OTHER INFORMATION: N= A, U, G or C
<220> FEATURE:
<221> NAME/KEY: misc_feature
<222> LOCATION: (1144)..(1151)
```

```
<223> OTHER INFORMATION: N= A, U, G or C
<220> FEATURE:
<221> NAME/KEY: misc_feature
<222> LOCATION: (1157)..(1162)
<223> OTHER INFORMATION: N= A, U, G or C
<220> FEATURE:
<221> NAME/KEY: misc_feature
<222> LOCATION: (1164)..(1185)
<223> OTHER INFORMATION: N= A, U, G or C
<220> FEATURE:
<221> NAME/KEY: misc_feature
<222> LOCATION: (1191)..(1192)
<223> OTHER INFORMATION: N= A, U, G or C
<220> FEATURE:
<221> NAME/KEY: misc_feature
<222> LOCATION: (1199)..(1211)
<223> OTHER INFORMATION: N= A, U, G or C
<220> FEATURE:
<221> NAME/KEY: misc_feature
<222> LOCATION: (1216)..(1222)
<223> OTHER INFORMATION: N= A, U, G or C
<220> FEATURE:
<221> NAME/KEY: misc_feature
<222> LOCATION: (1224)..(1225)
<223> OTHER INFORMATION: N= A, U, G or C
<220> FEATURE:
<221> NAME/KEY: misc_feature
<222> LOCATION: (1227)..(1233)
<223> OTHER INFORMATION: N= A, U, G or C
<220> FEATURE:
<221> NAME/KEY: misc_feature
<222> LOCATION: (1238)..(1246)
<223> OTHER INFORMATION: N= A, U, G or C
<220> FEATURE:
<221> NAME/KEY: misc_feature
<222> LOCATION: (1251)..(1251)
<223> OTHER INFORMATION: N= A, U, G or C
<220> FEATURE:
<221> NAME/KEY: misc_feature
<222> LOCATION: (1253)..(1253)
<223> OTHER INFORMATION: N= A, U, G or C
<220> FEATURE:
<221> NAME/KEY: misc_feature
<222> LOCATION: (1257)..(1258)
<223> OTHER INFORMATION: N= A, U, G or C
<220> FEATURE:
<221> NAME/KEY: misc_feature
<222> LOCATION: (1260)..(1261)
<223> OTHER INFORMATION: N= A, U, G or C
<220> FEATURE:
<221> NAME/KEY: misc_feature
<222> LOCATION: (1264)..(1264)
<223> OTHER INFORMATION: N= A, U, G or C
<220> FEATURE:
<221> NAME/KEY: misc_feature
<222> LOCATION: (1269)..(1269)
<223> OTHER INFORMATION: N= A, U, G or C
<220> FEATURE:
<221> NAME/KEY: misc_feature
<222> LOCATION: (1273)..(1280)
<223> OTHER INFORMATION: N= A, U, G or C
<220> FEATURE:
<221> NAME/KEY: misc_feature
<222> LOCATION: (1285)..(1285)
<223> OTHER INFORMATION: N= A, U, G or C
<220> FEATURE:
<221> NAME/KEY: misc_feature
<222> LOCATION: (1287)..(1288)
<223> OTHER INFORMATION: N= A, U, G or C
<220> FEATURE:
<221> NAME/KEY: misc_feature
<222> LOCATION: (1290)..(1294)
<223> OTHER INFORMATION: N= A, U, G or C
<220> FEATURE:
<221> NAME/KEY: misc_feature
<222> LOCATION: (1296)..(1296)
<223> OTHER INFORMATION: N= A, U, G or C
<220> FEATURE:
<221> NAME/KEY: misc_feature
```

```
<222> LOCATION: (1300)..(1300)
<223> OTHER INFORMATION: N= A, U, G or C
<220> FEATURE:
<221> NAME/KEY: misc_feature
<222> LOCATION: (1302)..(1304)
<223> OTHER INFORMATION: N= A, U, G or C
<220> FEATURE:
<221> NAME/KEY: misc_feature
<222> LOCATION: (1306)..(1306)
<223> OTHER INFORMATION: N= A, U, G or C
<220> FEATURE:
<221> NAME/KEY: misc_feature
<222> LOCATION: (1311)..(1311)
<223> OTHER INFORMATION: N= A, U, G or C
<220> FEATURE:
<221> NAME/KEY: misc_feature
<222> LOCATION: (1316)..(1321)
<223> OTHER INFORMATION: N= A, U, G or C
<220> FEATURE:
<221> NAME/KEY: misc_feature
<222> LOCATION: (1323)..(1323)
<223> OTHER INFORMATION: N= A, U, G or C
<220> FEATURE:
<221> NAME/KEY: misc_feature
<222> LOCATION: (1325)..(1325)
<223> OTHER INFORMATION: N= A, U, G or C
<220> FEATURE:
<221> NAME/KEY: misc_feature
<222> LOCATION: (1327)..(1328)
<223> OTHER INFORMATION: N= A, U, G or C
<220> FEATURE:
<221> NAME/KEY: misc_feature
<222> LOCATION: (1331)..(1336)
<223> OTHER INFORMATION: N= A, U, G or C
<220> FEATURE:
<221> NAME/KEY: misc_feature
<222> LOCATION: (1341)..(1341)
<223> OTHER INFORMATION: N= A, U, G or C
<220> FEATURE:
<221> NAME/KEY: misc_feature
<222> LOCATION: (1347)..(1349)
<223> OTHER INFORMATION: N= A, U, G or C
<220> FEATURE:
<221> NAME/KEY: misc_feature
<222> LOCATION: (1356)..(1357)
<223> OTHER INFORMATION: N= A, U, G or C
<220> FEATURE:
<221> NAME/KEY: misc_feature
<222> LOCATION: (1361)..(1361)
<223> OTHER INFORMATION: N= A, U, G or C
<220> FEATURE:
<221> NAME/KEY: misc_feature
<222> LOCATION: (1363)..(1363)
<223> OTHER INFORMATION: N= A, U, G or C
<220> FEATURE:
<221> NAME/KEY: misc_feature
<222> LOCATION: (1366)..(1366)
<223> OTHER INFORMATION: N= A, U, G or C
<220> FEATURE:
<221> NAME/KEY: misc_feature
<222> LOCATION: (1368)..(1368)
<223> OTHER INFORMATION: N= A, U, G or C
<220> FEATURE:
<221> NAME/KEY: misc_feature
<222> LOCATION: (1370)..(1371)
<223> OTHER INFORMATION: N= A, U, G or C
<220> FEATURE:
<221> NAME/KEY: misc_feature
<222> LOCATION: (1375)..(1376)
<223> OTHER INFORMATION: N= A, U, G or C
<220> FEATURE:
<221> NAME/KEY: misc_feature
<222> LOCATION: (1382)..(1383)
<223> OTHER INFORMATION: N= A, U, G or C
<220> FEATURE:
<221> NAME/KEY: misc_feature
<222> LOCATION: (1385)..(1387)
<223> OTHER INFORMATION: N= A, U, G or C
<220> FEATURE:
```

-continued

```
<221> NAME/KEY: misc_feature
<222> LOCATION: (1391)..(1392)
<223> OTHER INFORMATION: N= A, U, G or C
<220> FEATURE:
<221> NAME/KEY: misc_feature
<222> LOCATION: (1400)..(1402)
<223> OTHER INFORMATION: N= A, U, G or C
<220> FEATURE:
<221> NAME/KEY: misc_feature
<222> LOCATION: (1405)..(1425)
<223> OTHER INFORMATION: N= A, U, G or C
<220> FEATURE:
<221> NAME/KEY: misc_feature
<222> LOCATION: (1430)..(1435)
<223> OTHER INFORMATION: N= A, U, G or C
<220> FEATURE:
<221> NAME/KEY: misc_feature
<222> LOCATION: (1437)..(1454)
<223> OTHER INFORMATION: N= A, U, G or C
<220> FEATURE:
<221> NAME/KEY: misc_feature
<222> LOCATION: (1457)..(1564)
<223> OTHER INFORMATION: N= A, U, G or C
<220> FEATURE:
<221> NAME/KEY: misc_feature
<222> LOCATION: (1566)..(1567)
<223> OTHER INFORMATION: N= A, U, G or C
<220> FEATURE:
<221> NAME/KEY: misc_feature
<222> LOCATION: (1573)..(1599)
<223> OTHER INFORMATION: N= A, U, G or C
<220> FEATURE:
<221> NAME/KEY: misc_feature
<222> LOCATION: (1606)..(1607)
<223> OTHER INFORMATION: N= A, U, G or C
<220> FEATURE:
<221> NAME/KEY: misc_feature
<222> LOCATION: (1622)..(1622)
<223> OTHER INFORMATION: N= A, U, G or C
<220> FEATURE:
<221> NAME/KEY: misc_feature
<222> LOCATION: (1624)..(1627)
<223> OTHER INFORMATION: N= A, U, G or C
<220> FEATURE:
<221> NAME/KEY: misc_feature
<222> LOCATION: (1629)..(1630)
<223> OTHER INFORMATION: N= A, U, G or C
<220> FEATURE:
<221> NAME/KEY: misc_feature
<222> LOCATION: (1634)..(1634)
<223> OTHER INFORMATION: N= A, U, G or C
<220> FEATURE:
<221> NAME/KEY: misc_feature
<222> LOCATION: (1636)..(1637)
<223> OTHER INFORMATION: N= A, U, G or C
<220> FEATURE:
<221> NAME/KEY: misc_feature
<222> LOCATION: (1639)..(1640)
<223> OTHER INFORMATION: N= A, U, G or C
<220> FEATURE:
<221> NAME/KEY: misc_feature
<222> LOCATION: (1644)..(1644)
<223> OTHER INFORMATION: N= A, U, G or C
<220> FEATURE:
<221> NAME/KEY: misc_feature
<222> LOCATION: (1646)..(1648)
<223> OTHER INFORMATION: N= A, U, G or C
<220> FEATURE:
<221> NAME/KEY: misc_feature
<222> LOCATION: (1650)..(1653)
<223> OTHER INFORMATION: N= A, U, G or C
<220> FEATURE:
<221> NAME/KEY: misc_feature
<222> LOCATION: (1656)..(1663)
<223> OTHER INFORMATION: N= A, U, G or C
<220> FEATURE:
<221> NAME/KEY: misc_feature
<222> LOCATION: (1672)..(1673)
<223> OTHER INFORMATION: N= A, U, G or C
```

```
<220> FEATURE:
<221> NAME/KEY: misc_feature
<222> LOCATION: (1679)..(1679)
<223> OTHER INFORMATION: N= A, U, G or C
<220> FEATURE:
<221> NAME/KEY: misc_feature
<222> LOCATION: (1681)..(1684)
<223> OTHER INFORMATION: N= A, U, G or C
<220> FEATURE:
<221> NAME/KEY: misc_feature
<222> LOCATION: (1690)..(1690)
<223> OTHER INFORMATION: N= A, U, G or C
<220> FEATURE:
<221> NAME/KEY: misc_feature
<222> LOCATION: (1697)..(1697)
<223> OTHER INFORMATION: N= A, U, G or C
<220> FEATURE:
<221> NAME/KEY: misc_feature
<222> LOCATION: (1699)..(1699)
<223> OTHER INFORMATION: N= A, U, G or C
<220> FEATURE:
<221> NAME/KEY: misc_feature
<222> LOCATION: (1704)..(1707)
<223> OTHER INFORMATION: N= A, U, G or C
<220> FEATURE:
<221> NAME/KEY: misc_feature
<222> LOCATION: (1709)..(1749)
<223> OTHER INFORMATION: N= A, U, G or C
<220> FEATURE:
<221> NAME/KEY: misc_feature
<222> LOCATION: (1751)..(1754)
<223> OTHER INFORMATION: N= A, U, G or C
<220> FEATURE:
<221> NAME/KEY: misc_feature
<222> LOCATION: (1756)..(1758)
<223> OTHER INFORMATION: N= A, U, G or C
<220> FEATURE:
<221> NAME/KEY: misc_feature
<222> LOCATION: (1760)..(1762)
<223> OTHER INFORMATION: N= A, U, G or C
<220> FEATURE:
<221> NAME/KEY: misc_feature
<222> LOCATION: (1764)..(1770)
<223> OTHER INFORMATION: N= A, U, G or C
<220> FEATURE:
<221> NAME/KEY: misc_feature
<222> LOCATION: (1772)..(1772)
<223> OTHER INFORMATION: N= A, U, G or C
<220> FEATURE:
<221> NAME/KEY: misc_feature
<222> LOCATION: (1781)..(1782)
<223> OTHER INFORMATION: N= A, U, G or C
<220> FEATURE:
<221> NAME/KEY: misc_feature
<222> LOCATION: (1793)..(1794)
<223> OTHER INFORMATION: N= A, U, G or C
<220> FEATURE:
<221> NAME/KEY: misc_feature
<222> LOCATION: (1796)..(1797)
<223> OTHER INFORMATION: N= A, U, G or C
<220> FEATURE:
<221> NAME/KEY: misc_feature
<222> LOCATION: (1801)..(1801)
<223> OTHER INFORMATION: N= A, U, G or C
<220> FEATURE:
<221> NAME/KEY: misc_feature
<222> LOCATION: (1804)..(1805)
<223> OTHER INFORMATION: N= A, U, G or C
<220> FEATURE:
<221> NAME/KEY: misc_feature
<222> LOCATION: (1808)..(1808)
<223> OTHER INFORMATION: N= A, U, G or C
<220> FEATURE:
<221> NAME/KEY: misc_feature
<222> LOCATION: (1812)..(1813)
<223> OTHER INFORMATION: N= A, U, G or C
<220> FEATURE:
<221> NAME/KEY: misc_feature
<222> LOCATION: (1816)..(1816)
```

```
<223> OTHER INFORMATION: N= A, U, G or C
<220> FEATURE:
<221> NAME/KEY: misc_feature
<222> LOCATION: (1822)..(1822)
<223> OTHER INFORMATION: N= A, U, G or C
<220> FEATURE:
<221> NAME/KEY: misc_feature
<222> LOCATION: (1825)..(1826)
<223> OTHER INFORMATION: N= A, U, G or C
<220> FEATURE:
<221> NAME/KEY: misc_feature
<222> LOCATION: (1831)..(1831)
<223> OTHER INFORMATION: N= A, U, G or C
<220> FEATURE:
<221> NAME/KEY: misc_feature
<222> LOCATION: (1839)..(1839)
<223> OTHER INFORMATION: N= A, U, G or C
<220> FEATURE:
<221> NAME/KEY: misc_feature
<222> LOCATION: (1844)..(1845)
<223> OTHER INFORMATION: N= A, U, G or C
<220> FEATURE:
<221> NAME/KEY: misc_feature
<222> LOCATION: (1855)..(1856)
<223> OTHER INFORMATION: N= A, U, G or C
<220> FEATURE:
<221> NAME/KEY: misc_feature
<222> LOCATION: (1858)..(1866)
<223> OTHER INFORMATION: N= A, U, G or C
<220> FEATURE:
<221> NAME/KEY: misc_feature
<222> LOCATION: (1868)..(1872)
<223> OTHER INFORMATION: N= A, U, G or C
<220> FEATURE:
<221> NAME/KEY: misc_feature
<222> LOCATION: (1874)..(1884)
<223> OTHER INFORMATION: N= A, U, G or C
<220> FEATURE:
<221> NAME/KEY: misc_feature
<222> LOCATION: (1886)..(1888)
<223> OTHER INFORMATION: N= A, U, G or C
<220> FEATURE:
<221> NAME/KEY: misc_feature
<222> LOCATION: (1895)..(1896)
<223> OTHER INFORMATION: N= A, U, G or C
<220> FEATURE:
<221> NAME/KEY: misc_feature
<222> LOCATION: (1899)..(1899)
<223> OTHER INFORMATION: N= A, U, G or C
<220> FEATURE:
<221> NAME/KEY: misc_feature
<222> LOCATION: (1908)..(1909)
<223> OTHER INFORMATION: N= A, U, G or C
<220> FEATURE:
<221> NAME/KEY: misc_feature
<222> LOCATION: (1921)..(1922)
<223> OTHER INFORMATION: N= A, U, G or C
<220> FEATURE:
<221> NAME/KEY: misc_feature
<222> LOCATION: (1963)..(1963)
<223> OTHER INFORMATION: N= A, U, G or C
<220> FEATURE:
<221> NAME/KEY: misc_feature
<222> LOCATION: (1971)..(1971)
<223> OTHER INFORMATION: N= A, U, G or C
<220> FEATURE:
<221> NAME/KEY: misc_feature
<222> LOCATION: (1974)..(1974)
<223> OTHER INFORMATION: N= A, U, G or C
<220> FEATURE:
<221> NAME/KEY: misc_feature
<222> LOCATION: (1976)..(1976)
<223> OTHER INFORMATION: N= A, U, G or C
<220> FEATURE:
<221> NAME/KEY: misc_feature
<222> LOCATION: (1979)..(1979)
<223> OTHER INFORMATION: N= A, U, G or C
<220> FEATURE:
<221> NAME/KEY: misc_feature
```

```
<222> LOCATION: (1982)..(1989)
<223> OTHER INFORMATION: N= A, U, G or C
<220> FEATURE:
<221> NAME/KEY: misc_feature
<222> LOCATION: (1997)..(2005)
<223> OTHER INFORMATION: N= A, U, G or C
<220> FEATURE:
<221> NAME/KEY: misc_feature
<222> LOCATION: (2007)..(2007)
<223> OTHER INFORMATION: N= A, U, G or C
<220> FEATURE:
<221> NAME/KEY: misc_feature
<222> LOCATION: (2009)..(2009)
<223> OTHER INFORMATION: N= A, U, G or C
<220> FEATURE:
<221> NAME/KEY: misc_feature
<222> LOCATION: (2011)..(2011)
<223> OTHER INFORMATION: N= A, U, G or C
<220> FEATURE:
<221> NAME/KEY: misc_feature
<222> LOCATION: (2015)..(2015)
<223> OTHER INFORMATION: N= A, U, G or C
<220> FEATURE:
<221> NAME/KEY: misc_feature
<222> LOCATION: (2018)..(2019)
<223> OTHER INFORMATION: N= A, U, G or C
<220> FEATURE:
<221> NAME/KEY: misc_feature
<222> LOCATION: (2021)..(2021)
<223> OTHER INFORMATION: N= A, U, G or C
<220> FEATURE:
<221> NAME/KEY: misc_feature
<222> LOCATION: (2023)..(2026)
<223> OTHER INFORMATION: N= A, U, G or C
<220> FEATURE:
<221> NAME/KEY: misc_feature
<222> LOCATION: (2029)..(2029)
<223> OTHER INFORMATION: N= A, U, G or C
<220> FEATURE:
<221> NAME/KEY: misc_feature
<222> LOCATION: (2037)..(2040)
<223> OTHER INFORMATION: N= A, U, G or C
<220> FEATURE:
<221> NAME/KEY: misc_feature
<222> LOCATION: (2042)..(2042)
<223> OTHER INFORMATION: N= A, U, G or C
<220> FEATURE:
<221> NAME/KEY: misc_feature
<222> LOCATION: (2044)..(2044)
<223> OTHER INFORMATION: N= A, U, G or C
<220> FEATURE:
<221> NAME/KEY: misc_feature
<222> LOCATION: (2048)..(2052)
<223> OTHER INFORMATION: N= A, U, G or C
<220> FEATURE:
<221> NAME/KEY: misc_feature
<222> LOCATION: (2067)..(2068)
<223> OTHER INFORMATION: N= A, U, G or C
<220> FEATURE:
<221> NAME/KEY: misc_feature
<222> LOCATION: (2070)..(2070)
<223> OTHER INFORMATION: N= A, U, G or C
<220> FEATURE:
<221> NAME/KEY: misc_feature
<222> LOCATION: (2072)..(2072)
<223> OTHER INFORMATION: N= A, U, G or C
<220> FEATURE:
<221> NAME/KEY: misc_feature
<222> LOCATION: (2080)..(2081)
<223> OTHER INFORMATION: N= A, U, G or C
<220> FEATURE:
<221> NAME/KEY: misc_feature
<222> LOCATION: (2083)..(2085)
<223> OTHER INFORMATION: N= A, U, G or C
<220> FEATURE:
<221> NAME/KEY: misc_feature
<222> LOCATION: (2087)..(2089)
<223> OTHER INFORMATION: N= A, U, G or C
<220> FEATURE:
```

```
<221> NAME/KEY: misc_feature
<222> LOCATION: (2091)..(2091)
<223> OTHER INFORMATION: N= A, U, G or C
<220> FEATURE:
<221> NAME/KEY: misc_feature
<222> LOCATION: (2094)..(2108)
<223> OTHER INFORMATION: N= A, U, G or C
<220> FEATURE:
<221> NAME/KEY: misc_feature
<222> LOCATION: (2112)..(2113)
<223> OTHER INFORMATION: N= A, U, G or C
<220> FEATURE:
<221> NAME/KEY: misc_feature
<222> LOCATION: (2116)..(2116)
<223> OTHER INFORMATION: N= A, U, G or C
<220> FEATURE:
<221> NAME/KEY: misc_feature
<222> LOCATION: (2123)..(2123)
<223> OTHER INFORMATION: N= A, U, G or C
<220> FEATURE:
<221> NAME/KEY: misc_feature
<222> LOCATION: (2128)..(2128)
<223> OTHER INFORMATION: N= A, U, G or C
<220> FEATURE:
<221> NAME/KEY: misc_feature
<222> LOCATION: (2130)..(2132)
<223> OTHER INFORMATION: N= A, U, G or C
<220> FEATURE:
<221> NAME/KEY: misc_feature
<222> LOCATION: (2135)..(2142)
<223> OTHER INFORMATION: N= A, U, G or C
<220> FEATURE:
<221> NAME/KEY: misc_feature
<222> LOCATION: (2145)..(2146)
<223> OTHER INFORMATION: N= A, U, G or C
<220> FEATURE:
<221> NAME/KEY: misc_feature
<222> LOCATION: (2149)..(2155)
<223> OTHER INFORMATION: N= A, U, G or C
<220> FEATURE:
<221> NAME/KEY: misc_feature
<222> LOCATION: (2160)..(2160)
<223> OTHER INFORMATION: N= A, U, G or C
<220> FEATURE:
<221> NAME/KEY: misc_feature
<222> LOCATION: (2162)..(2166)
<223> OTHER INFORMATION: N= A, U, G or C
<220> FEATURE:
<221> NAME/KEY: misc_feature
<222> LOCATION: (2169)..(2170)
<223> OTHER INFORMATION: N= A, U, G or C
<220> FEATURE:
<221> NAME/KEY: misc_feature
<222> LOCATION: (2175)..(2175)
<223> OTHER INFORMATION: N= A, U, G or C
<220> FEATURE:
<221> NAME/KEY: misc_feature
<222> LOCATION: (2178)..(2178)
<223> OTHER INFORMATION: N= A, U, G or C
<220> FEATURE:
<221> NAME/KEY: misc_feature
<222> LOCATION: (2181)..(2194)
<223> OTHER INFORMATION: N= A, U, G or C
<220> FEATURE:
<221> NAME/KEY: misc_feature
<222> LOCATION: (2201)..(2211)
<223> OTHER INFORMATION: N= A, U, G or C
<220> FEATURE:
<221> NAME/KEY: misc_feature
<222> LOCATION: (2213)..(2213)
<223> OTHER INFORMATION: N= A, U, G or C
<220> FEATURE:
<221> NAME/KEY: misc_feature
<222> LOCATION: (2215)..(2223)
<223> OTHER INFORMATION: N= A, U, G or C
<220> FEATURE:
<221> NAME/KEY: misc_feature
<222> LOCATION: (2228)..(2228)
<223> OTHER INFORMATION: N= A, U, G or C
```

```
<220> FEATURE:
<221> NAME/KEY: misc_feature
<222> LOCATION: (2231)..(2233)
<223> OTHER INFORMATION: N= A, U, G or C
<220> FEATURE:
<221> NAME/KEY: misc_feature
<222> LOCATION: (2235)..(2236)
<223> OTHER INFORMATION: N= A, U, G or C
<220> FEATURE:
<221> NAME/KEY: misc_feature
<222> LOCATION: (2240)..(2240)
<223> OTHER INFORMATION: N= A, U, G or C
<220> FEATURE:
<221> NAME/KEY: misc_feature
<222> LOCATION: (2246)..(2246)
<223> OTHER INFORMATION: N= A, U, G or C
<220> FEATURE:
<221> NAME/KEY: misc_feature
<222> LOCATION: (2258)..(2259)
<223> OTHER INFORMATION: N= A, U, G or C
<220> FEATURE:
<221> NAME/KEY: misc_feature
<222> LOCATION: (2265)..(2265)
<223> OTHER INFORMATION: N= A, U, G or C
<220> FEATURE:
<221> NAME/KEY: misc_feature
<222> LOCATION: (2269)..(2270)
<223> OTHER INFORMATION: N= A, U, G or C
<220> FEATURE:
<221> NAME/KEY: misc_feature
<222> LOCATION: (2281)..(2281)
<223> OTHER INFORMATION: N= A, U, G or C
<220> FEATURE:
<221> NAME/KEY: misc_feature
<222> LOCATION: (2283)..(2284)
<223> OTHER INFORMATION: N= A, U, G or C
<220> FEATURE:
<221> NAME/KEY: misc_feature
<222> LOCATION: (2286)..(2286)
<223> OTHER INFORMATION: N= A, U, G or C
<220> FEATURE:
<221> NAME/KEY: misc_feature
<222> LOCATION: (2292)..(2294)
<223> OTHER INFORMATION: N= A, U, G or C
<220> FEATURE:
<221> NAME/KEY: misc_feature
<222> LOCATION: (2297)..(2297)
<223> OTHER INFORMATION: N= A, U, G or C
<220> FEATURE:
<221> NAME/KEY: misc_feature
<222> LOCATION: (2299)..(2302)
<223> OTHER INFORMATION: N= A, U, G or C
<220> FEATURE:
<221> NAME/KEY: misc_feature
<222> LOCATION: (2305)..(2306)
<223> OTHER INFORMATION: N= A, U, G or C
<220> FEATURE:
<221> NAME/KEY: misc_feature
<222> LOCATION: (2309)..(2310)
<223> OTHER INFORMATION: N= A, U, G or C
<220> FEATURE:
<221> NAME/KEY: misc_feature
<222> LOCATION: (2314)..(2321)
<223> OTHER INFORMATION: N= A, U, G or C
<220> FEATURE:
<221> NAME/KEY: misc_feature
<222> LOCATION: (2325)..(2326)
<223> OTHER INFORMATION: N= A, U, G or C
<220> FEATURE:
<221> NAME/KEY: misc_feature
<222> LOCATION: (2329)..(2330)
<223> OTHER INFORMATION: N= A, U, G or C
<220> FEATURE:
<221> NAME/KEY: misc_feature
<222> LOCATION: (2332)..(2332)
<223> OTHER INFORMATION: N= A, U, G or C
<220> FEATURE:
<221> NAME/KEY: misc_feature
<222> LOCATION: (2334)..(2334)
```

```
<223> OTHER INFORMATION: N= A, U, G or C
<220> FEATURE:
<221> NAME/KEY: misc_feature
<222> LOCATION: (2338)..(2340)
<223> OTHER INFORMATION: N= A, U, G or C
<220> FEATURE:
<221> NAME/KEY: misc_feature
<222> LOCATION: (2343)..(2343)
<223> OTHER INFORMATION: N= A, U, G or C
<220> FEATURE:
<221> NAME/KEY: misc_feature
<222> LOCATION: (2345)..(2345)
<223> OTHER INFORMATION: N= A, U, G or C
<220> FEATURE:
<221> NAME/KEY: misc_feature
<222> LOCATION: (2350)..(2351)
<223> OTHER INFORMATION: N= A, U, G or C
<220> FEATURE:
<221> NAME/KEY: misc_feature
<222> LOCATION: (2354)..(2357)
<223> OTHER INFORMATION: N= A, U, G or C
<220> FEATURE:
<221> NAME/KEY: misc_feature
<222> LOCATION: (2360)..(2363)
<223> OTHER INFORMATION: N= A, U, G or C
<220> FEATURE:
<221> NAME/KEY: misc_feature
<222> LOCATION: (2371)..(2373)
<223> OTHER INFORMATION: N= A, U, G or C
<220> FEATURE:
<221> NAME/KEY: misc_feature
<222> LOCATION: (2380)..(2381)
<223> OTHER INFORMATION: N= A, U, G or C
<220> FEATURE:
<221> NAME/KEY: misc_feature
<222> LOCATION: (2384)..(2386)
<223> OTHER INFORMATION: N= A, U, G or C
<220> FEATURE:
<221> NAME/KEY: misc_feature
<222> LOCATION: (2398)..(2398)
<223> OTHER INFORMATION: N= A, U, G or C
<220> FEATURE:
<221> NAME/KEY: misc_feature
<222> LOCATION: (2402)..(2407)
<223> OTHER INFORMATION: N= A, U, G or C
<220> FEATURE:
<221> NAME/KEY: misc_feature
<222> LOCATION: (2414)..(2414)
<223> OTHER INFORMATION: N= A, U, G or C
<220> FEATURE:
<221> NAME/KEY: misc_feature
<222> LOCATION: (2418)..(2418)
<223> OTHER INFORMATION: N= A, U, G or C
<220> FEATURE:
<221> NAME/KEY: misc_feature
<222> LOCATION: (2437)..(2437)
<223> OTHER INFORMATION: N= A, U, G or C
<220> FEATURE:
<221> NAME/KEY: misc_feature
<222> LOCATION: (2441)..(2441)
<223> OTHER INFORMATION: N= A, U, G or C
<220> FEATURE:
<221> NAME/KEY: misc_feature
<222> LOCATION: (2443)..(2443)
<223> OTHER INFORMATION: N= A, U, G or C
<220> FEATURE:
<221> NAME/KEY: misc_feature
<222> LOCATION: (2458)..(2458)
<223> OTHER INFORMATION: N= A, U, G or C
<220> FEATURE:
<221> NAME/KEY: misc_feature
<222> LOCATION: (2461)..(2464)
<223> OTHER INFORMATION: N= A, U, G or C
<220> FEATURE:
<221> NAME/KEY: misc_feature
<222> LOCATION: (2474)..(2474)
<223> OTHER INFORMATION: N= A, U, G or C
<220> FEATURE:
<221> NAME/KEY: misc_feature
```

```
<222> LOCATION: (2477)..(2477)
<223> OTHER INFORMATION: N= A, U, G or C
<220> FEATURE:
<221> NAME/KEY: misc_feature
<222> LOCATION: (2486)..(2489)
<223> OTHER INFORMATION: N= A, U, G or C
<220> FEATURE:
<221> NAME/KEY: misc_feature
<222> LOCATION: (2513)..(2513)
<223> OTHER INFORMATION: N= A, U, G or C
<220> FEATURE:
<221> NAME/KEY: misc_feature
<222> LOCATION: (2516)..(2516)
<223> OTHER INFORMATION: N= A, U, G or C
<220> FEATURE:
<221> NAME/KEY: misc_feature
<222> LOCATION: (2530)..(2530)
<223> OTHER INFORMATION: N= A, U, G or C
<220> FEATURE:
<221> NAME/KEY: misc_feature
<222> LOCATION: (2533)..(2534)
<223> OTHER INFORMATION: N= A, U, G or C
<220> FEATURE:
<221> NAME/KEY: misc_feature
<222> LOCATION: (2547)..(2548)
<223> OTHER INFORMATION: N= A, U, G or C
<220> FEATURE:
<221> NAME/KEY: misc_feature
<222> LOCATION: (2560)..(2561)
<223> OTHER INFORMATION: N= A, U, G or C
<220> FEATURE:
<221> NAME/KEY: misc_feature
<222> LOCATION: (2568)..(2568)
<223> OTHER INFORMATION: N= A, U, G or C
<220> FEATURE:
<221> NAME/KEY: misc_feature
<222> LOCATION: (2571)..(2571)
<223> OTHER INFORMATION: N= A, U, G or C
<220> FEATURE:
<221> NAME/KEY: misc_feature
<222> LOCATION: (2575)..(2575)
<223> OTHER INFORMATION: N= A, U, G or C
<220> FEATURE:
<221> NAME/KEY: misc_feature
<222> LOCATION: (2586)..(2586)
<223> OTHER INFORMATION: N= A, U, G or C
<220> FEATURE:
<221> NAME/KEY: misc_feature
<222> LOCATION: (2588)..(2588)
<223> OTHER INFORMATION: N= A, U, G or C
<220> FEATURE:
<221> NAME/KEY: misc_feature
<222> LOCATION: (2606)..(2606)
<223> OTHER INFORMATION: N= A, U, G or C
<220> FEATURE:
<221> NAME/KEY: misc_feature
<222> LOCATION: (2617)..(2617)
<223> OTHER INFORMATION: N= A, U, G or C
<220> FEATURE:
<221> NAME/KEY: misc_feature
<222> LOCATION: (2619)..(2620)
<223> OTHER INFORMATION: N= A, U, G or C
<220> FEATURE:
<221> NAME/KEY: misc_feature
<222> LOCATION: (2622)..(2622)
<223> OTHER INFORMATION: N= A, U, G or C
<220> FEATURE:
<221> NAME/KEY: misc_feature
<222> LOCATION: (2624)..(2624)
<223> OTHER INFORMATION: N= A, U, G or C
<220> FEATURE:
<221> NAME/KEY: misc_feature
<222> LOCATION: (2626)..(2626)
<223> OTHER INFORMATION: N= A, U, G or C
<220> FEATURE:
<221> NAME/KEY: misc_feature
<222> LOCATION: (2628)..(2630)
<223> OTHER INFORMATION: N= A, U, G or C
<220> FEATURE:
```

```
<221> NAME/KEY: misc_feature
<222> LOCATION: (2633)..(2635)
<223> OTHER INFORMATION: N= A, U, G or C
<220> FEATURE:
<221> NAME/KEY: misc_feature
<222> LOCATION: (2640)..(2642)
<223> OTHER INFORMATION: N= A, U, G or C
<220> FEATURE:
<221> NAME/KEY: misc_feature
<222> LOCATION: (2644)..(2646)
<223> OTHER INFORMATION: N= A, U, G or C
<220> FEATURE:
<221> NAME/KEY: misc_feature
<222> LOCATION: (2649)..(2650)
<223> OTHER INFORMATION: N= A, U, G or C
<220> FEATURE:
<221> NAME/KEY: misc_feature
<222> LOCATION: (2652)..(2652)
<223> OTHER INFORMATION: N= A, U, G or C
<220> FEATURE:
<221> NAME/KEY: misc_feature
<222> LOCATION: (2670)..(2674)
<223> OTHER INFORMATION: N= A, U, G or C
<220> FEATURE:
<221> NAME/KEY: misc_feature
<222> LOCATION: (2677)..(2678)
<223> OTHER INFORMATION: N= A, U, G or C
<220> FEATURE:
<221> NAME/KEY: misc_feature
<222> LOCATION: (2680)..(2680)
<223> OTHER INFORMATION: N= A, U, G or C
<220> FEATURE:
<221> NAME/KEY: misc_feature
<222> LOCATION: (2682)..(2682)
<223> OTHER INFORMATION: N= A, U, G or C
<220> FEATURE:
<221> NAME/KEY: misc_feature
<222> LOCATION: (2689)..(2691)
<223> OTHER INFORMATION: N= A, U, G or C
<220> FEATURE:
<221> NAME/KEY: misc_feature
<222> LOCATION: (2693)..(2693)
<223> OTHER INFORMATION: N= A, U, G or C
<220> FEATURE:
<221> NAME/KEY: misc_feature
<222> LOCATION: (2699)..(2701)
<223> OTHER INFORMATION: N= A, U, G or C
<220> FEATURE:
<221> NAME/KEY: misc_feature
<222> LOCATION: (2706)..(2708)
<223> OTHER INFORMATION: N= A, U, G or C
<220> FEATURE:
<221> NAME/KEY: misc_feature
<222> LOCATION: (2712)..(2713)
<223> OTHER INFORMATION: N= A, U, G or C
<220> FEATURE:
<221> NAME/KEY: misc_feature
<222> LOCATION: (2716)..(2716)
<223> OTHER INFORMATION: N= A, U, G or C
<220> FEATURE:
<221> NAME/KEY: misc_feature
<222> LOCATION: (2718)..(2719)
<223> OTHER INFORMATION: N= A, U, G or C
<220> FEATURE:
<221> NAME/KEY: misc_feature
<222> LOCATION: (2726)..(2727)
<223> OTHER INFORMATION: N= A, U, G or C
<220> FEATURE:
<221> NAME/KEY: misc_feature
<222> LOCATION: (2729)..(2730)
<223> OTHER INFORMATION: N= A, U, G or C
<220> FEATURE:
<221> NAME/KEY: misc_feature
<222> LOCATION: (2733)..(2736)
<223> OTHER INFORMATION: N= A, U, G or C
<220> FEATURE:
<221> NAME/KEY: misc_feature
<222> LOCATION: (2742)..(2743)
<223> OTHER INFORMATION: N= A, U, G or C
```

-continued

```
<220> FEATURE:
<221> NAME/KEY: misc_feature
<222> LOCATION: (2750)..(2750)
<223> OTHER INFORMATION: N= A, U, G or C
<220> FEATURE:
<221> NAME/KEY: misc_feature
<222> LOCATION: (2760)..(2762)
<223> OTHER INFORMATION: N= A, U, G or C
<220> FEATURE:
<221> NAME/KEY: misc_feature
<222> LOCATION: (2766)..(2766)
<223> OTHER INFORMATION: N= A, U, G or C
<220> FEATURE:
<221> NAME/KEY: misc_feature
<222> LOCATION: (2768)..(2770)
<223> OTHER INFORMATION: N= A, U, G or C
<220> FEATURE:
<221> NAME/KEY: misc_feature
<222> LOCATION: (2772)..(2775)
<223> OTHER INFORMATION: N= A, U, G or C
<220> FEATURE:
<221> NAME/KEY: misc_feature
<222> LOCATION: (2779)..(2780)
<223> OTHER INFORMATION: N= A, U, G or C
<220> FEATURE:
<221> NAME/KEY: misc_feature
<222> LOCATION: (2783)..(2785)
<223> OTHER INFORMATION: N= A, U, G or C
<220> FEATURE:
<221> NAME/KEY: misc_feature
<222> LOCATION: (2788)..(2788)
<223> OTHER INFORMATION: N= A, U, G or C
<220> FEATURE:
<221> NAME/KEY: misc_feature
<222> LOCATION: (2790)..(2809)
<223> OTHER INFORMATION: N= A, U, G or C
<220> FEATURE:
<221> NAME/KEY: misc_feature
<222> LOCATION: (2812)..(2814)
<223> OTHER INFORMATION: N= A, U, G or C
<220> FEATURE:
<221> NAME/KEY: misc_feature
<222> LOCATION: (2816)..(2820)
<223> OTHER INFORMATION: N= A, U, G or C
<220> FEATURE:
<221> NAME/KEY: misc_feature
<222> LOCATION: (2824)..(2825)
<223> OTHER INFORMATION: N= A, U, G or C
<220> FEATURE:
<221> NAME/KEY: misc_feature
<222> LOCATION: (2827)..(2830)
<223> OTHER INFORMATION: N= A, U, G or C
<220> FEATURE:
<221> NAME/KEY: misc_feature
<222> LOCATION: (2833)..(2833)
<223> OTHER INFORMATION: N= A, U, G or C
<220> FEATURE:
<221> NAME/KEY: misc_feature
<222> LOCATION: (2840)..(2842)
<223> OTHER INFORMATION: N= A, U, G or C
<220> FEATURE:
<221> NAME/KEY: misc_feature
<222> LOCATION: (2844)..(2846)
<223> OTHER INFORMATION: N= A, U, G or C
<220> FEATURE:
<221> NAME/KEY: misc_feature
<222> LOCATION: (2849)..(2849)
<223> OTHER INFORMATION: N= A, U, G or C
<220> FEATURE:
<221> NAME/KEY: misc_feature
<222> LOCATION: (2853)..(2856)
<223> OTHER INFORMATION: N= A, U, G or C
<220> FEATURE:
<221> NAME/KEY: misc_feature
<222> LOCATION: (2858)..(2859)
<223> OTHER INFORMATION: N= A, U, G or C
<220> FEATURE:
<221> NAME/KEY: misc_feature
<222> LOCATION: (2861)..(2864)
```

```
<223> OTHER INFORMATION: N= A, U, G or C
<220> FEATURE:
<221> NAME/KEY: misc_feature
<222> LOCATION: (2866)..(2867)
<223> OTHER INFORMATION: N= A, U, G or C
<220> FEATURE:
<221> NAME/KEY: misc_feature
<222> LOCATION: (2870)..(2872)
<223> OTHER INFORMATION: N= A, U, G or C
<220> FEATURE:
<221> NAME/KEY: misc_feature
<222> LOCATION: (2875)..(2877)
<223> OTHER INFORMATION: N= A, U, G or C
<220> FEATURE:
<221> NAME/KEY: misc_feature
<222> LOCATION: (2885)..(2888)
<223> OTHER INFORMATION: N= A, U, G or C
<220> FEATURE:
<221> NAME/KEY: misc_feature
<222> LOCATION: (2890)..(2895)
<223> OTHER INFORMATION: N= A, U, G or C
<220> FEATURE:
<221> NAME/KEY: misc_feature
<222> LOCATION: (2899)..(2904)
<223> OTHER INFORMATION: N= A, U, G or C

<400> SEQUENCE: 4
nnnnaagnnn nnaagngnnn nngguggaug ccunggcnnn nnnagncgan gaaggangnn      60
nnnnncnncn nnanncnnng gnnagnngnn nnnnnncnnn nnanccnnng nunuccgaau     120
ggggnaaccc nnnnnnnnnn nnnnnnnnan nnnnnnnnnn nnnnnnnnnn nnnnnnngnn     180
nacnnnnnga anugaaacau cunaguannn nnaggaanag aaannaannn ngauuncnnn     240
nguagnggcg agcgaannng nannagncnn nnnnnnnnnn nnnnnnnnnn nnnannngaa     300
nnnnnuggna agnnnnnnnn nannngguna nanccngua nnnnaaannn nnnnnnnnnn     360
nnnnnnnnnn aguannncnn nncncgngnn annnngunng aannngnnnn gaccannnnn     420
naagncuaaa uacunnnnnn ngaccnauag ngnannagua cngugangga aaggngaaaa     480
gnacccnnnn nangggagug aaanagnncc ugaaaccnnn nncnuanaan nngunnnagn     540
nnnnnnnnnn nnnugannnc gunccuuuug nannaugnnn cngnganuun nnnunnnnng     600
cnagnuuaan nnnnnnnngn agncgnagng aaancgagun nnaanngngc gnnnagunnn     660
nngnnnnaga cncgaanncn ngugancuan nnaugnncag gnugaagnnn nnguaanann     720
nnnuggaggn ccgaacnnnn nnnnguugaa aannnnnngg augannugug nnungnggng     780
aaanncnaan cnaacnnngn nauagcuggu ucucnncgaa annnnuuuag gnnnngcnun     840
nnnnnnnnnn nnnngngu agagcacugn nnnnnnnnng gnnnnnnnnn nnnnuacnna     900
nnnnnnnnaa acuncgaaun ccnnnnnnnn nnnnnnnngn agnnanncnn ngngngnuaa     960
nnuncnnngu nnanagggna acanccagaa ncnncnnnua aggncccnaa nnnnnnnnua    1020
aguggnaaan gangugnnnn nncnnanaca nnnaggangu uggcuuagaa gcagccancn    1080
uunaaagann gcguaanagc ucacnnnucn agnnnnnnng cgcngannau nuancgggnc    1140
uaannnnnnn nccgaannnn nngnnnnnnn nnnnnnnnnn nnnnngguag nngagcgunn    1200
nnnnnnnnnn ngaagnnnnn nngnnannnn nnnuggannn nnnnnnagug ngnaugnngn    1260
naunaguanc gannnnnnnn gugananncn nnnncnccgn annncnaagg nuuccnnnnn    1320
nangnunnuc nnnnnngggu nagucgnnnc cuaagnngag ncnganangn nuagnngaug    1380
gnnannnggu nnauauuccn nnacnnnnnn nnnnnnnnnn nnnnngacgn nnnnngnnnn    1440
nnnnnnnnnn nnnggnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
```

```
nnnncnngaa aannnnnnnn nnnnnnnnnn nnnnnnnnnc guaccnnaaa ccgacacagg      1620
ungnnnngnn gagnanncnn aggngnnngn nnnaannnnn nnnaaggaac unngcaaanu      1680
nnnnccguan cuucggnana aggnnnncnn nnnnnnnnnn nnnnnnnnnn nnnnnnnnnn      1740
nnnnnnnnng nnnnannnan nngnnnnnnn cnacuguuua nnaaaaacac agnncnnugc      1800
naanncgnaa gnnganguau anggnnugac nccugcccng ugcnngaagg uuaanngnnn      1860
nnnnnngnnn nngnnnnnnn nnnnannnaa gcccnnguna acggcggnng uaacuauaac      1920
nnuccuaagg uagcgaaauu ccuugucggg uaaguuccga ccngcacgaa ngngngnaang     1980 annnnnnnnc ugucucnnnn nnnnncncng ngaanuunna nunnnnguna agaugcnnnn      2040
uncncgcnnn nngacggaaa gaccccnngn ancuuuacun nannnunnna nugnnnnnnn      2100
nnnnnnnnug unnagnauag gunggagncn nngannnnnn nncgnnagnn nnnnnggagn      2160
cnnnnnnugn auacnacncu nnnnnnnnnn nnnnucuaac nnnnnnnnnn nancnnnnnn      2220
nnngacanug nnngnngggn aguuunacug gggcggunnc cuccnaaann guaacggagg      2280
ngnncnaagg unnncunann nnggnnggnn aucnnnnnnn nagunnaann gnanaagnnn      2340
gcnunacugn nagnnnnacn nnncgagcag nnncgaaagn nggnnnuagu gauccggngg      2400
unnnnnnugg aagngccnuc gcucaacgga uaaaagnuac ncngggggaua acaggcunau     2460 nnnncccaag aguncanauc gacggnnnng uuuggcaccu cgaugucggc ucnucncauc      2520
cuggggcugn agnnggucccc aagggunngg cguucgccn nuuaaagngg nacgngagcu      2580
ggguunanaa cgucgugaga caguungguc ccuaucngnn gngngngnnn gannnuugan      2640
nngnnnugnn cnuaguacga gaggaccggn nngnacnnan cncuggugnn ncnguugunn      2700
ngccannngc anngcngnnu agcuannunn ggnnnngaua anngcugaan gcaucuaagn      2760
nngaancnnn cnnnnagann agnnnucncn nnnnnnnnnn nnnnnnnnna gnnncnnnnn      2820
agannannnn gungauaggn nngnnnugna agnnnngnna nnnnunnagn nnacnnnuac      2880
uaaunnnncn nnnnncuunn nnnn                                             2904

<210> SEQ ID NO 5
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 5
cgtggtgacc ctt                                                           13

<210> SEQ ID NO 6
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 6
cgtcgtcacc gcta                                                          14

<210> SEQ ID NO 7
```

```
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 7
cgtggtaccc ctt                                                          13

<210> SEQ ID NO 8
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 8
tcacgcgata gcattgcg                                                     18

<210> SEQ ID NO 9
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 9
tctcacggga gctctccatg c                                                 21

<210> SEQ ID NO 10
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 10
tgactcaccc atcaacaacc gc                                                22

<210> SEQ ID NO 11
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 11
tgactcaccc atcaacaacc gc                                                22

<210> SEQ ID NO 12
<211> LENGTH: 22
<212> TYPE: DNA
<213> ORGANISM: Artificial Sequence
<220> FEATURE:
```

-continued

```
<223> OTHER INFORMATION: Synthetic
<220> FEATURE:
<221> NAME/KEY: misc_feature
<223> OTHER INFORMATION: PCR Primer

<400> SEQUENCE: 12
tgactcaccc atcaacaacc gc                                           22

<210> SEQ ID NO 13
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 13
gaagcagatt tgggtaccac c                                            21

<210> SEQ ID NO 14
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 14
tacggtcaat gctctgaaat ctgtgg                                       26

<210> SEQ ID NO 15
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 15
ttatgtaaaa tccattgtcg catccacc                                     28

<210> SEQ ID NO 16
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 16
tcccattact aaacccacac tcaacag                                      27

<210> SEQ ID NO 17
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer
```

<400> SEQUENCE: 17
taaggccttc gatacgggat aatccta                                27

<210> SEQ ID NO 18
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 18
tactccaatg ctaaaactaa tcgtcccaac                             30

<210> SEQ ID NO 19
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 19
tcctaggaat cacctcccat tccga                                  25

<210> SEQ ID NO 20
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 20
tggcagccta gcattagcag gaata                                  25

<210> SEQ ID NO 21
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 21
tcgctgacgc cataaaactc ttcac                                  25

<210> SEQ ID NO 22
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 22
taactaatac taacatctca gacgctcagg a                           31

<210> SEQ ID NO 23
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 23
tactcccacc ctggagcctc                                              20

<210> SEQ ID NO 24
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 24
ttatcacctt tcatgatcac gccct                                        25

<210> SEQ ID NO 25
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 25
tgtatgaatg gctccacgag ggt                                          23

<210> SEQ ID NO 26
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 26
tggtttggca gagatgtgtt taagt                                        25

<210> SEQ ID NO 27
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 27
tctgttaaaa gtgcataccg cca                                          23

<210> SEQ ID NO 28
<211> LENGTH: 21

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 28
tgaggatggt ggtcaaggga c                                              21

<210> SEQ ID NO 29
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 29
tggatttgac tgtaatgtgc ta                                             22

<210> SEQ ID NO 30
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 30
tgaagggatt tgactgtaat gtgctatg                                       28

<210> SEQ ID NO 31
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 31
gtgtgtgtgc tgggtaggat g                                              21

<210> SEQ ID NO 32
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 32
tggtaagaag tgggctaggg catt                                           24

<210> SEQ ID NO 33
<211> LENGTH: 24
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<223> OTHER INFORMATION: PCR Primer

<400> SEQUENCE: 33
tggtgatagc gcctaagcat agtg                                        24

<210> SEQ ID NO 34
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 34
tttcgtgcaa gaataggagg tggag                                       25

<210> SEQ ID NO 35
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 35
tagggtcgaa gccgcactcg                                             20

<210> SEQ ID NO 36
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 36
tgtgaggcgt attataccat agccg                                       25

<210> SEQ ID NO 37
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 37
tagaatctta gctttgggtg ctaatggtg                                   29

<210> SEQ ID NO 38
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer
```

```
<400> SEQUENCE: 38
tggctgaaca ttgtttgttg gtgt                                        24

<210> SEQ ID NO 39
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 39
taagtaatgc tagggtgagt ggtaggaag                                   29

<210> SEQ ID NO 40
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 40
tttatgggct ttggtgaggg aggta                                       25

<210> SEQ ID NO 41
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 41
tgctcctatt gataggacat agtggaagtg                                  30

<210> SEQ ID NO 42
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 42
tggcatttca ctgtaaagag gtgttgg                                     27

<210> SEQ ID NO 43
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR Primer

<400> SEQUENCE: 43
tcggtaagca ttaggaatgc cattgc                                      26
```

```
<210> SEQ ID NO 44
<211> LENGTH: 52
<212> TYPE: DNA
<213> ORGANISM: Artificial Sequence
<220> FEATURE:
<223> OTHER INFORMATION: Synthetic

<400> SEQUENCE: 44
acataaaaac ccaatccaca tcaaacccccc cccccatgc ttacaagcaa gt          52

<210> SEQ ID NO 45
<211> LENGTH: 53
<212> TYPE: DNA
<213> ORGANISM: Artificial Sequence
<220> FEATURE:
<223> OTHER INFORMATION: Synthetic

<400> SEQUENCE: 45
acataaaaac ccaatccaca tcaaacccccc ccccccatg cttacaagca agt         53

<210> SEQ ID NO 46
<211> LENGTH: 79
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t

<400> SEQUENCE: 46
accacctgta gtacataaaa acccaatcca catcaaaccc ccccccccct nggtttanaa   60
gnangtnngg nantnancc                                               79

<210> SEQ ID NO 47
<211> LENGTH: 80
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (65)..(68)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t

<400> SEQUENCE: 47
gagggttgat tgctgtactt gcttgtaagc atgggggggg gggntttaat ngnanttgnt     60
ttttnnnncc ccccgggn                                                  80
```